(12) United States Patent
Blein et al.

(10) Patent No.: US 9,683,053 B2
(45) Date of Patent: *Jun. 20, 2017

(54) HETERO-DIMERIC IMMUNOGLOBULINS

(71) Applicant: Glenmark Pharmaceuticals S.A., La Chaux-de-Fonds (CH)

(72) Inventors: Stanislas Blein, La Chaux-de-Fonds (CH); Darko Skegro, La Chaux-de-Fonds (CH); Paul Wassmann, La Chaux-de-Fonds (CH)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/167,712

(22) Filed: Jan. 29, 2014

(65) Prior Publication Data

US 2014/0187753 A1 Jul. 3, 2014

Related U.S. Application Data

(63) Continuation of application No. 13/695,773, filed as application No. PCT/IB2012/051410 on Mar. 23, 2012.

(60) Provisional application No. 61/467,727, filed on Mar. 25, 2011.

(51) Int. Cl.
| | |
|---|---|
| *C07K 16/46* | (2006.01) |
| *C07K 16/18* | (2006.01) |
| *C07K 16/28* | (2006.01) |
| *C07K 16/32* | (2006.01) |

(52) U.S. Cl.
CPC ............... *C07K 16/46* (2013.01); *C07K 16/18* (2013.01); *C07K 16/2803* (2013.01); *C07K 16/2842* (2013.01); *C07K 16/2863* (2013.01); *C07K 16/32* (2013.01); *C07K 16/468* (2013.01); *C07K 2317/50* (2013.01); *C07K 2317/52* (2013.01); *C07K 2317/526* (2013.01); *C07K 2317/55* (2013.01); *C07K 2317/622* (2013.01); *C07K 2317/94* (2013.01); *C07K 2319/00* (2013.01)

(58) Field of Classification Search
CPC ............... C07K 16/46; C07K 2317/50; C07K 2317/526; C07K 2317/52
USPC ....................... 530/387.3; 435/69.9
See application file for complete search history.

(56) References Cited

U.S. PATENT DOCUMENTS

| | | |
|---|---|---|
| 5,807,706 A | 9/1998 | Carter et al. |
| 5,821,337 A | 10/1998 | Carter et al. |
| 2013/0178605 A1* | 7/2013 | Blein et al. ............... 530/387.3 |
| 2014/0066599 A2 | 3/2014 | Blein et al. |

FOREIGN PATENT DOCUMENTS

| | | |
|---|---|---|
| WO | WO 96/40210 A1 | 12/1996 |
| WO | 9850431 | 11/1998 |
| WO | WO 98/50431 A2 | 11/1998 |
| WO | 2004-003019 | 1/2004 |
| WO | 2007110205 | 10/2007 |
| WO | WO 2007/110205 A2 | 10/2007 |
| WO | 2007147901 | 12/2007 |
| WO | WO 2007/147901 A1 | 12/2007 |
| WO | 2009089004 | 7/2009 |
| WO | WO 2009/089004 A1 | 7/2009 |
| WO | WO 2010/095031 A2 | 8/2010 |
| WO | 2012058768 | 5/2012 |
| WO | WO 2012/058768 A1 | 5/2012 |
| WO | WO 2012/131555 A2 | 10/2012 |

OTHER PUBLICATIONS

Dall'Acqua, et al., "Modulation of the Effector Functions of a Human IgG1 through Engineering of its Hinge Region", The Journal of Immunology, 2006, vol. 117, pp. 1129-1138.

Ibragimova, et al., "Stability of the Beta-Sheet of the WW Domain: A Molecular Dynamics Simulation Study", Biophysical Journal, 1999, vol. 77, pp. 2191-2198.

Kumar, et al., "Molecular Cloning and Expressions of the Fabs of Human Autoantibodies in *Escherichia coli*", The Journal of Biological Chemistry, 2000, vol. 275, pp. 35129-35136.

Salfeld, et al., "Isotype Selection in Antibody Engineering", Nature Biotechnology, 2007, vol. 25, No. 12, pp. 1369-1372.

Song, et al., "Light Chain of Natural Antibody Plays a Dominant Role in Protein Antigen Binding", Biochemical and Biophysical Research Communications, 2000, vol. 268, pp. 390-394.

Smith-Gill, et al., "Contributions of immunoglobulin heavy and light chains to antibody specificity for lysozyme and two haptens", Journal of Immunology, 1987, vol. 139, pp. 4135-4144.

Ward, et al., "Binding Activities of a Repertoire of a Single Immunoglobulin Variable Domains Secreted from *Escherichia coli*", Nature, 1989, vol. 341, pp. 544-546.

Carter (2001) "Bispecific Human IgG by Design" J Immunol Methods 248(1-2):7-15.

Gunasekaran et al. (2010) "Enhancing Antibody Fc Heterodimer Formation through Electrostatic Steering Effects: Applications to Bispecific Molecules and Monovalent IgG" J Biol Chem 285(25):19637-19646.

Ridgway et al. (1996) "'Knobs-into-Holes' Engineering of AntibodyCH3 Domains for Heavy Chain Heterodimerization" Protein Eng 9(7):617-621.

Allison, T.J., et al., "Structure of a human γδ T-cell antigen receptor," Nature 411:820-824, Nature Publishing Group, England (2001).

Arnold, K., et al., "The Swiss-Model workspace: a web-based environment for protein structure homology modelling," *Bioinformatics* 22(2): 195-201, Oxford University Press, England (2006).

Baselga, J. and Swain, S.M., "Novel anticancer targets: revisiting ERBB2 and discovering ERBB3," *Nat Rev Cancer* 9(7):463-475, Macmillan Publishers Ltd., England (2009).

(Continued)

*Primary Examiner* — Lynn Bristol

(74) *Attorney, Agent, or Firm* — Sterne, Kessler, Goldstein & Fox P.L.L.C.

(57) ABSTRACT

The present invention relates to engineered hetero-dimeric immunoglobulins or fragments thereof and methods of making the same.

21 Claims, 72 Drawing Sheets

(56) References Cited

OTHER PUBLICATIONS

Berman, H.M., et al., "The Protein Data Bank," *Nucleic Acids Res.* 28(1):235-242, Oxford University Press, England (2000).

Bernstein, F.C., et al., "The Protein Data Bank: A Computer-Based Archival File for Macromolecular Structures," *Eur J Biochem* 80:319-324, Federation of European Biochemical Societies, England (1977).

Carter, P., "Bispecific human IgG by design," *J Immunol Methods* 248:7-15, Elsevier Science B.V., Netherlands (2001).

Chacko, S., et al., "Structural Studies of Human Autoantibodies: crystal structure of a thyroid peroxidase autoantibody Fab," *J Biol Chem* 271(21):12191-12198, American Society for Biochemistry and Molecular Biology, United States (1996).

Chirino, A.J., et al., "Minimizing the immunogenicity of protein therapeutics," *Drug Discov Today* 9(2):82-90, Elsevier Ltd., England (2004).

Emsley, P., and Cowtan, K., "Coot: model-building tools for molecular graphics," *Acta Crystallogr D Biol Crystallogr* 60(Pt 12 Pt 1):2126-2132, International Union of Crystallography, Denmark (2004).

Engelman, J.A. and Jänne, P.A., "Mechanisms of Acquired Resistance to Epidermal Growth Factor Receptor Tyrosine Kinase Inhibitors in Non-Small Cell Lung Cancer," *Clin Cancer Res* 14(10):2895-2899, American Association for Cancer Research, United States (2008).

Gadola, S.D., et al.. "Structure and binding kinetics of three different human CD1d-α-galetosylceramide-specific T cell receptors," *J Exp Med* 203(3):699-710, The Rockefeller University Press, United States (2006).

Garber, E. and Demarest, S.J., "A broad range of Fab stabilities within a host of therapeutic IgGs," *Biochem Biophys Res Commun* 355:751-757, Elsevier Inc., United States (2007).

Gunasekaran, K., et al., "Enhancing Antibody Fc Heterodimer Formation through Electrostatic Steering Effects: Applications to Bispecific Molecules and Monovalent IgG," *J Biol Chem* 285(25):19637-19646, American Society for Biochemistry and Molecular Biology, United States (2010).

Hennecke, J. and Wiley. D.C., "Structure of a Complex of the Human α/βT Cell Receptor (TCR) HA1.7, Influenza Hemagglutinin Peptide, and Major Histocompatibility Complex Class II Molecule, HLA-DR4 (DRA*0101 and DRB1*0401): Insight into TCR Cross-Restriction and Alloreactivity," *J Exp Med* 195(5):571-581, The Rockefeller University Press, United States (2002).

Herr, A.B., et al., "Insights into IgA-mediated immune responses from the crystal structures of human FcαRI and its complex with IgA1-Fc," *Nature* 423:614-620, Nature Publishing Group, England (2003).

Hynes, N. E., and Lane, H.A. "ERBB Receptors and Cancer: The Complexity of Targeted Inhibitors," *Nat Rev Cancer* 5(5):341-354, Nature Publishing Group, England (2005).

Jones, K.L. and Buzdar, A.U., "Evolving novel anti-HER2 strategies," *Lance Oncol* 10:1179-1187, Lancet Publishing Group, England (2009).

Kaas, Q., et al., "IG, TR and IgSF, MHC and MhcSF: what do we learn from the IMGT Colliers de Perles?," *Briefings in Functional Genomics & Proteomics* 6(4):253-264, Oxford University Press, England (2008).

Kjer-Nielsen, L., et al., "The 1.5 Å Crystal Structure of a Highly Selected Antiviral T cell Receptor Provides Evidence for a Structural Basis of Immunodominance," *Structure* 10(11):1521-1532, Elsevier Science Ltd., England (2002).

Krapp, S., et al., "Structural Analysis of Human IgG-Fc Glycoforms Reveals a Correlation between Glycosylation and Structural Integrity," *J Mol Biol* 325(5):979-989, Elsevier Science Ltd.., England (2003).

Kufer, P., et al., "A revival of bispecific antibodies," *Trends Biotechnol* 22(5):238-244, Elsevier Ltd., England (2004).

Lefranc, M-P., et al., "IMGT, the international ImMunoGeneTics database," *Nucleic Acids Res* 27(1):209-212, Oxford University Press, England (1999).

Lefranc, M-P., "IMGT, the international ImMunoGeneTics database," *Nucleic Acids Res* 29(1):207-209, Oxford University Press. England (2001).

Lefranc, M-P., "IMGT, the international ImMunoGeneTics database," *Nucleic Acids Res* 31(1):307-310, Oxford University Press, England (2003).

Lefranc, M-P., et al., "IMGT unique numbering for immunoglobulin and T cell receptor constant domains and Ig superfamily C-like domains," *Dev Comp Immunol* 29(3):185-203, Elsevier Science, United States (2005).

Liu, H., et al., "Effect of posttranslational modifications on the thermal stability of a recombinant monoclonal antibody," *Immunol Lett* 106(2):144-153, Elsevier B.V., Netherlands (2006).

Merchant, A.M., et al., "An efficient route to human bispecific IgG," *Nat Biotechnol* 16(7):677-681, Nature America Publishing, United States (1998).

Milstein, C., and Cuello, A.C., "Hybrid hybridomas and their use in immunohistochemistry," *Nature* 305(5934):537-540, Macmillan Publishing Ltd., England (1983).

Nilson, B.H.K., et al., "Protein L from *Peptostreptococcus magnus* Binds to the κ Light Chain Variable Domain," *J Biol Chem* 267(4):2234-2239, The American Society for Biochemistry and Molecular Biology, Inc., United States (1992).

Pecorari, F., et al., "Folding, Heterodimeric Association and Specific Peptide Recognition of a Murine αβ T-cell Receptor Expressed in *Escherichia coli*," *J Mol Biol* 285:1831-1843, Academic Press, England (1999).

Retter, I., et al., "VBASE2, an integrative V gene database," *Nucleic Acids Research* 33(Database issue):D671-D674, Oxford University Press, England (2005).

Ridgway, J.B.B., et al., "'Knobs-into-holes' engineering of antibody $C_H3$ domains for heavy chain heterodimerization," *Protein Eng* 9(7):617-621, Oxford University Press, England (1996).

Robert, C., et al., "Cutaneous side-effects of kinase inhibitors and blocking antibodies," *Lancet Oncol* 6(7):491-500, Lancet Publishing Group, England (2005).

Rowinsky, E.K., "The erbB family: Targets for Therapeutic Development Against Cancer and Therapeutic Strategies using Monoclonal Antibodies and Tyrosine Kinase Inhibitors," *Annu Rev Med* 55:433-457, Annual Reviews, Inc., United States (2004).

Ruiz, M., et al., "IMGT, the international ImMunoGeneTics database," *Nucleic Acids Research* 28(1):219-221, Oxford University Press, England (2000).

Tina, K.G., et al., "PIC: Protein Interactions Calculator," *Nucleic Acids Res* 35(Web Server Issue):W473-W476, Oxford University Press, England (2007).

Willcox, B.E., et al., "Production of soluble αβ T-cell receptor heterodimers suitable for biophysical analysis of ligand binding," *Protein Sci* 8:2418-2423, Cambridge University Press, United States (1999).

International Search Report for International Patent Application PCT/IB2012/051410, European Patent Office, Rijswijk, Netherlands, mailed on Nov. 6, 2012.

Written Opinion for International Patent Application PCT/IB2012/051410, European Patent Office, Rijswijk, Netherlands, mailed on Dec. 27, 2012.

Dall'Acqua, W., et al., "Contribution of domain interface residues to the stability of antibody CH3 domain homodimers," *Biochemistry* 37(26):9266-9273, American Chemical Society, United States (1998).

Potapov, V., et al., "Protein-Protein Recognition: Juxtaposition of Domain and Interface Cores in Immunoglobulins and Other Sandwich-like Proteins," *J Mol Biol* 342:665-679, Elsevier Ltd., England (2004).

International Preliminary Report on Patentability for International Patent Application No. PCT/IB2012/051410, European Patent Office, issued on Oct. 1, 2013.

Office Action mailed Aug. 8, 2014, in U.S. Appl. No. 13/695,773, inventors Blein, S., et al., filed Nov. 1, 2012.

Office Action mailed Feb. 6. 2015, in U.S. Appl. No. 13/695,773, inventors Blein, S., et al., filed Nov. 1, 2012.

Office Action mailed Sep. 1, 2015, in U.S. Appl. No. 13/695,773, inventors Blein, S., et al., filed Nov. 1, 2012.

(56) References Cited

OTHER PUBLICATIONS

Office Action mailed Dec. 9, 2015, in U.S. Appl. No. 13/695,773, Blein, S., et al, filed Nov. 1, 2012.
Office Action mailed Jul. 5, 2016, in U.S. Appl. No. 13/695,773, Blein, S., et al, filed Nov. 1, 2012.

* cited by examiner

FIG. 1

```
                        340       350       360       370       380
                        .|....|....|....|....|....|....|....|....|....|...
Human IgG1 CH3 domain   ~~GQPREPQVYTLPPSRDELTKNQVSLTCLVKGFYPSDIAVEWESNGQPE
CH3-BT alpha domain     ~~.......................K.V...T.................
CH3-BT beta domain      ~~......E.A.F............T.V...T.................

390       400       410       420       430
                        .|....|....|....|....|....|....|....|....|....|...
Human IgG1 CH3 domain   NNYKTTPPVLDSDGSFFLYSKLTVDKSRWQQGNVFSCSVMHEALHNHYTQ
CH3-BT alpha domain     ...Y............S.V.W.N...........................
CH3-BT beta domain      .....D..L.E.....C.S.R.R...........................

440
                        .|....|..
Human IgG1 CH3 domain   KSLSLSPGK
CH3-BT alpha domain     .........
CH3-BT beta domain      .........
```

FIG. 19A

| CH1 | | | | | | | | | | | | | | | | | |
|---|---|---|---|---|---|---|---|---|---|---|---|---|---|---|---|---|---|
| IMGT® | 1.4 | 1.3 | 1.2 | 1.1 | 1 | 2 | 3 | 4 | 5 | 6 | 7 | 8 | 9 | 10 | 11 | 12 | 13 | 14 |
| EU | 118 | 119 | 120 | 121 | 122 | 123 | 124 | 125 | 126 | 127 | 128 | 129 | 130 | 131 | 132 | 133 | 134 | 135 |
| IGHG1 | A | S | T | K | G | P | S | V | F | P | L | A | P | S | S | K | S | T |
| IGHG2 | | | | | | | | | | | | | | C | | R | | |
| IGHG3 | | | | | | | | | | | | | | C | | R | | |
| IGHG4 | | | | | | | | | | | | | | C | | R | | |

| IMGT® | 15 | 16 | 17 | 18 | 19 | 20 | 21 | 22 | 23 | 24 | 25 | 26 | 27 | 28 | 29 | 30 | 35 | 36 |
|---|---|---|---|---|---|---|---|---|---|---|---|---|---|---|---|---|---|---|
| EU | 136 | 137 | 138 | 139 | 140 | 141 | 142 | 143 | 144 | 145 | 146 | 147 | 148 | 149 | 150 | 151 | 152 | 153 |
| IGHG1 | S | G | G | T | A | A | L | G | C | L | V | K | D | Y | F | P | E | P |
| IGHG2 | E | S | | | | | | | | | | | | | | | | |
| IGHG3 | | | | | | | | | | | | | | | | | | |
| IGHG4 | E | | S | | | | | | | | | | | | | | | |

| IMGT® | 37 | 38 | 39 | 40 | 41 | 42 | 43 | 44 | 45 | 45.1 | 45.2 | 45.3 | 77 | 78 | 79 | 80 | 81 | 82 |
|---|---|---|---|---|---|---|---|---|---|---|---|---|---|---|---|---|---|---|
| EU | 154 | 155 | 156 | 157 | 158 | 159 | 160 | 161 | 162 | 163 | 164 | 165 | 166 | 167 | 168 | 169 | 170 | 171 |
| IGHG1 | V | T | V | S | W | N | S | G | A | L | T | S | G | V | H | T | F | P |
| IGHG2 | | | | | | | | | | | | | | | | | | |
| IGHG3 | | | | | | | | | | | | | | | | | | |
| IGHG4 | | | | | | | | | | | | | | | | | | |

FIG. 19A (cont.)

| IMGT® | 83 | 84 | 84.1 | 84.2 | 84.3 | 84.4 | 85.4 | 85.3 | 85.2 | 85.1 | 85 | 86 | 87 | 88 | 89 | 90 | 91 | 92 |
|---|---|---|---|---|---|---|---|---|---|---|---|---|---|---|---|---|---|---|
| EU | 172 | 173 | 174 | 175 | 176 | 177 | 178 | 179 | 180 | 181 | 182 | 183 | 184 | 185 | 186 | 187 | 188 | 189 |
| IGHG1 | A | V | L | Q | S | S | G | L | Y | S | L | S | S | V | V | T | V | P |
| IGHG2 | | | | | | | | | | | | | | | | | | |
| IGHG3 | | | | | | | | | | | | | | | | | | |
| IGHG4 | | | | | | | | | | | | | | | | | | |

| IMGT® | 93 | 94 | 95 | 96 | 98 | 99 | 100 | 101 | 102 | 103 | 104 | 105 | 106 | 107 | 108 | 109 | 110 | 113 |
|---|---|---|---|---|---|---|---|---|---|---|---|---|---|---|---|---|---|---|
| EU | 190 | 191 | 192 | 193 | 194 | 195 | 196 | 197 | 198 | 199 | 200 | 201 | 202 | 203 | 204 | 205 | 206 | 207 |
| IGHG1 | S | S | N | F | G | T | Q | T | Y | I | C | N | V | N | H | K | P | S |
| IGHG2 | | | | | | | | | | T | | | | D | | | | |
| IGHG3 | | | | | | | | | | T | | | | | | | | |
| IGHG4 | | | | | | | K | | | T | | | | D | | | | |

| IMGT® | 114 | 115 | 116 | 117 | 118 | 119 | 120 | 121 |
|---|---|---|---|---|---|---|---|---|
| EU | 208 | 209 | 210 | 211 | 212 | 213 | 214 | 215 |
| IGHG1 | N | T | K | V | D | K | T | V |
| IGHG2 | | | | | | | R | |
| IGHG3 | | | | | | | R | |
| IGHG4 | | | | | | | | |

FIG. 19B

| IMGT® | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| EU | 216 | 217 | 218 | 219 | 220 | 221 | 222 | 223 | 224 | 225 | 226 | 227 | 228 | 229 | 230 |
| IGHG1-hinge | E | P | K | S | C | D | K | T | H | T | C | P | P | C | P |

| IMGT® | 1.6 | 1.5 | 1.4 | 1.3 | 1.2 | 1.1 | 1 | 2 | 3 | 4 | 5 | 6 | 7 | 8 | 9 | 10 | 11 | 12 |
|---|---|---|---|---|---|---|---|---|---|---|---|---|---|---|---|---|---|---|
| EU | 231 | 232 | 233 | 234 | 235 | 236 | 237 | 238 | 239 | 240 | 241 | 242 | 243 | 244 | 245 | 246 | 247 | 248 |
| IGHG1 | A | P | E | L | L | G | G | P | S | V | F | L | F | P | P | K | P | K |
| IGHG2 |  |  | ~ | P | V | A |  |  |  |  |  |  |  |  |  |  |  |  |
| IGHG3 |  |  |  |  |  |  |  |  |  |  |  |  |  |  |  |  |  |  |
| IGHG4 |  |  |  | F |  |  |  |  |  |  |  |  |  |  |  |  |  |  |

| IMGT® | 13 | 14 | 15 | 15.1 | 15.2 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|
| EU | 249 | 250 | 251 | 252 | 253 | 254 | 255 | 256 | 257 | 258 | 259 | 260 | 261 | 262 | 263 | 264 | 265 | 266 |
| IGHG1 | D | T | L | M | I | S | R | T | P | E | V | T | C | V | V | V | D | V |
| IGHG2 |  |  |  |  |  |  |  |  |  |  |  |  |  |  |  |  |  |  |
| IGHG3 |  |  |  |  |  |  |  |  |  |  |  |  |  |  |  |  |  |  |
| IGHG4 |  |  |  |  |  |  |  |  |  |  |  |  |  |  |  |  |  |  |

| IMGT® | 29 | 30 | 31 | 34 | 35 | 36 | 37 | 38 | 39 | 40 | 41 | 42 | 43 | 44 | 45 | 45.1 | 45.2 | 45.3 |
|---|---|---|---|---|---|---|---|---|---|---|---|---|---|---|---|---|---|---|
| EU | 267 | 268 | 269 | 270 | 271 | 272 | 273 | 274 | 275 | 276 | 277 | 278 | 279 | 280 | 281 | 282 | 283 | 284 |
| IGHG1 | S | H | E | D | P | E | V | K | F | N | W | Y | V | D | G | V | E | V |
| IGHG2 |  |  |  |  |  |  |  | Q |  |  |  |  |  |  |  |  |  |  |
| IGHG3 |  |  |  |  |  |  |  | Q |  |  |  |  |  |  |  |  |  |  |
| IGHG4 |  | Q |  |  |  |  |  | Q |  | K |  |  |  |  |  |  |  |  |

FIG. 19C (cont.)

| IMGT® | 45.4 | 77 | 78 | 79 | 80 | 81 | 82 | 83 | 84 | 84.1 | 84.2 | 84.3 | 84.4 | 85.4 | 85.3 | 85.2 | 85.1 | 85 |
|---|---|---|---|---|---|---|---|---|---|---|---|---|---|---|---|---|---|---|
| EU | 285 | 286 | 287 | 288 | 289 | 290 | 291 | 292 | 293 | 294 | 295 | 296 | 297 | 298 | 299 | 300 | 301 | 302 |
| IGHG1 | H | N | A | K | T | K | P | R | E | E | Q | Y | N | S | T | Y | R | V |
| IGHG2 | | | | | | | | | | | | F | | | | F | | |
| IGHG3 | | | | | | | | | | | | | | | | | | |
| IGHG4 | | | | | | | | | | | | F | | | | F | | |

| IMGT® | 86 | 87 | 88 | 89 | 90 | 91 | 92 | 93 | 94 | 95 | 96 | 97 | 98 | 99 | 100 | 101 | 102 | 103 |
|---|---|---|---|---|---|---|---|---|---|---|---|---|---|---|---|---|---|---|
| EU | 303 | 304 | 305 | 306 | 307 | 308 | 309 | 310 | 311 | 312 | 313 | 314 | 315 | 316 | 317 | 318 | 319 | 320 |
| IGHG1 | V | S | V | L | T | V | L | H | Q | D | W | L | N | G | K | E | Y | K |
| IGHG2 | | | | | | | V | | | | | | | | | | | |
| IGHG3 | | | | | | | | | | | | | | | | | | |
| IGHG4 | | | | | | | | | | | | | | | | | | |

| IMGT® | 104 | 105 | 106 | 107 | 108 | 109 | 110 | 113 | 114 | 115 | 116 | 117 | 118 | 119 | 120 | 121 | 122 | 123 |
|---|---|---|---|---|---|---|---|---|---|---|---|---|---|---|---|---|---|---|
| EU | 321 | 322 | 323 | 324 | 325 | 326 | 327 | 328 | 329 | 330 | 331 | 332 | 333 | 334 | 335 | 336 | 337 | 338 |
| IGHG1 | C | K | V | S | N | K | A | L | P | A | P | I | E | K | T | I | S | K |
| IGHG2 | | | | | | | | | | S | S | | | | | | | |
| IGHG3 | | | | | | | | | | | | | | | | | | |
| IGHG4 | | | | | | | | | | | | | | | | | | |

| IMGT® | 124 | 125 |
|---|---|---|
| EU | 339 | 340 |
| IGHG1 | A | K |
| IGHG2 | T | |
| IGHG3 | T | |
| IGHG4 | | |

FIG. 19D

| CH3 | | | | | | | | | | | | | | | | |
|---|---|---|---|---|---|---|---|---|---|---|---|---|---|---|---|---|
| IMGT® | 1.4 | 1.3 | 1.2 | 1.1 | 1 | 2 | 3 | 4 | 5 | 6 | 7 | 8 | 9 | 10 | 11 | 12 | 13 | 14 |
| EU | 341 | 342 | 343 | 344 | 345 | 346 | 347 | 348 | 349 | 350 | 351 | 352 | 353 | 354 | 355 | 356 | 357 | 358 |
| IGHG1 | G | Q | P | R | E | P | Q | V | Y | T | L | P | P | S | R | D | E | L |
| IGHG2 | | | | | | | | | | | | | | | | | | M |
| IGHG3 | | | | | | | | | | | | | | | | E | | M |
| IGHG4 | | | | | | | | | | | | | | | Q | E | | M |

| IMGT® | 15 | 16 | 17 | 18 | 19 | 20 | 21 | 22 | 23 | 24 | 25 | 26 | 27 | 28 | 29 | 30 | | | 36 |
|---|---|---|---|---|---|---|---|---|---|---|---|---|---|---|---|---|---|---|---|
| EU | 359 | 360 | 361 | 362 | 363 | 364 | 365 | 366 | 367 | 368 | 369 | 370 | 371 | 372 | 373 | 374 | | | 376 |
| IGHG1 | T | K | N | Q | V | S | L | T | C | L | V | K | G | F | Y | P | | | D |
| IGHG2 | | | | | | | | | | | | | | | | | | | |
| IGHG3 | | | | | | | | | | | | | | | | | | | |
| IGHG4 | | | | | | | | | | | | | | | | | | | |

| IMGT® | 37 | 38 | 39 | 40 | 41 | 42 | 43 | 44 | 45 | 45.1 | 45.2 | 45.3 | 45.4 | 77 | 78 | 79 | 80 | 81 |
|---|---|---|---|---|---|---|---|---|---|---|---|---|---|---|---|---|---|---|
| EU | 377 | 378 | 379 | 380 | 381 | 382 | 383 | 384 | 385 | 386 | 387 | 388 | 389 | 390 | 391 | 392 | 393 | 394 |
| IGHG1 | I | A | V | E | W | E | S | N | G | Q | P | E | N | N | Y | K | T | T |
| IGHG2 | | | | | | | | | | | | | | | | | | |
| IGHG3 | | | | | | | | | S | | | | | | | N | | |
| IGHG4 | | | | | | | | | | | | | | | | | | |

FIG. 19D (cont.)

| IMGT® | 82 | 83 | 84 | 84.1 | 84.2 | 84.3 | 84.4 | 85.4 | 85.3 | 85.2 | 85.1 | 85 | 86 | 87 | 88 | 89 | 90 | 91 |
|---|---|---|---|---|---|---|---|---|---|---|---|---|---|---|---|---|---|---|
| EU | 395 | 396 | 397 | 398 | 399 | 400 | 401 | 402 | 403 | 404 | 405 | 406 | 407 | 408 | 409 | 410 | 411 | 412 |
| IGHG1 | P | P | V | L | D | S | D | G | S | F | F | L | Y | S | K | L | T | V |
| IGHG2 | | | M | | | | | | | | | | | | | | | |
| IGHG3 | | | M | | | | | | | | | | | | | | | |
| IGHG4 | | | | | | | | | | | | | | | R | | | |

| IMGT® | 92 | 93 | 94 | 95 | 96 | 97 | 98 | 99 | 100 | 101 | 102 | 103 | 104 | 105 | 106 | 107 | 108 | 109 |
|---|---|---|---|---|---|---|---|---|---|---|---|---|---|---|---|---|---|---|
| EU | 413 | 414 | 415 | 416 | 417 | 418 | 419 | 420 | 421 | 422 | 423 | 424 | 425 | 426 | 427 | 428 | 429 | 430 |
| IGHG1 | D | K | S | R | W | Q | Q | G | N | V | F | S | C | S | V | M | H | E |
| IGHG2 | | | | | | | | | | I | | | | | | | | |
| IGHG3 | | | | | | | | | | | | | | | | | | |
| IGHG4 | | | | | | | E | | | | | | | | | | | |

| IMGT® | 110 | 112 | 113 | 114 | 115 | 116 | 117 | 118 | 119 | 120 | 121 | 122 | 123 | 124 | 125 | 129 | 130 | |
|---|---|---|---|---|---|---|---|---|---|---|---|---|---|---|---|---|---|---|
| EU | 431 | 432 | 433 | 434 | 435 | 436 | 437 | 438 | 439 | 440 | 441 | 442 | 443 | 444 | 445 | 446 | 447 | |
| IGHG1 | A | L | H | N | H | Y | T | Q | K | S | L | S | L | S | P | G | K | |
| IGHG2 | | | | | | | | | | | | | | | | | | |
| IGHG3 | | | | | R | F | | | | | | | | | | | | |
| IGHG4 | | | | | | | | | | | | | | | L | | | |

FIG. 20A

| IMGT® | 1.4 | 1.3 | 1.2 | 1.1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| EU | 118 | 119 | 120 | 121 | 122 | 123 | 124 | 125 | 126 | 127 | 128 | 129 | 130 | 131 | 132 | 133 | 134 | 135 |
| CH1 | A | S | T | K | G | P | S | V | F | P | L | A | P | S | S | K | S | T |
| ALPHA | | | | | | | | | | | | | | | | | | |
| BETA | | | | | E | | | | A | | F | | | | | | | |
| DELTA | | | | | | | | | | | M | | | | | | | |
| GAMMA | | | | | | | K | | T | | | | | | | | | |
| CH3 | | | | | | | Q | | Y | | | | | | | D | E | |

| IMGT® | 15 | 16 | 17 | 18 | 19 | 20 | 21 | 22 | 23 | 24 | 25 | 26 | 27 | 28 | 29 | 30 | 35 | 36 |
|---|---|---|---|---|---|---|---|---|---|---|---|---|---|---|---|---|---|---|
| EU | 136 | 137 | 138 | 139 | 140 | 141 | 142 | 143 | 144 | 145 | 146 | 147 | 148 | 149 | 150 | 151 | 152 | 153 |
| CH1 | S | G | G | T | A | A | L | G | C | L | V | K | D | Y | F | P | E | P |
| ALPHA | | | | | | K | | V | T | | | T | | | | | | |
| BETA | | | | | | T | | V | T | | | T | | | | | | |
| DELTA | | | | | | N | | A | | | | E | E | | | | | |
| GAMMA | | | | Q | | T | | L | | | | | K | | | | | |
| CH3 | | | | | | S | | T | | | | | | | | | | |

| IMGT® | 37 | 38 | 39 | 40 | 41 | 42 | 43 | 44 | 45 | 45.1 | 45.2 | 45.3 | 77 | 78 | 79 | 80 | 81 | 82 |
|---|---|---|---|---|---|---|---|---|---|---|---|---|---|---|---|---|---|---|
| EU | 154 | 155 | 156 | 157 | 158 | 159 | 160 | 161 | 162 | 163 | 164 | 165 | 166 | 167 | 168 | 169 | 170 | 171 |
| CH1 | V | T | V | S | W | N | S | G | A | L | T | S | G | V | H | T | F | P |
| ALPHA | | | | | | | | | | | | | | | | | | |
| BETA | | | | | | | | | | | | | | | Y | | D | |
| DELTA | | | | | | | | | | | | | | | | | A | |
| GAMMA | | | | | | | | | | | | | | | | | G | |
| CH3 | | | | | | | | | | | | | | | K | | T | |

FIG. 20A (cont.)

| IMGT® | 83 | 84 | 84.1 | 84.2 | 84.3 | 84.4 | 85.4 | 85.3 | 85.2 | 85.1 | 85 | 86 | 87 | 88 | 89 | 90 | 91 | 92 |
|---|---|---|---|---|---|---|---|---|---|---|---|---|---|---|---|---|---|---|
| EU | 172 | 173 | 174 | 175 | 176 | 177 | 178 | 179 | 180 | 181 | 182 | 183 | 184 | 185 | 186 | 187 | 188 | 189 |
| CH1 | A | V | L | Q | S | S | G | L | Y | S | L | S | S | V | V | T | V | P |
| ALPHA | | | | | | | | | | | | | | W | | N | | |
| BETA | | L | | E | | | | | | A | | V | | R | | R | | |
| DELTA | | | | S | | | | | | N | | | | | | K | | |
| GAMMA | | M | | | | | | | | M | | V | | L | | | | |
| CH3 | | | | D | | | | | | F | | F | | W | | | | |

| IMGT® | 93 | 94 | 95 | 96 | 98 | 99 | 100 | 101 | 102 | 103 | 104 | 105 | 106 | 107 | 108 | 109 | 110 | 113 |
|---|---|---|---|---|---|---|---|---|---|---|---|---|---|---|---|---|---|---|
| EU | 190 | 191 | 192 | 193 | 194 | 195 | 196 | 197 | 198 | 199 | 200 | 201 | 202 | 203 | 204 | 205 | 206 | 207 |
| CH1 | S | S | S | L | G | T | Q | T | Y | I | C | N | V | N | H | K | P | S |
| ALPHA | | | | | | | | | | | | | | | | | | |
| BETA | | | | | | | | | | | | | | | | | | |
| DELTA | | | | | | | | | | | | | | | | | | |
| GAMMA | | | | | | | | | | | | | | | | | | |
| CH3 | | | | | | | | | | | | | | K | | | | |

| IMGT® | 114 | 115 | 116 | 117 | 118 | 119 | 120 | 121 |
|---|---|---|---|---|---|---|---|---|
| EU | 208 | 209 | 210 | 211 | 212 | 213 | 214 | 215 |
| CH1 | N | T | K | V | D | K | K | V |
| ALPHA | | | | | | | | |
| BETA | | | | | | | | |
| DELTA | | | | | | | | |
| GAMMA | | | | | | | | |
| CH3 | | | | | | | | |

FIG. 20B

| IMGT® | 1.6 | 1.5 | 1.4 | 1.3 | 1.2 | 1.1 | 1 | 2 | 3 | 4 | 5 | 6 | 7 | 8 | 9 | 10 | 11 | 12 |
|---|---|---|---|---|---|---|---|---|---|---|---|---|---|---|---|---|---|---|
| EU | 231 | 232 | 233 | 234 | 235 | 236 | 237 | 238 | 239 | 240 | 241 | 242 | 243 | 244 | 245 | 246 | 247 | 248 |
| CH2 | A | P | E | L | L | G | G | P | S | V | F | L | F | P | P | K | P | K |
| ALPHA | | | | | | | | | | | | | | | | | | |
| BETA | | | | | | | | | E | | A | | M | | | | | |
| DELTA | | | | | | | | | | | | | | | | | | |
| GAMMA | | | | | | | | | K | | T | | L | | | | | |
| CH3 | | | | | | | | | | | Y | | | | | | | |

| IMGT® | 13 | 14 | 15 | 15.1 | 15.2 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|
| EU | 249 | 250 | 251 | 252 | 253 | 254 | 255 | 256 | 257 | 258 | 259 | 260 | 261 | 262 | 263 | 264 | 265 | 266 |
| CH2 | D | T | L | M | I | S | R | T | P | E | V | T | C | V | V | V | D | V |
| ALPHA | | | | | | | | | | K | | V | | | | T | | |
| BETA | | | | | | | | | | T | | V | | | | T | | |
| DELTA | | | | | | | | | | N | | A | | | | | | |
| GAMMA | | | | | | | | | | S | | L | | | | | | |
| CH3 | | | | | | | | | | | | | | | | E | E | |
| | | | | | | | | | | | | | | | | | K | |

| IMGT® | 29 | 30 | 31 | 34 | 35 | 36 | 37 | 38 | 39 | 40 | 41 | 42 | 43 | 44 | 45 | 45.1 | 45.2 | 45.3 |
|---|---|---|---|---|---|---|---|---|---|---|---|---|---|---|---|---|---|---|
| EU | 267 | 268 | 269 | 270 | 271 | 272 | 273 | 274 | 275 | 276 | 277 | 278 | 279 | 280 | 281 | 282 | 283 | 284 |
| CH2 | S | H | E | D | P | E | V | K | F | N | W | Y | V | D | G | V | E | V |
| ALPHA | | | | | | | | | | | | | | | | | | |
| BETA | | | | | | | | | | | | | | | | | | |
| DELTA | | | | | | | | | | | | | | | | | | |
| GAMMA | | | | | | | | | | | | | | | | | | |
| CH3 | | | | | | | | | | | | | | | | | | |

FIG. 20B (cont.)

| IMGT® | 45.4 | 77 | 78 | 79 | 80 | 81 | 82 | 83 | 84 | 84.1 | 84.2 | 84.3 | 84.4 | 85.4 | 85.3 | 85.2 | 85.1 | 85 |
|---|---|---|---|---|---|---|---|---|---|---|---|---|---|---|---|---|---|---|
| EU | 285 | 286 | 287 | 288 | 289 | 290 | 291 | 292 | 293 | 294 | 295 | 296 | 297 | 298 | 299 | 300 | 301 | 302 |
| CH2 | H | N | A | K | T | K | P | R | E | E | Q | Y | N | S | T | Y | R | V |
| ALPHA | | | | Y | | | | | | | | | | | | | S | |
| BETA | | | | | | D | | | L | | E | | | | | | A | |
| DELTA | | | | F | | A | | | | | S | | | | | | N | |
| GAMMA | | | | | | G | | M | | | | D | | | | | M | |
| CH3 | | | | | | | | T | | | | | | | | | F | |

| IMGT® | 86 | 87 | 88 | 89 | 90 | 91 | 92 | 93 | 94 | 95 | 96 | 97 | 98 | 99 | 100 | 101 | 102 | 103 |
|---|---|---|---|---|---|---|---|---|---|---|---|---|---|---|---|---|---|---|
| EU | 303 | 304 | 305 | 306 | 307 | 308 | 309 | 310 | 311 | 312 | 313 | 314 | 315 | 316 | 317 | 318 | 319 | 320 |
| CH2 | V | S | W | L | T | V | L | H | Q | D | W | L | N | G | K | E | Y | K |
| ALPHA | | | | | | | | | | | | | | | | | | |
| BETA | S | | R | | R | | | | | | | | | | | | | |
| DELTA | | | L | | | | | | | | | | | | | | | |
| GAMMA | F | | W | | K | | | | | | | | | | | | | |
| CH3 | Y | | K | | | | | | | | | | | | | | | |

FIG. 20B (cont.)

| IMGT® | 104 | 105 | 106 | 107 | 108 | 109 | 110 | 113 | 114 | 115 | 116 | 117 | 118 | 119 | 120 | 121 | 122 | 123 |
|---|---|---|---|---|---|---|---|---|---|---|---|---|---|---|---|---|---|---|
| EU | 321 | 322 | 323 | 324 | 325 | 326 | 327 | 328 | 329 | 330 | 331 | 332 | 333 | 334 | 335 | 336 | 337 | 338 |
| CH2 | C | K | V | S | N | K | A | L | P | A | P | I | E | K | T | I | S | K |
| ALPHA | | | | | | | | | | | | | | | | | | |
| BETA | | | | | | | | | | | | | | | | | | |
| DELTA | | | | | | | | | | | | | | | | | | |
| GAMMA | | | | | | | | | | | | | | | | | | |
| CH3 | | | | | | | | | | | | | | | | | | |

| IMGT® | 124 | 125 |
|---|---|---|
| EU | 339 | 340 |
| CH2 | A | K |
| ALPHA | | |
| BETA | | |
| DELTA | | |
| GAMMA | | |
| CH3 | | |

FIG. 20C

| IMGT® | 1.4 | 1.3 | 1.2 | 1.1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| EU | 341 | 342 | 343 | 344 | 345 | 346 | 347 | 348 | 349 | 350 | 351 | 352 | 353 | 354 | 355 | 356 | 357 | 358 |
| CH3 | G | Q | P | R | E | P | Q | V | Y | T | L | P | P | S | R | D | E | L |
| ALPHA | | | | | | | | | | | | | | | | | | |
| BETA | | | | | | | E | | A | | F | | | | | | | |
| DELTA | | | | | | | | | | | M | | | | | | | |
| GAMMA | | | | | | | K | | T | | | | | | | | | |

| IMGT® | 15 | 16 | 17 | 18 | 19 | 20 | 21 | 22 | 23 | 24 | 25 | 26 | 27 | 28 | 29 | 30 | 35 | 36 |
|---|---|---|---|---|---|---|---|---|---|---|---|---|---|---|---|---|---|---|
| EU | 359 | 360 | 361 | 362 | 363 | 364 | 365 | 366 | 367 | 368 | 369 | 370 | 371 | 372 | 373 | 374 | 375 | 376 |
| CH3 | T | K | N | Q | V | S | L | T | C | L | V | K | G | F | Y | P | S | D |
| ALPHA | | | | | | K | L | V | | | | | | | | | | |
| BETA | | | | | | T | | V | | | | T | | | | | | |
| DELTA | | | | | | N | | A | | | | E | E | | | | | |
| GAMMA | | | | | | T | | L | | | | | K | | | | | |

| IMGT® | 37 | 38 | 39 | 40 | 41 | 42 | 43 | 44 | 45 | 45.1 | 45.2 | 45.3 | 45.4 | 77 | 78 | 79 | 80 | 81 |
|---|---|---|---|---|---|---|---|---|---|---|---|---|---|---|---|---|---|---|
| EU | 377 | 378 | 379 | 380 | 381 | 382 | 383 | 384 | 385 | 386 | 387 | 388 | 389 | 390 | 391 | 392 | 393 | 394 |
| CH3 | I | A | V | E | W | E | S | N | G | Q | P | E | N | N | Y | K | T | T |
| ALPHA | | | | | | | | | | | | | | | | Y | | |
| BETA | | | | | | | | | | | | | | | | | | D |
| DELTA | | | | | | | | | | | | | | | | F | | A |
| GAMMA | | | | | | | | | | | | | | | | | | G |

FIG. 20C (cont.)

| IMGT® | 82 | 83 | 84 | 84.1 | 84.2 | 84.3 | 84.4 | 85.4 | 85.3 | 85.2 | 85.1 | 85 | 86 | 87 | 88 | 89 | 90 | 91 |
|---|---|---|---|---|---|---|---|---|---|---|---|---|---|---|---|---|---|---|
| EU | 395 | 396 | 397 | 398 | 399 | 400 | 401 | 402 | 403 | 404 | 405 | 406 | 407 | 408 | 409 | 410 | 411 | 412 |
| CH3 | P | P | V | L | D | S | D | G | S | F | F | L | Y | S | K | L | T | V |
| ALPHA | | | | | | | | | | | | | | | | | | |
| BETA | | | L | | E | | | | | | S | | V | | W | | R | |
| DELTA | | | | | S | | | | | | A | | S | | R | | K | |
| GAMMA | | | M | | | | | | | | M | | F | | W | | | |

| IMGT® | 92 | 93 | 94 | 95 | 96 | 97 | 98 | 99 | 100 | 101 | 102 | 103 | 104 | 105 | 106 | 107 | 108 | 109 |
|---|---|---|---|---|---|---|---|---|---|---|---|---|---|---|---|---|---|---|
| EU | 413 | 414 | 415 | 416 | 417 | 418 | 419 | 420 | 421 | 422 | 423 | 424 | 425 | 426 | 427 | 428 | 429 | 430 |
| CH3 | D | K | S | R | W | Q | Q | G | N | V | F | S | C | S | V | M | H | E |
| ALPHA | | | | | | | | | | | | | | | | | | |
| BETA | | | | | | | | | | | | | | | | | | |
| DELTA | | | | | | | | | | | | | | | | | | |
| GAMMA | | | | | | | | | | | | | | | | | | |

| IMGT® | 110 | 112 | 113 | 114 | 115 | 116 | 117 | 118 | 119 | 120 | 121 | 122 | 123 | 124 | 125 | 129 | 130 | |
|---|---|---|---|---|---|---|---|---|---|---|---|---|---|---|---|---|---|---|
| EU | 431 | 432 | 433 | 434 | 435 | 436 | 437 | 438 | 439 | 440 | 441 | 442 | 443 | 444 | 445 | 446 | 447 | |
| CH3 | A | L | H | N | H | Y | T | Q | K | S | L | S | L | S | P | G | K | |
| ALPHA | | | | | | | | | | | | | | | | | | |
| BETA | | | | | | | | | | | | | | | | | | |
| DELTA | | | | | | | | | | | | | | | | | | |
| GAMMA | | | | | | | | | | | | | | | | | | |

FIG. 21A

| IMGT® | 1.4 | 1.3 | 1.2 | 1.1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| IGHE CH4 | G | P | R | A | A | P | E | V | Y | A | F | A | T | P | E | W | P | G |
| ALPHA | | | | | | | | | | | | | | | | | | |
| BETA | | | | | | | | | | | | | M | | | | | |
| DELTA | | | | | | | | | A | | | | | | | | | |
| GAMMA | | | | | | | K | | T | | | | | | | D | | |
| CH3 | | | | | | | Q | | | | | | | | | | E | |

| IMGT® | 15 | 16 | 17 | 18 | 19 | 20 | 21 | 22 | 23 | 24 | 25 | 26 | 27 | 28 | 29 | 30 | 35. | 36 |
|---|---|---|---|---|---|---|---|---|---|---|---|---|---|---|---|---|---|---|
| IGHE CH4 | S | R | D | K | R | T | L | A | C | L | I | Q | N | F | M | P | E | D |
| ALPHA | | | | | | K | | V | | | | T | | | | | | |
| BETA | | | | | | | | V | | | | T | | | | | | |
| DELTA | | | | | | N | | | | | | | E | | | | | |
| GAMMA | | | | | | | | L | | | | E | K | | | | | |
| CH3 | | | | Q | | S | Q | T | | | | | | | | | | |

| IMGT® | 37 | 38 | 39 | 40 | 41 | 42 | 43 | 44 | 45 | 45.1 | 45.2 | 45.3 | 45.4 | 45.5 | 45.6 | 77 | 78 | 79 |
|---|---|---|---|---|---|---|---|---|---|---|---|---|---|---|---|---|---|---|
| IGHE CH4 | I | S | V | Q | W | L | H | N | E | V | Q | L | P | D | A | R | H | S |
| ALPHA | | | | | | | | | | | | | | | | | | Y |
| BETA | | | | | | | | | | | | | | | | | | |
| DELTA | | | | | | | | | | | | | | | | | | F |
| GAMMA | | | | | | | | | | | | | | | | | | |
| CH3 | | | | | | | | | | | | | | | | | | K |

FIG. 21A (cont.)

| IMGT® | 80 | 81 | 82 | 83 | 84 | 84.1 | 84.2 | 84.3 | 84.4 | 85.4 | 85.3 | 85.2 | 85.1 | 85 | 86 | 87 | 88 | 89 |
|---|---|---|---|---|---|---|---|---|---|---|---|---|---|---|---|---|---|---|
| IGHE CH4 | T | T | Q | P | R | K | T | K | G | S | G | F | F | V | F | S | R | L |
| ALPHA | | | | | | | | | | | | | | | V | | W | |
| BETA | | D | | | L | | E | | | | | | S | | S | | | |
| DELTA | | A | | | | | S | | | | | | A | | V | | L | |
| GAMMA | | G | | | M | | | | | | | | N | | | | W | |
| CH3 | | | | | | | D | | | | | | M | | Y | | K | |

| IMGT® | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|
| IGHE CH4 | E | V | T | R | A | E | W | E | Q | K | D | E | F | I | C | R | A | V |
| ALPHA | N | | | | | | | | | | | | | | | | | |
| BETA | R | | | | | | | | | | | | | | | | | |
| DELTA | K | | | | | | | | | | | | | | | | | |
| GAMMA | | | | | | | | | | | | | | | | | | |
| CH3 | | | | | | | | | | | | | | | | | | |

| IMGT® | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|
| IGHE CH4 | H | E | A | A | S | P | S | Q | T | V | Q | R | A | V | S | V | N | P |
| ALPHA | | | | | | | | | | | | | | | | | | |
| BETA | | | | | | | | | | | | | | | | | | |
| DELTA | | | | | | | | | | | | | | | | | | |
| GAMMA | | | | | | | | | | | | | | | | | | |
| CH3 | | | | | | | | | | | | | | | | | | |

FIG. 21B

| IMGT® | 1.4 | 1.3 | 1.2 | 1.1 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|---|---|
| IGHM CH4 | V | A | L | H | R | P | D | V | Y | L | L | P | P | A | R | E | Q | L | N |
| ALPHA | | | | | | | | | | | | | | | | | | | |
| BETA | | | | | | | E | | A | | F | | | | | | | | |
| DELTA | | | | | | | | | | | M | | | | | | | | |
| GAMMA | | | | | | | K | | T | | | | | | | D | | | |
| CH3 | | | | Q | | | | | | | | | | | | | E | | |

| IMGT® | 15.1 | 16 | 17 | 18 | 19 | 20 | 21 | 22 | 23 | 24 | 25 | 26 | 27 | 28 | 29 | 30 | 35 | 36 | 37 |
|---|---|---|---|---|---|---|---|---|---|---|---|---|---|---|---|---|---|---|---|
| IGHM CH4 | L | R | E | S | A | T | I | T | C | L | V | T | G | F | S | P | A | D | V |
| ALPHA | | | | | | | | | | | | | | | | | | | |
| BETA | | | | | K | | | V | | | | | | | | | | | |
| DELTA | | | | | | | | V | | | | | | | | | | | |
| GAMMA | | | | | N | | | A | | | | | E | | | | | | |
| CH3 | | | | Q | | S | | L | | | | | K | | | | | | |

| IMGT® | 38 | 39 | 40 | 41 | 42 | 43 | 44 | 45 | 45.1 | 45.2 | 45.3 | 45.4 | 45.5 | 45.6 | 77 | 78 | 79 | 80 | 81 |
|---|---|---|---|---|---|---|---|---|---|---|---|---|---|---|---|---|---|---|---|
| IGHM CH4 | F | V | Q | W | M | Q | R | G | Q | P | L | S | P | E | K | Y | V | T | S |
| ALPHA | | | | | | | | | | | | | | | | | | | |
| BETA | | | | | | | | | | | | | | | | | Y | | D |
| DELTA | | | | | | | | | | | | | | | | | F | | A |
| GAMMA | | | | | | | | | | | | | | | | | | | G |
| CH3 | | | | | | | | | | | | | | | K | | | | T |

FIG. 21B (cont.)

| IMGT® | 82 | 83 | 84 | 84.1 | 84.2 | 84.3 | 84.4 | 84.5 | 85.5 | 85.4 | 85.3 | 85.2 | 85.1 | 85 | 86 | 87 | 88 | 89 | 90 |
|---|---|---|---|---|---|---|---|---|---|---|---|---|---|---|---|---|---|---|---|
| IGHM CH4 | A | P | M | P | E | P | Q | A | P | G | R | Y | F | A | H | S | I | L | T |
| ALPHA | | | | | | | | | | | | | | | V | | W | | N |
| BETA | | | L | | | | | | | | | | S | | S | | R | | R |
| DELTA | | | | | S | | | | | | | | A | | V | | | | |
| GAMMA | | | | | | | | | | | | | N | | F | | L | | R |
| CH3 | | | | | D | | | | | | | | M | | Y | | W | | K |

| IMGT® | 91 | 92 | 93 | 94 | 95 | 96 | 97 | 98 | 99 | 100 | 101 | 102 | 103 | 104 | 105 | 106 | 107 | 108 | 109 |
|---|---|---|---|---|---|---|---|---|---|---|---|---|---|---|---|---|---|---|---|
| IGHM CH4 | V | S | E | E | E | W | N | T | G | E | T | Y | T | C | V | V | A | H | E |
| ALPHA | | | | | | | | | | | | | | | | | | | |
| BETA | | | | | | | | | | | | | | | | | | | |
| DELTA | | | | | | | | | | | | | | | | | | | |
| GAMMA | | | | | | | | | | | | | | | | | | | |
| CH3 | | | | | | | | | | | | | | | | | | | |

| IMGT® | 110 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|
| IGHM CH4 | A | L | P | N | R | V | T | E | R | T | V | D | K | S | T |
| ALPHA | | | | | | | | | | | | | | | |
| BETA | | | | | | | | | | | | | | | |
| DELTA | | | | | | | | | | | | | | | |
| GAMMA | | | | | | | | | | | | | | | |
| CH3 | | | | | | | | | | | | | | | |

FIG. 22

| IMGT® | 1.4 | 1.3 | 1.2 | 1.1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| EU | 108 | 109 | 110 | 111 | 112 | 113 | 114 | 115 | 116 | 117 | 118 | 119 | 120 | 121 | 122 | 123 | 124 | 125 |
| IGKC | R | T | V | A | A | P | S | V | F | I | F | P | P | S | D | E | Q | L |
| ALPHA | | | | | | | | | | | | | | | | | | |
| BETA | | | | | | E | | A | | | | | | | | | | |
| DELTA | | | | | | | | | | | M | | | | | | | |
| GAMMA | | | | | | K | | T | | | | | | | D | | | |
| CH3 | | | | | | Q | | Y | | L | | | | | | | E | |

| IMGT® | 15 | 16 | 17 | 18 | 19 | 20 | 21 | 22 | 23 | 24 | 25 | 26 | 27 | 28 | 29 | 30 | 35 | 36 |
|---|---|---|---|---|---|---|---|---|---|---|---|---|---|---|---|---|---|---|
| EU | 126 | 127 | 128 | 129 | 130 | 131 | 132 | 133 | 134 | 135 | 136 | 137 | 138 | 139 | 140 | 141 | 142 | 143 |
| IGKC | K | S | G | T | A | S | V | V | C | L | L | N | N | F | Y | P | R | E |
| ALPHA | | | | | | K | | | | | | T | | | | | | |
| BETA | | | | | | T | | | | | | T | | | | | | |
| DELTA | | | | | | N | | A | | | | | E | | | | | |
| GAMMA | | | | | | T | | L | | | | | K | | | | | |
| CH3 | | | | | | | | T | | | | K | | | | | | |

| IMGT® | 37 | 38 | 39 | 40 | 41 | 42 | 43 | 44 | 45 | 45.1 | 45.2 | 45.3 | 45.4 | 45.5 | 77 | 78 | 79 | 80 |
|---|---|---|---|---|---|---|---|---|---|---|---|---|---|---|---|---|---|---|
| EU | 144 | 145 | 146 | 147 | 148 | 149 | 150 | 151 | 152 | 153 | 154 | 155 | 156 | 157 | 158 | 159 | 160 | 161 |
| IGKC | A | K | V | Q | W | K | V | D | N | A | L | Q | S | G | N | S | Q | E |
| ALPHA | | | | | | | | | | | | | | | | | | |
| BETA | | | | | | | | | | | | | | | | | | |
| DELTA | | | | | | | | | | | | | | | | | F | |
| GAMMA | | | | | | | | | | | | | | | | | Y | |
| CH3 | | | | | | | | | | | | | | | | | | K |

FIG. 22 (cont.)

| IMGT® | 81 | 82 | 83 | 84 | 84.1 | 84.2 | 84.3 | 84.4 | 84.5 | 85.4 | 85.3 | 85.2 | 85.1 | 85 | 86 | 87 | 88 | 89 |
|---|---|---|---|---|---|---|---|---|---|---|---|---|---|---|---|---|---|---|
| EU | 162 | 163 | 164 | 165 | 166 | 167 | 168 | 169 | 170 | 171 | 172 | 173 | 174 | 175 | 176 | 177 | 178 | 179 |
| IGKC | S | V | T | E | Q | D | S | K | D | S | T | Y | S | L | S | S | T | L |
| ALPHA | | | | | | | | | | | | | | | | | | |
| BETA | D | | | L | | E | | | | | | | A | | V | | W | |
| DELTA | A | | | | | S | | | | | | | N | | | | R | |
| GAMMA | G | | M | | | | | | | | | | M | | F | | L | |
| CH3 | T | | V | | | | | | | | | | F | | Y | | W | |
|  | | | | | | | | | | | | | | | | | K | |

| IMGT® | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|
| EU | 180 | 181 | 182 | 183 | 184 | 185 | 186 | 187 | 188 | 189 | 190 | 191 | 192 | 193 | 194 | 195 | 196 | 197 |
| IGKC | T | L | S | K | A | D | Y | E | K | H | K | V | Y | A | C | E | V | T |
| ALPHA | N | | | | | | | | | | | | | | | | | |
| BETA | R | | | | | | | | | | | | | | | | | |
| DELTA | K | | | | | | | | | | | | | | | | | |
| GAMMA | | | | | | | | | | | | | | | | | | |
| CH3 | | | | | | | | | | | | | | | | | | |

| IMGT® | 108 | 109 | 110 | 113 | 114 | 115 | 116 | 117 | 118 | 119 | 120 | 121 | 122 | 123 | 124 | 125 | 126 |
|---|---|---|---|---|---|---|---|---|---|---|---|---|---|---|---|---|---|
| EU | 198 | 199 | 200 | 201 | 202 | 203 | 204 | 205 | 206 | 207 | 208 | 209 | 210 | 211 | 212 | 213 | 214 |
| IGKC | H | Q | G | L | S | S | P | V | T | K | S | F | N | R | G | E | C |
| ALPHA | | | | | | | | | | | | | | | | | |
| BETA | | | | | | | | | | | | | | | | | |
| DELTA | | | | | | | | | | | | | | | | | |
| GAMMA | | | | | | | | | | | | | | | | | |
| CH3 | | | | | | | | | | | | | | | | | |

FIG. 23A

| IMGT® | 1.4 | 1.3 | 1.2 | 1.1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|
| KABAT | 108 | 109 | 110 | 111 | 112 | 113 | 114 | 115 | 116 | 117 | 118 | 119 | 120 | 121 | 122 | 123 | 124 | 125 |
| IGLC1 | Q | P | K | A | N | P | T | V | T | L | F | P | P | S | S | E | E | L |
| IGLC2 | | | | | A | | S | | | | | | | | | | | |
| IGLC3 | | | | | A | | S | | | | | | | | | | | |
| IGLC6 | | | | | A | | S | | | | | | | | | | | |
| IGLC7 | | | | | A | | S | | | | | | | | | | | |
| ALPHA | | | | | | | E | | A | | | | | | | | | |
| BETA | | | | | | | | | | | | | | | | | | |
| DELTA | | | | | | | | | | | M | | | | | | | |
| GAMMA | | | | | | | K | | | | | | | | | | | |
| CH3 | | | | | | | Q | | Y | | L | | | | D | | | |

| IMGT® | 15 | 16 | 17 | 18 | 19 | 20 | 21 | 22 | 23 | 24 | 25 | 26 | 27 | 28 | 29 | 30 | 35 | 36 |
|---|---|---|---|---|---|---|---|---|---|---|---|---|---|---|---|---|---|---|
| KABAT | 126 | 127 | 128 | 129 | 130 | 131 | 132 | 133 | 134 | 135 | 136 | 137 | 138 | 139 | 140 | 141 | 142 | 143 |
| IGLC1 | Q | A | N | K | A | T | L | V | C | L | I | S | D | F | Y | P | G | A |
| IGLC2 | | | | | | | | | | | | | | | | | | |
| IGLC3 | | | | | | | | | | | | | | | | | | |
| IGLC6 | | | | | | | | | | | | | | | | | | |
| IGLC7 | | | | | | | | | | | | | | | | | | |
| ALPHA | | | | | | K | | | | | | T | | | | | | |
| BETA | | | | | | | | | | | V | T | | | | | | |
| DELTA | | | | | | N | | A | | | | | E | | | | | |
| GAMMA | | | | | | | | L | | | | E | K | | | | | |
| CH3 | | | | | | | | T | | | | K | | | | | | |

FIG. 23A (cont.)

| IMGT® | 37 | 38 | 39 | 40 | 41 | 42 | 43 | 44 | 45 | 45.1 | 45.2 | 45.3 | 45.4 | 45.5 | 77 | 78 | 79 | 80 |
|---|---|---|---|---|---|---|---|---|---|---|---|---|---|---|---|---|---|---|
| KABAT | 144 | 145 | 146 | 147 | 148 | 149 | 150 | 151 | 152 | 153 | 154 | 155 | 156 | 157 | 158 | 159 | 160 | 161 |
| IGLC1 | V | T | V | A | W | K | A | D | G | S | P | V | K | A | G | V | E | T |
| IGLC2 | | | | | | | | | S | | | | | | | | | |
| IGLC3 | | | | | | | | | S | | | | | | | | | |
| IGLC6 | | K | | | | | | | | | | | N | T | | | | |
| IGLC7 | | | | | | | | | | | | | | V | | | | |
| ALPHA | | | | | | | | | | | | | | | | | Y | |
| BETA | | | | | | | | | | | | | | | | | | |
| DELTA | | | | | | | | | | | | | | | | | F | |
| GAMMA | | | | | | | | | | | | | | | | | | |
| CH3 | | | | | | | | | | | | | | | | | K | |

FIG. 23B

| IMGT® | 81 | 82 | 83 | 84 | 84.1 | 84.2 | 84.3 | 84.4 | 85.4 | 85.3 | 85.2 | 85.1 | 85 | 86 | 87 | 88 | 89 | 90 |
|---|---|---|---|---|---|---|---|---|---|---|---|---|---|---|---|---|---|---|
| KABAT | 162 | 163 | 164 | 165 | 166 | 167 | 168 | 170 | 171 | 172 | 173 | 174 | 175 | 176 | 177 | 178 | 179 | 180 |
| IGLC1 | T | K | P | S | K | Q | S | N | N | K | Y | A | A | S | S | Y | L | S |
| IGLC2 |   | T |   |   |   |   |   |   |   |   |   |   |   |   |   |   |   |   |
| IGLC3 |   | T |   |   |   |   |   |   |   |   |   |   |   |   |   |   |   |   |
| IGLC6 |   | T |   |   |   |   |   |   |   |   |   |   |   |   |   |   |   |   |
| IGLC7 |   |   |   |   |   |   |   |   |   |   |   |   |   |   |   |   |   |   |
| ALPHA |   |   |   |   |   |   |   |   |   |   |   |   |   |   |   |   |   |   |
| BETA | D |   |   | L |   | E |   |   |   |   |   | S |   | V |   | W |   | N |
| DELTA | A |   |   |   |   | S |   |   |   |   |   | N |   | V |   | R |   | R |
| GAMMA | G |   |   | M |   |   |   |   |   |   |   | M |   | F |   | L |   | K |
| CH3 |   |   |   |   |   |   |   |   |   |   |   | F |   | Y |   | W |   |   |

| IMGT® | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|
| KABAT | 181 | 182 | 183 | 184 | 185 | 186 | 187 | 188 | 189 | 190 | 191 | 192 | 193 | 194 | 195 | 196 | 197 | 198 |
| IGLC1 | L | T | P | E | Q | W | K | S | H | R | S | Y | S | C | Q | V | T | H |
| IGLC2 |   |   |   |   |   |   |   |   |   |   |   |   |   |   |   |   |   |   |
| IGLC3 |   |   |   |   |   |   |   |   |   | K |   |   |   |   |   |   |   |   |
| IGLC6 |   |   |   |   |   |   |   |   |   |   |   |   |   |   |   |   |   |   |
| IGLC7 |   |   |   |   |   |   |   |   |   |   |   |   |   |   | R |   |   |   |
| ALPHA |   |   |   |   |   |   |   |   |   |   |   |   |   |   |   |   |   |   |
| BETA |   |   |   |   |   |   |   |   |   |   |   |   |   |   |   |   |   |   |
| DELTA |   |   |   |   |   |   |   |   |   |   |   |   |   |   |   |   |   |   |
| GAMMA |   |   |   |   |   |   |   |   |   |   |   |   |   |   |   |   |   |   |
| CH3 |   |   |   |   |   |   |   |   |   |   |   |   |   |   |   |   |   |   |

FIG. 23B (cont.)

| IMGT® | 109 | 114 | 115 | 116 | 117 | 118 | 119 | 120 | 121 | 122 | 123 | 124 | 125 | 126 | 127 |
|---|---|---|---|---|---|---|---|---|---|---|---|---|---|---|---|
| KABAT | 199 | 200 | 203 | 204 | 205 | 206 | 207 | 208 | 209 | 210 | 211 | 212 | 213 | 214 | 215 |
| IGLC1 | E | G | S | T | V | E | K | T | V | A | P | T | E | C | S |
| IGLC2 | | | | | | | | | | | | | | | |
| IGLC3 | | | | | | | | | | | | | | | |
| IGLC6 | | | | | | | | | | | | A | | | |
| IGLC7 | | | | | | | | | | | | A | | | |
| ALPHA | | | | | | | | | | | | | | | |
| BETA | | | | | | | | | | | | | | | |
| DELTA | | | | | | | | | | | | | | | |
| GAMMA | | | | | | | | | | | | | | | |
| CH3 | | | | | | | | | | | | | | | |

FIG. 42

```
                    A              AB      B                       BC              C              CD
                  (1-15)                 (16-26)                 (27-38)         (39-45)
                                   --->         --->           --->         --->
                1       10     15  16      23 26              27         38   39 41    45
             87654321|........|...,|123|..|...,|....|.........|............|   |.|....|1234567
CH1
J00220 IGHA1    ASPTSPKVFPLSLCSTQP....DGNVVIACLVQ  GFFPQ.EPLS  VTWSESGQGV....
J00221 IGHA2    ASPTSPKVFPLSLDSTPQ....DGNVVVACLVQ  GFFPQ.EPLS  VTWSESGQNV....
K02875 IGHD     APTKAPDVFPIISGCRHPKD..NSPVVLACLIT  GYHP..TSVT  VTWYMGTQSQ....
J00222 IGHE     ASTQSPSVFPLTRCCKNIPSN.ATSVTLGCLAT  GYFP..EPVM  VTCDTGSLNG....
J00228 IGHG1    ASTKGPSVFPLAPSSKSTS...GGTAALGCLVK  DYFP..EPVT  VSWNSGALTS....
J00230 IGHG2    ASTKGPSVFPLAPCSRSTS...ESTAALGCLVK  DYFP..EPVT  VSWNSGALTS....
X03604 IGHG3    ASTKGPSVFPLAPCSRSTS...GGTAALGCLVK  DYFP..EPVT  VSWNSGALTS....
K01316 IGHG4    ASTKGPSVFPLAPCSRSTS...ESTAALGCLVK  DYFP..EPVT  VSWNSGALTS....
X06766 IGHGP    ASTKGPSVFPLVPSSRSVS...EGTAALGCLVK  DYFP..EPVT  VSWNSGALTR....
X14940 IGHM     GSASAPTLFPLVSCENSPSD..TSSVAVGCLAQ  DFLP..DSIT  LSWKYKNNSDIS..

CH2
J00220 IGHA1    CCHPRLSLHRPALEDLLL...GSEANLTCTLT  GLRDA.SGVT  FTWTPSSGKS....
J00221 IGHA2    CCHPRLSLHRPALEDLLL...GSEANLTCTLT  GLRDA.SGAT  FTWTPSSGKS....
K02878 IGHD     ECPSHTQPLGVYLLTPAVQDLWL..RDKATFTCFVV  GSDL..KDAH  LTWEVAGKVPTG..
J00222 IGHE     VCSRDFTPPTVKILQSSCDGGGHF.PPTIQLLCLVS  GYTP..GTIN  ITWLEDGQVMD...
J00223 IGHEP1   .....NPRGVSAYLSRPSPFDLFI.RKSPTITCLVV  DLAPSKWTVN  LTWSRASGKPV...
J00228 IGHG1    APELLGGPSVFLFPPKPKDTLMI.SRTPEVTCVVV  DVSHEDPEVK  FNWYVDGVEVH...
J00230 IGHG2    AP.PVAGPSVFLFPPKPKDTLMI.SRTPEVTCVVV  DVSHEDPEVQ  FNWYVDGVEVH...
X03604 IGHG3    APELLGGPSVFLFPPKPKDTLMI.SRTPEVTCVVV  DVSHEDPEVQ  FKWYVDGVEVH...
K01316 IGHG4    APEFLGGPSVFLFPPKPKDTLMI.SRTPEVTCVVV  DVSQEDPEVQ  FNWYVDGVEVH...
X06766 IGHGP    TTEPLGGPSVFLFPPKPKDTLMI.SRTPEVTCVVV  DVSHEDPEVK  FNWYVDGVEVH...
X14940 IGHM     VIAELPPKVSVFVPPRDGFFGN.PRKSKLICQAT  GFSP..RQIQ  VSWLREGKQVGS..
```

FIG. 42 (cont.)

```
                      A            AB       B              BC          C          CD
                    (1-15)       (16-26)                 (27-38)     (39-45)
                 ----------->    ------->              |........|   ----->
                 1      10  15   16   23 26 27         38     39  41    45
         87654321|........|....|123|........|...|     ........|   |.|...|1234567
CH3
J00220 IGHA1     GNTFRPEVHLLPPPSEELAL..NELVTLTCLAR GFSP..KDVL  VRWLQGSQELPRE.
J00221 IGHA2     GNTFRPEVHLLPPPSEELAL..NELVTLTCLAR GFSP..KDVL  VRWLQGSQELPRE.
K02879 IGHD      AAQAPVKLSLNLLASSDPP..EAASWLLCEVS GFSP..PNIL  LMWLEDQREVNTS.
J00222 IGHE      DSNPRGVSAYLSRPSPFDLFI..RKSPTITCLVV DLAPSKGTVN LTWSRASGKPV...
J00223 IGHEP1    GPRAAPEVYAFATPEWLGS...RDKRTLTCLIQ NFMP..EDIS  VQWLHNEVQLPDA.
J00228 IGHG1     GQPREPQVYTLPPSRDELT...KNQVSLTCLVK GFYP..SDIA  VEWESNGQPEN...
J00230 IGHG2     GQPREPQVYTLPPSREEMT...KNQVSLTCLVK GFYP..SDIA  VEWESNGQPEN...
X03604 IGHG3     GQPREPQVYTLPPSREEMT...KNQVSLTCLVK GFYP..SDIA  VEWESSGQPEN...
K01316 IGHG4     GQPREPQVYTLPPSQEEMT...KNQVSLTCLVK GFYP..SDIA  VEWESNGQPEN...
X06766 IGHGP     GQPREPQVYTLPPSQK.MT...KNQVTLTCLVK GFYP..SDIT  VEWESNGQPEN...
X14940 IGHM      DQDTAIRVFAIPPSFASIFL..TKSTKLTCLVT DLTTY.DSVT  ISWTRQNGEAV...
CH4
J00222 IGHE      GPRAAPEVYAFATPEWPGS...RDKRTLACLIQ NFMP..EDIS  VQWLHNEVQLPDA.
X14940 IGHM      GVALHRPDVYLLPPAREQLNL..RESATITCLVT GFSP..ADVF  VQWMQRGQPLSPE.
```

FIG. 42 (cont.)

```
              D            DE                  E                    EF     F              FG           G
            (77-84)                          (85-96)              (97-104)            (105-117)    (118-128)
        --------->                      ---------------->         -------->           -------->    -------->
         77     84                       85    89    96    97         104             105    117   118    128
        |     |123456776543 21|        |    |    | 12|          |        |           |        |   |        |
CH1
J00220 IGHA1   TARNFPPSQDASG....DLYTTSSQLTLPATQC..LAGKSVTC    HVKHY...TNPSQ    DVTVPCP
J00221 IGHA2   TARNFPPSQDASG....DLYTTSSQLTLPATQC..PDGKSVTC    HVKHY...TNPSQ    DVTVPCP
K02875 IGHD    PQRTFPEIQRRD.....SYMTSSQLSTPLQQW..RQGEYKC      VVQHT..ASKSK     KEIFRWP
J00222 IGHE    TTMTLPATTLTLS....GHYATISLLTVSGAW....AKQMFTC    RVAHTPSSTDWVD    NKTFS
J00228 IGHG1   GVHTFPAVLQSS.....GLYSLSSVVTVPSSSL...GTQTYIC    NVNHKP..SNTKV    DKKV
J00230 IGHG2   GVHTFPAVLQSS.....GLYSLSSVVTVPSSNF...GTQTYTC    NVDHKP..SNTKV    DKTV
X03604 IGHG3   GVHTFPAVLQSS.....GLYSLSSVVTVPSSSL...GTQTYTC    NVNHKP..SNTKV    DKRV
K01316 IGHG4   GVHTFPAVLQSS.....GLYSLSSVVTVPSSSL...GTKTYTC    NVDHKP..SNTKV    DKRV
X06766 IGHGP   SVHTFPAVLQSS.....GLYSLSSVVTVPSSSL...GTQTYTC    NVDHKP..SNTKV    DKTV
X14940 IGHM    STRGFPSVLRGG.....KYAATSQVLLPSKDVMQGTDEHVVC     KVQHP...NGNK     EKNVPLP
CH2
J00220 IGHA1   .AVQGPPERDLCG.....CYSVSSVLPGCAEPW..NHGKTFTC    TAAYPE..SKTPL    TATLSKS
J00221 IGHA2   .AVQGPPERDLCG.....CYSVSSVLPGCAQPW..NHGETFTC    TAAHPE..LKTPL    TANITKS
K02878 IGHD    GVEEGLLERHSN......GSQSQHSRLTLPRSLW..NAGTSVTC   TLNHPS..LPPQR    LMALREP
J00222 IGHE    VDLSTASTTQEG......ELASTQSELTLSQKHW..LSDRTYC    QVTYQ...GHTF     EDSTKKCA
J00223 IGHEP1  NHSTRKEEKQRN......GTLTVTSTVPVGTRDW..IEGETYQC   RVTHPQ..LPRAL    VRSTTKTS
J00228 IGHG1   NAKTKPREEQYN......STYRVVSVLTVLHQDW..LNGKEYKC   KVSNKA..LPAPI    EKTISKAK
J00230 IGHG2   NAKTKPREEQFN......STFRVVSVLTVVHQDW..LNGKEYKC   KVSNKG..LPAPI    EKTISKTK
X03604 IGHG3   NAKTKPREEQYN......STFRVVSVLTVLHQDW..LNGKEYKC   KVSNKA..LPAPI    EKTISKTK
K01316 IGHG4   NAKTKPREEQFN......STYRVVSVLTVLHQDW..LNGKEYKC   KVSNKG..LPSSI    EKTISKAK
X06766 IGHGP   NAKTKPWEEQYN......STYHVVSVLTVVHQNW..LNGREYKC   KVSNKG..LPSSI    EKTISKTK
X14940 IGHM    GVTTDQVQAEAKES....GPTTYKVTSTLTIKESDW..LGQSMFTC RVDHR...GLTF     QQNASSMCVP
```

FIG. 42 (cont.)

```
             D          DE             E              EF   F              FG              G
          (77-84)                    (85-96)              (97-104)     (105-117)        (118-128)
          -------->                 ---------------->    -------->    ------------>    ----------->
          77      84                85           96      97      104  105         117  118      128
          |       |1234567765432 1|...........|    |12|.......|   |............|   |.........|
CH3
J00220 IGHA1    KYLTWASRQEPSQG...TTTFAVTSILRVAAEDW..KKGDTFSC MVGHEA.LPLAFT QKTIDRLA
J00221 IGHA2    KYLTWASRQEPSQG...TTTFAVTSILRVAAEDW..KKGDTFSC MVGHEA.LPLAFT QKTIDRLA
K02879 IGHD     GFAPARPPPQPRS....TTFWAWSVLRVPAPPS..PQPATYTC VVSHEDSRTLLNA SRSLEVS
J00222 IGHE     NHSTRKEEKQRN.....GTLTVTSTLPVGTRDW..IEGETYQC RVTHPH..LPRAL MRSTTKTS
J00223 IGHEP1   RHSTTQPRKTKG.....SGFFIFSRLEVTRAEW..EQKDEFIC RAVHEAAIPSQTV QRAVSVNP
J00228 IGHG1    NYKTTPPVLDSD.....GSFFLYSKLTVDKSRW..QQGNVFSC SVMHEA.LHNHYT QKSLSLSP
J00230 IGHG2    NYKTTPPMLDSD.....GSFFLYSKLTVDKSRW..QQGNVFSC SVMHEA.LHNHYT QKSLSLSP
J00230 IGHG3    NYNTTPPMLDSD.....GSFFLYSKLTVDKSRW..QQGNIFSC SVMHEA.LHNRFT QKSLSLSP
X03604 IGHG4    NYKTTPPVLDSD.....GSFFLYSRLTVDKSRW..QEGNVFSC SVMHEA.LHNHYT QKSLSLSL
K01316 IGHGP    NYKTTPPMLDSN.....GSFFLYSKLTVDKSRW..QQGNVFSC SVMHEG.LHNHYT QKSLSLSP
X06766 IGHM     KTHTNISESHPN.....ATFSAVGEASICEDDW..NSGERFTC TVTHTD..LPSPL KQTISRPK
CH4
J00222 IGHE     RHSTTQPRKTKG.....SGFFVFSRLEVTRAEW..EQKDEFIC RAVHEAASPSQTV QRAVSVNP
X14940 IGHM     KYVTSAPMPEPQA....PGRYFAHSILTVSEEEW..NTGETYTC VVAHEA.LPNRVT ERTVDKST
```

FIG. 43

```
              A              AB        B                BC              C         CD
           (1-15)                   (16-26)          (27-38)         (39-45)
           ─────────>                ─────────>       ─────────>      ─────────>
         1         10     15      16        23 26 27             38 39 41 45      1234567
87654321|........|.....|  |123|........|..|     |........|     |.|....|1234567
J00241 IGKC  RTVAAPSVFIFPPSDEQLK...SGTASVVCLLN NFYP..REAK VQWKVDNALQSG..

D              DE        E                EF      F         FG              G
           (77-84)                   (85-96)          (97-104)         (105-117)        (118-128)
           ─────────>                ─────────>       ─────────>      ─────────>         ─────────>
         77       84             85        89 96          97    104  105       117      118
|......|12345677654321|....|........|....|12|........|     |........|     |........
J00241 IGKC  NSQESVTEQDSKD.....STYSLSSTLTLSKADY..EKHKVYAC EVTHQG...LSSPV TKSFNRGEC
```

FIG. 44

```
                              A                     AB          B                          BC                      C          CD
                           (1-15)                            (16-26)                     (27-38)                 (39-45)
                      |_____>                  |_____>               |_____>              |_____>
                      1        10    15                 16      23 26 27          38                         38  3941 45
                87654321|........|....|123|..........|....|123|..........|....|  |..........|..........|  |....|1234567
J00252 IGLC1             PKANPTVTLFPPSSEELQ...ANKATLVCLIS DFYP..GAVT  VAWKADGSPVKA..
J00253 IGLC2             GQPKAAPSVTLFPPSSEELQ...ANKATLVCLIS DFYP..GAVT VAWKADSSPVKA..
J00254 IGLC3             PKAAPSVTLFPPSSEELQ...ANKATLVCLIS DFYP..GAVT VAWKADSSPVKA..
J03011 IGLC6             GQPKAAPSVTLFPPSSEELQ...ANKATLVCLIS DFYP..GAVK VAWKADGSPVNT..
X51755 IGLC7             GQPKAAPSVTLFPPSSEELQ...ANKATLVCLVS DFYP..GAVT VAWKADGSPVKV..

D                         DE                  E                         EF    F                 FG                    G
                       (77-84)                                       (85-96)                         (97-104)          (105-117)           (118-128)
                    |_____>                                     |_____>                    |_____>         |_____>         |_____>
                    77      84                                  85      89    96              97     104          105                  117 118
                    |......|12345677654321|.......|..|........|....|....|..|  |12|..........|....| |..........|..........|..........| |...........|
J00252 IGLC1        GVETTKPSKQSN......NKYAASSYLSLTPEQW..KSHRSYSC QVTHE....GSTV EKTVAPTECS
J00253 IGLC2        GVETTTPSKQSN......NKYAASSYLSLTPEQW..KSHRSYSC QVTHE....GSTV EKTVAPTECS
J00254 IGLC3        GVETTTPSKQSN......NKYAASSYLSLTPEQW..KSHKSYSC QVTHE....GSTV EKTVAPTECS
J03011 IGLC6        GVETTTPSKQSN......NKYAASSYLSLTPEQW..KSHRSYSC QVTHE....GSTV EKTVAPAECS
X51755 IGLC7        GVETTKPSKQSN......NKYAASSYLSLTPEQW..KSHRSYSC RVTHE....GSTV EKTVAPAECS
```

FIG. 45

```
                              A              AB       B           BC          C       CD
                           (1-15)         (16-26)   (27-38)     (39-45)
                            1       10  15       16    23 26 27        38   39 41 45
                   87654321|........|....|123|........|....|........|   |.|...|1234567
X02883 TRAC         XIQNPDPAVYQLRDSK.......SSDKSVCLFT DFDS...QTN   VSQSKDS.......
M12887 TRBC1        EDLNKVFPPEVAVFEPSEAEISH..TQKATLVCLAT GFFP..DHVE  LSWWVNGKEVHS..
M12888 TRBC2        EDLKNVFPPEVAVFEPSEAEISH..TQKATLVCLAT GFYP..DHVE  LSWWVNGKEVHS..
M22148 TRDC         XSQPHTKPSVFVMKNG.......TNVACLVK EFYP..KDIR   INLVSSKKI.....
M14996 TRGC1        DKQLDADVSPKPTIFLPSIAETKL..QKAGTYLCLLE KFFP..DVIK  IHWQEKKSNTIL..
M15002 TRGC2 (2x)   DKQLDADVSPKPTIFLPSIAETKL..QKAGTYLCLLE KFFP DIIK   IHWQEKKSNTIL..
M17323 TRGC2 (3x)   DKQLDADVSPKPTIFLPSIAETKL..QKAGTYLCLLE KFFP..DIIK  IHWQEKKSNTIL..

D             DE          E          EF      F          FG                    G
                      (77-84)                    (85-96)            (97-104)    (105-117)           (118-128)
                        77   84              85    89    96 97     104 105                117   118
                      |.....|12345677654321|....|.....|12|........|   |.|...123456654321|......| |...|
X02883 TRAC           DVYITDKTVLDMRSM.DFKSNSAVAWSNKS.......DFAC ANAFNN QVQFYGLSENDEWTQDRAKPVTQIV SIIPE DTFFPSP
M12887 TRBC1          GVSTDPQPLKEQPAL.NDSRYCLSSRLRVSATFWQ.NPRNHFRC QVQFYGLSENDEWTQDRAKPVTQIV SAEAWGRA
M12888 TRBC2          GVSTDPQPLKEQPAL.NDSRYCLSSRLRVSATFWQ.NPRNHFRC QVQFYGLSENDEWTQDRAKPVTQIV SAEAWGRA
M22148 TRDC           TEFDPAIVISPS......GKYNAVKLGKYED......SNSVTC SVQHDNK......TVHST DFEVKTDST
M14996 TRGC1          GSQEGNTMKTND........TYMKFSWLTVPEK....SLDKEHRC IVRHENN.............KNGVDQ EIIFPPIKT
M15002 TRGC2 (2x)     GSQEGNTMKTND........TYMKFSWLTVPEE....SLDKEHRC IVRHENN.............KNGIDQ EIIFPPIKT
M17323 TRGC2 (3x)     GSQEGNTMKTND........TYMKFSWLTVPEE....SLDKEHRC IVRHENN.............KNGIDQ EIIFPPIKT
```

HETERO-DIMERIC IMMUNOGLOBULINS

RELATED APPLICATION

This application claims benefit of U.S. provisional application No. 61/467,727 filed on Mar. 25, 2011; all of which are hereby incorporated by reference in their entirety.

REFERENCE TO A SEQUENCE LISTING SUBMITTED ELECTRONICALLY

The content of the electronically submitted sequence listing (Name: 3305_0180002_SeqListing_ST25.txt; Size: 308,633 bytes; and Date of Creation: Jul. 6, 2015) is herein incorporated by reference in its entirety.

THE FIELD OF THE INVENTION

The present invention relates to engineered hetero-dimeric immunoglobulins or fragments thereof and methods of making the same.

BACKGROUND OF THE INVENTION

Methods for making hetero-dimeric proteins have been reported. The first approach to construct and produce hetero-dimeric bispecific antibodies was the quadroma technology (Milstein C and Cuello A C, *Nature*, 305(5934):537-40 (1983)) which consists of a somatic fusion of two different hybridoma cell lines expressing murine monoclonal antibodies with the desired specificities of the bispecific antibody. Because of the random pairing of two different immunoglobulin (Ig) heavy and light chains within the resulting hybrid-hybridoma (or quadroma) cell line, up to ten different immunogloblin species are generated of which only one is the functional bispecific antibody (Kufer P et al., *Trends Biotechnol*, 22(5):238-44 (2004)). The presence of mis-paired by-products reduces significantly the production yield and requires sophisticated purification procedures to achieve product homogeneity. The mispairing of Ig heavy chains can be reduced by using several rational design strategies, most of which engineer the antibody heavy chains for hetero-dimerization via the design of man-made complementary hetero-dimeric interfaces between the two subunits of the CH3 domain homo-dimer. The first report of an engineered CH3 hetero-dimeric domain pair was made by Carter et al. describing a "protuberance-into-cavity" approach for generating a hetero-dimeric Fc moiety (U.S. Pat. No. 5,807,706; 'knobs-into-holes'; Merchant A M et al., *Nat Biotechnol*, 16(7):677-81 (1998)). Alternative designs have been recently developed and involved either the design of a new CH3 module pair by modifying the core composition of the modules as described in WO2007/110205 or the design of complementary salt bridges between modules as described in WO2007/147901 or WO2009/089004. The disadvantage of the CH3 engineering strategies is that these techniques still result in the production of a significant amount of undesirable homo-dimers. Hence there remains a need for an engineering technique which minimizes the content of homo-dimeric species.

Regardless of the various approaches at hetero-dimerizing Ig heavy chains as described in these patent publications, the major obstacle facing the development of full bispecific antibodies (i.e., two FAB fragments, each having a unique set of variable heavy and light chain domains that creates a unique antigen binding site and one dimeric Fc region) based on any CH3 domain rational engineering or others, is the requirement of having a common light chain to both FABs in order to circumvent the mispairing of their light chains (Carter P, *J Immunol Methods*, 248(1-2):7-15 (2001)). Although, this can be accomplished by using antibodies with identical light chains that bind to different antigens by virtue of their distinct heavy chains, it does requires the isolation of such antibodies, which usually involves the use of display technologies, and here are no current technologies that will enable the direct use of two distinct human monoclonal antibodies with the desired specificities to be reassembled without further CDR or light chain engineering into a full bispecific antibody. Thus there is a need for generating full, correctly assembled, bispecific antibodies that are similar in their overall structure to natural antibodies, i.e., comprising two FAB fragments, each having a unique set of variable heavy and light chain domains that creates a unique antigen binding site and one dimeric Fc region.

SUMMARY OF THE INVENTION

The present disclosure relates generally to engineer hetero-dimeric immunoglobulins or fragments thereof and methods of making the same.

In one aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 12 and the protein-protein interface of the parent domain of the second engineered immunoglobulin chain is substituted with an amino acid residue at position 119, the substituted amino acid residue at position 12 and the substituted amino acid residue at position 119 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 26 and the protein-protein interface of the parent domain of the second engineered immunoglobulin chain is substituted with an amino acid residue at position 13, the substituted amino acid residue at position 26 and the substituted amino acid residue at position 13 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 27 and the protein-protein interface of the parent domain of the second engineered immunoglobulin chain is substituted with an amino acid residue at position 18, the substituted amino acid residue at position 27 and the substituted amino acid residue at position 18 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 79 and the protein-protein interface of the parent domain of the second engineered immunoglobulin chain is substituted with an amino acid residue at position 84.3, the substituted amino acid residue at position 79 and the substituted amino acid residue at position 84.3 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, if the parent domain of the first engineered immunoglobulin chain is an IGKC domain and the amino acid residue which is substituted in the protein-protein interface of the parent domain of the first engineered immunoglobulin chain is at position 11 and the parent domain of the second engineered immunoglobulin chain is a domain which comprises a hinge region, the parent domain of the second engineered immunoglobulin chain is not substituted at position 3 of the hinge region, wherein the amino acid position of each group member is indicated according to the IMGT® numbering.

In a further aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, wherein the amino acid position of each group member is indicated according to the IMGT® numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 88, and optionally a further amino acid residue at a position selected from the group consisting of 3, 5, 7, 20, 22, 26, 27, 79, 81, 84, 84.2, 85.1, 86, and 90 and, wherein the amino acid residue which is substituted in the protein-protein interface of the parent domain of the second engineered immunoglobulin chain comprises the amino acid residue at position 85.1 and/or 86 and optionally a further amino acid residue at a position selected from the group consisting of 3, 5, 7, 20, 22, 26, 27, 79, 81, 84, 84.2, 88, and 90 or at a position selected from the group consisting of 3, 5, 7, 20, 22, 26, 27, 79, 81, 84, 84.2, 85.1, 88, and 90 or at a position selected from the group consisting of 3, 5, 7, 20, 22, 26, 27, 79, 81, 84, 84.2, 86, 88, and 90,
wherein the amino acid residue substituted at position 88 in the parent domain of the first engineered immunoglobulin chain is interacting with the amino acid residue substituted at position 85.1 and/or 86 in the parent domain of the second engineered immunoglobulin chain,
wherein the amino acid position of each group member is indicated according to the IMGT® numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 84, 84.2, 85.1, 86, 88 and 90 and, wherein the amino acid residues which are substituted in the protein-protein interface of the parent domain of the second engineered immunoglobulin chain comprise the amino acid residue at position 26 and at a further position selected from the group consisting of 3, 22, 27, 79, 81, 84, 85.1, 86, and 88, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 88, and optionally a further amino acid residue at a position selected from the group consisting of 3, 5, 7, 20, 22, 26, 27, 79, 81, 83, 84, 84.2, 84.3, 85.1, 86 and 90 and, wherein the amino acid residue which is substituted in the protein-protein interface of the parent domain of the second engineered immunoglobulin chain comprises the amino acid residue at position 85.1 and/or 86 and optionally a further amino acid residue at a position selected from the group consisting of 3, 5, 7, 20, 22, 26, 27, 79, 81, 83, 84, 84.2, 84.3 and 90 or at a position selected from the group consisting of 3, 5, 7, 20, 22, 26, 27, 79, 81, 83, 84, 84.2, 84.3, 85.1 and 90 or at a position selected from the group consisting of 3, 5, 7, 20, 22, 26, 27, 79, 81, 83, 84, 84.2, 84.3, 86 and 90, wherein the amino acid residue substituted at position 88 in the parent domain of the first engineered immunoglobulin chain is interacting with the amino acid residue substituted at position 85.1 and/or 86 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 83, 84, 84.2, 84.3, 85.1, 86, 88 and 90 and, wherein the amino acid residue which is substituted in the protein-protein interface of the parent domain of the second engineered immunoglobulin chain comprises the amino acid residue at position 26 and optionally a further amino acid residue at a position selected from the group consisting of 3, 5, 7, 20, 22, 27, 79, 81, 83, 84, 84.2, 84.3, 85.1, 86, 88 and 90, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH4 domain, wherein the protein-protein interface of the parent domain of the first engineered immunoglobulin chain comprises an amino acid residue substitution at a position selected from the group consisting of 20, 22, 85.1, 86, and 88, and/or wherein the protein-protein interface of the parent domain of the second engineered immunoglobulin chain comprises an amino acid residue substitution at a position selected from the group consisting of 22, 26, 85.1, 86, and 88, wherein the amino acid position of each group member is indicated according to the IMGT® numbering.

In another aspect, the present disclosure provides a method to produce a hetero-dimeric immunoglobulin or hetero-dimeric fragment thereof comprising:
(a) substituting at least one amino acid residue of the protein-protein interface of a parent domain of a first parent immunoglobulin chain at the equivalent 3D structural position from a protein-protein interface of a donor domain of a first member of the naturally occurring immunoglobulin super-family to obtain a first engineered immunoglobulin chain comprising an engineered domain,
(b) substituting at least one amino acid residue of the protein-protein interface of the parent domain of a second parent immunoglobulin chain at the equivalent 3D structural position from a protein-protein interface of a donor domain of a second member of the naturally occurring immunoglobulin super-family to obtain a second engineered immunoglobulin chain comprising an engineered domain, (c) culturing a host cell comprising a nucleic acid encoding said engineered immunoglobulin chains, wherein the culturing is such that the nucleic acid is expressed and the engineered immunoglobulin chains produced; and (d) recovering the hetero-dimeric immunoglobulin or hetero-dimeric fragment thereof from the host cell culture.

In another aspect, the present disclosure provides a method to engineer a protein-protein interface of a domain of a multidomain protein comprising:

(a) providing a multidomain protein comprising a domain with a protein-protein interface;

(b) selecting as a donor domain a naturally occurring immunoglobulin super-family member comprising a domain with a protein-protein interface which is different from the domain of (a);

(c) overlaying 3D structures of the domain with the protein-protein interface of (a) and the donor domain with the protein-protein interface of (b);

(d) identifying exposed protein-protein interface residues in the overlayed 3D structures of the domain with the protein-protein interface of (a) and the donor domain with the protein-protein interface of (b);

(e) substituting at least one amino acid residue of the identified exposed protein-protein interface amino acid residues of the domain with the protein-protein interface of (a) with amino acid residues at the equivalent 3D structural position from the identified exposed protein-protein interface amino acid residues from the donor domain with the protein-protein interface of (b).

In a further aspect, the present disclosure provides the use of a donor domain of a first and a second member of the naturally occurring immunoglobulin super-family to engineer a hetero-dimeric immunoglobulin or hetero-dimeric fragment thereof comprising a first engineered immunoglobulin chain comprising at least one engineered domain which has a protein-protein interface which is substituted with at least one amino acid residue from the protein-protein interface of the donor domain of the first member of the naturally occurring immunoglobulin super-family and a second engineered immunoglobulin chain comprising at least one engineered domain which has a protein-protein interface which is substituted with at least one amino acid residue from the protein-protein interface of the donor domain of the second member of the naturally occurring immunoglobulin super-family.

BRIEF DESCRIPTION OF THE FIGURES

FIG. 1: Depicts the amino-acid sequence alignment of engineered 0113 domain BT alpha chain and engineered CH3 domain BT beta chain with human IgG1 CH3 domain. EU numbering is used. (Human IgG1CH3 domain: SEQ ID NO: 122; CH3-BT alpha domain: SEQ ID NO: 123 CH3-BT beta domain: SEQ ID NO: 124).

EU numberings are used; shaded position means no substitution. FIG. 19C: Sequences of human IGHG1, IGHG2, IGHG3 and IGHG4 CH2 domains; the IMGT® and EU numberings are used; shaded position means no substitution; (~) indicates a shift in sequence alignment. FIG. 19D: Sequences of human IGHG1, IGHG2, IGHG3 and IGHG4 CH3 domains; the IMGT® and EU numberings are used; shaded position means no substitution.

FIG. 20A: Sequences of engineered human IGHG1 CH1 domains having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; the IMGT® and EU numberings are used; shaded position means no substitution. FIG. 20B: Sequences of engineered human IGHG1 CH2 domains having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; the IMGT® and EU numberings are used; shaded position means no substitution. FIG. 20C: Sequences of engineered human IGHG1 CH3 domains having protein-protein interfaces based on the human TRAC (abbreviated ALPHA), TRBC2 (abbreviated BETA), TRDC (abbreviated DELTA), and TRGC1 (abbreviated GAMMA) constant domains; the IMGT® and EU numberings are used; shaded position means no substitution.

FIG. 21A: Sequences of engineered human IGHE CH4 domains having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; the IMGT® and EU numberings are used; shaded position means no substitution. FIG. 21B: Sequences of engineered human IGHM CH4 domains having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; the IMGT® and EU numberings are used; shaded position means no substitution.

FIG. 22: Sequences of engineered human IGKC domains having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; the IMGT® and EU numberings are used; shaded position means no substitution.

FIG. 23A: Sequences of human IGLC1, IGLC2, IGLC3, IGLC6, IGLC7 and engineered variants having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; Kabat residues 108 to 161 are shown—both the IMGT® and Kabat numberings are used; shaded position means no substitution. FIG. 23B: Sequences of human IGLC1, IGLC2, IGLC3, IGLC6, IGLC7 and engineered variants having protein-protein interfaces based on the human TRAC (abbreviated ALPHA), TRBC2 (abbreviated BETA), TRDC (abbreviated DELTA), TRGC1 (abbreviated GAMMA), and IGHG1 CH3 (abbreviated CH3) constant domains; Kabat residues 162 to 215 are shown—both the IMGT® and Kabat numberings are used; shaded position means no substitution.

C and D: HT1080 cells were stained with the anti-hCD19 antibody (grey histogram) as an isotype control or the anti-hCD19_anti-VLA2 bispecific antibody (white histogram). Binding of the primary antibodies was revealed by (C) a mouse anti c-myc tag antibody or (D) a mouse anti His tag antibody and stained with a PE-labelled anti-mouse Ig antibody.

Figure 32:
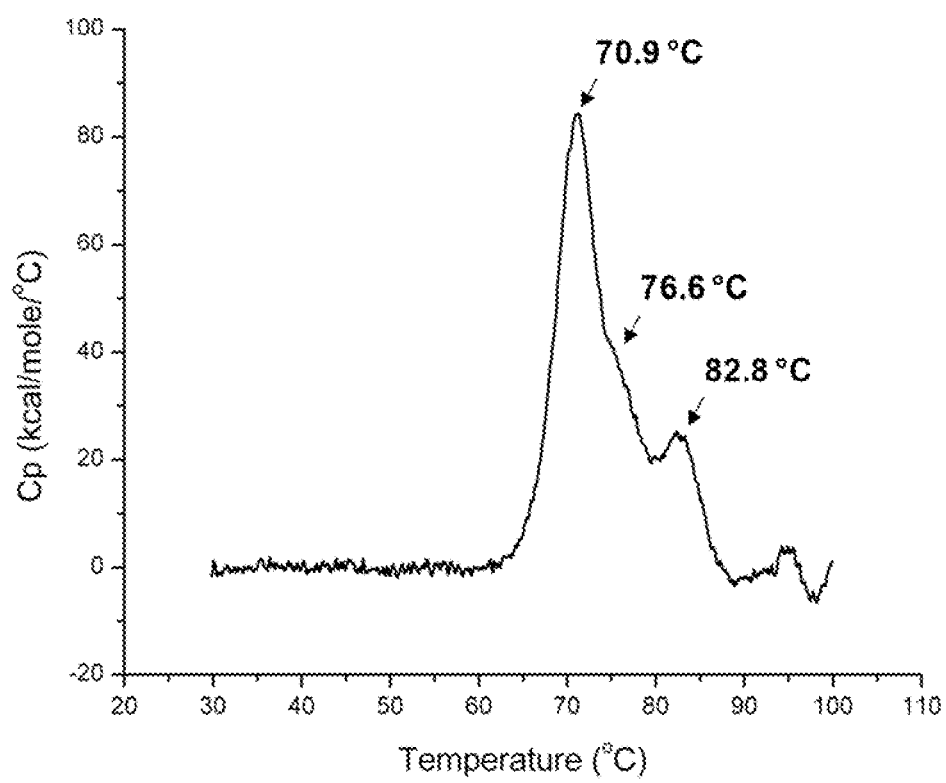

FIG. 32: DSC thermogram of the anti-hCD19_anti-hVLA2 bispecific antibody.

Figure 33:
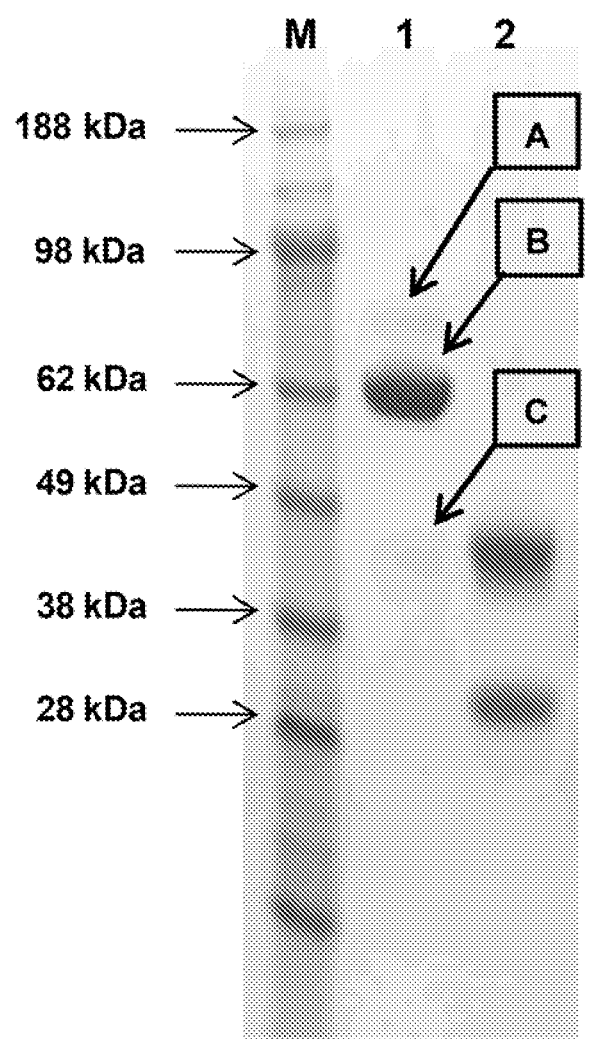

FIG. 33: SDS-PAGE analysis demonstrating production of the BT alpha IGHG3_VL-BT beta F405A hetero-dimer (4-12% SDS Tris-glycine polyacrylamide gel). (M) molecular weight marker as indicated. (1) BT alpha IGHG3_VL-BT beta F405A transfection output after protein-A purification, non-reducing conditions. (2) BT alpha IGHG3_VL-BT beta F405A transfection output after protein-A purification, reducing conditions. (A) VL-BT beta F405A_VL-BT beta F405A homo-dimer (B) BT alpha IGHG3_VL-BT beta F405A hetero-dimer, (C) VL-BT beta F405A chain (half molecule).

Figure 34:
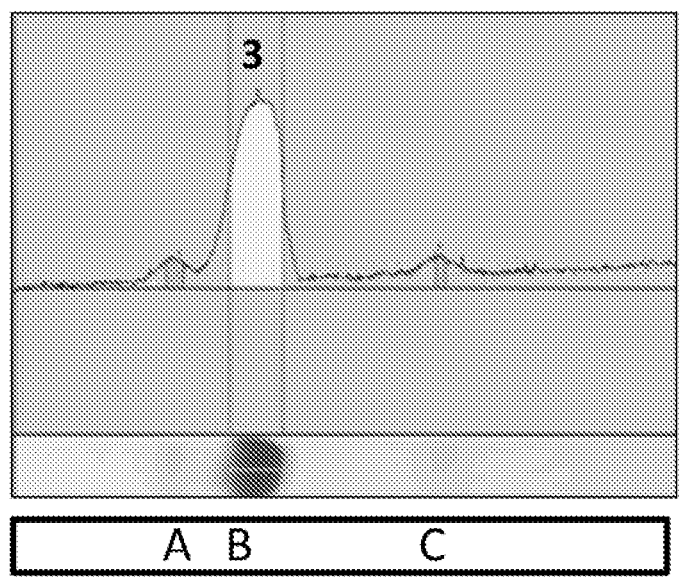

FIG. 34: Scanning densitometry analysis assessing the relative proportion of the BT alpha IGHG3_VL-BT beta F405A hetero-dimer after protein-A purification (4-12% SDS Tris-glycine polyacrylamide gel). (A) VL-BT beta F405A_VL-BT beta F405A homo-dimer (B) BT alpha IGHG3_VL-BT beta F405A hetero-dimer (C) VL-BT beta F405A chain (half molecule).

Figure 35:
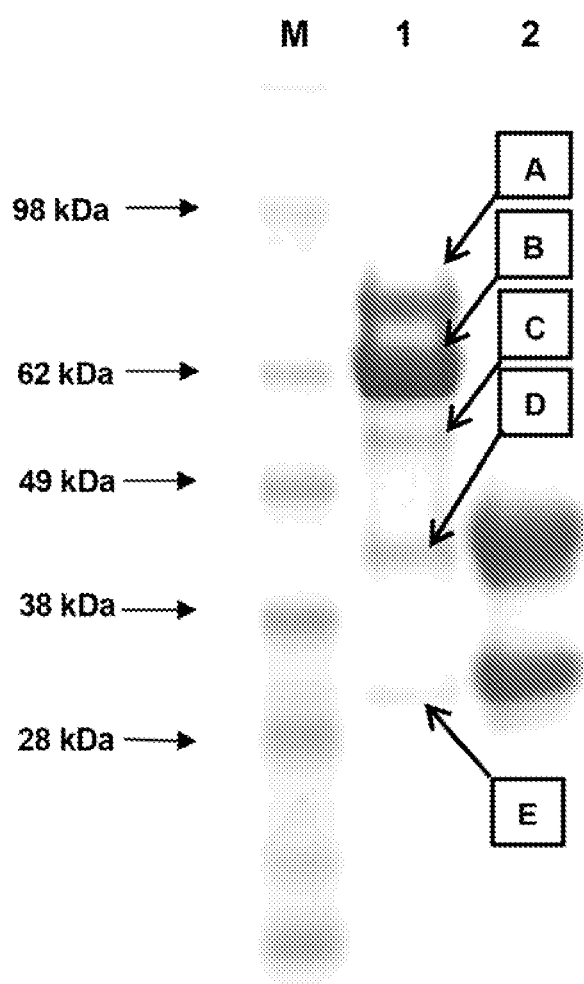

FIG. 35: SDS-PAGE analysis demonstrating production of the Fc IGHAG_VL-Fc IGHGA hetero-dimer (4-12% SDS Tris-glycine polyacrylamide gel). (M) molecular weight marker as indicated. (1) Fc IGHAG_VL-Fc IGHGA hetero-dimer transfection output after protein-A purification, non-reducing conditions. (2) Fc IGHAG_VL-Fc IGHGA hetero-dimer transfection output after protein-A purification, reducing conditions. (A) VL-Fc IGHGA_VL-Fc IGHGA homo-dimer (B) Fc IGHAG_VL-Fc IGHGA hetero-dimer (C) Fc IGHAG_Fc IGHAG homo-dimer (D) VL-Fc IGHGA chain (half molecule). (E) Fc IGHAG chain (half molecule).

Figure 36:
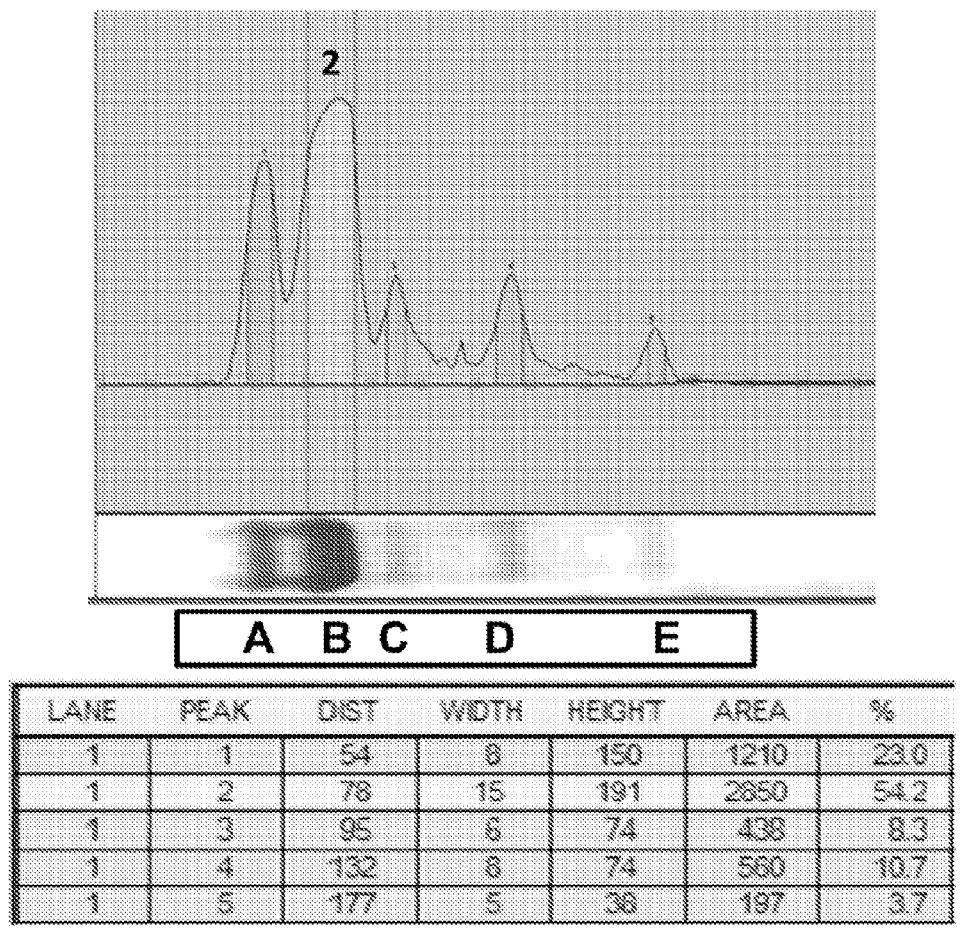

FIG. 36: Scanning densitometry analysis assessing the relative proportion of the Fc IGHAG_VL-Fc IGHGA hetero-dimer after protein-A purification (4-12% SDS Tris-glycine polyacrylamide gel). (A) VL-Fc IGHGA_VL-Fc IGHGA homo-dimer (B) Fc IGHAG_VL-Fc IGHGA hetero-dimer (C) Fc IGHAG_Fc IGHAG homo-dimer (D) VL-Fc IGHGA chain (half molecule). (E) Fc IGHAG chain (half molecule).

Figure 37:
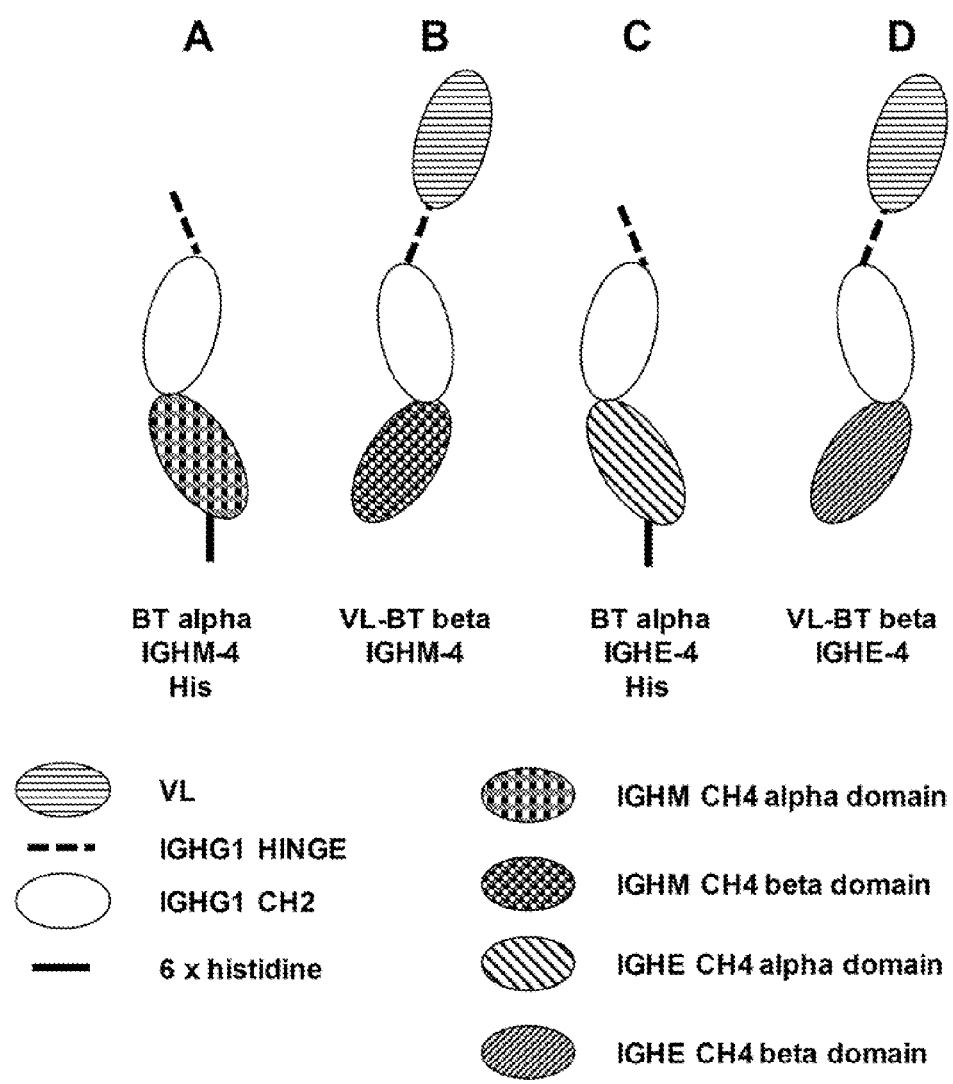

FIG. 37: Schematic diagram of engineered CH4 based Fc chains. (A) BT alpha IGHM-4 His chain. (B) VL-BT beta IGHM-4 chain. (C) BT alpha IGHE-4 His chain. (D) VL-BT beta IGHE-4 chain.

Figure 38:
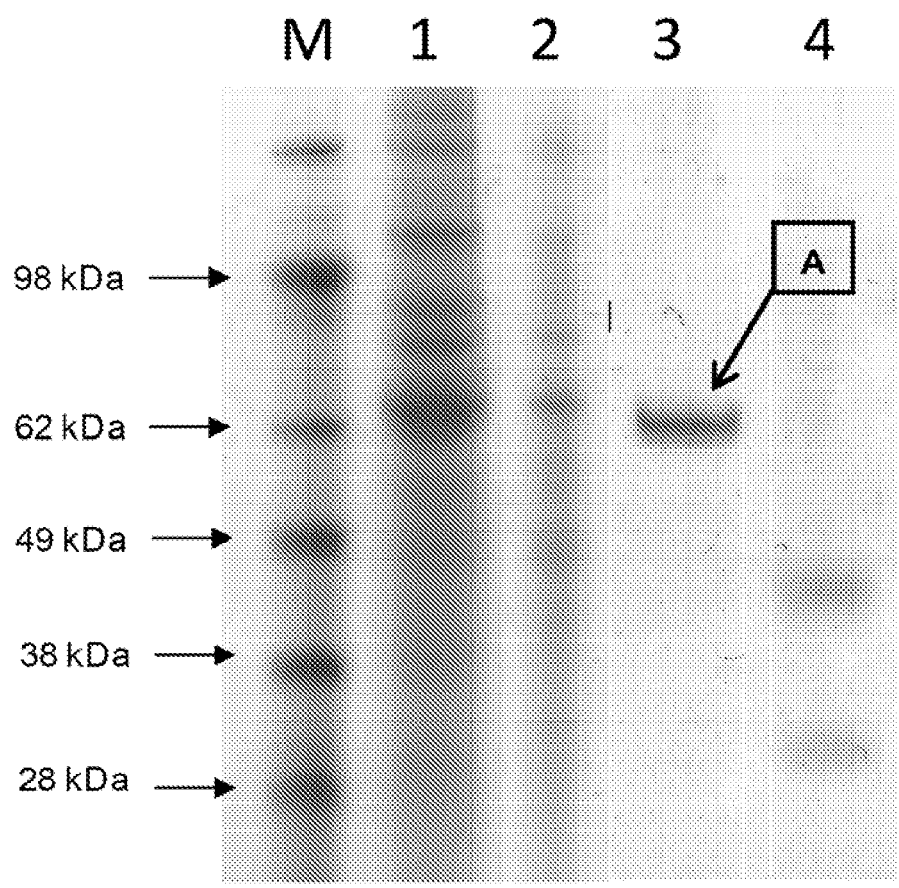
Figure 39:
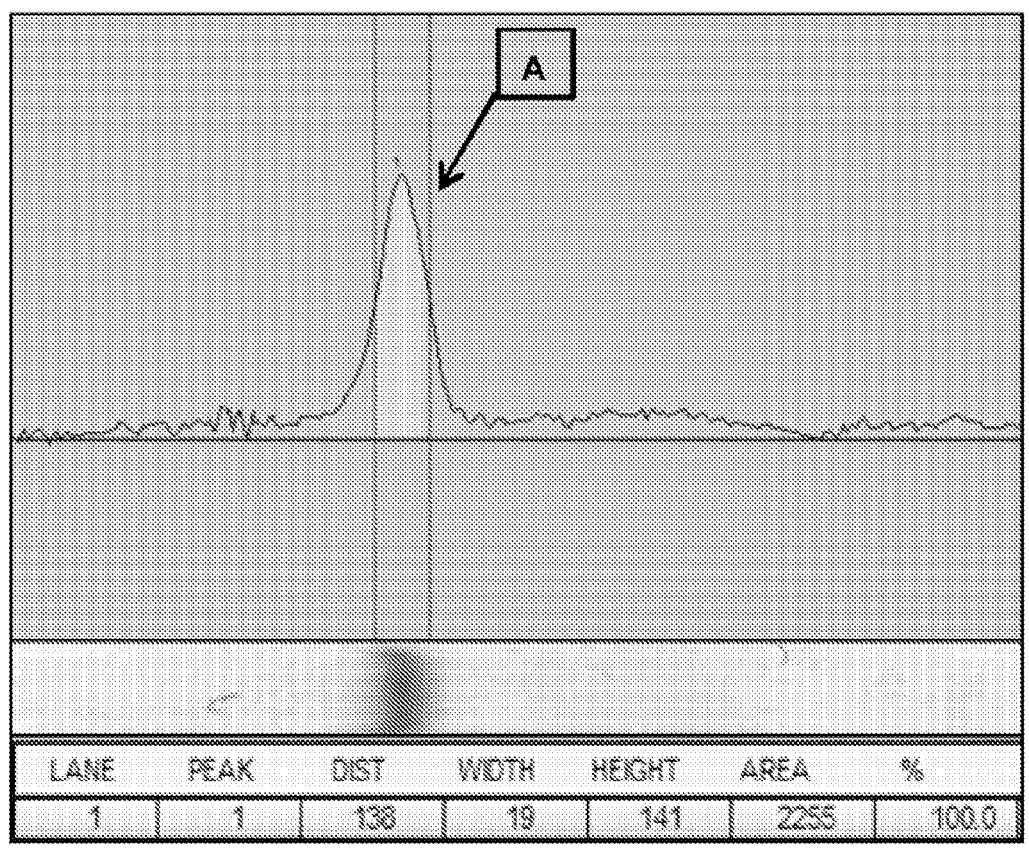

FIG. 38: SDS-PAGE analysis demonstrating production of the BT alpha IGHM-4 His_VL-BT beta IGHM-4 hetero-dimer (4-12% SDS Tris-glycine polyacrylamide gel). (M) molecular weight marker as indicated. (1) BT alpha IGHM-4 His_VL-BT beta IGHM-4 hetero-dimer transfection output, non-reducing conditions. (2) BT alpha IGHM-4 His_VL-BT beta IGHM-4 hetero-dimer transfection output, reducing conditions. (3) BT alpha IGHM-4 His_VL-BT beta IGHM-4 hetero-dimer transfection output after protein-L purification, non reducing conditions. (4) BT alpha IGHM-4 His_VL-BT beta IGHM-4 hetero-dimer transfection output after protein-L purification, reducing conditions. (A) BT alpha IGHM-4 His_VL-BT beta IGHM-4 beta hetero-dimer FIG. 39: Scanning densitometry analysis assessing the relative proportion of the BT alpha IGHM-4 His_VL-BT IGHM-4 beta hetero-dimer after protein-L purification (4-12% SDS Tris-glycine polyacrylamide gel).

Figure 40:
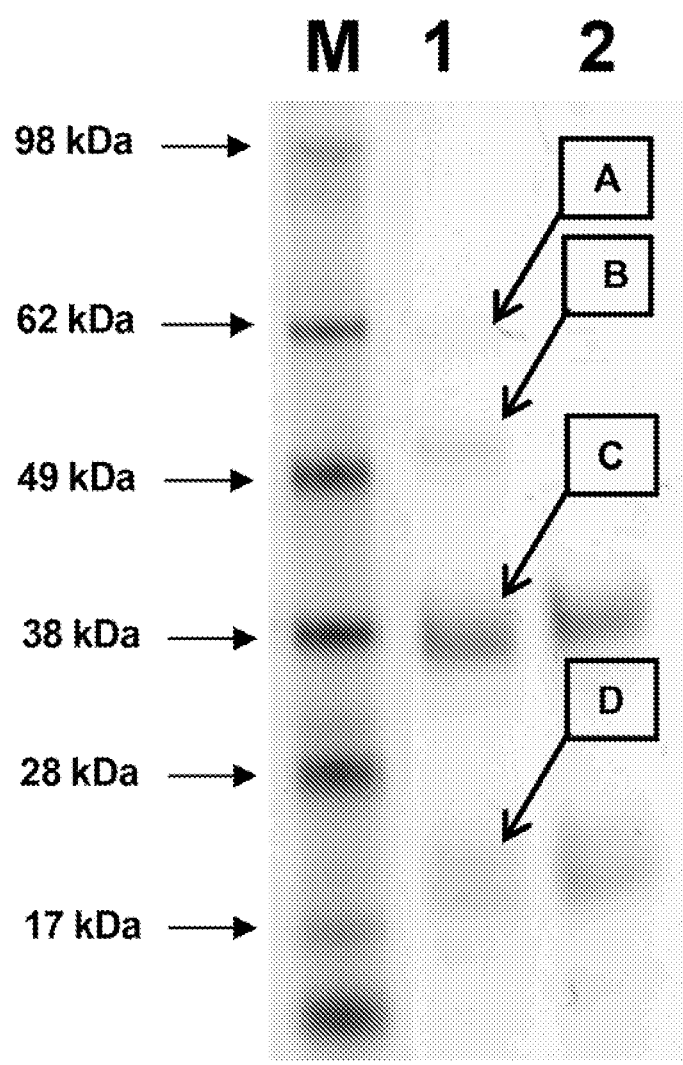

FIG. 40: SDS-PAGE analysis demonstrating production of the BT alpha IGHE-4 His_VL-BT beta IGHE-4 hetero-dimer (4-12% SDS Tris-glycine polyacrylamide gel). (M) molecular weight marker as indicated. (1) BT alpha IGHE-4 His_VL-BT beta IGHE-4 hetero-dimer transfection output after protein-A purification, non-reducing conditions. (2) BT alpha IGHE-4 His_VL-BT beta IGHE-4 hetero-dimer transfection output after protein-A purification, reducing conditions. (A) BT alpha IGHE-4 His_VL-BT beta IGHE-4 hetero-dimer (B) BT alpha IGHE-4 His_BT alpha IGHE-4 His homo-dimer. (C) VL-BT beta IGHE-4 chain (half molecule). (D) BT alpha IGHE-4 His chain (half molecule).

Figure 41:
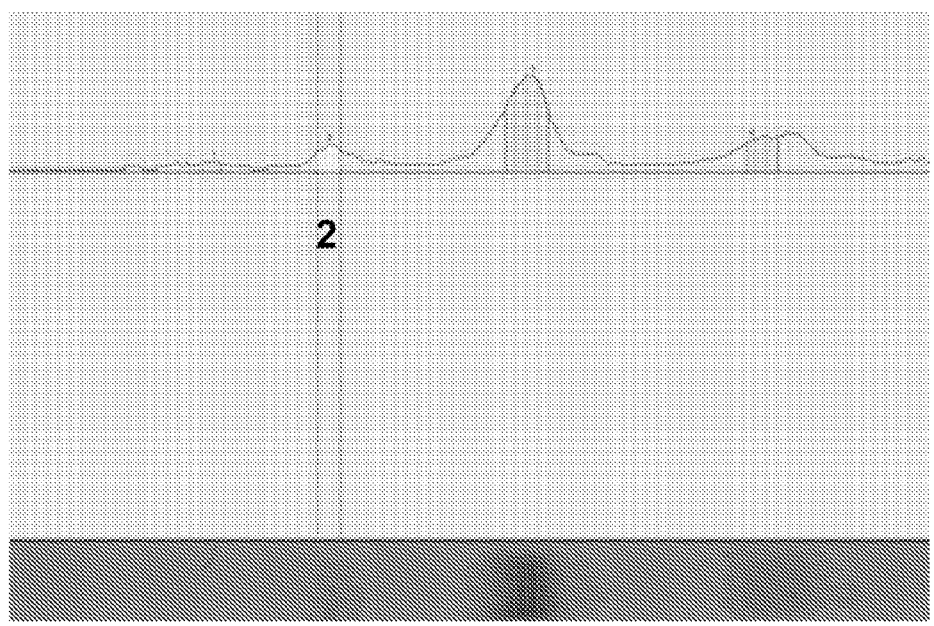

FIG. 41: Scanning densitometry analysis assessing the relative proportion of the BT alpha IGHE-4 His_VL-BT beta IGHE-4 hetero-dimer after protein-A purification (4-12% SDS Tris-glycine polyacrylamide gel).

FIG. 42: IMGT® unique numbering as used herein e.g. in example 1, 2, 3, 4, 7, 8, 9, 10, 11, and 12 to identify 3D equivalent positions for human CH1, CH2, CH3, and CH4 constant domains of IGHA1 (SEQ ID NO: 98), IGHA2 (SEQ ID NO: 99), IGHD (SEQ ID NO: 100), IGHE (SEQ ID NO: 101). IGHEP1 (SEQ ID NO: 121), IGHG1 (SEQ ID NO: 102), IGHG2 (SEQ ID NO: 103), IGHG3 (SEQ ID NO: 104j, IGHG4 (SEQ ID NO: 105), IGHGP (SEQ ID NO: 106), and IGHM (SEQ ID NO: 107). GenBank accession numbers are indicated.

FIG. 43: IMGT® unique numbering as used herein e.g. in example 5, 6, 7, and 9 to identify 3D equivalent positions for human IGKC constant domain (SEQ ID NO: 108). GenBank accession number is indicated.

FIG. 44: IMGT® unique numbering as used herein e.g. in example 7 to identify 3D equivalent positions for human IGLC1 (SEQ ID NO: 109), IGLC2 (SEQ ID NO: 110), IGLC3 (SEQ ID NO: 111), IGLC6 (SEQ ID NO: 112), and IGLC7 (SEQ ID NO: 113) constant domains. GenBank accession numbers are indicated.

FIG. 45: IMGT® unique numbering as used herein e.g. in example 1, 2, 3, 4, 5, 7, 8, 9, 10, and 12 to identify 3D equivalent positions for human TRAC (SEQ ID NO: 114), TRBC1 (SEQ ID NO: 115), TRBC2 (SEQ ID NO: 116), TRDC (SEQ ID NO: 117), TRGC1 (SEQ ID NO: 118), TRGC2 (2x) (SEQ ID NO: 119), and TRGC2 (3x) (SEQ ID NO: 120) constant domains. GenBank accession numbers are indicated.

DETAILED DESCRIPTION OF THE INVENTION

The present disclosure relates generally to engineer hetero-dimeric immunoglobulins or fragments thereof and methods of making the same.

The term "antibody" as referred to herein includes full-length antibodies and any antigen binding fragment or single chains thereof. Antibodies and specifically naturally occurring antibodies are glycoproteins which exist as one or more copies of a Y-shaped unit, composed of four polypeptide chains. Each "Y" shape contains two identical copies of a heavy (H) chain, and two identical copies of a light (L) chain, named as such by their relative molecular weights. Each light chain pairs with a heavy chain, and each heavy chain pairs with another heavy chain. Covalent interchain disulfide bonds and non covalent interactions link the chains together. Antibodies and specifically naturally occurring antibodies contain variable regions, which are the two copies of the antigen binding site. Papain, a proteolytic enzyme splits the "Y" shape into three separate molecules, two so called "Fab" fragments (Fab=fragment antigen binding), and one so called "Fc" fragment or "Fc region" (Fc=fragment crystallizable). A Fab fragment consists of the entire light chain and part of the heavy chain. The heavy chain contains one variable domain (VH) and either three or four constant domains (CH1, CH2, CH3, and CH4, depending on the antibody class or isotype). The region between the CH1 and CH2 domains is called the hinge region and permits flexibility between the two Fab arms of the Y-shaped antibody molecule, allowing them to open and close to accommodate binding to two antigenic determinants separated by a fixed distance. The "hinge region" as referred to herein is a sequence region of 6-62 amino acids in length, only present in IgA, IgD, and IgG, which encompasses the cysteine residues that bridge the two heavy chains. The heavy chains of IgA, IgD, and IgG each have four domains, i.e. one variable domain (VH) and three constant domains (CH1-3). IgE and IgM have one variable and four constant domains (CH1-4) on the heavy chain. The constant regions of the antibodies may mediate the binding to host tissues or factors, including various cells of the immune system (e.g., effector cells) and the first component (C1q) of the complement system classical pathway. Each light chain is usually linked to a heavy chain by one covalent disulfide bond. Each light chain contains one variable domain (VL) and one light chain constant domain. The light chain constant domain is a kappa light chain constant domain designated herein as IGKC or is a lambda light chain constant domain designated herein as IGLC. IGKC is used herein equivalently to Cκ or CK and has the same meaning. IGLC is used herein equivalently to Cλ or CL and has the same meaning. The term "an IGLC domain" as used herein refer to all lambda light chain constant domains e.g. to all lambda light chain constant domains selected from the group consisting of IGLC1, IGLC2, IGLC3, IGLC6, and IGLC7. The VH and VL regions can be further subdivided into regions of hypervariability, termed complementarity determining regions (CDR), interspersed with regions that are more conserved, termed framework regions (FR or FW). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and a light chain constant region, and each heavy chain comprising immunoglobulin domains VH, CH1 (C[γ]1), CH2 (C[γ]2), CH3 (C[γ]3), and CH4 (C[γ]4), depending on the antibody class or isotype). In some mammals, for example in camels and llamas, IgG antibodies may consist of only two heavy chains, each heavy chain comprising a variable domain attached to the Fc region.

Antibodies are grouped into classes, also referred to as isotypes, as determined genetically by the constant region. Human constant light chains are classified as kappa (CK) and lambda (C[λ]) light chains. Heavy chains are classified as mu (μ), delta (δ), gamma (γ), alpha (α), or epsilon (ε), and define the antibody's isotype as IgM, IgD, IgG, IgA, and IgE, respectively. Thus, "isotype" as used herein is meant any of the classes and/or subclasses of immunoglobulins defined by the chemical and antigenic characteristics of their constant regions. The known human immunoglobulin isotypes are IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), and IgE (IGHE). The so-called human immunoglobulin pseudo-gamma IGHGP gene represents an additional human immunoglobulin heavy constant region gene which has been sequenced but does not encode a protein due to an altered switch region (Bensmana M et al., Nucleic Acids Res, 16(7):3108 (1988)). In spite of having an altered switch region, the human immunoglobulin pseudo-gamma IGHGP gene has open reading frames for all heavy constant domains (CH1-CH3) and hinge. All open reading frames for its heavy constant domains encode protein domains which align well with all human immunoglobulin constant domains with the predicted structural features. This additional pseudo-gamma isotype is referred herein as IgGP or IGHGP. Other pseudo immunoglobulin genes have been reported such as the human immunoglobulin heavy constant domain epsilon P1 and P2 pseudo-genes (IGHEP1 and IGHEP2). The IgG class is the most commonly used for therapeutic purposes. In humans this class comprises subclasses IgG1, IgG2, IgG3, and IgG4. In mice this class comprises subclasses IgG1, IgG2a, IgG2b, IgG2c and IgG3.

The term "naturally occurring immunoglobulin super-family" as used herein refers to members of the immunoglobulin super-family which can be found in nature (Williams A F and Barclay A N, *Annu Rev Immunol,* 6:381-405 (1988)) i.e. which have not been genetically engineered, and includes, but is not limited to Antigen receptors like antibodies; immunoglobulins; T cell receptor chains including the TCR constant domain family; Antigen presenting molecules like Class I MHC, Class II MHC or beta-2 microglobulin; Co-receptors like CD4, CD8, or CD19; Antigen receptor accessory molecules like CD3-γ, -δ and -ε chains, CD79a or CD79b; Co-stimulatory or inhibitory molecules like CD28, CD80 or CD86 (also known as B7.1 and B7.2 molecules); Receptors on Natural killer cells like Killer-cell immunoglobulin-like receptors (KIR); Adhesion molecules like CD2, CD48, the SIGLEC family (e.g. CD22, CD83), the CTX family (e.g. CTX, JAMs, BT-IgSF, CAR, VSIG, ESAM), Intercellular adhesion molecules (ICAMs), Vascular cell adhesion molecules (e.g. VCAM-1), Neural Cell Adhesion Molecule (NCAM); Cytokine and growth factor receptors like Interleukin-1 receptor type I, Interleukin-1 receptor type II precursor (IL-1R-2, IL-1R-beta, CD121b antigen), Platelet-derived growth factor receptor (PDGFR), Interleukin-6 receptor alpha chain precursor (IL-6R-alpha, CD126 antigen), Colony stimulating factor 1 receptor precursor (CSF-1-R, CD115 antigen, macrophage colony stimulating factor I receptor), Mast/stem cell growth factor receptor precursor (SCFR, c-kit, CD117 antigen), Basic fibroblast growth factor receptor 1 precursor (FGFR-1, Tyrosine kinase receptor CEK1); Receptor tyrosine kinases/phosphatases like Tyrosine-protein kinase receptor Tie-1 precursor or Receptor-type tyrosine-protein phosphatase mu precursor; Ig binding receptors like Polymeric immunoglobulin receptor (PIGR), or selected Fc receptors; and others like CD147, Thymocyte differentiation antigen-1 (Thy-1), also known as CD90, CD7, Butyrophilins (Btn), Sodium channel subunit beta-1 precursor, Titin (a huge intracellular muscle protein also known as Connectin).

The T cell receptor (TCR) constant domain family as used herein include the human TCR constant domain alpha which is referred herein as "human TCR constant domain alpha" or "TRAC" (SEQ ID NO: 1; GenBank database accession number AAO72258.1 (residues 135-225) which is equivalent to the complete sequence of IMGT® reference TRAC, the human TCR constant domain beta which is referred herein as "human TCR constant domain beta" or "TRBC2" (SEQ ID NO: 2; GenBank database accession number AAA61026.1 (residues 134-261), which is equivalent to residues 1.8-124 of IMGT® reference TRBC2), the human TCR constant domain delta which is referred herein as "human TCR constant domain delta" or "TRDC" (SEQ ID NO: 32; GenBank database accession number AAA61125.1 (residues 135-221) which is equivalent to residues 1.7-120 of IMGT® reference TRDC), the human TCR constant domain gamma which is referred herein as "human TCR constant domain gamma" or "TRGC1" (SEQ ID NO: 33; GenBank database accession number AAA61110.1 (residues 145-245) which is equivalent to residues 1.1-124 of IMGT® reference TRGC1), and the pre T-cell antigen receptor chains (pre-TCR) as disclosed in Pang S S et al., Nature, 467(7317):844-8 (2010). Within the scope of the invention, allotype variants of the human TCR beta and gamma constant domains (IMGT® reference TRBC1, and TRGC2 (2×) or TRGC2 (3×), respectively) are equally included.

IMGT® references are according to IMGT® (the international ImMunoGeneTics information System®) (Lefranc M P et al., Nucleic Acids Res, 27(1):209-12 (1999); Ruiz M et al., Nucleic Acids Res, 28(1):219-21 (2000); Lefranc M P, Nucleic Acids Res, 29(1):207-9 (2001); Lefranc M P, Nucleic Acids Res, 31(1):307-10 (2003); Lefranc M P et al., Dev Comp Immunol, 29(3):185-203 (2005); Kaas Q et al., Briefings in Functional Genomics & Proteomics, 6(4):253-64 (2007)).

Preferred naturally occurring immunoglobulin super-family members which can be used for the present invention as donor domains are selected from the group consisting of the human TCR constant domain alpha, the human TCR constant domain beta, the human TCR constant domain gamma, the human TCR constant domain delta, the human TCR variable domain alpha, the human TCR variable domain beta, the human TCR variable domain gamma, the human TCR variable domain delta, pre T-cell antigen receptor chains and the CH1, CH2, CH3, CH4, IGKC, IGLC1, IGLC2, IGLC3, IGLC6, and IGLC7 domains. More preferred are donor domains selected from the group consisting of the human TCR constant domain alpha, the human TCR constant domain beta, the human TCR constant domain gamma, the human TCR constant domain delta, and the CH3 domain, in particular donor domains selected from the group consisting of the human TCR constant domain alpha, the human TCR constant domain beta, the human TCR constant domain gamma and the human TCR constant domain delta. Preferably naturally occurring immunoglobulin super-family members referred to in the present invention are human naturally occurring immunoglobulins.

The term "Immunoglobulin fragments" as used herein include, but is not limited to, (i) a domain, (ii) the Fab fragment consisting of VL, VH, CL or CK and CH1 domains, including Fab' and Fab'-SH, (ii) the Fd fragment consisting of the VH and CH1 domains, (iii) the dAb fragment (Ward E S et al., Nature, 341(6242):544-6 (1989)) which consists of a single variable domain (iv) F(ab')$_2$ fragments, a bivalent fragment comprising two linked Fab fragments (v) single chain Fv molecules (scFv), wherein a VH domain and a VL domain are linked by a peptide linker which allows the two domains to associate to form an antigen binding site (Bird R E et al., Science, 242(4877): 423-6 (1988); Huston J S et al., Proc Natl Acad Sci USA, 85(16):5879-83 (1988)), (vi) "diabodies" or "triabodies", multivalent or multispecific fragments constructed by gene fusion (Holliger P et al., Proc Natl Acad Sci USA, 90(14): 6444-8 (1993); Tomlinson I and Holliger P, Methods Enzymol, 326:461-79 (2000)), (vii) scFv, diabody or domain antibody fused to an Fc region and (viii) scFv fused to the same or a different antibody.

The term "hetero-dimeric immunoglobulin" or "hetero-dimeric fragment" or "hetero-dimer" as used herein includes an immunoglobulin molecule or part of comprising at least a first and a second polypeptide, like a first and a second domain, wherein the second polypeptide differs in amino acid sequence from the first polypeptide. Preferably, a hetero-dimeric immunoglobulin comprises two polypeptide chains, wherein the first chain has at least one non identical domain to the second chain, and wherein both chains assemble, i.e. interact through their non identical domains. Specifically, a hetero-dimeric immunoglobulin comprises at least two domains, wherein the first domain is non identical to the second domain, and wherein both domains assemble, i.e. interact through their protein-protein interfaces. More preferably the hetero-dimeric immunoglobulin, has binding specificity for at least two different ligands, antigens or binding sites, i.e. is bispecific. Hetero-dimeric immunoglobulin as used herein includes but is not limited to full length bispecific antibodies, bispecifc Fab, bispecifc F(ab')$_2$, bispecific scFv fused to an Fc region, diabody fused to an Fc region and domain antibody fused to an Fc region. Preferably, a hetero-dimeric immunoglobulin fragment comprises at least two domains, wherein the first domain is non identical to the second domain, and wherein both domains assemble, i.e. interact through their protein-protein interfaces. More preferably, a hetero-dimeric immunoglobulin fragment comprises at least two engineered domains, wherein the first engineered domain is non identical to the second engineered domain i.e. the first engineered domain differs in amino acid sequence from the second engineered domain, and wherein both engineered domains assemble by interaction through their protein-protein interfaces.

"Naturally occurring hetero-dimers" as used herein includes but are not limited to an IGKC domain or an IGLC domain (IGLC1 or IGLC2 or IGLC3 or IGLC6 or IGLC7) which hetero-dimerizes with any heavy chain CH1 domain (IGHA1 CH1, IGHA2 CH1, IGHD CH1, IGHE CH1, IGHG1 CH1, IGHG2 CH1, IGHG3 CH1, IGHG4 CH1, IGHGP CH1, IGHM CH1), e.g. IGKC/IGHA1 CH1, IGLC2/IGHA1 CH1, IGLC3/IGHA1 CH1, IGLC6/IGHA1 CH1, IGLC7/IGHA1 CH1, IGKC/IGHA2 CH1, IGLC2/IGHA2 CH1, IGLC3/IGHA2 CH1, IGLC6/IGHA2 CH1, IGLC7/IGHA2 CH1, IGKC/IGHD CH1, IGLC2/IGHD CH1, IGLC3/IGHD CH1, IGLC6/IGHD CH1, IGLC7/IGHD CH1, IGKC/IGHE CH1, IGLC2/IGHE CH1, IGLC3/IGHE CH1, IGLC6/IGHE CH1, IGLC7/IGHE CH1, IGKC/IGHG1 CH1, IGLC2/IGHG1 CH1, IGLC3/IGHG1 CH1, IGLC6/IGHG1 CH1, IGLC7/IGHG1 CH1, IGKC/IGHG2 CH1, IGLC2/IGHG2 CH1, IGLC3/IGHG2 CH1, IGLC6/IGHG2 CH1, IGLC7/IGHG2 CH1, IGKC/IGHG3 CH1, IGLC2/IGHG3 CH1, IGLC3/IGHG3 CH1, IGLC6/IGHG3 CH1, IGLC7/IGHG3 CH1, IGKC/IGHG4 CH1, IGLC2/IGHG4 CH1, IGLC3/IGHG4 CH1, IGLC6/IGHG4 CH1, IGLC7/IGHG4 CH1, IGKC/IGHGP CH1, IGLC2/IGHGP CH1, IGLC3/IGHGP CH1, IGLC6/IGHGP CH1, IGLC7/IGHGP CH1, IGKC/IGHM CH1, IGLC2/IGHM CH1, IGLC3/IGHM CH1, IGLC6/IGHM CH1, IGLC7/IGHM CH1. Other examples of "naturally occurring hetero-dimers" encompass an antibody variable heavy chain domain which hetero-dimerizes with an antibody variable light chain domain (kappa or lambda), a TCR alpha variable domain which hetero-dimerizes with a TCR beta variable domain, a TCR gamma variable domain which hetero-dimerizes with a TCR delta variable domain, a TCR alpha constant domain which hetero-dimerizes with a TCR beta constant domain, a TCR gamma constant domain which hetero-dimerizes with a TCR delta constant domain.

The term "homo-dimeric immunoglobulin" or "homo-dimeric fragment" or "homo-dimer" as used herein includes an immunoglobulin molecule or part of comprising at least a first and a second polypeptide, like a first and a second domain, wherein the second polypeptide is identical in amino acid sequence to the first polypeptide. Preferably, a homo-dimeric immunoglobulin comprises two polypeptide chains, wherein the first chain has at least one identical domain to the second chain, and wherein both chains assemble, i.e. interact through their identical domains. Specifically, a homo-dimeric immunoglobulin comprises at least two identical domains and wherein both domains assemble, i.e. interact through their protein-protein interfaces. Preferably, a homo-dimeric immunoglobulin fragment comprises at least two domains, wherein the first domain is identical to the second domain, and wherein both domains assemble, i.e. interact through their protein-protein interfaces. "Naturally occurring homo-dimers" as used herein include but are not limited to e.g. two CH3 domains of the same species, isotype and subclass e g human IGHG1 CH3/IGHG1 CH3, human IGHG2 CH3/IGHG2 CH3, human IGHG3 CH3/IGHG3 CH3, human IGHG4 CH3/IGHG4 CH3, human IGHA1 CH3/IGHA1 CH3, human IGHA2 CH3/IGHA2 CH3, human IGHE CH3/IGHE CH3, human IGHEP1 CH3/IGHEP1 CH3, human IGHM CH3/IGHM CH3, human IGHD CH3/IGHD CH3, human IGHGP CH3/IGHGP CH3, two CH2 domains of the same species, isotype and subclass e.g. human IGHG1 CH2/IGHG1 CH2, human IGHG2 CH2/IGHG2 CH2, human IGHG3 CH2/IGHG3 CH2, human IGHG4 CH2/IGHG4 CH2, human IGHA1 CH2/IGHA1 CH2, human IGHA2 CH2/IGHA2 CH2, human IGHE CH2/IGHE CH2, human IGHEP1 CH2/IGHEP1 CH2, human IGHM CH2/IGHM CH2, human IGHD CH2/IGHD CH2, human IGHGP CH2/IGHGP CH2, or two CH4 domains of the same species, isotype and subclass e.g. human IGHE CH4/IGHE CH4, human IGHM CH4/IGHM CH4. Preferred "Naturally occurring homo-dimers" are selected from the group consisting of human IGHG1 CH3/IGHG1 CH3, human IGHG2 CH3/IGHG2 CH3, human IGHG3 CH3/IGHG3 CH3, human IGHG4 CH3/IGHG4 CH3, human IGHA1 CH3/IGHA1 CH3, human IGHA2 CH3/IGHA2 CH3, human IGHE CH3/IGHE CH3, human IGHM CH3/IGHM CH3, human IGHD CH3/IGHD CH3, human IGHGP CH3/IGHGP CH3, human IGHE CH2/IGHE CH2, human IGHM CH2/IGHM CH2, human IGHE CH4/IGHE CH4, and human IGHM CH4/IGHM CH4.

Most immunoglobulin light chains associate into dimers (Novotny J and Haber E, *Proc Natl Acad Sci USA*, 82(14): 4592-6 (1985)). Both kappa and lambda light chains have been reported to homo-dimerize, and several crystal structures of kappa and lambda light chain dimers are available from the Protein Data Bank (PDB) database (Roussel A et al., *Eur J Biochem*, 260(1):192-9 (1999), Huang D B et al., *Proc Natl Acad Sci USA*, 93(14):7017-21 (1996); www.pdb.org; Bernstein F C et al., *Eur J Biochem*, 80(2):319-24 (1977)). Within the scope of the invention homo-dimers of an IGKC domain or an IGLC domain (IGLC1 or IGLC2 or IGLC3 or IGLC6 or IGLC7) can be considered as parent or donor domains for protein-protein interface engineering. Thus, "naturally occurring homo-dimers" as used herein also include but are not limited to two IGKC domains of the same species, isotype and subclass e.g. human IGKC/IGKC, two IGLC domains of the same species, isotype and subclass e.g. human IGLC1/IGLC1, human IGLC2/IGLC2, human IGLC3/IGLC3, human IGLC6/IGLC6, human IGLC7/IGLC7 and any other pairwise combination of IGLC1, IGLC2, IGLC3, IGLC6, and IGLC7.

The term "formation of a hetero-dimer" or "forming a hetero-dimer" or "capable to form a hetero-dimer" in relation to two domains e.g. in relation to two parent domains or to two donor domains as used herein means that the first domain is not identical to the second domain and wherein both domains assemble, i.e. interact through their protein-protein interface wherein the protein-protein interfaces are normally not identical. The first domain is not identical to the second domain if both domains differ in amino acid sequence by at least one amino acid residue. The protein-protein interfaces are normally not identical if the protein-protein interface of the first parent or donor domain has at least one 3D structural position with a different amino acid residue compared to the protein-protein interface of the second parent or donor domain.

The term "formation of a naturally occurring hetero-dimer" or "forming a naturally occurring hetero-dimer" or "capable to form a naturally occurring hetero-dimer" in relation to two domains e.g. in relation to two naturally occurring parent domains or to two naturally occurring donor domains as used herein means that the first domain is not identical to the second domain and wherein both domains assemble, i.e. interact through their protein-protein interface wherein the protein-protein interfaces are normally not identical. The first domain is not identical to the second domain if both domains differ in amino acid sequence by at least one amino acid residue. The protein-protein interfaces are normally not identical if the protein-protein interface of the first parent or donor domain has at least one 3D structural position with a different amino acid residue compared to the protein-protein interface of the second parent or donor domain.

The term "formation of a homo-dimer" or "forming a homo-dimer" or "capable to form a homo-dimer" in relation to two domains e.g. in relation to two parent domains or to two donor domains as used herein means that the first domain is identical to the second domain and wherein both domains assemble, i.e. interact through their protein-protein interface, wherein the protein-protein interfaces are normally identical. The first domain is identical to the second domain if their amino acid sequences are identical. The protein-protein interfaces are normally identical if the protein-protein interface of the first parent or donor domain has the identical amino acid at the identical 3D structural position compared to the protein-protein interface of the second parent or donor domain.

The term "formation of a naturally occurring homo-dimer" or "forming a naturally occurring homo-dimer" or "capable to form a naturally occurring homo-dimer" in relation to two domains e.g. in relation to two naturally occurring parent domains or to two naturally occurring donor domains as used herein means that the first domain is identical to the second domain and wherein both domains assemble, i.e. interact through their protein-protein interface, wherein the protein-protein interfaces are normally identical. The first domain is identical to the second domain if their amino acid sequences are identical. The protein-protein interfaces are normally identical if the protein-protein interface of the first parent or donor domain has the identical amino acid at the identical 3D structural position compared to the protein-protein interface of the second parent or donor domain.

The term "domain" as used herein includes any region of a polypeptide that is responsible for selectively assembling with a protein partner (i.e., another protein (or region of) or another domain) and/or can perform a complete biological function or part of like binding a receptor, or a substrate, independently or within a multidomain entity. Usually a domain as referred to herein is not a hinge region and/or does not contain a hinge region. The domain can exist independently of the rest of a protein chain. A domain forms a compact three-dimensional structure and is independently stable and folded. Domains vary in length from between about 25 amino acids up to 500 amino acids in length. Preferably the domains as used herein vary in length from between about 70 amino acids up to about 120 amino acids in length. The shortest domains such as zinc fingers are stabilized by metal ions or disulfide bridges. Domains often form functional units, such as the calcium-binding EF hand domain of calmodulin. Because they are self-stable, domains can be "swapped" by genetic engineering between one protein and another to make chimeric proteins. Immunoglobulins are made of variable and constant domains belonging to the immunoglobulin superfamily (Williams A F and Barclay A N, *Annu Rev Immunol*, 6:381-405 (1988); Bork P et al., *J Mol Biol*, 242(4):309-20 (1994)). Domains, which are included herein are CH1 and CH3, specifically naturally occurring CH1 and CH3, from IGHA1, IGHA2, IGHD, IGHE, IGHG1, IGHG2, IGHG3, IGHG4, IGHGP and IGHM; CH4, specifically naturally occurring CH4, from IGHE and IGHM; IGKC, IGLC1, IGLC2, IGLC3, IGLC6, and IGLC7, specifically naturally occurring IGKC, IGLC1, IGLC2, IGLC3, IGLC6, and IGLC7. Further domains which are included herein are CH2, specifically naturally occurring CH2, from IGHA1, IGHA2, IGHD, IGHE, IGHG1, IGHG2, IGHG3, IGHG4, IGHGP and IGHM. Preferably unglycosylated CH2 domains are used herein which in their unglycosylated form are homo-dimers as referred herein. The CH2 domains in an unglycosylated Fc fragment approach each other much more closely compared to the CH2 domains in a naturally glycosylated Fc fragment. The crystal structure of the murine unglycosylated IgG1 Fc fragment has shown that a fully unglycosylated Fc fragment can adopt a "closed" structure with the distance between the Pro 332 from the CH2 domain of the first unglycosylated immunoglobulin chain and the Pro 332 from the CH2 domain of the second unglycosylated immunoglobulin chain is only 11.6 Å (Feige M J et al., *J Mol Biol*, 391(3):599-608 (2009)). Further domains which are included herein are VH and VL domains which do not have an engineered protein-protein interface according to the invention, i.e. which are not specifically engineered to modify its naturally occurring protein-protein interface except for backmutations arising out of the humanization process. The term "naturally occurring domain" as used herein refers to domains which can be found in nature i.e. which have not been genetically engineered.

For all immunoglobulin constant domains included in the present invention, numbering can be according to the IMGT® (IMGT®, the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005); Kaas Q et al., *Briefings in Functional Genomics & Proteomics*, 6(4):253-64 (2007)).

For all human CH1, CH2, CH3 immunoglobulin heavy chain constant domains selected from the group consisting of IGHG1, IGHG2, IGHG3, and IGHG4, numbering can be according to the "EU numbering system" (Edelman G M et al., *Proc Natl Acad Sci USA*, 63(1):78-85 (1969)). The correspondence between the IMGT unique numbering and the EU numbering for all human CH1, CH2, CH3 immunoglobulin heavy chain constant domains selected from the group consisting of IGHG1, IGHG2, IGHG3, and IGHG4 is shown in FIG. 19. A complete correspondence for the human CH1, hinge, CH2, and CH3 constant regions of IGHG1 can be found at the IMGT database (IMGT®, the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005)); Kaas Q et al., *Briefings in Functional Genomics & Proteomics*, 6(4):253-64 (2007)).

For the human kappa immunoglobulin light chain constant domain (IGKC), numbering can be according to the "EU numbering system" (Edelman G M et al., *Proc Natl Acad Sci USA*, 63(1):78-85 (1969)). The correspondence between the IMGT unique numbering and the EU numbering for the human IGKC immunoglobulin light chain constant domain is shown in FIG. 22. A complete correspondence for the human CK domain can be found at IMGT database (IMGT®, the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005)); Kaas Q et al., *Briefings in Functional Genomics & Proteomics*, 6(4):253-64 (2007)).

For the human lambda immunoglobulin light chain constant domains (IGLC1, IGLC2, IGLC3, IGLC6, and IGLC7), numbering can be according to the "Kabat numbering system" (Kabat E A et al., *Sequences of proteins of immunological interest*. 5$^{th}$ Edition—US Department of Health and Human Services, NIH publication n° 91-3242 (1991)) as described by Dariavach P et al., *Proc Natl Acad Sci USA*, 84(24):9074-8 (1987) and Frangione B et al., *Proc Natl Acad Sci USA*, 82(10):3415-9 (1985). The correspondence between the IMGT unique numbering and the Kabat numbering for human immunoglobulin light chain constant domains (IGLC1, IGLC2, IGLC3, IGLC6, and IGLC7) is shown in FIG. 23. A complete correspondence for human IGLC domains can be found at the IMGT database (IMGT®, the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005)); Kaas Q et al., *Briefings in Functional Genomics & Proteomics*, 6(4):253-64 (2007)).

The human IGHG1 immunoglobulin heavy chain constant domains referred herein as the following domain boundaries: CH1 [EU numbering: 118-215], Hinge γ1 [EU numbering: 216-230], CH2 [EU numbering: 231-340], and CH3 [EU numbering: 341-447]. The human CK domain referred herein spans residues 108 to 214 (EU numbering). The human IGLC1, IGLC2, IGLC3, IGLC6, and IGLC7 domains referred herein span residues 108-215 (Kabat numbering).

A "multidomain entity" or "multidomain protein" as used herein comprises at least two domains. These two domains can be on one immunoglobulin chain (one polypeptide) or can be on two immunoglobulin chains (two polypeptides).

The term "engineered immunoglobulin chain" as used herein includes an immunoglobulin chain comprising at least one engineered domain with a protein-protein interface which differs from the parent domain.

The term "parent immunoglobulin chain" as used herein includes any existing immunoglobulin chain, specifically naturally occurring immunoglobulin chains, which can be used as a parent sequence for designing an engineered immunoglobulin chain. Preferably, the parent immunoglobulin chains, e.g. the parent immunoglobulin chain of the first engineered immunoglobulin chain and/or the parent immunoglobulin chain of the second engineered immunoglobulin chain and/or the parent immunoglobulin chain of the third engineered immunoglobulin chain are naturally occurring immunoglobulin chains.

The term "parent domain" as used herein includes any existing domain, specifically naturally occurring domains, more specifically naturally occurring domains which form a naturally occurring hetero-dimer or a naturally occurring homo-dimer, which can be used as a parent sequence for designing an engineered domain. The parent domain of the engineered domain of the first, second, third and fourth engineered immunoglobulin chain is not a zinc finger. The parent domain is usually an immunoglobulin domain, e.g. a domain of an immunoglobulin chain. Preferably, the parent domains, e.g. the parent domain of a first and/or a second engineered immunoglobulin chain and/or the parent domain of a further engineered domain of the first and/or the second engineered immunoglobulin chain and/or the parent domain of an engineered domain of a third engineered immunoglobulin chain are naturally occurring domains.

The term "donor domain" as used herein includes naturally occurring domains, specifically naturally occurring domains which form a naturally occurring hetero-dimer or a naturally occurring homo-dimer, which can be used as a donor sequence for designing an engineered domain, i.e. which can be used as donor sequence for substituting amino acid residues at the equivalent 3D structural position in a parent domain.

The term "engineered domain" as used herein includes a domain engineered from a parent domain and a donor domain.

The term "protein-protein interface" as used herein includes amino acid residues that mediate direct-contact association of a protein domain with amino acid residues of another protein domain thereby defining a 3D interface. These amino acid residues that mediate direct-contact association between two domains include any amino acid from one partner interacting with one or more amino acid from the other partner. The term "interacting" in relation to interacting amino acid residues as used herein includes any amino acid from one partner having at least one heavy atom that is less than 15 Å away from any heavy atom of an amino acid residue in the other partner. The term "heavy atom of an amino acid residue" refers herein to any atom of an amino acid residue which is not a hydrogen atom. Preferably, interacting amino acid residues include any amino acids from one partner having at least one heavy atom that is less than 10 Å away from any heavy atom of an amino acid residue in the other partner. Most preferably, interacting amino acid residues include any amino acids from one partner having at least one heavy atom that is less than 5 Å away from any heavy atom of an amino acid residue in the other partner. The interaction of amino acid residues can be mediated by forces which include van der Waals forces, hydrogen bonds, water-mediated hydrogen bonds, salt bridges or electrostatic forces, hydrophobic contacts, and disulfide bonds or other forces known to one skilled in the art. Protein-protein interfaces are more hydrophobic and bury twice as much protein surfaces as in protein complexes, and usually assemble at the time they fold (Bahadur R P et al., *Proteins*, 53(3):708-19 (2003)). Analysis of 47 FAB fragments experimentally determined 3D structures showed that up to 50 residues in the constant domain light chain and up to 52 residues in the constant domain heavy chain compose the domain protein-protein interfaces (Potapov V et al., *J Mol Biol*, 342(2):665-79 (2004)). The CH3 protein interface involves 16 residues located on four antiparallel beta-strands that make intermolecular contacts and are buried 1090 Å2 from each surface (Dall'Acqua W et al., *Biochemistry*, 37(26):9266-73 (1998)).

The protein-protein interfaces of the engineered domains are considered to interact by homo-dimerization if the protein-protein interface of the donor domain of e.g. the first member of the naturally occurring immunoglobulin super-family and the protein-protein interface of the donor domain of e.g. the second member of the naturally occurring immunoglobulin super-family interact by homo-dimerization, e.g. if both donor domains form a homo-dimer, and if all amino acid residues of the protein-protein interfaces of the parent domains are substituted with amino acid residues of the donor domain of the first member of the naturally occurring immunoglobulin super-family and the donor domain of the second member of the naturally occurring immunoglobulin super-family. Thus protein-protein interfaces of the engineered domains are considered to interact by homo-dimerization if all amino acid residues of the protein-protein interface of the first engineered domain are identical to the amino acid residues of the protein-protein interface of the second engineered domain at identical 3D positions.

The protein-protein interfaces of the engineered domains are considered to interact by hetero-dimerization if the protein-protein interface of the donor domain of e.g. the first member of the naturally occurring immunoglobulin super-family and the protein-protein interface of the donor domain of e.g. the second member of the naturally occurring immunoglobulin super-family interact by homo-dimerization, e.g. if both donor domains form a homo-dimer, and if not all amino acid residues of the protein-protein interfaces of the parent domains are substituted with amino acid residues of the donor domain of the first member of the naturally occurring immunoglobulin super-family and the donor domain of the second member of the naturally occurring immunoglobulin super-family. More specifically the protein-protein interfaces of the engineered domains are considered to interact by hetero-dimerization if the protein-protein interface of the donor domain of e.g. the first member of the naturally occurring immunoglobulin super-family and the protein-protein interface of the donor domain of e.g. the second member of the naturally occurring immunoglobulin super-family interact by homo-dimerization, e.g. if both donor domains form a homo-dimer, and if at least one amino acid residue in the first parent domain is substituted with an amino acid residue at the 3D equivalent structural position in the donor domain of the first member of the naturally occurring immunoglobulin super-family and wherein the second parent domain is not substituted with the identical amino acid residue which was substituted in the first parent domain at the identical 3D structural position.

The protein-protein interfaces of the engineered domains are considered to interact by hetero-dimerization if the protein-protein interface of the donor domain of e.g. the first member of the naturally occurring immunoglobulin super-family and the protein-protein interface of the donor domain of e.g. the second member of the naturally occurring immunoglobulin super-family interact by hetero-dimerization e.g. if both donor domains form a hetero-dimer, and if all or not all amino acid residues of the protein-protein interfaces of the parent domains are substituted with amino acid residues of the donor domain of the first member of the naturally occurring immunoglobulin super-family and the donor domain of the second member of the naturally occurring immunoglobulin super-family.

Thus protein-protein interfaces of the engineered domains are considered to interact by hetero-dimerization if not all amino acid residues of the protein-protein interface of the first engineered domain are identical to the amino acid residues of the protein-protein interface of the second engineered domain at identical 3D positions.

The term "equivalent 3D structural position" or "equivalent 3D position" or "3D equivalent structural position" or "3D equivalent position" are used interchangeably herein and include the position of an amino acid residue in the protein-protein interface of a donor domain which when overlaid on the protein-protein interface of a parent domain by superimposing the carbon alpha traces of both domains, occupies a 3D position within less than a distance of 6 Å to the closest residue of the parent domain, wherein the donor domain is different from the parent domain. Superimposition can be performed by comparing the coordinates of the atoms in the same frame of reference. Beside the carbon alpha traces, backbone atoms (N, C and O) of both domains can be superimposed. The 3D structural positions can be selected as well based on visual inspection (i.e. intuition based design or knowledge based design) or positions can be selected after enumerating energy terms like van der Waals interaction, hydrogen bond interaction etc. (i.e. rational design). 3D structures of the domains as used herein includes experimentally solved 3D structure in crystalline or solution state which can be retrieved the Protein Data Bank (www.pdb.org; Bernstein F C et al., *Eur J Biochem*, 80(2):319-24 (1977); Berman H M et al., *Nucleic Acids Res*, 28(1):235-42 (2000)) or other databases. In addition, 3D structures of the domains which are not available from public databases or have not been solved can be modelled using a number of computational methods such as Ab initio prediction methods where only the amino acid sequence of the protein is required or threading and homology modeling methods where a 3D model for the protein domain is build from experimental structures of evolutionary related proteins (Zhang Y, *Curr Opin Struct Biol*, 18(3):342-8 (2008)). Without being bound by theory, alternatively the IMGT® numbering system can be used to identify equivalent 3D structural positions in immunoglobulin domains since this system is based on the comparative analysis of the 3D structure of the immunoglobulin super-family domains.

The term "Non essential to the core integrity of the domain" as used herein includes residues which are non-essential for correct folding and/or the hydrophobic core of the protein domain. Folded proteins usually have a hydrophobic core in which side chain packing stabilizes the folded state, and charged or polar side chains occupy the solvent-exposed surface where they interact with surrounding water, ions or others ligands such as other proteins or protein domains or carbohydrates. Formation of intramolecular hydrogen bonds provides another important contribution to protein core stability. Non essential residues to the core integrity of a protein domain include but are not limited to non-proline residues, non cysteine residues involved in an intramolecular disulfide bond, exposed residues, and residues which are not involved intramolecular hydrogen bonds.

The terms "protein" and "polypeptide" as used herein have the same meaning and are used interchangeably.

The terms "amino acid" or "amino acid residue" as used herein includes natural amino acids as well as non-natural amino acids. Preferably natural amino acids are included.

The term "charged amino acid" as used herein includes the amino acids lysine (positively charged), arginine (positively charged), histidine (positively charged), aspartic acid (negatively charged) and glutamic acid (negatively charged). Normally, charged amino acid as used herein are lysine, arginine, histidine, aspartic acid and glutamic acid. The term "charged pair" or "charged pair of amino acids" or "charged amino acid pair" have the same meaning and are used interchangeably and include any combination of one positively charged amino acid with one negatively charged amino acid. This includes the following pairs of charged amino acids: lysine/aspartic acid, lysine/glutamic acid, arginine/aspartic acid, arginine/glutamic acid, histidine/aspartic acid, and histidine/glutamic acid.

The terms "substitution" or "amino acid substitution" or "amino acid residue substitution" as used herein refers to a substitution of a first amino acid residue in an amino acid sequence with a second amino acid residue, whereas the first amino acid residue is different from the second amino acid residue i.e. the substituted amino acid residue is different from the amino acid which has been substituted.

The term "amino acid residues which are not adjacent" or "not adjacent amino acid residues" as used herein refers to two amino acids within an amino acid sequence which are not immediately adjoining i.e. which have at least one intervening amino acid residue in between them.

The term "Fab" or "Fab region" as used herein includes the polypeptides that comprise the VH, CH1, VL, and light chain constant immunoglobulin domains. Fab may refer to this region in isolation, or this region in the context of a full length antibody or antibody fragment.

The term "Fc" or "Fc region", as used herein includes the polypeptide comprising the constant region of an antibody heavy chain excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (C[γ]2 and C[γ]3) and the hinge between Cgamma1 (C[γ]1) and Cgamma2 (C[γ]2). Although the boundaries of the Fc region may vary, the human IgG heavy chain Fc region is usually defined to comprise residues C226 or P230 to its carboxyl-terminus, wherein the numbering is according to the EU index. Fc may refer to this region in isolation or this region in the context of an Fc polypeptide, for example an antibody.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in which the arginine at position 94 is replaced with a lysine. For example 94K indicates the substitution of position 94 with a lysine. For the purposes herein, multiple substitutions are typically separated by a slash or a comma. For example, "R94K/L78V" or "R94K, L78V" refers to a double variant comprising the substitutions R94K and L78V. By "amino acid insertion" or "insertion" as used herein is meant the addition of an amino acid at a particular position in a parent polypeptide sequence. For example, insert −94 designates an insertion at position 94. By "amino acid deletion" or "deletion" as used herein is meant the removal of an amino acid at a particular position in a parent polypeptide sequence. For example, R94− designates the deletion of arginine at position 94.

The term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis.

"Conservative amino acid substitutions" as used herein includes amino acid substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Hetero-Dimeric Immunoglobulins

In one aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 12 and the protein-protein interface of the parent domain of the second engineered immunoglobulin chain is substituted with an amino acid residue at position 119, the substituted amino acid residue at position 12 and the substituted amino acid residue at position 119 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 26 and the protein-protein interface of the parent domain of the second engineered immunoglobulin chain is substituted with an amino acid residue at position 13, the substituted amino acid residue at position 26 and the substituted amino acid residue at position 13 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 27 and the protein-protein interface of the parent domain of the second engineered immunoglobulin chain is substituted with an amino acid residue at position 18, the substituted amino acid residue at position 27 and the substituted amino acid residue at position 18 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 79 and the protein-protein interface of the parent domain of the second engineered immunoglobulin chain is substituted with an amino acid residue at position 84.3, the substituted amino acid residue at position 79 and the substituted amino acid residue at position 84.3 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, if the parent domain of the first engineered immunoglobulin chain is an IGKC domain and the amino acid residue which is substituted in the protein-protein interface of the parent domain of the first engineered immunoglobulin chain is at position 11 and the parent domain of the second engineered immunoglobulin chain is a domain which comprises a hinge region, the parent domain of the second engineered immunoglobulin chain is not substituted at position 3 of the hinge region, wherein the amino acid position of each group member is indicated according to the IMGT® numbering.

Preferably, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 12 and the protein-protein interface of the parent domain of the second engineered immunoglobulin chain is substituted with an amino acid residue at position 119, the substituted amino acid residue at position 12 and the substituted amino acid residue at position 119 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 26 and the protein-protein interface of the parent domain of the second engineered immunoglobulin chain is substituted with an amino acid residue at position 13, the substituted amino acid residue at position 26 and the substituted amino acid residue at position 13 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 27 and the protein-protein interface of the parent domain of the second engineered immunoglobulin chain is substituted with an amino acid residue at position 18, the substituted amino acid residue at position 27 and the substituted amino acid residue at position 18 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and/or the protein-protein interface of the parent domain of the second engineered immunoglobulin chain is substituted with an amino acid residue at position 26, the substituted amino acid residue at position 20 and the unsubstituted or substituted amino acid residue at position 26 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 79 and/or the protein-protein interface of the parent domain of the second engineered immunoglobulin chain is substituted with an amino acid residue at position 84.3, the unsubstituted or substituted amino acid residue at position 79 and the substituted amino acid residue at position 84.3 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, if the parent domain of the first engineered immunoglobulin chain is an IGKC domain and the amino acid residue which is substituted in the protein-protein interface of the parent domain of the first engineered immunoglobulin chain is at position 11 and the parent domain of the second engineered immunoglobulin chain is a domain which comprises a hinge region, the parent domain of the second engineered immunoglobulin chain is not substituted at position 3 of the hinge region, wherein the amino acid position of each group member is indicated according to the IMGT® numbering.

Even more preferably, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 12 and the protein-protein interface of the parent domain of the second engineered immunoglobulin chain is substituted with an amino acid residue at position 119, the substituted amino acid residue at position 12 and the substituted amino acid residue at position 119 are not charged amino acids, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 26 and the protein-protein interface of the parent domain of the second engineered immunoglobulin chain is substituted with an amino acid residue at position 13, the substituted amino acid residue at position 26 and the substituted amino acid residue at position 13 are not charged amino acids, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not charged amino acids, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 27 and the protein-protein interface of the parent domain of the second engineered immunoglobulin chain is substituted with an amino acid residue at position 18, the substituted amino acid residue at position 27 and the substituted amino acid residue at position 18 are not charged amino acids, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not charged amino acids, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 79 and the protein-protein interface of the parent domain of the second engineered immunoglobulin chain is substituted with an amino acid residue at position 84.3, the substituted amino acid residue at position 79 and the substituted amino acid residue at position 84.3 are not charged amino acids, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not charged amino acids, if the parent domain of the first engineered immunoglobulin chain is an IGKC domain and the amino acid residue which is substituted in the protein-protein interface of the parent domain of the first engineered immunoglobulin chain is at position 11 and the parent domain of the second engineered immunoglobulin chain is a domain which comprises a hinge region, the parent domain of the second engineered immunoglobulin chain is not substituted at position 3 of the hinge region, wherein the amino acid position of each group member is indicated according to the IMGT® numbering.

Position 5 of an IGLC domain in the protein-protein interface of the parent domain of the first engineered immunoglobulin chain indicated according to the IMGT® numbering correspond to position 116 according to Kabat numbering.

Position 12 of an IGLC domain in the protein-protein interface of the parent domain of the first engineered immunoglobulin chain indicated according to the IMGT® numbering correspond to position 123 according to Kabat numbering.

Position 13 of an IGLC domain in the protein-protein interface of the parent domain of the first engineered immunoglobulin chain indicated according to the IMGT® numbering correspond to position 124 according to Kabat numbering.

Position 18 of an IGLC domain in the protein-protein interface of the parent domain of the first engineered immunoglobulin chain indicated according to the IMGT® numbering correspond to position 129 according to Kabat numbering.

Position 20 of an IGLC domain in the protein-protein interface of the parent domain of the first engineered immunoglobulin chain indicated according to the IMGT® numbering correspond to position 131 according to Kabat numbering.

Position 79 of an IGLC domain in the protein-protein interface of the parent domain of the first engineered immunoglobulin chain indicated according to the IMGT® numbering correspond to position 160 according to Kabat numbering.

Position 11 of the IGKC domain in the protein-protein interface of the parent domain of the first engineered immunoglobulin chain indicated according to the IMGT® numbering correspond to position 122 according to EU numbering.

Position 12 of the IGKC domain in the protein-protein interface of the parent domain of the first engineered immunoglobulin chain indicated according to the IMGT® numbering correspond to position 123 according to EU numbering.

Position 20 of an IGKC domain in the protein-protein interface of the parent domain of the first engineered immunoglobulin chain indicated according to the IMGT® numbering correspond to position 131 according to EU numbering.

Position 86 of an IGKC domain in the protein-protein interface of the parent domain of the first engineered immunoglobulin chain indicated according to the IMGT® numbering correspond to position 176 according to EU numbering.

Position 20 of a CH1 domain in the protein-protein interface of the parent domain of the second engineered immunoglobulin chain indicated according to the IMGT® numbering correspond to position 141 according to EU numbering.

Position 26 of a CH1 domain in the protein-protein interface of the parent domain of the second engineered immunoglobulin chain indicated according to the IMGT® numbering correspond to position 147 according to EU numbering.

Position 27 of a CH1 domain in the protein-protein interface of the parent domain of the second engineered immunoglobulin chain indicated according to the IMGT® numbering correspond to position 148 according to EU numbering.

Position 84.3 of a CH1 domain in the protein-protein interface of the parent domain of the second engineered immunoglobulin chain indicated according to the IMGT® numbering correspond to position 176 according to EU numbering.

Position 86 of the CH1 domain in the protein-protein interface of the parent domain of the second engineered immunoglobulin chain indicated according to the IMGT® numbering correspond to position 183 according to EU numbering.

Position 119 of a CH1 domain in the protein-protein interface of the parent domain of the second engineered immunoglobulin chain indicated according to the IMGT® numbering correspond to position 213 according to EU numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein,
if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair,
if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair,
if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, wherein the amino acid position of each group member is indicated according to the IMGT® numbering.

Preferably the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and/or the protein-protein interface of the parent domain of the second engineered immunoglobulin chain is substituted with an amino acid residue at position 26, the substituted amino acid residue at position 20 and the unsubstituted or substituted amino acid residue at position 26 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, wherein the amino acid position of each group member is indicated according to the IMGT® numbering.

Even more preferably the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not charged amino acids, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not charged amino acids, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not charged amino acids, wherein the amino acid position of each group member is indicated according to the IMGT® numbering.

In a further aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, wherein the amino acid position of each group member is indicated according to the IMGT® numbering.

Preferably the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and/or the protein-protein interface of the parent domain of the second engineered immunoglobulin chain is substituted with an amino acid residue at position 26, the substituted amino acid residue at position 20 and the unsubstituted or substituted amino acid residue at position 26 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, wherein the amino acid position of each group member is indicated according to the IMGT® numbering.

Even more preferably the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not charged amino acids, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not charged amino acids, wherein the amino acid position of each group member is indicated according to the IMGT® numbering.

In some aspects the present disclosure provides a hetero-dimeric immunoglobulin or hetero-dimeric fragment comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 5, the substituted amino acid residue at position 5 and the substituted amino acid residue at position 20 are not a charged pair, preferably are not charged amino acids, and wherein, if the parent domain of the first engineered immunoglobulin chain is a CH1 domain and the parent domain of the second engineered immunoglobulin chain is an IGLC domain or an IGKC domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, preferably are not charged amino acids, wherein the amino acid position of each group member is indicated according to the IMGT® numbering.

In some aspects the present disclosure provides a hetero-dimeric immunoglobulin or hetero-dimeric fragment comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 20, 22, 85.1, 86, and 88, and wherein, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, preferably are not charged amino acids, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, preferably are not charged amino acids, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 5, the substituted amino acid residue at position 5 and the substituted amino acid residue at position 20 are not a charged pair, preferably are not charged amino acids, and wherein, if the parent domain of the first engineered immunoglobulin chain is a CH1 domain and the parent domain of the second engineered immunoglobulin chain is an IGLC domain or an IGKC domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, preferably are not charged amino acids, wherein the amino acid position of each group member is indicated according to the IMGT® numbering.

In a further aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the engineered domain of the first engineered immunoglobulin chain and the engineered domain of the second engineered immunoglobulin chain are not identical and, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 88, and optionally a further amino acid residue at a position selected from the group consisting of 3, 5, 7, 20, 22, 26, 27, 79, 81, 84, 84.2, 85.1, 86, and 90 and, wherein the amino acid residue which is substituted in the protein-protein interface of the parent domain of the second engineered immunoglobulin chain comprises the amino acid residue at position 85.1 and/or 86 and optionally a further amino acid residue at a position selected from the group consisting of 3, 5, 7, 20, 22, 26, 27, 79, 81, 84, 84.2, 88, and 90 or at a position selected from the group consisting of 3, 5, 7, 20, 22, 26, 27, 79, 81, 84, 84.2, 85.1, 88, and 90 or at a position selected from the group consisting of 3, 5, 7, 20, 22, 26, 27, 79, 81, 84, 84.2, 86, 88, and 90, wherein the amino acid residue substituted at position 88 in the parent domain of the first engineered immunoglobulin chain is interacting with the amino acid residue substituted at position 85.1 and/or 86 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the engineered domain of the first engineered immunoglobulin chain and the engineered domain of the second engineered immunoglobulin chain are not identical and, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 84, 84.2, 85.1, 86, 88 and 90 and, wherein the amino acid residues which are substituted in the protein-protein interface of the parent domain of the second engineered immunoglobulin chain comprise the amino acid residue at position 26 and at a further position selected from the group consisting of 3, 22, 27, 79, 81, 84, 85.1, 86, and 88, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the engineered domain of the first engineered immunoglobulin chain and the engineered domain of the second engineered immunoglobulin chain are not identical and, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 88, and optionally a further amino acid residue at a position selected from the group consisting of 3, 5, 7, 20, 22, 26, 27, 79, 81, 83, 84, 84.2, 84.3, 85.1, 86 and 90 and, wherein the amino acid residue which is substituted in the protein-protein interface of the parent domain of the second engineered immunoglobulin chain comprises the amino acid residue at position 85.1 and/or 86 and optionally a further amino acid residue at a position selected from the group consisting of 3, 5, 7, 20, 22, 26, 27, 79, 81, 83, 84, 84.2, 84.3 and 90 or at a position selected from the group consisting of 3, 5, 7, 20, 22, 26, 27, 79, 81, 83, 84, 84.2, 84.3, 85.1 and 90 or at a position selected from the group consisting of 3, 5, 7, 20, 22, 26, 27, 79, 81, 83, 84, 84.2, 84.3, 86 and 90, wherein the amino acid residue substituted at position 88 in the parent domain of the first engineered immunoglobulin chain is interacting with the amino acid residue substituted at position 85.1 and/or 86 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:

(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and (b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family, wherein the engineered domain of the first engineered immunoglobulin chain and the engineered domain of the second engineered immunoglobulin chain are not identical and, wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 83, 84, 84.2, 84.3, 85.1, 86, 88 and 90 and, wherein the amino acid residue which is substituted in the protein-protein interface of the parent domain of the second engineered immunoglobulin chain comprises the amino acid residue at position 26 and optionally a further amino acid residue at a position selected from the group consisting of 3, 5, 7, 20, 22, 27, 79, 81, 83, 84, 84.3, 85.1, 86, 88 and 90, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In a further aspect, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH4 domain, wherein the protein-protein interface of the parent domain of the first engineered immunoglobulin chain comprises an amino acid residue substitution at a position selected from the group consisting of 20, 22, 85.1, 86, and 88, and/or wherein the protein-protein interface of the parent domain of the second engineered immunoglobulin chain comprises an amino acid residue substitution at a position selected from the group consisting of 22, 26, 85.1, 86, and 88, wherein the amino acid position of each group member is indicated according to the IMGT® numbering.

In some embodiments the donor domain of the first member of the naturally occurring immunoglobulin super-family and the donor domain of the second member of the naturally occurring immunoglobulin super-family form a naturally occurring hetero-dimer or a naturally occurring homo-dimer. In some embodiments the donor domain of the third member of the naturally occurring immunoglobulin super-family and the donor domain of the fourth member of the naturally occurring immunoglobulin super-family form a naturally occurring hetero-dimer or a naturally occurring homo-dimer.

In some embodiments, the first member of the naturally occurring immunoglobulin super-family and its donor domain is identical in amino acid sequence to the second member of the naturally occurring immunoglobulin super-family and its donor domain respectively.

In some embodiments, the first member of the naturally occurring immunoglobulin super-family and its donor domain is different in amino acid sequence from the second member of the naturally occurring immunoglobulin super-family and its donor domain respectively.

In some embodiments the third and the fourth member of the naturally occurring immunoglobulin super-family, in particular the donor domains of the third and the fourth member of the naturally occurring immunoglobulin super-family, are different from the first and the second member of the naturally occurring immunoglobulin super-family, in particular the donor domains of the first and the second member of the naturally occurring immunoglobulin super-family. In some embodiments the first, second, third and fourth member of the naturally occurring immunoglobulin super-family, in particular its donor domains are each different from the other.

In some embodiments the engineered domain of the first engineered immunoglobulin chain and the engineered domain of the second engineered immunoglobulin chain are not identical.

In some embodiments the first engineered immunoglobulin chain and its engineered domain are not identical to the second engineered immunoglobulin chain and its engineered domain, i.e. the engineered immunoglobulin chains, in particular its engineered domains are different in amino acid sequence from each other e.g. the first and the second engineered immunoglobulin chains in particular its engineered domains have amino acid sequences which are different from each other by at least one amino acid or by at least two amino acids or by at least three amino acids or by at least four amino acids or by at least five amino acids or by at least five to ten amino acids or by at least ten to thirty amino acids.

In some embodiments, the first engineered immunoglobulin chain and/or its engineered domain is different in amino acid sequence from the second engineered immunoglobulin chain and/or its engineered domain, wherein the protein-protein interfaces of the engineered domains of the engineered immunoglobulin chains interact by hetero-dimerization.

In some embodiments, the first engineered immunoglobulin chain and/or its engineered domain is different in amino acid sequence from the second engineered immunoglobulin chain and/or its engineered domain, wherein the protein-protein interfaces of the engineered domains of the engineered immunoglobulin chains interact by homo-dimerization.

In some embodiments, at least one substituted amino acid residue in the protein-protein interface of the parent domain of the first engineered immunoglobulin chain is interacting with at least one substituted amino acid residue in the protein-protein interface of the parent domain of the second engineered immunoglobulin chain. Preferably at least two, more preferably at least three, most preferably at least four, in particular at least five substituted amino acid residue in the protein-protein interface of the parent domain of the first engineered immunoglobulin chain are interacting with at least one substituted amino acid residue in the protein-protein interface of the parent domain of the second engineered immunoglobulin chain.

In some embodiments at least one, preferably at least two, more preferably at least three, most preferably at least four, in particular at least five amino acid residue of the protein-protein interface of the engineered domain of the first engineered immunoglobulin chain is different from the protein-protein interface of the engineered domain of the second engineered immunoglobulin chain.

In some embodiments, each of the first and second engineered immunoglobulin chains and its engineered domains are different in amino acid sequence from the first and second member of the naturally occurring immunoglobulin super-family and its donor domains.

In some embodiments, the parent domain of the first engineered immunoglobulin chain is different in amino acid sequence from the first member of the naturally occurring immunoglobulin super-family and its donor domain. In some embodiments, the parent domain of the second engineered immunoglobulin chain is different in amino acid sequence from second member of the naturally occurring immunoglobulin super-family and its donor domain.

In some embodiments, the protein-protein interface of the parent domain of the first engineered immunoglobulin chain and the protein-protein interface of the parent domain of the second engineered immunoglobulin chain are not substituted with charged amino acids, preferably are not substituted with a charged pair.

In some embodiments, the protein-protein interface of the parent domain of the first engineered immunoglobulin chain is not substituted with 26A and/or 26E and/or 86T and/or the protein-protein interface of the parent domain of the second engineered immunoglobulin chain is not substituted with 20T and/or 26K and/or 85.1A and/or 88T, wherein the amino acid position is indicated according to the IMGT® numbering.

In some embodiments, the protein-protein interface of the engineered domain of the first engineered immunoglobulin chain is interacting with the protein-protein interface of the engineered domain of the second engineered immunoglobulin chain by homo-dimerization, wherein the engineered domains of the first engineered immunoglobulin chain and the second engineered immunoglobulin chain are not identical in amino acid sequence.

In some embodiments, the parent domains of the engineered domains of the engineered immunoglobulin chains are not substituted in the loop region of the domain.

In some embodiments, at least one 3D structural position of the protein-protein interface of the engineered domain of the first engineered immunoglobulin chain is different in amino acid residue compared to the identical 3D structural position of the protein-protein interface of the engineered domain of the second engineered immunoglobulin chain.

In some embodiments, the further engineered domain of the first engineered immunoglobulin chain and/or the second engineered immunoglobulin chain are not identical to the third engineered immunoglobulin chain and its engineered domain, i.e. the engineered immunoglobulin chains, in particular its engineered domains are different in amino acid sequence from each other e.g. the first engineered immunoglobulin chain and/or the second engineered immunoglobulin chain and/or the third engineered immunoglobulin chain, in particular the further engineered domain of the first engineered immunoglobulin chain and/or the second engineered immunoglobulin chain and the engineered domain of the third engineered immunoglobulin chain have amino acid sequences which are different from each other by at least one amino acid or by at least two amino acids or by at least three amino acids or by at least four amino acids or by at least five amino acids or by at least five to ten amino acids or by at least ten to thirty amino acids.

In some embodiments, the further engineered domain of the first engineered immunoglobulin chain and/or the second engineered immunoglobulin chain is different in amino acid sequence from the engineered domain of the third engineered immunoglobulin chain, wherein the protein-protein interfaces of the engineered domains of the engineered immunoglobulin chains interact by hetero-dimerization.

In some embodiments, the further engineered domain of the first engineered immunoglobulin chain and/or the second engineered immunoglobulin chain is different in amino acid sequence from the engineered domain of the third engineered immunoglobulin chain, wherein the protein-protein interfaces of the engineered domains of the engineered immunoglobulin chains interact by homo-dimerization.

In some embodiments, the third member of the naturally occurring immunoglobulin super-family and its donor domain is different in amino acid sequence from the fourth member of the naturally occurring immunoglobulin super-family and its donor domain respectively.

In some embodiments, the third member of the naturally occurring immunoglobulin super-family and its donor domain is identical in amino acid sequence to the fourth member of the naturally occurring immunoglobulin super-family and its donor domain respectively.

In some embodiments, each of the further engineered domain of the first engineered immunoglobulin chain and/or the second engineered immunoglobulin chain and the engineered domain of the third engineered immunoglobulin chain are different in amino acid sequence from the third and fourth member of the naturally occurring immunoglobulin super-family and its donor domains.

In some embodiments, the parent domain of the further engineered domain of the first engineered immunoglobulin chain and/or the second engineered immunoglobulin chain is different in amino acid sequence from the third member of the naturally occurring immunoglobulin super-family and its donor domain.

In some embodiments, the parent domain of the engineered domain of the third engineered immunoglobulin chain is different in amino acid sequence from the fourth member of the naturally occurring immunoglobulin super-family and its donor domain.

In some embodiments the first and second engineered immunoglobulin chains have parent domains which are identical. In some embodiments the first and second engineered immunoglobulin chains have parent domains which are not identical. In some embodiments the first and second engineered immunoglobulin chains have parent domains which have amino acid sequences which are different from each other by one amino acid or by two amino acids or by three amino acids or by four amino acids or by five amino acids or by five to ten amino acids or by ten to thirty amino acids, preferably by at least one amino acid or by at least two amino acids or by at least three amino acids or by at least four amino acids or by at least five amino acids or by at least five to ten amino acids or by at least ten to thirty amino acids.

In some embodiments the parent domain of the further engineered domain of the first and/or second engineered immunoglobulin chains and the parent domain of the engineered domain of the third engineered immunoglobulin chain are identical. In some embodiments the parent domain of the further engineered domain of the first and/or second engineered immunoglobulin chains and the parent domain of the engineered domain of the third engineered immunoglobulin chain are not identical. In some embodiments the parent domain of the further engineered domain of the first and/or second engineered immunoglobulin chains and the parent domain of the engineered domain of the third engineered immunoglobulin chain are different from each other by one amino acid or by two amino acids or by three amino acids or by four amino acids or by five amino acids or by five to ten amino acids or by ten to thirty amino acids, preferably by at least one amino acid or by at least two amino acids or by at least three amino acids or by at least four amino acids or by at least five amino acids or by at least five to ten amino acids or by at least ten to thirty amino acids.

In some embodiments the present disclosure provides a hetero-dimeric immunoglobulin or fragment thereof comprising a parent domain of the first and/or second engineered immunoglobulin chain, in particular a parent domain of the first and second engineered immunoglobulin chain which is selected from the group consisting of CH1, CH2, CH3, CH4, IGKC, IGLC1, IGLC2, IGLC3, IGLC6, and IGLC7. CH1, CH3 can be from IGHA1, IGHA2, IGHD, IGHE, IGHG1, IGHG2, IGHG3, IGHG4, IGHGP and IGHM. CH4 can be from IGHE and IGHM. CH2 can be from IGHA1, IGHA2, IGHD, IGHE, IGHG1, IGHG2, IGHG3, IGHG4, IGHGP and IGHM.

In some embodiments the parent domain of the first and/or the second engineered immunoglobulin chain, in particular the parent domain of the first and second engineered immunoglobulin chain, is a domain selected from the group consisting of CH1 domain, CH4 domain, IGKC domain, IGLC1 domain, IGLC2 domain, IGLC3 domain, IGLC6 domain, and IGLC7 domain, preferably from the group consisting of CH1 domain, IGKC domain, IGLC1 domain, IGLC2 domain, IGLC3 domain, IGLC6 domain, and IGLC7 domain.

Normally the parent domain of the first and/or second engineered immunoglobulin chain is a naturally occurring domain. Usually the parent domain of the first and/or second engineered immunoglobulin chain is from human e.g a naturally occurring human domain. Preferably the parent domain of the first and/or second engineered immunoglobulin chain is from human and from the same isotype, species and subclass. In some embodiments, the preferred parent domain of the first and/or second engineered immunoglobulin chain, in particular the parent domain of the first and second engineered immunoglobulin chain, is a CH3 domain, more preferably a human CH3 domain, in particular a human CH3 domain from IGHG1. Equally preferred, the parent domains of the first and second engineered immunoglobulin chain are from a different isotype. In some embodiments the parent domain of the first engineered immunoglobulin chain is a CH3 domain from IGHG1, preferably a human CH3 domain from IGHG1 and the parent domain of the second engineered immunoglobulin chain is a CH3 domain from IGHG3 preferably a human CH3 domain from IGHG3.

In some embodiments, the parent domain of the first and/or second engineered immunoglobulin chain, in particular the parent domain of the first and second engineered immunoglobulin chain, is a CH4 domain, more preferably a human CH4 domain, in particular a human CH4 domain from IGHM or a human CH4 domain from IGHE.

Equally, the preferred the parent domain of the first engineered immunoglobulin chain is a CH1 domain and the parent domain of the second engineered immunoglobulin chain is a light chain constant domain such as an IGLC domain or an IGKC domain. Equally, the preferred parent domain of the first engineered immunoglobulin chain is a light chain constant domain such as an IGLC domain or an IGKC domain and the preferred parent domain of the second engineered immunoglobulin chain is a CH1 domain. More preferred is a human CH1 domain selected from the group consisting of IGHG1, IGHG2, IGHG3, and IGHG4, in particular a human CH1 domain from IGHG1. Most preferably the parent domain of the first engineered immunoglobulin chain is an IGLC domain selected from the group consisting of IGLC1, IGLC2, IGLC3, IGLC6, and IGLC7 or is an IGKC domain and the parent domain of the second engineered immunoglobulin chain is a CH1 domain or the parent domain of the first engineered immunoglobulin chain is a CH1 domain and the parent domain of the second engineered immunoglobulin chain is an IGLC domain selected from the group consisting of IGLC1, IGLC2, IGLC3, IGLC6, and IGLC7 or is an IGKC domain.

In some embodiments the parent domain of the further engineered domain of the first engineered immunoglobulin chain and/or the second engineered immunoglobulin chain and the engineered domain of the third engineered immunoglobulin chain are selected from the group consisting of CH1, CH2, CH3, CH4, IGKC, IGLC1, IGLC2, IGLC3, IGLC6 and IGLC7. Normally the parent domain of the further engineered domain of the first engineered immunoglobulin chain and/or the second engineered immunoglobulin chain and the parent domain of the engineered domain of the third engineered immunoglobulin chain is a naturally occurring domain. Usually the parent domain of the further engineered domain of the first engineered immunoglobulin chain and/or the second engineered immunoglobulin chain and the engineered domain of the third engineered immunoglobulin chain is from human. Preferably the parent domain of the further engineered domain of the first engineered immunoglobulin chain and/or the second engineered immunoglobulin chain and the engineered domain of the third engineered immunoglobulin chain is from human and from the same isotype, species and subclass. The preferred parent domain of the further engineered domain of the first engineered immunoglobulin chain and/or the second engineered immunoglobulin chain and the engineered domain of the third engineered immunoglobulin chain is a CH3 domain, more preferably a human CH3 domain, in particular a human CH3 domain from IGHG1. Equally preferred, the parent domains of the further engineered domain of the first engineered immunoglobulin chain and/or the second engineered immunoglobulin chain and/or the engineered domain of the third engineered immunoglobulin chain are from a different isotype. In some embodiments the parent domain of the further engineered domain of the first engineered immunoglobulin chain and/or the second engineered immunoglobulin chain is a CH3 domain from IGHG1, preferably a human CH3 domain from IGHG1, and the parent domain of the engineered domain of the third engineered immunoglobulin chain is a CH3 domain from IGHG3 preferably a human CH3 domain from IGHG3.

In some embodiments, the parent domains of the further engineered domain of the first engineered immunoglobulin chain and/or the second engineered immunoglobulin chain and/or the engineered domain of the third engineered immunoglobulin chain is a CH4 domain, more preferably a human CH4 domain, in particular a human CH4 domain from IGHM or a human CH4 domain from IGHE. Equally preferred the parent domain of the further engineered domain of the first engineered immunoglobulin chain and/or the second engineered immunoglobulin is a CH1 domain and the parent domain of the engineered domain of the third engineered immunoglobulin chain is a light chain constant domain such as an IGLC domain or an IGKC domain. Equally, the preferred parent domain of the further engineered domain of the first engineered immunoglobulin chain and/or the second engineered immunoglobulin is a light chain constant domain such as an IGLC domain or an IGKC domain and the preferred parent domain of the engineered domain of the third engineered immunoglobulin chain is a CH1 domain. More preferred is a human CH1 domain selected from the group consisting of IGHG1, IGHG2, IGHG3, and IGHG4, in particular a human CH1 domain from IGHG1.

Parent domains from the same species, isotype and subclass, e g human CH3 domain from IGHG1 as parent domain of e.g. the first and second engineered immunoglobulin chain, form a homo-dimer. In some embodiments the parent domains of the first and the second engineered immunoglobulin chain form a homo-dimer, specifically a naturally occurring homo-dimer.

In some embodiments the parent domains of the first and the second engineered immunoglobulin chain form a hetero-dimer specifically a naturally occurring hetero-dimer, e.g. a CH1 domain and an IGKC domain or a CH1 domain and an IGLC domain.

In some embodiments the parent domains of the first and the second engineered immunoglobulin chain form a hetero-dimer e.g. a CH3 domain from IGHG1 and a CH3 domain from IGHG3.

In some embodiments the parent domains of the further engineered domain of the first and/or second engineered immunoglobulin chain and the parent domain of the engineered domain of the third engineered immunoglobulin chain form a homo-dimer, specifically a naturally occurring homo-dimer.

In some embodiments the parent domains of the further engineered domain of the first and/or second engineered immunoglobulin chain and the parent domain of the engineered domain of the third engineered immunoglobulin chain form a hetero-dimer, specifically a naturally occurring hetero-dimer, e.g. a CH1 domain and an IGKC domain or a CH1 domain and an IGLC domain.

In some embodiments the parent domains of the further engineered domain of the first and/or second engineered immunoglobulin chain and the parent domain of the engineered domain of the third engineered immunoglobulin chain form a hetero-dimer e.g. a CH3 domain from IGHG1 and a CH3 domain from IGHG3.

In some embodiments the parent domains of the first and the second engineered immunoglobulin chain are not a CH2 domain.

In some embodiments the parent domains of the first and the second engineered immunoglobulin chain are not a CH3 domain.

In some embodiments the parent domains of the first and the second engineered immunoglobulin chains are not a VH domain and not a VL domain.

In some embodiments the parent domains of the first and the second engineered immunoglobulin chain are not from IgG2.

In some embodiments the preferred parent domain of the first engineered immunoglobulin chain is a CH1 domain and the preferred parent domain of the second engineered immunoglobulin chain is an IGKC domain or, the preferred parent domain of the first engineered immunoglobulin chain is an IGKC domain and the preferred parent domain of the second engineered immunoglobulin chain is a CH1 domain. Even more preferably, the preferred parent domain of the first engineered immunoglobulin chain is a human CH1 domain and the preferred parent domain of the second engineered immunoglobulin chain is a human IGKC domain or, the preferred parent domain of the first engineered immunoglobulin chain is a human IGKC domain and the preferred parent domain of the second engineered immunoglobulin chain is a human CH1 domain, more preferably a human CH1 domain selected from the group consisting of IGHG1, IGHG2, IGHG3, and IGHG4, in particular a human CH1 domain from IGHG1.

In some embodiments the preferred parent domain of the first engineered immunoglobulin chain is a CH1 domain and the preferred parent domain of the second engineered immunoglobulin chain is an IGLC domain or, the preferred parent domain of the first engineered immunoglobulin chain is an IGLC domain and the preferred parent domain of the second engineered immunoglobulin chain is a CH1 domain. Even more preferably, the preferred parent domain of the first engineered immunoglobulin chain is a human CH1 domain and the preferred the parent domain of the second engineered immunoglobulin chain is a human IGLC domain or, the preferred parent domain of the first engineered immunoglobulin chain is a human IGLC domain and the preferred parent domain of the second engineered immunoglobulin chain is a human CH1 domain, more preferably a human CH1 domain selected from the group consisting of IGHG1, IGHG2, IGHG3, and IGHG4, in particular a human CH1 domain from IGHG1.

In some embodiments the preferred parent domain of the further engineered domain of the first and/or second engineered immunoglobulin chain is a CH1 domain and the preferred parent domain of the engineered domain of the third engineered immunoglobulin chain is an IGKC domain or, the preferred parent domain of the further engineered domain of the first and/or second engineered immunoglobulin chain is an IGKC domain and the preferred parent domain of the engineered domain of the third engineered immunoglobulin chain. Even more preferably, the preferred parent domain of the further engineered domain of the first and/or second engineered immunoglobulin chain is a human CH1 domain and the preferred parent domain of the engineered domain of the third engineered immunoglobulin chain is a human IGKC domain or, the preferred parent domain of the further engineered domain of the first and/or second engineered immunoglobulin chain is a human IGKC domain and the preferred parent domain of the engineered domain of the third engineered immunoglobulin chain is a human CH1 domain, more preferably a human CH1 domain selected from the group consisting of IGHG1, IGHG2, IGHG3, and IGHG4, in particular a human CH1 domain from IGHG1.

In some embodiments the preferred parent domain of the further engineered domain of the first and/or second engineered immunoglobulin chain is a CH1 domain and the preferred parent domain of the engineered domain of the third engineered immunoglobulin chain is an IGLC domain or, the preferred parent domain of the further engineered domain of the first and/or second engineered immunoglobulin chain is an IGLC domain and the preferred parent domain of the engineered domain of the third engineered immunoglobulin chain. Even more preferably, the preferred parent domain of the further engineered domain of the first and/or second engineered immunoglobulin chain is a human CH1 domain and the preferred parent domain of the engineered domain of the third engineered immunoglobulin chain is a human IGLC domain or, the preferred parent domain of the further engineered domain of the first and/or second engineered immunoglobulin chain is a human IGLC domain and the preferred parent domain of the engineered domain of the third engineered immunoglobulin chain is a human CH1 domain. More preferred is a human CH1 domain selected from the group consisting of IGHG1, IGHG2, IGHG3, and IGHG4, in particular a human CH1 domain from IGHG1.

In some embodiments the parent domain of the first and/or second engineered immunoglobulin chain, in particular the parent domain of the first and second engineered immunoglobulin chain, is a CH3 domain, preferably a CH3 domain of the same species, isotype and subclass, and the parent domain of the further engineered domain of the first engineered immunoglobulin chain and/or the second engineered immunoglobulin is a light chain constant domain such as an IGLC domain or an IGKC domain and the parent domain of the engineered domain of the third engineered immunoglobulin chain is a CH1 domain.

In some embodiments the parent domain of the first engineered immunoglobulin chain is a light chain constant domain such as an IGLC domain or an IGKC domain and the parent domain of the engineered domain of the second engineered immunoglobulin chain is a CH1 domain, and the parent domain of the further engineered domain of the first engineered immunoglobulin chain and/or the second engineered immunoglobulin and the parent domain of the engineered domain of the third engineered immunoglobulin chain is a CH3 domain, preferably a CH3 domain of the same species, isotype and subclass.

In some embodiments e.g if the hetero-dimeric immunoglobulin is a F(ab')$_2$, the parent domain of the engineered domain of the first engineered immunoglobulin chain is a CH1 domain and the parent domain of the engineered domain of the second engineered immunoglobulin chain is a light chain constant domain such as an IGLC domain or an IGKC domain and the parent domain of the further engineered domain of the first engineered immunoglobulin chain is a CH1 domain, and the parent domain of the further engineered domain of the second engineered immunoglobulin chain is a light chain constant domain such as an IGLC domain or an IGKC domain, wherein the first engineered immunoglobulin chain comprises a hinge region between the parent domain of the engineered domain and the parent domain of the further engineered domain.

In some embodiments the present disclosure provides a hetero-dimeric immunoglobulin or fragment thereof, wherein the amino acid residues from the protein-protein interface of the donor domain of the first and second member of the naturally occurring immunoglobulin super-family are amino acids non essential to the core integrity of the domain, preferably wherein the amino acid residues from the protein-protein interface of the donor domain of the first and second member of the naturally occurring immunoglobulin super-family used for substitution of the protein-protein interface of the parent domain of the first and/or second engineered immunoglobulin chain are amino acids non essential to the core integrity of the domain.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the second engineered immunoglobulin chain comprises an amino acid residue substitution at a position selected from the group consisting of 22, 26, 85.1, 86, and 88, preferably the protein-protein interface of the parent domain of the first engineered immunoglobulin chain comprises an amino acid residue substitution at a position selected from the group consisting of 22, 85.1, 86, and 88, and the protein-protein interface of the parent domain of the second engineered immunoglobulin chain comprises an amino acid residue substitution at a position selected from the group consisting of 22, 85.1, 86, and 88 or comprises an amino acid residue substitution at a position selected from the group consisting of 85.1 and 86, more preferably the protein-protein interface of the parent domain of the first engineered immunoglobulin chain comprises an amino acid residue substitution at a position selected from the group consisting of 22, 85.1 and 88, and the protein-protein interface of the parent domain of the second engineered immunoglobulin chain comprises an amino acid residue substitution at a position selected from the group consisting of 22, 85.1, 86, and 88 or comprises an amino acid residue substitution at a position selected from the group consisting of 85.1 and 86, in particular the protein-protein interface of the parent domain of the first engineered immunoglobulin chain comprises an amino acid residue substitution at position 88, and the protein-protein interface of the parent domain of the second engineered immunoglobulin chain comprises an amino acid residue substitution at a position selected from the group consisting of 22, 85.1, 86, and 88 or comprises an amino acid residue substitution at a position selected from the group consisting of 85.1 and 86, wherein the amino acid position of each group member is indicated according to the IMGT® numbering.

Thus in some embodiments, the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domains of the first and the second engineered immunoglobulin chain are not a CH2 domain, not a CH3 domain, not a VL domain and not a VH domain and, wherein the protein-protein interface of the parent domain of the first engineered immunoglobulin chain comprises an amino acid residue substitution at a position selected from the group consisting of 22, 85.1, 86, 88 and/or, wherein the protein-protein interface of the parent domain of the second engineered immunoglobulin chain comprises an amino acid residue substitution at a position selected from the group consisting of 22, 85.1, 86, 88, wherein if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, preferably not charged amino acids,
wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the first engineered immunoglobulin chain comprises an amino acid residue substitution at position 20 selected from the group consisting of 20A, 20E, 20K, 20N, 20Q, 20S, 20T, 20V and 20W and/or conservative amino substitutions thereof, preferably selected from the group consisting of 20A, 20N, 20Q, 20S, 20T, 20V and 20W and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the first engineered immunoglobulin chain comprises an amino acid residue substitution at position 22 selected from the group consisting of 22A, 22G, 22I, 22L, 22T and 22V and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the first engineered immunoglobulin chain comprises an amino acid residue substitution at position 85.1 selected from the group consisting of 85.1A, 85.1C, 85.1F, 85.1H, 85.1K, 85.1M, 85.1N, 85.1R, 85.1S, 85.1T, and 85.1W and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the first engineered immunoglobulin chain comprises an amino acid residue substitution at position 86 selected from the group consisting of 86F, 86H, 86I, 86T, 86Q, 86S, 86V, 86W, 86Y and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the first engineered immunoglobulin chain comprises an amino acid residue substitution at position 88 selected from the group consisting of 88E, 88I, 88K, 88L, 88Q, 88R, 88T, 88V, 88W, 88Y and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and the protein-protein interface of the parent domain of the second engineered immunoglobulin chain comprises an amino acid residue substitution at a position selected from the group consisting of 22, 26, 85.1, 86, and 88, the protein-protein interface of the parent domain of the second engineered immunoglobulin chain comprises an amino acid residue substitution at position 22 selected from the group consisting of 22A, 22G, 22I, 22L, 22T and 22V and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and the protein-protein interface of the parent domain of the second engineered immunoglobulin chain comprises an amino acid residue substitution at a position selected from the group consisting of 22, 26, 85.1, 86, and 88, the protein-protein interface of the parent domain of the second engineered immunoglobulin chain comprises an amino acid residue substitution at position 26 selected from the group consisting of 26K, 26Q, 26R, 26S, 26T, and 26V and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and the protein-protein interface of the parent domain of the second engineered immunoglobulin chain comprises an amino acid residue substitution at a position selected from the group consisting of 22, 26, 85.1, 86, and 88, the protein-protein interface of the parent domain of the second engineered immunoglobulin chain comprises an amino acid residue substitution at position 85.1 selected from the group consisting of 85.1A, 85.1C, 85.1F, 85.1H, 85.1K, 85.1M, 85.1N, 85.1R, 85.1S, 85.1T, and 85.1W and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and the protein-protein interface of the parent domain of the second engineered immunoglobulin chain comprises an amino acid residue substitution at a position selected from the group consisting of 22, 26, 85.1, 86, and 88, the protein-protein interface of the parent domain of the second engineered immunoglobulin chain comprises an amino acid residue substitution at position 86 selected from the group consisting of 86F, 86H, 86I, 86T, 86Q, 86S, 86V, 86W, 86Y and/or conservative amino substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and the protein-protein interface of the parent domain of the second engineered immunoglobulin chain comprises an amino acid residue substitution at a position selected from the group consisting of 22, 26, 85.1, 86, and 88, the protein-protein interface of the parent domain of the second engineered immunoglobulin chain comprises an amino acid residue substitution at position 88 selected from the group consisting of 88E, 88I, 88K, 88L, 88Q, 88R, 88T, 88V, 88W, 88Y and/or conservative amino substitutions thereof, wherein the amino acid position of each group member is indicated according to the IMGT® numbering.

In some embodiments, if the substitution in the parent domain of the first engineered immunoglobulin chain is at position 88, the substituted amino acid residue in the parent domain of the second engineered immunoglobulin chain which interacts with the substituted amino acid residue at position 88 in the parent domain of the first engineered immunoglobulin chain is at position 85.1 and/or 86, or if the substitution in the parent domain of the second engineered immunoglobulin chain is at position 88, the substituted amino acid residue in the parent domain of the first engineered immunoglobulin chain which interacts with the substituted amino acid residue at position 88 in the parent domain of the second engineered immunoglobulin chain is at position 85.1 and/or 86, wherein the amino acid position of each group member is indicated according to the IMGT® numbering.

In some embodiments, the substituted amino acid residue in the parent domain of the first engineered immunoglobulin chain comprises an amino acid residue at position 88 and the substituted amino acid residue in the parent domain of the second engineered immunoglobulin chain comprises an amino acid residue at position 85.1 and/or 86, preferably at position 85.1 and 86, wherein the amino acid position is indicated according to the IMGT® numbering. Usually the substituted amino acid residue in the parent domain of the first engineered immunoglobulin chain at position 88 and the substituted amino acid residue in the parent domain of the second engineered immunoglobulin chain at position 85.1 and/or 86 interact with each other, wherein the amino acid position is indicated according to the IMGT® numbering.

In some embodiments, if the substitution in the parent domain of the first engineered immunoglobulin chain is at position 85.1, the substituted amino acid residue in the parent domain of the second engineered immunoglobulin chain which interacts with the substituted amino acid residue at position 85.1 in the parent domain of the first engineered immunoglobulin chain is at position 86, or if the substitution in the parent domain of the second engineered immunoglobulin chain is at position 85.1, the substituted amino acid residue in the parent domain of the first engineered immunoglobulin chain which interacts with the substituted amino acid residue at position 85.1 in the parent domain of the second engineered immunoglobulin chain is at position 86, wherein the amino acid position of each group member is indicated according to the IMGT® numbering.

In some embodiments, the substituted amino acid residue in the parent domain of the first engineered immunoglobulin chain comprises an amino acid residue at position 85.1 and the substituted amino acid residue in the parent domain of the second engineered immunoglobulin chain comprises an amino acid residue at position 86, wherein the amino acid position is indicated according to the IMGT® numbering. Usually the substituted amino acid residue in the parent domain of the first engineered immunoglobulin chain at position 85.1 and the substituted amino acid residue in the parent domain of the second engineered immunoglobulin chain at position 86 interact with each other, wherein the amino acid position is indicated according to the IMGT® numbering.

In some embodiments, if the substitution in the parent domain of the first engineered immunoglobulin chain is at position 22, the substituted amino acid residue in the parent domain of the second engineered immunoglobulin chain which interacts with the substituted amino acid residue at position 22 in the parent domain of the first engineered immunoglobulin chain is at position 22 and/or 86, or if the substitution in the parent domain of the second engineered immunoglobulin chain is at position 22, the substituted amino acid residue in the parent domain of the first engineered immunoglobulin chain which interacts with the substituted amino acid residue at position 22 in the parent domain of the second engineered immunoglobulin chain is at position 22 and/or 86, wherein the amino acid position of each group member is indicated according to the IMGT® numbering.

In some embodiments, the substituted amino acid residue in the parent domain of the first engineered immunoglobulin chain comprises an amino acid residue at position 22 and the substituted amino acid residue in the parent domain of the second engineered immunoglobulin chain comprises an amino acid residue at position 22 and/or 86, preferably at position 22 and 86, wherein the amino acid position is indicated according to the IMGT® numbering. Usually the substituted amino acid residue in the parent domain of the first engineered immunoglobulin chain at position 22 and the substituted amino acid residue in the parent domain of the second engineered immunoglobulin chain at position 22 and/or 86 interact with each other, wherein the amino acid position is indicated according to the IMGT® numbering.

In some embodiments, if the substitution in the parent domain of the first engineered immunoglobulin chain is at position 20, the substituted amino acid residue in the parent domain of the second engineered immunoglobulin chain which interacts with the substituted amino acid residue at position 20 in the parent domain of the first engineered immunoglobulin chain is at position 26, or if the substitution in the parent domain of the second engineered immunoglobulin chain is at position 20, the substituted amino acid residue in the parent domain of the first engineered immunoglobulin chain which interacts with the substituted amino acid residue at position 20 in the parent domain of the second engineered immunoglobulin chain is at position 26, wherein the amino acid position of each group member is indicated according to the IMGT® numbering.

In some embodiments, the substituted amino acid residue in the parent domain of the first engineered immunoglobulin chain comprises an amino acid residue at position 20 and the substituted amino acid residue in the parent domain of the second engineered immunoglobulin chain comprises an amino acid residue at position 26, wherein the amino acid position is indicated according to the IMGT® numbering. Usually the substituted amino acid residue in the parent domain of the first engineered immunoglobulin chain at position 20 and the substituted amino acid residue in the parent domain of the second engineered immunoglobulin chain at position 26 interact with each other, wherein the amino acid position is indicated according to the IMGT® numbering.

In some embodiments, the donor domains of the first and second member of the naturally occurring immunoglobulin super-family are a human IGHA1 CH2 or a human IGHA2 CH2, wherein the amino acid substitutions in the protein-protein interface of the engineered domain of the first immunoglobulin chain comprise 88V and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domains of the first and second member of the naturally occurring immunoglobulin super-family are a human IGHA1 CH2 or a human IGHA2 CH2, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domains of the first and second member of the naturally occurring immunoglobulin super-family are a human IGHA1 CH2 or a human IGHA2 CH2, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHD CH2, wherein the amino acid substitutions in the protein-protein interface of the engineered domain of the first immunoglobulin chain comprise 88R and conservative amino acid substitutions thereof, and the amino acid substitutions in the protein-protein interface of the engineered domain of the second immunoglobulin chain comprise 86H and conservative amino acid substitutions thereof, and/or 85.1S and conservative amino acid substitutions thereof, wherein the amino acid position is indicated according to the IMGT® numbering.

In some embodiments, the donor domains of the first and second member of the naturally occurring immunoglobulin super-family are a human IGHD CH2, wherein the amino acid substitutions in the protein-protein interface of the engineered domain of the first immunoglobulin chain comprise 86H and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domains of the first and second member of the naturally occurring immunoglobulin super-family are a human IGHD CH2, wherein the amino acid substitutions in the protein-protein interface of the engineered domain of the first immunoglobulin chain comprise 86H and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHE CH2, wherein the amino acid substitutions in the protein-protein interface of the engineered domain of the first immunoglobulin chain comprise 88E and conservative amino acid substitutions thereof, and the amino acid substitutions in the protein-protein interface of the engineered domain of the second immunoglobulin chain comprise 86Q and conservative amino acid substitutions thereof, and/or 85.1S and conservative amino acid substitutions thereof, wherein the amino acid position is indicated according to the IMGT® numbering.

In some embodiments, the donor domains of the first and second member of the naturally occurring immunoglobulin super-family are a human IGHE CH2, wherein the amino acid substitutions in the protein-protein interface of the engineered domain of the first immunoglobulin chain comprise 86Q and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domains of the first and second member of the naturally occurring immunoglobulin super-family are a human IGHE CH2, wherein the amino acid substitutions in the protein-protein interface of the engineered domain of the first immunoglobulin chain comprise 86Q and conservative amino acid substitutions thereof, and the amino acid substitutions in the protein-protein interface of the engineered domain of the second immunoglobulin chain comprise 22L and conservative amino acid substitutions thereof, wherein the amino acid position is indicated according to the IMGT® numbering.

In some embodiments, the donor domains of the first and second member of the naturally occurring immunoglobulin super-family are a human IGHG1 CH2 or a human IGHG2 CH2 or a human IGHG3 CH2 or a human IGHG4 CH2, wherein the amino acid substitutions in the protein-protein interface of the engineered domain of the first immunoglobulin chain comprise 88V and conservative amino acid substitutions thereof, and the amino acid substitutions in the protein-protein interface of the engineered domain of the second immunoglobulin chain comprise 86V and conservative amino acid substitutions thereof, and/or 85.1R and conservative amino acid substitutions thereof, wherein the amino acid position is indicated according to the IMGT® numbering.

In some embodiments, the donor domains of the first and second member of the naturally occurring immunoglobulin super-family are a human IGHG1 CH2 or a human IGHG2 CH2 or a human IGHG3 CH2 or a human IGHG4 CH2, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 85.1R and conservative amino acid substitutions thereof, wherein the amino acid position is indicated according to the IMGT® numbering.

In some embodiments, the donor domains of the first and second member of the naturally occurring immunoglobulin super-family are a human IGHG1 CH2 or a human IGHG2 CH2 or a human IGHG3 CH2 or a human IGHG4 CH2, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHP CH2, wherein the amino acid substitutions in the protein-protein interface of the engineered domain of the first immunoglobulin chain comprise 88V and conservative amino acid substitutions thereof, and the amino acid substitutions in the protein-protein interface of the engineered domain of the second immunoglobulin chain comprise 86V and conservative amino acid substitutions thereof, and/or 85.1H and conservative amino acid substitutions thereof, wherein the amino acid position is indicated according to the IMGT® numbering.

In some embodiments, the donor domains of the first and second member of the naturally occurring immunoglobulin super-family are a human IGHP CH2, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 85.1H and conservative amino acid substitutions thereof, wherein the amino acid position is indicated according to the IMGT® numbering. In some embodiments, the donor domains of the first and second member of the naturally occurring immunoglobulin super-family are a human IGHP CH2, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHM CH2, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86T and conservative amino acid substitutions thereof, and/or 85.1K and conservative amino acid substitutions thereof, wherein the amino acid position is indicated according to the IMGT® numbering.

In some embodiments, the donor domains of the first and second member of the naturally occurring immunoglobulin super-family are a human IGHM CH2, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 85.1K and conservative amino acid substitutions thereof, wherein the amino acid position is indicated according to the IMGT® numbering.

In some embodiments, the donor domains of the first and second member of the naturally occurring immunoglobulin super-family are a human IGHM CH2, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 22I and conservative amino acid substitutions thereof, wherein the amino acid position is indicated according to the IMGT® numbering.

In some embodiments, the donor domains of the first and second member of the naturally occurring immunoglobulin super-family are a human IGHA1 CH3 or a human IGHA2 CH3, wherein the amino acid substitutions in the protein-protein interface of the engineered domain of the first immunoglobulin chain comprise 88I and conservative amino acid substitutions thereof, and the amino acid substitutions in the protein-protein interface of the engineered domain of the second immunoglobulin chain comprise 86T and conservative amino acid substitutions thereof, and/or 85.1A and conservative amino acid substitutions thereof, wherein the amino acid position is indicated according to the IMGT® numbering. In some embodiments, the donor domains of the first and second member of the naturally occurring immunoglobulin super-family are a human IGHA1 CH3 or a human IGHA2 CH3, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domains of the first and second member of the naturally occurring immunoglobulin super-family are a human IGHA1 CH3 or a human IGHA2 CH3, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHD CH3, wherein the amino acid substitutions in the protein-protein interface of the engineered domain of the first immunoglobulin chain comprise 88V and conservative amino acid substitutions thereof, and the amino acid substitutions in the protein-protein interface of the engineered domain of the second immunoglobulin chain comprise 86W and conservative amino acid substitutions thereof, and/or 85.1W and conservative amino acid substitutions thereof, wherein the amino acid position is indicated according to the IMGT® numbering.

In some embodiments, the donor domains of the first and second member of the naturally occurring immunoglobulin super-family are a human IGHD CH3, wherein the amino acid substitutions in the protein-protein interface of the engineered domain of the first immunoglobulin chain comprise 86W and conservative amino acid substitutions thereof, and the amino acid substitutions in the protein-protein interface of the engineered domain of the second immunoglobulin chain comprise 85.1W and conservative amino acid substitutions thereof, wherein the amino acid position is indicated according to the IMGT® numbering.

In some embodiments, the donor domains of the first and second member of the naturally occurring immunoglobulin super-family are a human IGHD CH3, wherein the amino acid substitutions in the protein-protein interface of the engineered domain of the first immunoglobulin chain comprise 86W and conservative amino acid substitutions thereof, and the amino acid substitutions in the protein-protein interface of the engineered domain of the second immunoglobulin chain comprise 22L and conservative amino acid substitutions thereof, wherein the amino acid position is indicated according to the IMGT® numbering. In some embodiments, the donor domains of the first and second member of the naturally occurring immunoglobulin super-family are a human IGHE CH3, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86T and conservative amino acid substitutions thereof, and/or 85.1T and conservative amino acid substitutions thereof, wherein the amino acid position is indicated according to the IMGT® numbering.

In some embodiments, the donor domains of the first and second member of the naturally occurring immunoglobulin super-family are a human IGHE CH3, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 85.1T and conservative amino acid substitutions thereof, wherein the amino acid position is indicated according to the IMGT® numbering.

In some embodiments, the donor domains of the first and second member of the naturally occurring immunoglobulin super-family are a human IGHE CH3, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHG1 CH3 or a human IGHG2 CH3 or a human IGHG3 CH3, wherein the amino acid substitutions in the protein-protein interface of the engineered domain of the first immunoglobulin chain comprise 88K and conservative amino acid substitutions thereof, and the amino acid substitutions in the protein-protein interface of the engineered domain of the second immunoglobulin chain comprise 86Y and conservative amino acid substitutions thereof, and/or 85.1F and conservative amino acid substitutions thereof, wherein the amino acid position of each group member is indicated according to the IMGT® numbering.

In some embodiments, the donor domains of the first and second member of the naturally occurring immunoglobulin super-family are a human IGHG1 CH3 or a human IGHG2 CH3 or a human IGHG3 CH3, wherein the amino acid substitutions in the protein-protein interface of the engineered domain of the first immunoglobulin chain comprise 86Y and conservative amino acid substitutions thereof, and the amino acid substitutions in the protein-protein interface of the engineered domain of the second immunoglobulin chain comprise 85.1F and conservative amino acid substitutions thereof, wherein the amino acid position is indicated according to the IMGT® numbering.

In some embodiments, the donor domains of the first and second member of the naturally occurring immunoglobulin super-family are a human IGHG1 CH3 or a human IGHG2 CH3 or a human IGHG3 CH3, wherein the amino acid substitutions in the protein-protein interface of the engineered domain of the first immunoglobulin chain comprise 86Y and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHG4 CH3, wherein the amino acid substitutions in the protein-protein interface of the engineered domain of the first immunoglobulin chain comprise 88R and conservative amino acid substitutions thereof, and the amino acid substitutions in the protein-protein interface of the engineered domain of the second immunoglobulin chain comprise 86Y and conservative amino acid substitutions thereof, and/or 85.1F and conservative amino acid substitutions thereof, wherein the amino acid position is indicated according to the IMGT® numbering.

In some embodiments, the donor domains of the first and second member of the naturally occurring immunoglobulin super-family are a human IGHG4 CH3, wherein the amino acid substitutions in the protein-protein interface of the engineered domain of the first immunoglobulin chain comprise 86Y and conservative amino acid substitutions thereof, and the amino acid substitutions in the protein-protein interface of the engineered domain of the second immunoglobulin chain comprise 85.1F and conservative amino acid substitutions thereof, wherein the amino acid position is indicated according to the IMGT® numbering.

In some embodiments, the donor domains of the first and second member of the naturally occurring immunoglobulin super-family are a human IGHG4 CH3, wherein the amino acid substitutions in the protein-protein interface of the engineered domain of the first immunoglobulin chain comprise 86Y and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering. In some embodiments, the donor domains of the first and second member of the naturally occurring immunoglobulin super-family are a human IGHP CH3, wherein the amino acid substitutions in the protein-protein interface of the engineered domain of the first immunoglobulin chain comprise 88K and conservative amino acid substitutions thereof, and the amino acid substitutions in the protein-protein interface of the engineered domain of the second immunoglobulin chain comprise 86Y and conservative amino acid substitutions thereof, and/or 85.1F and conservative amino acid substitutions thereof, wherein the amino acid position is indicated according to the IMGT® numbering.

In some embodiments, the donor domains of the first and second member of the naturally occurring immunoglobulin super-family are a human IGHP CH3, wherein the amino acid substitutions in the protein-protein interface of the engineered domain of the first immunoglobulin chain comprise 86Y and conservative amino acid substitutions thereof, and the amino acid substitutions in the protein-protein interface of the engineered domain of the second immunoglobulin chain comprise 85.1F and conservative amino acid substitutions thereof, wherein the amino acid position is indicated according to the IMGT® numbering.

In some embodiments, the donor domains of the first and second member of the naturally occurring immunoglobulin super-family are a human IGHP CH3, wherein the amino acid substitutions in the protein-protein interface of the engineered domain of the first immunoglobulin chain comprise 86Y and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHM CH3, wherein the amino acid substitutions in the protein-protein interface of the engineered domain of the first immunoglobulin chain comprise 88E and conservative amino acid substitutions thereof, and the amino acid substitutions in the protein-protein interface of the engineered domain of the second immunoglobulin chain comprise 86V and conservative amino acid substitutions thereof, and/or 85.1S and conservative amino acid substitutions thereof, wherein the amino acid position is indicated according to the IMGT® numbering.

In some embodiments, the donor domains of the first and second member of the naturally occurring immunoglobulin super-family are a human IGHM CH3, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering. In some embodiments, the donor domains of the first and second member of the naturally occurring immunoglobulin super-family are a human IGHM CH3, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGHE CH4, wherein the amino acid substitutions in the protein-protein interface of the engineered domain of the first immunoglobulin chain comprise 88R and conservative amino acid substitutions thereof, and the amino acid substitutions in the protein-protein interface of the engineered domain of the second immunoglobulin chain comprise 86F and conservative amino acid substitutions thereof, and/or 85.1F and conservative amino acid substitutions thereof, wherein the amino acid position is indicated according to the IMGT® numbering.

In some embodiments, the donor domains of the first and second member of the naturally occurring immunoglobulin super-family are a human IGHE CH4, wherein the amino acid substitutions in the protein-protein interface of the engineered domain of the first immunoglobulin chain comprise 86F and conservative amino acid substitutions thereof, and the amino acid substitutions in the protein-protein interface of the engineered domain of the second immunoglobulin chain comprise 85.1F and conservative amino acid substitutions thereof, wherein the amino acid position is indicated according to the IMGT® numbering. In some embodiments, the donor domains of the first and second member of the naturally occurring immunoglobulin super-family are a human IGHE CH4, wherein the amino acid substitutions in the protein-protein interface of the engineered domain of the first immunoglobulin chain comprise 86F and conservative amino acid substitutions thereof, and the amino acid substitutions in the protein-protein interface of the engineered domain of the second immunoglobulin chain comprise 22A and conservative amino acid substitutions thereof, wherein the amino acid position is indicated according to the IMGT® numbering.

In some embodiments, the donor domains of the first and second member of the naturally occurring immunoglobulin super-family are a human IGHM CH4, wherein the amino acid substitutions in the protein-protein interface of the engineered domain of the first immunoglobulin chain comprise 88I and conservative amino acid substitutions thereof, and the amino acid substitutions in the protein-protein interface of the engineered domain of the second immunoglobulin chain comprise 86H and conservative amino acid substitutions thereof, and/or 85.1F and conservative amino acid substitutions thereof, wherein the amino acid position is indicated according to the IMGT® numbering.

In some embodiments, the donor domains of the first and second member of the naturally occurring immunoglobulin super-family are a human IGHM CH4, wherein the amino acid substitutions in the protein-protein interface of the engineered domain of the first immunoglobulin chain comprise 86H and conservative amino acid substitutions thereof, and the amino acid substitutions in the protein-protein interface of the engineered domain of the second immunoglobulin chain comprise 85.1F and conservative amino acid substitutions thereof, wherein the amino acid position is indicated according to the IMGT® numbering.

In some embodiments, the donor domains of the first and second member of the naturally occurring immunoglobulin super-family are a human IGHM CH4, wherein the amino acid substitutions in the protein-protein interface of the engineered domain of the first immunoglobulin chain comprise 86H and conservative amino acid substitutions thereof, and the amino acid substitutions in the protein-protein interface of the engineered domain of the second immunoglobulin chain comprise 22T and conservative amino acid substitutions thereof, wherein the amino acid position is indicated according to the IMGT® numbering.

In some embodiments, the donor domains of the first and second member of the naturally occurring immunoglobulin super-family are a human IGKC, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domains of the first and second member of the naturally occurring immunoglobulin super-family are a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domains of the first and second member of the naturally occurring immunoglobulin super-family are a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domains of the first and second member of the naturally occurring immunoglobulin super-family are a human IGLC1 or a human IGLC2 or a human IGLC3 or a human IGLC6 or a human IGLC7, wherein the amino acid substitutions in the protein-protein interface of the engineered domain of the first immunoglobulin chain comprise 88Y and conservative amino acid substitutions thereof, and the amino acid substitutions in the protein-protein interface of the engineered domain of the second immunoglobulin chain comprise 86S and conservative amino acid substitutions thereof, and/or 85.1A and conservative amino acid substitutions thereof, wherein the amino acid position of each group member is indicated according to the IMGT® numbering.

In some embodiments, the donor domains of the first and second member of the naturally occurring immunoglobulin super-family are a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domains of the first and second member of the naturally occurring immunoglobulin super-family are a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHA1 CH1 or human IGHA2 CH1, and the donor domain of the second member of the naturally occurring immunoglobulin super-family is a human IGKC, wherein the amino acid substitutions in the protein-protein interface of the engineered domain of the first immunoglobulin chain comprise 88Q and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGHA1 CH1 or human IGHA2 CH1, and the donor domain of the second member of the naturally occurring immunoglobulin super-family is a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human IGHA1 CH1 or human IGHA2 CH1, and the donor domain of the second member of the naturally occurring immunoglobulin super-family is a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHD CH1, and the donor domain of the second member of the naturally occurring immunoglobulin super-family is a human IGKC, wherein the amino acid substitutions in the protein-protein interface of the engineered domain of the first immunoglobulin chain comprise 88Q and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGHD CH1, and the donor domain of the second member of the naturally occurring immunoglobulin super-family is a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering. In some embodiments, the donor domain of the first member of the naturally occurring immunoglobulin super-family is a human IGHD CH1, and the donor domain of the second member of the naturally occurring immunoglobulin super-family is a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHE CH1, and the donor domain of the second member of the naturally occurring immunoglobulin super-family is a human IGKC, wherein the amino acid substitutions in the protein-protein interface of the engineered domain of the first immunoglobulin chain comprise 88L and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGHE CH1, and the donor domain of the second member of the naturally occurring immunoglobulin super-family is a human IGKC, wherein the amino acid substitutions in the protein-protein interface of the engineered domain of the first immunoglobulin chain comprise 86I and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human IGHE CH1, and the donor domain of the second member of the naturally occurring immunoglobulin super-family is a human IGKC, wherein the amino acid substitutions in the protein-protein interface of the engineered domain of the first immunoglobulin chain comprise 86I and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHG1 CH1 or a human IGHG2 CH1 or a human IGHG3 CH1 or a human IGHG4 CH1 or a human IGHGP CH1, and the donor domain of the second member of the naturally occurring immunoglobulin super-family is a human IGKC, wherein the amino acid substitutions in the protein-protein interface of the engineered domain of the first immunoglobulin chain comprise 88V and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGHG1 CH1 or a human IGHG2 CH1 or a human IGHG3 CH1 or a human IGHG4 CH1 or a human IGHGP CH1, and the donor domain of the second member of the naturally occurring immunoglobulin super-family is a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human IGHG1 CH1 or a human IGHG2 CH1 or a human IGHG3 CH1 or a human IGHG4 CH1 or a human IGHGP CH1, and the donor domain of the second member of the naturally occurring immunoglobulin super-family is a human IGKC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHM CH1, and the donor domain of the second member of the naturally occurring immunoglobulin super-family is a human IGKC, wherein the amino acid substitutions in the protein-protein interface of the engineered domain of the first immunoglobulin chain comprise 88Q and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGHM CH1, and the donor domain of the second member of the naturally occurring immunoglobulin super-family is a human IGKC, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human IGHM CH1, and the donor domain of the second member of the naturally occurring immunoglobulin super-family is a human IGKC, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHA1 CH1 or a human IGHA2 CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 88Q and conservative amino acid substitutions thereof, and the amino acid substitutions in the protein-protein interface of the engineered domain of the second immunoglobulin chain comprise 86S and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGHA1 CH1 or a human IGHA2 CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGHA1 CH1 or a human IGHA2 CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHD CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 88Q and conservative amino acid substitutions thereof, and the amino acid substitutions in the protein-protein interface of the engineered domain of the second immunoglobulin chain comprise 86S and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGHD CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGHD CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHE CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 88L and conservative amino acid substitutions thereof, and the amino acid substitutions in the protein-protein interface of the engineered domain of the second immunoglobulin chain comprise 86S and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGHE CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86I and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering. In some embodiments, the donor domain of the first member of the naturally occurring immunoglobulin super-family is a human IGHE CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86I and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHG1 CH1 or a human IGHG2 CH1 or a human IGHG3 CH1 or a human IGHG4 CH1 or a human IGHGP CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 88V and conservative amino acid substitutions thereof, and the amino acid substitutions in the protein-protein interface of the engineered domain of the second immunoglobulin chain comprise 86S and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGHG1 CH1 or a human IGHG2 CH1 or a human IGHG3 CH1 or a human IGHG4 CH1 or a human IGHGP CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering. In some embodiments, the donor domain of the first member of the naturally occurring immunoglobulin super-family is a human IGHG1 CH1 or a human IGHG2 CH1 or a human IGHG3 CH1 or a human IGHG4 CH1 or a human IGHGP CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGHM CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 88Q and conservative amino acid substitutions thereof, and the amino acid substitutions in the protein-protein interface of the engineered domain of the second immunoglobulin chain comprise 86S and conservative amino acid substitutions thereof, and/or 85.1A and conservative amino acid substitutions thereof, wherein the amino acid position is indicated according to the IMGT® numbering. In some embodiments, the donor domain of the first member of the naturally occurring immunoglobulin super-family is a human IGHM CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGHM CH1, and the donor domain of the second member of the naturally occurring immunoglobulin super-family is a human IGLC1 or a human IGLC2 or a human IGLC3 or a human IGLC6 or a human IGLC7, wherein the amino acid substitutions in the protein-protein interface of the engineered domain of the first immunoglobulin chain comprise 86T and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHA1 CH1 or a human IGHA2 CH1, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86S and conservative amino acid substitutions thereof, and/or 85.1T and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHA1 CH1 or a human IGHA2 CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1T and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHA1 CH1 or a human IGHA2 CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22A and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHD CH1, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86S and conservative amino acid substitutions thereof, and/or 85.1M and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHD CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1M and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHD CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22A and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHE CH1, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86I and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHE CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHE CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22G and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHG1 CH1 or a human IGHG2 CH1 or a human IGHG3 CH1 or a human IGHG4 CH1 or a human IGHGP CH1, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHG1 CH1 or a human IGHG2 CH1 or a human IGHG3 CH1 or a human IGHG4 CH1 or a human IGHGP CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHG1 CH1 or a human IGHG2 CH1 or a human IGHG3 CH1 or a human IGHG4 CH1 or a human IGHGP CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22G and conservative amino acid substitutions thereof, wherein the amino acid position is indicated according to the IMGT® numbering.

In some embodiments, the donor domain of the first member of the naturally occurring immunoglobulin superfamily is a human IGKC, and the donor domain of the second member of the naturally occurring immunoglobulin super-family is a human IGHM CH1, wherein the amino acid substitutions in the protein-protein interface of the engineered domain of the first immunoglobulin chain comprise 88T and conservative amino acid substitutions thereof, and the amino acid substitutions in the protein-protein interface of the engineered domain of the second immunoglobulin chain comprise 86T and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHM CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGKC, and the donor domain of the second member of the naturally occurring immunoglobulin super-family is a human IGHM CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22G and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHA1 CH1 or a human IGHA2 CH1, wherein the amino acid substitutions in the protein-protein interface of the engineered domain of the first immunoglobulin chain comprise 88Y and conservative amino acid substitutions thereof, and the amino acid substitutions in the protein-protein interface of the engineered domain of the second immunoglobulin chain comprise 86S and conservative amino acid substitutions thereof, and/or 85.1T and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHA1 CH1 or a human IGHA2 CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1T and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHA1 CH1 or a human IGHA2 CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22A and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHD CH1, wherein the amino acid substitutions in the protein-protein interface of the engineered domain of the first immunoglobulin chain comprise 88Y and conservative amino acid substitutions thereof, and the amino acid substitutions in the protein-protein interface of the engineered domain of the second immunoglobulin chain comprise 86S and conservative amino acid substitutions thereof, and/or 85.1M and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHD CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1M and conservative amino acid substitutions thereof, wherein the amino acid position is indicated according to the IMGT® numbering. In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHD CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22A and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHE CH1, wherein the amino acid substitutions in the protein-protein interface of the engineered domain of the first immunoglobulin chain comprise 88Y and conservative amino acid substitutions thereof, and the amino acid substitutions in the protein-protein interface of the engineered domain of the second immunoglobulin chain comprise 86I and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHE CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHE CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22G and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHG1 CH1 or a human IGHG2 CH1 or a human IGHG3 CH1 or a human IGHG4 CH1 or a human IGHGP CH1, wherein the amino acid substitutions in the protein-protein interface of the engineered domain of the first immunoglobulin chain comprise 88Y and conservative amino acid substitutions thereof, and the amino acid substitutions in the protein-protein interface of the engineered domain of the second immunoglobulin chain comprise 86S and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHG1 CH1 or a human IGHG2 CH1 or a human IGHG3 CH1 or a human IGHG4 CH1 or a human IGHGP CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHG1 CH1 or a human IGHG2 CH1 or a human IGHG3 CH1 or a human IGHG4 CH1 or a human IGHGP CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22G and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHM CH1, wherein the amino acid substitutions in the protein-protein interface of the engineered domain of the first immunoglobulin chain comprise 88Y and conservative amino acid substitutions thereof, and the amino acid substitutions in the protein-protein interface of the engineered domain of the second immunoglobulin chain comprise 86T and conservative amino acid substitutions thereof, and/or 85.1A and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHM CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1A and conservative amino acid substitutions thereof, wherein the amino acid position is indicated according to the IMGT® numbering.

In some embodiments, the donor domain of the first member of the naturally occurring immunoglobulin super-family is a human IGLC1 or a human IGLC2 or a human IGLC3 or a human IGLC6 or a human IGLC7, and the donor domain of the second member of the naturally occurring immunoglobulin super-family is a human IGHM CH1, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22G and conservative amino acid substitutions thereof, wherein the amino acid position is indicated according to the IMGT® numbering.

In some embodiments, the donor domain of the first member of the naturally occurring immunoglobulin super-family is a human TRAC, and the donor domain of the second member of the naturally occurring immunoglobulin super-family is a human TRBC1 or a human TRBC2, wherein the amino acid substitutions in the protein-protein interface of the engineered domain of the first immunoglobulin chain comprise 88W and conservative amino acid substitutions thereof, and the amino acid substitutions in the protein-protein interface of the engineered domain of the second immunoglobulin chain comprise 86S and conservative amino acid substitutions thereof, and/or 85.1C or 85.1A or 85.1C and conservative amino acid substitutions thereof, wherein the amino acid position is indicated according to the IMGT® numbering.

In some embodiments, the donor domain of the first member of the naturally occurring immunoglobulin super-family is a human TRAC, and the donor domain of the second member of the naturally occurring immunoglobulin super-family is a human TRBC1 or a human TRBC2, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 85.1C or 85.1A or 85.1C and conservative amino acid substitutions thereof, wherein the amino acid position is indicated according to the IMGT® numbering.

In some embodiments, the donor domain of the first member of the naturally occurring immunoglobulin super-family is a human TRAC, and the donor domain of the second member of the naturally occurring immunoglobulin super-family is a human TRBC1 or a human TRBC2, wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering.

In some embodiments, the donor domain of the first member of the naturally occurring immunoglobulin super-family is a human TRBC1 or a human TRBC2, and the donor domain of the second member of the naturally occurring immunoglobulin super-family is a human TRAC, wherein the amino acid substitutions in the protein-protein interface of the engineered domain of the first immunoglobulin chain comprise 88R and conservative amino acid substitutions thereof, and the amino acid substitutions in the protein-protein interface of the engineered domain of the second immunoglobulin chain comprise 86V and conservative amino acid substitutions thereof, and/or 85.1S and conservative amino acid substitutions thereof, wherein the amino acid position is indicated according to the IMGT® numbering.

In some embodiments, the donor domain of the first member of the naturally occurring immunoglobulin super-family is a human TRBC1 or a human TRBC2, and the donor domain of the second member of the naturally occurring immunoglobulin super-family is a human TRAC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 85.1S and conservative amino acid substitutions thereof, wherein the amino acid position is indicated according to the IMGT® numbering.

In some embodiments, the donor domain of the first member of the naturally occurring immunoglobulin super-family is a human TRBC1 or a human TRBC2, and the donor domain of the second member of the naturally occurring immunoglobulin super-family is a human TRAC, wherein the amino acid substitutions in the protein-protein interface of the engineered domain of the first immunoglobulin chain comprise 86S and conservative amino acid substitutions thereof, and the amino acid substitutions in the protein-protein interface of the engineered domain of the second immunoglobulin chain comprise 22V and conservative amino acid substitutions thereof, wherein the amino acid position is indicated according to the IMGT® numbering. In some embodiments, the donor domain of the first member of the naturally occurring immunoglobulin super-family is a human TRDC, and the donor domain of the second member of the naturally occurring immunoglobulin super-family is a human TRGC1 or a human TRGC2 (2x) or a human TRGC2 (3x), wherein the amino acid substitutions in the protein-protein interface of the engineered domain of the first immunoglobulin chain comprise 88L and conservative amino acid substitutions thereof, and the amino acid substitutions in the protein-protein interface of the engineered domain of the second immunoglobulin chain comprise 86F and conservative amino acid substitutions thereof, and/or 85.1M and conservative amino acid substitutions thereof, wherein the amino acid position is indicated according to the IMGT® numbering.

In some embodiments, the donor domain of the first member of the naturally occurring immunoglobulin super-family is a human TRDC, and the donor domain of the second member of the naturally occurring immunoglobulin super-family is a human TRGC1 or a human TRGC2 (2x) or a human TRGC2 (3x), wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 85.1M and conservative amino acid substitutions thereof, wherein the amino acid position is indicated according to the IMGT® numbering. In some embodiments, the donor domain of the first member of the naturally occurring immunoglobulin super-family is a human TRDC, and the donor domain of the second member of the naturally occurring immunoglobulin super-family is a human TRGC1 or a human TRGC2 (2x) or a human TRGC2 (3x), wherein the amino acid substitutions in the protein-protein interface of the engineered domain of the first immunoglobulin chain comprise 86V and conservative amino acid substitutions thereof, and the amino acid substitutions in the protein-protein interface of the engineered domain of the second immunoglobulin chain comprise 22L and conservative amino acid substitutions thereof, wherein the amino acid position is indicated according to the IMGT® numbering.

In some embodiments, the donor domain of the first member of the naturally occurring immunoglobulin super-family is a human TRGC1 or a human TRGC2 (2x) or a human TRGC2 (3x), and the donor domain of the second member of the naturally occurring immunoglobulin super-family is a human TRDC, wherein the amino acid substitutions in the protein-protein interface of the engineered domain of the first immunoglobulin chain comprise 88W and conservative amino acid substitutions thereof, and the amino acid substitutions in the protein-protein interface of the engineered domain of the second immunoglobulin chain comprise 86V and conservative amino acid substitutions thereof, and/or 85.1N and conservative amino acid substitutions thereof, wherein the amino acid position is indicated according to the IMGT® numbering. In some embodiments, the donor domain of the first member of the naturally occurring immunoglobulin super-family is a human TRGC1 or a human TRGC2 (2×) or a human TRGC2 (3×), and the donor domain of the second member of the naturally occurring immunoglobulin super-family is a human TRDC, wherein the amino acid substitutions in the protein-protein interface of the engineered domain of the first immunoglobulin chain comprise 86F and conservative amino acid substitutions thereof, and the amino acid substitutions in the protein-protein interface of the engineered domain of the second immunoglobulin chain comprise 85.1N and conservative amino acid substitutions thereof, wherein the amino acid position is indicated according to the IMGT® numbering.

In some embodiments, the donor domain of the first member of the naturally occurring immunoglobulin super-family is a human TRGC1 or a human TRGC2 (2×) or a human TRGC2 (3×), and the donor domain of the second member of the naturally occurring immunoglobulin super-family is a human TRDC, wherein the amino acid substitutions in the protein-protein interface of the engineered domain of the first immunoglobulin chain comprise 86F and conservative amino acid substitutions thereof, and the amino acid substitutions in the protein-protein interface of the engineered domain of the second immunoglobulin chain comprise 22A and conservative amino acid substitutions thereof, wherein the amino acid position is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and/or the protein-protein interface of the parent domain of the second engineered immunoglobulin chain comprises an amino acid residue substitution at a position selected from the group consisting of 22, 26, 85.1, 86, and 88, the protein-protein interface of the parent domain of the first engineered immunoglobulin chain comprises an amino acid residue substitution selected from the group consisting of 20V, 20T, 20A, 20N, 20Q, 20E, 20K, 20W, 20S, 22A, 22G, 22T, 22L, 22I, 22V, 85.1T, 85.1M, 85.1A, 85.1S, 85.1R, 85.1H, 85.1K, 85.1W, 85.1F, 85.1C, 85.1N, 86S, 86I, 86T, 86H, 86Q, 86V, 86W, 86Y, 86F, 88Q, 88L, 88V, 88R, 88E, 88T, 88I, 88K, 88Y, and 88W and/or wherein the protein-protein interface of the parent domain of the second engineered immunoglobulin chain comprises an amino acid residue substitution selected from the group consisting of 22A, 22G, 22T, 22L, 22I, 22V, 26Q, 26T, 26K, 26V, 26S, 26R, 26N, 26E, 85.1T, 85.1M, 85.1A, 85.1S, 85.1R, 85.1H, 85.1K, 85.1W, 85.1F, 85.1C, 85.1N, 86S, 86I, 86T, 86H, 86Q, 86V, 86W, 86Y, 86F, 88Q, 88L, 88V, 88R, 88E, 88I, 88T, 88K, 88Y, and 88W, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and/or the protein-protein interface of the parent domain of the second engineered immunoglobulin chain comprises an amino acid residue substitution at a position selected from the group consisting of 22, 26, 85.1, 86, and 88, the protein-protein interface of the parent domain of the first engineered immunoglobulin chain comprises an amino acid residue substitution selected from the group consisting of 20K, 20N, 20T, 20S, 22A, 22L, 22V, 22T, 85.1S, 85.1A, 85.1N, 85.1M, 85.1F, 86S, 86F, 86Y, 86V, 88W, 88R, 88L, and 88K and/or conservative amino acid substitutions thereof and/or the protein-protein interface of the parent domain of the second engineered immunoglobulin chain comprises an amino acid residue substitution selected from the group consisting of 22A, 22L, 22V, 22T, 26E, 26T, 26K, 85.1S, 85.1A, 85.1N, 85.1M, 85.1F, 86S, 86F, 86Y, 86V, 88W, 88R, 88L, and 88K and/or conservative amino acid substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and/or the protein-protein interface of the parent domain of the second engineered immunoglobulin chain comprises an amino acid residue substitution at a position selected from the group consisting of 22, 26, 85.1, 86, and 88, the protein-protein interface of the parent domain of the first engineered immunoglobulin chain comprises an amino acid residue substitution selected from the group consisting of 20K, 20N, 20T, 20S, 22A, 22L, 22V, 22T, 85.1S, 85.1A, 85.1N, 85.1M, 85.1F, 86S, 86T, 86F, 86Y, 86V, 88W, 88R, 88L, 88I, and 88K and/or conservative amino acid substitutions thereof and/or the protein-protein interface of the parent domain of the second engineered immunoglobulin chain comprises an amino acid residue substitution selected from the group consisting of 22A, 22L, 22V, 22T, 26E, 26T, 26K, 26R, 85.1S, 85.1A, 85.1N, 85.1M, 85.1F, 86S, 86T, 86F, 86Y, 86V, 88W, 88R, 88L, 88I and 88K and/or conservative amino acid substitutions thereof, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, the protein-protein interface of the parent domain of the first engineered immunoglobulin chain comprises a further amino acid residue substitution at a position selected from the group consisting of 3, 5, 7, 11, 12, 13, 18, 26, 27, 79, 81, 83, 84, 84.2 and 90, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and the protein-protein interface of the parent domain of the second engineered immunoglobulin chain comprises an amino acid residue substitution at a position selected from the group consisting of 22, 26, 85.1, 86, and 88, the protein-protein interface of the parent domain of the second engineered immunoglobulin chain comprises a further amino acid residue substitution at a position selected from the group consisting of 3, 5, 7, 11, 12, 13, 18, 20, 27, 79, 81, 83, 84, 84.2 and 90, wherein the amino acid position of each group member is indicated according to the IMGT® numbering.

Preferably the protein-protein interface of the parent domain of the first engineered immunoglobulin chain comprises an amino acid residue substitution at a position selected from the group consisting of 20, 22, 85.1, 86, 88 and a further amino acid residue substitution at a position selected from the group consisting of 26, 79, and 90, and the protein-protein interface of the parent domain of the second engineered immunoglobulin chain comprises an amino acid residue substitution at a position selected from the group consisting of 22, 26, 85.1, 86, 88 and a further amino acid residue substitution at a position selected from the group consisting of 3, 5, 7, 20, 81, 84, 84.2, and 90, wherein the amino acid position of each group member is indicated according to the IMGT® numbering.

Preferably the protein-protein interface of the parent domain of the first engineered immunoglobulin chain comprises an amino acid residue substitution at a position selected from the group consisting of 20, 22, 85.1, 86, 88 and a further amino acid residue substitution at a position selected from the group consisting of 3, 5, 26, 27, 81, 83, and 84, and the protein-protein interface of the parent domain of the second engineered immunoglobulin chain comprises an amino acid residue substitution at a position selected from the group consisting of 22, 85.1, 86, 88 and a further amino acid residue substitution at a position selected from the group consisting of 7, 20, 27, 79, 81, 84.2, and 90, wherein the amino acid position of each group member is indicated according to the IMGT® numbering.

Preferably the protein-protein interface of the parent domain of the first engineered immunoglobulin chain comprises an amino acid residue substitution at a position selected from the group consisting of 20, 22, 85.1, 86, 88 and a further amino acid residue substitution at a position selected from the group consisting of 3, 5, 7, 11, 12, 13, 18, 26, 79, 81, 83, and 84.2, and the protein-protein interface of the parent domain of the second engineered immunoglobulin chain comprises an amino acid residue substitution at a position selected from the group consisting of 22, 26, 85.1, 86, 88 and a further amino acid residue substitution at a position selected from the group consisting of 3, 5, 7, 11, 12, 13, 18, 20, 79, 81, 83, and 84.2, wherein the amino acid position of each group member is indicated according to the IMGT® numbering.

In some embodiments, wherein the protein-protein interface of the parent domain of the first engineered immunoglobulin chain comprises an amino acid residue substitution at a position selected from the group consisting of 20, 22, 85.1, 86, and 88, and/or the protein-protein interface of the parent domain of the second engineered immunoglobulin chain comprises an amino acid residue substitution at a position selected from the group consisting of 22, 26, 85.1, 86, and 88, the parent domain of the first and/or the second engineered immunoglobulin chain is a domain selected from the group consisting of CH1 domain, CH4 domain, IGKC domain, IGLC1 domain, IGLC2 domain, IGLC3 domain, IGLC6 domain, and IGLC7 domain, wherein the amino acid position of each group member is indicated according to the IMGT® numbering.

Preferably, the parent domain of the first engineered immunoglobulin chain is a CH1 domain and the parent domain of the second engineered immunoglobulin chain is selected from the group consisting of IGKC domain, IGLC1 domain, IGLC2 domain, IGLC3 domain, IGLC6 domain, and IGLC7 domain. Equally preferably the parent domain of the first and the second engineered immunoglobulin chain is a CH4 domain, in particular a CH4 domain of the same isotype, species and subclass.

Preferably, the parent domain of the first engineered immunoglobulin chain is a CH1 domain and the parent domain of the second engineered immunoglobulin chain is an IGKC domain or, the parent domain of the first engineered immunoglobulin chain is an IGKC domain and the parent domain of the second engineered immunoglobulin chain is a CH1 domain.

Preferably, the parent domain of the first engineered immunoglobulin chain is a CH1 domain and the parent domain of the second engineered immunoglobulin chain is an IGLC domain selected from the group consisting of IGLC1, IGLC2, IGLC3, IGLC6, and IGLC7 or, the parent domain of the first engineered immunoglobulin chain is an IGLC domain selected from the group consisting of IGLC1, IGLC2, IGLC3, IGLC6, and IGLC7 and the parent domain of the second engineered immunoglobulin chain is a CH1 domain.

In some embodiments, wherein the protein-protein interface of the parent domain of the first engineered immunoglobulin chain comprises an amino acid residue substitution at a position selected from the group consisting of 20, 22, 85.1, 86, and 88, and/or the protein-protein interface of the parent domain of the second engineered immunoglobulin chain comprises an amino acid residue substitution at a position selected from the group consisting of 22, 26, 85.1, 86, and 88, the parent domain of the first and/or the second engineered immunoglobulin chain is a domain selected from the group consisting of CH1 domain, CH4 domain, IGKC domain, IGLC1 domain, IGLC2 domain, IGLC3 domain, IGLC6 domain, and IGLC7 domain, wherein the amino acid position of each group member is indicated according to the IMGT® numbering.

In some embodiments, wherein the parent domains of the first and the second engineered immunoglobulin chain are not a CH2 domain, not a CH3 domain, not a VL domain and not a VH domain and wherein,
if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 12 and the protein-protein interface of the parent domain of the second engineered immunoglobulin chain is substituted with an amino acid residue at position 119, the substituted amino acid residue at position 12 and the substituted amino acid residue at position 119 are not a charged pair,
if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 26 and the protein-protein interface of the parent domain of the second engineered immunoglobulin chain is substituted with an amino acid residue at position 13, the substituted amino acid residue at position 26 and the substituted amino acid residue at position 13 are not a charged pair,
if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 5 and the protein-protein interface of the parent domain of the second engineered immunoglobulin chain is substituted with an amino acid residue at position 20, the substituted amino acid residue at position 5 and the substituted amino acid residue at position 20 are not a charged pair, if the parent domain of the first engineered immunoglobulin chain is a CH1 domain and the parent domain of the second engineered immunoglobulin chain is an IGLC domain and the protein-protein interface of the parent domain of the first engineered immunoglobulin chain is substituted with an amino acid residue at position 27 and the protein-protein interface of the parent domain of the second engineered immunoglobulin chain is substituted with an amino acid residue at position 18, the substituted amino acid residue at position 27 and the substituted amino acid residue at position 18 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 20 and the protein-protein interface of the parent domain of the second engineered immunoglobulin chain is substituted with an amino acid residue at position 26, the substituted amino acid residue at position 20 and the substituted amino acid residue at position 26 are not a charged pair, if the parent domain of the first engineered immunoglobulin chain is an IGLC domain and the parent domain of the second engineered immunoglobulin chain is a CH1 domain and the protein-protein interface of the parent domain of the first engineered immunoglobulin chain is substituted with an amino acid residue at position 79 and the protein-protein interface of the parent domain of the second engineered immunoglobulin chain is substituted with an amino acid residue at position 84.3, the substituted amino acid residue at position 79 and the substituted amino acid residue at position 84.3 are not a charged pair, if the parent domain of the first engineered immunoglobulin chain is an IGLC domain or an IGKC domain and the parent domain of the second engineered immunoglobulin chain is a CH1 domain and the protein-protein interface of the parent domain of the first engineered immunoglobulin chain is substituted with an amino acid residue at position 86 and the protein-protein interface of the parent domain of the second engineered immunoglobulin chain is substituted with an amino acid residue at position 86, the substituted amino acid residues at both positions 86 are not a charged pair, if the parent domain of the first engineered immunoglobulin chain is an IGKC domain and the amino acid residue which is substituted in the protein-protein interface of the parent domain of the first engineered immunoglobulin chain is at position 11 and the parent domain of the second engineered immunoglobulin chain is a domain which comprises a hinge region, the parent domain of the second engineered immunoglobulin chain is not substituted at position 3 of the hinge region, the parent domain of the first and/or the second engineered immunoglobulin chain is a domain selected from the group consisting of CH1 domain, CH4 domain, IGKC domain, IGLC1 domain, IGLC2 domain, IGLC3 domain, IGLC6 domain, and IGLC7 domain and/or the amino acid residue which is substituted in the protein-protein interface of the parent domain of the first and/or the second engineered immunoglobulin chain comprises an amino acid residue at a position selected from the group consisting of 3, 5, 7, 11, 12, 13, 18, 20, 22, 26, 27, 79, 81, 83, 84, 84.2, 85.1, 86, 88 and 90, wherein the amino acid position of each group member is indicated according to the IMGT® numbering.

Preferably the protein-protein interface of the parent domain of the first engineered immunoglobulin chain comprises an amino acid residue substitution at a position selected from the group consisting of 20, 22, 26, 79, 85.1, 86, 88 and 90 and the protein-protein interface of the parent domain of the second engineered immunoglobulin chain comprises an amino acid residue substitution at a position selected from the group consisting of 3, 5, 7, 20, 22, 26, 81, 84, 84.2, 85.1, 86, 88 and 90, wherein the amino acid position of each group member is indicated according to the IMGT® numbering.

Preferably the protein-protein interface of the parent domain of the first engineered immunoglobulin chain comprises an amino acid residue substitution at a position selected from the group consisting of 3, 5, 20, 22, 26, 27, 81, 83, 84, 85.1, 86, and 88, and the protein-protein interface of the parent domain of the second engineered immunoglobulin chain comprises an amino acid residue substitution at a position selected from the group consisting of 7, 20, 22, 27, 79, 81, 84.2, 85.1, 86, 88, and 90, wherein the amino acid position of each group member is indicated according to the IMGT® numbering.

Preferably the protein-protein interface of the parent domain of the first engineered immunoglobulin chain comprises an amino acid residue substitution at a position selected from the group consisting of 3, 5, 7, 11, 12, 13, 18, 20, 22, 26, 79, 81, 83, 84.2, 85.1, 86, and 88, and the protein-protein interface of the parent domain of the second engineered immunoglobulin chain comprises an amino acid residue substitution at a position selected from the group consisting of 3, 5, 7, 11, 12, 13, 18, 20, 22, 26, 79, 81, 83, 84.2, 85.1, 86, and 88, wherein the amino acid position of each group member is indicated according to the IMGT® numbering.

In some embodiments the first and the second member of the naturally occurring immunoglobulin super-family are selected from the TCR constant domain family. In some embodiments the third and the fourth member of the naturally occurring immunoglobulin super-family are selected from the TCR constant domain family.

Preferably the donor domain of first member of the naturally occurring immunoglobulin super-family is the TCR constant domain alpha (SEQ ID NO: 1) and the donor domain of the second member of the naturally occurring immunoglobulin super-family is the TCR constant domain beta (SEQ ID NO: 2). Equally the donor domain of the first member of the naturally occurring immunoglobulin super-family can be the TCR constant domain beta (SEQ ID NO: 2) and the donor domain of the second member of the naturally occurring immunoglobulin super-family can be the TCR constant domain alpha (SEQ ID NO: 1).

Preferably the donor domain of the third member of the naturally occurring immunoglobulin super-family is the TCR constant domain alpha (SEQ ID NO: 1) and the donor domain of the fourth member of the naturally occurring immunoglobulin super-family is the TCR constant domain beta (SEQ ID NO: 2). Equally the donor domain of the third member of the naturally occurring immunoglobulin super-family can be the TCR constant domain beta (SEQ ID NO: 2) and the donor domain of the fourth member of the naturally occurring immunoglobulin super-family can be the TCR constant domain alpha (SEQ ID NO: 1).

In a further embodiment the donor domain of the first member of the naturally occurring immunoglobulin super-family is the TCR constant domain alpha (SEQ ID NO: 1)

and the donor domain of the second member of the naturally occurring immunoglobulin super-family is the TCR constant domain beta (SEQ ID NO: 2), wherein the cysteine (C) at amino acid position 75 in SEQ ID NO: 2 is substituted with alanine (A) or serine (S), preferably with alanine (A).

In a further embodiment the donor domain of the third member of the naturally occurring immunoglobulin super-family is the TCR constant domain alpha (SEQ ID NO: 1) and the donor domain of the fourth member of the naturally occurring immunoglobulin super-family is the TCR constant domain beta (SEQ ID NO: 2), wherein the cysteine (C) at amino acid position 75 in SEQ ID NO: 2 is substituted with alanine (A) or serine (S), preferably with alanine (A).

In a further embodiment the donor domain of the third member of the naturally occurring immunoglobulin super-family is the TCR constant domain gamma (SEQ ID NO: 33) and the donor domain of the fourth member of the naturally occurring immunoglobulin super-family is the TCR constant domain delta (SEQ ID NO: 32) or wherein the donor domain of the third member of the naturally occurring immunoglobulin super-family is the TCR constant domain delta (SEQ ID NO: 32) and the donor domain of the fourth member of the naturally occurring immunoglobulin super-family is the TCR constant domain gamma (SEQ ID NO: 33).

In a further embodiment the donor domain of the first and/or second member of the naturally occurring immuno-globulin super-family is an IgA1 CH3 domain, preferably an IGHA1 CH3 domain, more preferably the human IGHA1 CH3 domain (SEQ ID NO: 96). In a further embodiment the donor domain of the first and/or second member of the naturally occurring immunoglobulin super-family is IgA2 CH3 domain, preferably an IGHA2 CH3 domain, more preferably the human IGHA2 CH3 domain (SEQ ID NO: 97).

In a further embodiment the donor domain of the third and/or fourth member of the naturally occurring immuno-globulin super-family is an IgA1 CH3 domain, preferably an IGHA1 CH3 domain, more preferably the human IGHA1 CH3 domain (SEQ ID NO: 96). In a further embodiment the donor domain of the third and/or fourth member of the naturally occurring immunoglobulin super-family is an IgA2 CH3 domain, preferably an IGHA2 CH3 domain, more preferably the human IGHA2 CH3 domain (SEQ ID NO: 97).

The IGHA1 CH3 domain or the IGHA2 CH3 domain as donor domains are particularly useful if the parent domains of the first engineered immunoglobulin chain and/or the second engineered immunoglobulin chain or the further engineered domain of the first engineered immunoglobulin chain and/or the second engineered immunoglobulin chain and the engineered domain of the third engineered immu-noglobulin chain are CH3 domains from an isotype different from IGHA1 or IGHA2, e.g. IGHG1 or IGHG2 or IGHG3 or IGHG4 CH3 domains or preferably IGHG1 CH3, more preferably human IGHG1 CH3.

In a further embodiment at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family and additionally at least one amino acid residue of the protein-protein interface of the parent domain of said first engineered immunoglobulin chain is substituted with an amino acid residue at the equivalent 3D structural position from a protein-protein interface of a donor domain of a third member of the naturally occurring immunoglobulin super-family and wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family and additionally at least one amino acid residue of the protein-protein interface of the parent domain of said second engineered immunoglobulin chain is substituted with an amino acid residue at the equivalent 3D structural position from a protein-protein interface of a donor domain of a fourth member of the naturally occurring immunoglobulin super-family.

In case the parent domains are from IgG1, the donor domain of the first member of the naturally occurring immunoglobulin super-family can be selected from e.g. a CH3 domain of IgA, IgM or IgE, the donor domain of the third member of the naturally occurring immunoglobulin super-family can be selected from e.g. a CH4 domain of IgM or IgE or from a CH3 domain of IgG2, IgG3 or IgG4, the donor domain of the second member of the naturally occur-ring immunoglobulin super-family can be selected from e.g. a CH3 domain of IgA, IgM or IgE and the donor domain of the fourth member of the naturally occurring immunoglobu-lin super-family can be selected from e.g. a CH4 domain of IgM or IgE or from a CH3 domain of IgG2, IgG3 or IgG4. Usually the donor domain of the first member of the natu-rally occurring immunoglobulin super-family and the donor domain of the second member of the naturally occurring immunoglobulin super-family which are selected are the same and the donor domain of the third member of the naturally occurring immunoglobulin super-family and the donor domain of the fourth member of the naturally occur-ring immunoglobulin super-family are the same.

Provided that the parent domain of the first engineered immunoglobulin chain and the parent domain of the second engineered immunoglobulin chain form a hetero-dimer, spe-cifically a naturally occurring hetero-dimer, or are specially a CH1 domain and an IGKC domain, the donor domain of the first member of the naturally occurring immunoglobulin super-family and the donor domain of the second member of the naturally occurring immunoglobulin can be domains which form a homo-dimer, usually domains of the same isotype, species and subclass, preferably a CH3 domain, more preferred a human CH3 domain, even more preferred an IgG1 CH3 domain, in particular a human IgG1 CH3 domain. Equally preferred is an IgA1 CH3 domain or an IgA2 CH3 domain, preferably the human IGHA1 CH3 domain or the human IGHA2 CH3 domain.

Provided that the parent domain of the first engineered immunoglobulin chain and the parent domain of the second engineered immunoglobulin chain form a hetero-dimer, spe-cifically a naturally occurring hetero-dimer, or are specially a CH1 domain and an IGKC domain, the donor domain of the first member of the naturally occurring immunoglobulin super-family and the donor domain of the second member of the naturally occurring immunoglobulin can be domains which form a hetero-dimer, preferably domains from the TCR constant domain family, more preferably TCR constant domain alpha (SEQ ID NO: 1) and TCR constant domain beta (SEQ ID NO: 2) or TCR constant domain gamma (SEQ ID NO: 33) and the TCR constant domain delta (SEQ ID NO: 32).

Provided that the parent domain of the first engineered immunoglobulin chain and the parent domain of the second engineered immunoglobulin chain form a homo-dimer, specifically a naturally occurring homo-dimer, or are specifically domains of the same isotype, species and subclass, the donor domain of the first member of the naturally occurring immunoglobulin super-family and the donor domain of the second member of the naturally occurring immunoglobulin are domains which form a hetero-dimer, preferably domains from the TCR constant domain family, more preferably TCR constant domain alpha (SEQ ID NO: 1) and TCR constant domain beta (SEQ ID NO: 2) or TCR constant domain gamma (SEQ ID NO: 33) and the TCR constant domain delta (SEQ ID NO: 32).

Provided that the parent domain of the further engineered domain of the first and/or second engineered immunoglobulin chain and the parent domain of the engineered domain of the third engineered immunoglobulin chain form a hetero-dimer, specifically a naturally occurring hetero-dimer, or are specifically a CH1 domain and a IGKC domain, the donor domain of the third member of the naturally occurring immunoglobulin super-family and the donor domain of the fourth member of the naturally occurring immunoglobulin are preferably domains which form a homo-dimer, usually domains of the same isotype, species and subclass, preferably a CH3 domain, more preferred a human CH3 domain, even more preferred an IgG1 CH3 domain, in particular a human IgG1 CH3 domain. Provided that the parent domain of the further engineered domain of the first and/or second engineered immunoglobulin chain and the parent domain of the engineered domain of the third engineered immunoglobulin chain form a homo-dimer, specifically a naturally occurring homo-dimer, or are specifically domains of the same isotype, species and subclass, the donor domain of the third member of the naturally occurring immunoglobulin super-family and the donor domain of the fourth member of the naturally occurring immunoglobulin are preferably domains which form a hetero-dimer, preferably domains from the TCR constant domain family, more preferably TCR constant domain alpha (SEQ ID NO: 1) and TCR constant domain beta (SEQ ID NO: 2) or TCR constant domain gamma (SEQ ID NO: 33) and the TCR constant domain delta (SEQ ID NO: 32).

Provided that the parent domain of the further engineered domain of the first and/or second engineered immunoglobulin chain and the parent domain of the engineered domain of the third engineered immunoglobulin chain form a hetero-dimer, specifically a naturally occurring hetero-dimer, the donor domain of the third member of the naturally occurring immunoglobulin super-family and the donor domain of the fourth member of the naturally occurring immunoglobulin are domains which form a hetero-dimer, preferably domains from the TCR constant domain family, more preferably TCR constant domain alpha (SEQ ID NO: 1) and TCR constant domain beta (SEQ ID NO: 2) or TCR constant domain gamma (SEQ ID NO: 33) and the TCR constant domain delta (SEQ ID NO: 32).

In some embodiments the donor domain of the first member of the naturally occurring immunoglobulin super-family is the TCR constant domain alpha (SEQ ID NO: 1), the donor domain of the second member of the naturally occurring immunoglobulin super-family is the TCR constant domain beta (SEQ ID NO: 2), the donor domain of the third member of the naturally occurring immunoglobulin super-family is the TCR constant domain delta (SEQ ID NO: 32) and the donor domain of the fourth member of the naturally occurring immunoglobulin super-family is the TCR constant domain gamma (SEQ ID NO: 33).

In some embodiments the donor domain of first member of the naturally occurring immunoglobulin super-family is the TCR constant domain delta (SEQ ID NO: 32), the donor domain of the second member of the naturally occurring immunoglobulin super-family is the TCR constant domain gamma (SEQ ID NO: 33), the donor domain of the third member of the naturally occurring immunoglobulin super-family is the TCR constant domain alpha (SEQ ID NO: 1) and the donor domain of the fourth member of the naturally occurring immunoglobulin super-family is the TCR constant domain beta (SEQ ID NO: 2).

In some embodiments the donor domain of the first member of the naturally occurring immunoglobulin super-family is the TCR constant domain alpha (SEQ ID NO: 1) or the TCR constant domain delta (SEQ ID NO: 32), the donor domain of the second member of the naturally occurring immunoglobulin super-family is the TCR constant domain beta (SEQ ID NO: 2) or the TCR constant domain gamma (SEQ ID NO: 33), the donor domain of the third and the fourth member of the naturally occurring immunoglobulin super-family is the IgG1 CH3 domain (SEQ ID NO: 47), with the proviso that if the donor domain of the first member of the naturally occurring immunoglobulin super-family is the TCR constant domain alpha (SEQ ID NO: 1), the donor domain of the second member of the naturally occurring immunoglobulin super-family is the TCR constant domain beta (SEQ ID NO: 2) and if the donor domain of the first member of the naturally occurring immunoglobulin super-family is the TCR constant domain delta (SEQ ID NO: 32), the donor domain of the second member of the naturally occurring immunoglobulin super-family is the TCR constant domain gamma (SEQ ID NO: 33).

In some embodiments the donor domain of the first member of the naturally occurring immunoglobulin super-family is the TCR constant domain alpha (SEQ ID NO: 1) or the TCR constant domain delta (SEQ ID NO: 32), the donor domain of the second member of the naturally occurring immunoglobulin super-family is the TCR constant domain beta (SEQ ID NO: 2) or the TCR constant domain gamma (SEQ ID NO: 33), the donor domain of the third and the fourth member of the naturally occurring immunoglobulin super-family is the human IGHA1 CH3 domain (SEQ ID NO: 96) or the human IGHA2 CH3 domain (SEQ ID NO: 97), with the proviso that if the first member of the naturally occurring immunoglobulin super-family is the TCR constant domain alpha (SEQ ID NO: 1), the donor domain of the second member of the naturally occurring immunoglobulin super-family is the TCR constant domain beta (SEQ ID NO: 2) and if the donor domain of the first member of the naturally occurring immunoglobulin super-family is the TCR constant domain delta (SEQ ID NO: 32), the donor domain of the second member of the naturally occurring immunoglobulin super-family is the TCR constant domain gamma (SEQ ID NO: 33).

In some embodiments the protein-protein interface of the engineered domain of the first engineered immunoglobulin chain is interacting with the protein-protein interface of the engineered domain of the second engineered immunoglobulin chain by hetero-dimerization.

In some embodiments the protein-protein interface of the engineered domain of the first engineered immunoglobulin chain is interacting with the protein-protein interface of the engineered domain of the second engineered immunoglobulin chain by homo-dimerization.

In some embodiments the parent domain of the first engineered immunoglobulin chain is an IGKC domain and the amino acid residue which is substituted in the protein-protein interface of the parent domain of the engineered domain of the first engineered immunoglobulin chain comprises an amino acid residue at a position selected from the group consisting of 114, 116, 118, 123, 124, 131, 133, 137, 138, 160, 162, 164, 165, 167, 174, 176, 178, and 180, wherein the amino acid position of each group member is indicated according to the EU numbering.

In some embodiments the parent domain of the first engineered immunoglobulin chain is an IGLC domain selected from the group consisting of IGLC1, IGLC2, IGLC3, IGLC6, and IGLC7 and the amino acid residue which is substituted in the protein-protein interface of the parent domain of the first engineered immunoglobulin chain comprises an amino acid residue at a position selected from the group consisting of 114, 116, 118, 122, 131, 133, 137, 138, 160, 162, 165, 167, 174, 176, 178, and 180, wherein the amino acid position of each group member is indicated according to the Kabat numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of S131V, S131T, S131A, S131N, S131Q, S131E, S131K, S131W, V133A, V133G, V133T, V133L, V133I, N137Q, N137T, N137K, N137V, N137S, N137R, N137E, S174T, S174M, S174A, S174R, S174H, S174K, S174W, S174F, S174C, S174N, S176I, S176T, S176H, S176Q, S176V, S176W, S176Y, S176F, T178Q, T178L, T178V, T178R, T178E, T178I, T178K, T178Y, and T178W, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of S114E, S114K, S114Q, F116A, F116T, F116Y, F118M, F118L, E123D, Q124E, S131K, S131T, S131N, V133L, V133A, V133T, N137T, N137E, N137K, N138K, N138E, Q160Y, Q160F, Q160K, S162A, S162G, S162D, S162T, T164V, T164M, E165L, D167E, D167S, S174A, S174M, S174N, S174F, S176F, S176V, S176Y, T178W, T178R, T178L, T178K, T180N, T180R, and T180K or is selected from the group consisting of S114E, S114K, S114Q, F116A, F116T, F116Y, F118M, F118L, E123D, Q124E, S131K, S131T, S131N, V133L, V133A, V133T, N137T, N137E, N137K, N138K, N138E, Q160Y, Q160F, Q160K, S162A, S162G, S162D, S162T, T164V, T164M, E165L, D167E, D167S, S174A, S174M, S174N, S174F, S176F, S176V, S176Y, T178W, T178R, T178L, T178K, T180N, T180R, and T180K and conservative amino acid substitutions thereof, wherein the amino acid position of each group member is indicated according to the EU numbering.

In some embodiments the parent domain of the first engineered immunoglobulin chain is an IGLC domain selected from the group consisting of IGLC1, IGLC2, IGLC3, IGLC6, and IGLC7 and the amino acid residue which is substituted in the protein-protein interface of the parent domain of the first engineered immunoglobulin chain comprises an amino acid residue selected from the group consisting of 131V, 131A, 131N, 131Q, 131E, 131K, 131W, 131S, 133A, 133G, 133T, 133L, 133I, 137Q, 137T, 137K, 137V, 137R, 137N, 137E, 174T, 174M, 174S, 174R, 174H, 174K, 174W, 174F, 174C, 174N, 176I, 176T, 176H, 176Q, 176W, 176Y, 176V, 176F, 178Q, 178L, 178V, 178R, 178E, 178T, 178I, 178K, 178E, and 178W, wherein the amino acid position of each group member is indicated according to the Kabat numbering.

In some embodiments the parent domain of the first engineered immunoglobulin chain is an IGLC domain selected from the group consisting of IGLC1, IGLC2, IGLC3, IGLC6, and IGLC7 and the amino acid residue which is substituted in the protein-protein interface of the parent domain of the first engineered immunoglobulin chain comprises an amino acid residue selected from the group consisting of 114E, 114K, 114Q, 116A, 116Y, 118M, 118L, 122D, 131K, 131N, 133A, 133L, 133T, 137T, 137E, 137K, 138E, 138K, 160Y, 160F, 160K, 162D, 162A, 162G, 165L, 165M, 167E, 167S, 174N, 174M, 174F, 174S, 176V, 176F, 176Y, 178W, 178R, 178L, 178K, 180N, 180R, and 180K or selected from the group consisting of 114E, 114K, 114Q, 116A, 116Y, 118M, 118L, 122D, 131K, 131N, 133A, 133L, 133T, 137T, 137E, 137K, 138E, 138K, 160Y, 160F, 160K, 162D, 162A, 162G, 165L, 165M, 167E, 167S, 174N, 174M, 174F, 174S, 176V, 176F, 176Y, 178W, 178R, 178L, 178K, 180N, 180R, and 180K and conservative amino acid substitutions thereof, wherein the amino acid position of each group member is indicated according to the Kabat numbering.

In some embodiments the parent domain of the second engineered immunoglobulin chain is a CH1 domain and the amino acid residue which is substituted in the protein-protein interface of the parent domain of the second engineered immunoglobulin chain comprises an amino acid residue at a position selected from the group consisting of 124, 126, 128, 133, 134, 139, 141, 143, 147, 148, 168, 170, 173, 175, 181, 183, 185, and 187, wherein the amino acid position of each group member is indicated according to the EU numbering.

In some embodiments the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of 141V, 141T, 141N, 141Q, 141E, 141K, 141W, 141S, 143A, 143T, 143L, 143I, 143V, 147Q, 147T, 147V, 147S, 147R, 147N, 147E, 181I, 181M, 181A, 181R, 181H, 181K, 181W, 181F, 181C, 181N, 183I, 183H, 183Q, 183V, 183T, 183W, 183Y, 183F, 185Q, 185L, 185R, 185E, 185I, 185T, 185K, 185Y, and 185W, wherein the amino acid position of each group member is indicated according to the EU numbering.

In some embodiments the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of S124E, S124K, S124Q, F126A, F126T, F126Y, L128F, L128M, K133D, S134E, T139Q, A141K, A141T, A141N, A141S, G143V, G143A, G143L, G143T, K147T, K147E, D148E, D148K, H168Y, H168F, H168K, F170D, F170A, F170G, F170T, V173L, V173M, Q175E, Q175S, Q175D, S181A, S181N, S181M, S181F, S183V, S183F, S183Y, V185W, V185R, V185L, V185K, T187N, T187K and T187R or is selected from the group consisting of S124E, S124K, S124Q, F126A, F126T, F126Y, L128F, L128M, K133D, S134E, T139Q, A141K, A141T, A141N, A141S, G143V, G143A, G143L, G143T, K147T, K147E, D148E, D148K, H168Y, H168F, H168K, F170D, F170A, F170G, F170T, V173L, V173M, Q175E, Q175S, Q175D, S181A, S181N, S181M, S181F, S183V, S183F, S183Y, V185W, V185R, V185L, V185K, T187N, T187K and T187R and conservative amino acid substitutions thereof, wherein the amino acid position of each group member is indicated according to the EU numbering.

Positions 114, 116, 118, 122, 131, 133, 137, 138, 160, 162, 165, 167, 174, 176, 178, and 180 in the protein-protein interface of an IGLC domain as parent domain according to Kabat numbering correspond in the same order to positions 3, 5, 7, 11, 20, 22, 26, 27, 79, 81, 84, 84.2, 85.1, 86, 88, and 90 indicated according to the IMGT® numbering.

Positions 114, 116, 118, 123, 124, 131, 133, 137, 138, 160, 162, 164, 165, 167, 174, 176, 178, and 180 in the protein-protein interface of the IGKC domain as parent domain according to EU numbering correspond in the same order to positions 3, 5, 7, 12, 13, 20, 22, 26, 27, 79, 81, 83, 84, 84.2, 85.1, 86, 88, and 90 indicated according to the IMGT® numbering.

Positions 124, 126, 128, 133, 134, 139, 141, 143, 147, 148, 168, 170, 173, 175, 181, 183, 185, and 187 in the protein-protein interface of the CH1 domain as parent domain according to EU numbering correspond in the same order to positions 3, 5, 7, 12, 13, 18, 20, 22, 26, 27, 79, 81, 84, 84.2, 85.1, 86, 88, and 90 indicated according to the IMGT® numbering.

Positions 124, 126, 128, 133, 134, 139, 141, 143, 147, 148, 168, 170, 173, 175, 181, 183, 185, and 187 in the protein-protein interface of the CH4 domain as parent domain according to EU numbering correspond in the same order to positions 3, 5, 7, 12, 13, 18, 20, 22, 26, 27, 79, 81, 84, 84.2, 85.1, 86, 88, and 90 indicated according to the IMGT® numbering.

Thus equivalently in some embodiments the present disclosure provides a hetero-dimeric immunoglobulin or fragment thereof, wherein the parent domain of the engineered domain of the first engineered immunoglobulin chain is an IGKC domain and the amino acid residue which is substituted in the protein-protein interface of the parent domain of the engineered domain of the first engineered immunoglobulin chain comprises an amino acid residue at a position selected from the group consisting of 3, 5, 7, 12, 13, 20, 22, 26, 27, 79, 81, 83, 84, 84.2, 85.1, 86, 88, and 90, wherein the amino acid position of each group member is indicated according to the IMGT® numbering.

Thus equivalently in some embodiments the present disclosure provides a hetero-dimeric immunoglobulin or fragment thereof, wherein the parent domain of the first engineered immunoglobulin chain is an IGLC domain selected from the group consisting of IGLC1, IGLC2, IGLC3, IGLC6, and IGLC7 and the amino acid residue which is substituted in the protein-protein interface of the parent domain of the first engineered immunoglobulin chain comprises an amino acid residue at a position selected from the group consisting of 3, 5, 7, 11, 20, 22, 26, 27, 79, 81, 84, 84.2, 85.1, 86, 88, and 90, wherein the amino acid position of each group member is indicated according to the IMGT® numbering.

Thus equivalently in some embodiments the present disclosure provides a hetero-dimeric immunoglobulin or fragment thereof, wherein the parent domain of the engineered domain of the second engineered immunoglobulin chain is a CH1 domain and the amino acid residue which is substituted in the protein-protein interface of the parent domain of the engineered domain of the second engineered immunoglobulin chain comprises an amino acid residue at a position selected from the group consisting of 3, 5, 7, 12, 13, 18, 20, 22, 26, 27, 79, 81, 84, 84.2, 85.1, 86, 88, and 90, wherein the amino acid position of each group member is indicated according to the IMGT® numbering.

Thus equivalently in some embodiments the present disclosure provides a hetero-dimeric immunoglobulin or fragment thereof, wherein the parent domain of the engineered domain of the first and/or second engineered immunoglobulin chain is a CH4 domain and the amino acid residue which is substituted in the protein-protein interface of the parent domain of the engineered domain of the first and/or second engineered immunoglobulin chain comprises an amino acid residue at a position selected from the group consisting of 3, 5, 7, 12, 13, 18, 20, 22, 26, 27, 79, 81, 84, 84.2, 85.1, 86, 88, and 90, wherein the amino acid position of each group member is indicated according to the IMGT® numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue at a position selected from the group consisting of 131, 137, 160, 176, 178, and 180, and/or the parent domain of the second engineered immunoglobulin chain is a CH1 domain and the amino acid residue which is substituted in the protein-protein interface of the parent domain of the second engineered immunoglobulin chain comprises an amino acid residue at a position selected from the group consisting of 124, 126, 128, 141, 143, 147, 170, 173, 175, 181, 185, and 187, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises the amino acid residue at position 178 or comprises T178W or comprises T178W and conservative amino acid substitutions thereof, and optionally a further amino acid residue selected from the group consisting of 131, 137, 160, 176, and 180, and/or the parent domain of the second engineered immunoglobulin chain is a CH1 domain and the amino acid residue which is substituted in the protein-protein interface of the parent domain of the second engineered immunoglobulin chain comprises an amino acid residue at position 181 or comprises S181A or comprises S181A and conservative amino acid substitutions thereof and optionally a further amino acid residue selected from the group consisting of 124, 126, 128, 141, 143, 147, 170, 173, 175, 185, and 187, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of S131K, N137T, Q160Y, S176V, T178W, and T180N or comprises an amino acid residue selected from the group consisting of S131K, N137T, Q160Y, S176V, T178W, and T180N and conservative amino acid substitutions thereof, and/or the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of S124E, F126A, L128F, A141T, G143V, K147T, F170D, V173L, Q175E, S181A, V185R or comprises an amino acid residue selected from the group consisting of S124E, F126A, L128F, A141T, G143V, K147T, F170D, V173L, Q175E, 5181A, V185R and T187R and conservative amino acid substitutions thereof, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue at a position selected from the group consisting of 114, 116, 131, 137, 162, 165, 167, 174, 178, and 180, and/or the parent domain of the second engineered immunoglobulin chain is a CH1 domain and the amino acid residue which is substituted in the protein-protein interface of the parent domain of the second engineered immunoglobulin chain comprises an amino acid residue at a position selected from the group consisting of 141, 143, 147, 168, 183, 185 and 187, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue at position 174 or comprises S174A or comprises S174A and conservative amino acid substitutions thereof and optionally a further amino acid residue selected from the group consisting of 114, 116, 131, 137, 162, 165, 167, 178, and 180, and/or the parent domain of the second engineered immunoglobulin chain is a CH1 domain and the amino acid residue which is substituted in the protein-protein interface of the parent domain of the second engineered immunoglobulin chain comprises an amino acid residue at position 185 or comprises V185W or comprises V185W and conservative amino acid substitutions thereof and optionally a further amino acid residue selected from the group consisting of 141, 143, 147, 168, 183, and 187, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of S114E, F116A, S131T, N137T, S162D, E165L, D167E, S174A, T178R, and T180R or comprises an amino acid residue selected from the group consisting of S114E, F116A, S131T, N137T, S162D, E165L, D167E, S174A, T178R, and T180R and conservative amino acid substitutions thereof, and/or the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of A141K, G143V, K147T, H168Y, S183V, V185W, and T187N or comprises an amino acid residue selected from the group consisting of A141K, G143V, K147T, H168Y, S183V, V185W, and T187N and conservative amino acid substitutions thereof, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue at a position selected from the group consisting of 114, 116, 131, 133, 137, 138, 162, 164, 174, 176, 178 and 180, and/or the parent domain of the second engineered immunoglobulin chain is a CH1 domain and the amino acid residue which is substituted in the protein-protein interface of the parent domain of the second engineered immunoglobulin chain comprises an amino acid residue at a position selected from the group consisting of 128, 141, 143, 148, 168, 170, 175, 181, 183, 185, and 187, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises the amino acid residue at position 178 or comprises T178W or comprises T178W and conservative amino acid substitutions thereof and optionally a further amino acid residue selected from the group consisting of 114, 116, 131, 133, 137, 138, 162, 164, 174, and 176, and/or the parent domain of the second engineered immunoglobulin chain is a CH1 domain and the amino acid residue which is substituted in the protein-protein interface of the parent domain of the second engineered immunoglobulin chain comprises an amino acid residue at position 183 or comprises S183V or comprises S183V and conservative amino acid substitutions thereof and optionally a further amino acid residue selected from the group consisting of 128, 141, 143, 148, 168, 170, 175, 181, 185, and 187, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of S114K, F116T, S131T, V133L, N137E, N138K, S162G, T164M, S174M, S176F, and T178W or comprises an amino acid residue selected from the group consisting of S114K, F116T, S131T, V133L, N137E, N138K, S162G, T164M, S174M, S176F, and T178W and conservative amino acid substitutions thereof, and/or the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of L128M, A141N, G143A, D148E, H168F, F170A, Q175S, S181N, S183V, V185L, and T187K or comprises an amino acid residue selected from the group consisting of L128M, A141N, G143A, D148E, H168F, F170A, Q175S, S181N, S183V, V185L, and T187K and conservative amino acid substitutions thereof, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue at a position selected from the group consisting of 118, 131, 133, 138, 160, 162, 167, 174, 176, 178, and 180 and/or the parent domain of the second engineered immunoglobulin chain is a CH1 domain and the amino acid residue which is substituted in the protein-protein interface of the parent domain of the second engineered immunoglobulin chain comprises an amino acid residue at a position selected from the group consisting of 124, 126, 141, 143, 147, 148, 170, 173, 181, 183 and 185, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the engineered domain of the first engineered immunoglobulin chain comprises the amino acid residue at position 176 or comprises S176V or comprises S176V and conservative amino acid substitutions thereof and optionally a further amino acid residue selected from the group consisting of 118, 131, 133, 138, 160, 162, 167, 174, 178, 180, and/or the parent domain of the second engineered immunoglobulin chain is a CH1 domain and the amino acid residue which is substituted in the protein-protein interface of the parent domain of the second engineered immunoglobulin chain comprises the amino acid residue at position 185 or comprises V185W or comprises V185W and conservative amino acid substitutions thereof and optionally a further amino acid residue selected from the group consisting of 124, 126, 141, 143, 147, 148, 170, 173, 181, and 183, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of F118M, S131N, V133A, N138E, Q160F, S162A, D167S, S174N, S176V, T178L, and T180K or comprises an amino acid residue selected from the group consisting of F118M, S131N, V133A, N138E, Q160F, S162A, D167S, S174N, S176V, T178L, and T180K and conservative amino acid substitutions thereof and/or the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of S124K, F126T, A141T, G143L, K147E, D148K, F170G, V173M, S181M, S183F, and V185W or comprises an amino acid residue selected from the group consisting of S124K, F126T, A141T, G143L, K147E, D148K, F170G, V173M, S181M, S183F, and V185W and conservative amino acid substitutions thereof, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue at a position selected from the group consisting of 114, 116, 118, 123, 124, 133, 137, 160, 162, 164, 174, 176, and 178, and/or the parent domain of the second engineered immunoglobulin chain is a CH1 domain and the amino acid residue which is substituted in the protein-protein interface of the parent domain of the second engineered immunoglobulin chain comprises an amino acid residue at a position selected from the group consisting of 124, 126, 133, 134, 139, 141, 143, 168, 170, 175, 181, 183, and 185, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises the amino acid residue at position 176 or comprises S176Y or comprises S176Y and conservative amino acid substitutions thereof and optionally a further amino acid residue selected from the group consisting of 114, 116, 118, 123, 124, 133, 137, 160, 162, 164, 174, and 178, and/or the parent domain of the second engineered immunoglobulin chain is a CH1 domain and the amino acid residue which is substituted in the protein-protein interface of the parent domain of the second engineered immunoglobulin chain comprises the amino acid residue at position 183 or comprises S183Y or comprises S183Y and conservative amino acid substitutions thereof and optionally a further amino acid residue selected from the group consisting of 124, 126, 133, 134, 139, 141, 143, 168, 170, 175, 181, and 185, wherein the amino acid position of each group member is indicated according to the EU numbering.

In some embodiments the parent domain of the first engineered immunoglobulin chain is an IGKC domain and the amino acid residue which is substituted in the protein-protein interface of the parent domain of the first engineered immunoglobulin chain comprises an amino acid residue selected from the group consisting of S114Q, F116Y, F118L, E123D, Q124E, V133T, N137K, Q160K, S162T, T164V, S174F, S176Y, and T178K or comprises an amino acid residue selected from the group consisting of S114Q, F116Y, F118L, E123D, Q124E, V133T, N137K, Q160K, S162T, T164V, S174F, S176Y, and T178K and conservative amino acid substitutions thereof, and/or the parent domain of the second engineered immunoglobulin chain is a CH1 domain and the amino acid residue which is substituted in the protein-protein interface of the parent domain of the second engineered immunoglobulin chain comprises an amino acid residue selected from the group consisting of S124Q, F126Y, K133D, S134E, T139Q, A141S, G143T, H168K, F170T, Q175D, S181F, S183Y, and V185K or comprises an amino acid residue selected from the group consisting of S124Q, F126Y, K133D, S134E, T139Q, A141S, G143T, H168K, F170T, Q175D, S181F, S183Y, and V185K and conservative amino acid substitutions thereof, wherein the amino acid position of each group member is indicated according to the EU numbering.

In some embodiments the parent domain of the first engineered immunoglobulin chain is a CH1 domain and the parent domain of the second engineered immunoglobulin chain is a IGKC domain, wherein the amino acid residue which are substituted in the protein-protein interface of the parent domain of the first engineered immunoglobulin chain comprises V185W and S183V or comprises V185W and S183V and conservative amino acid substitutions thereof, and/or wherein the amino acid residues which are substituted in the protein-protein interface of the parent domain of the second engineered immunoglobulin chain comprises S174A or S174A and conservative amino acid substitutions thereof and/or a further amino acid selected from the group consisting of S114E, F116A, F118F, S131T, N137T, S162D, E165L, D167E, T178R, T180R or selected from the group consisting of S114E, F116A, F118F, S131T, N137T, S162D, E165L, D167E, T178R, T180R and conservative amino acid substitutions thereof, wherein the amino acid position is indicated according to the EU numbering.

In some embodiments the parent domain of the first engineered immunoglobulin chain is an IGKC domain and the parent domain of the second engineered immunoglobulin chain is a CH1 domain, wherein the amino acid residues which are substituted in the protein-protein interface of the parent domain of the first engineered immunoglobulin chain comprises S176F and/or T178W or comprises S176F and/or T178W and conservative amino acid substitutions thereof, and/or wherein the amino acid residues which are substituted in the protein-protein interface of the parent domain of the second engineered immunoglobulin chain comprises H168F and/or F170A or comprises H168F and/or F170A and conservative amino acid substitutions thereof, wherein the amino acid position is indicated according to the EU numbering.

In some embodiments the parent domain of the first engineered immunoglobulin chain is an IGKC domain and the parent domain of the second engineered immunoglobulin chain is a CH1 domain, wherein the amino acid residues which are substituted in the protein-protein interface of the parent domain of the first engineered immunoglobulin chain comprises T178W or comprises T178W and conservative amino acid substitutions thereof, and/or wherein the amino acid residues which are substituted in the protein-protein interface of the parent domain of the second engineered immunoglobulin chain comprises L128M or comprises L128M and conservative amino acid substitutions thereof, wherein the amino acid position is indicated according to the EU numbering.

In some embodiments the parent domain of the first engineered immunoglobulin chain is an IGKC domain and the parent domain of the second engineered immunoglobulin chain is a CH1 domain, wherein the amino acid residues which are substituted in the protein-protein interface of the parent domain of the first engineered immunoglobulin chain comprises T178W or comprises T178W and conservative amino acid substitutions thereof, and/or wherein the amino acid residues which are substituted in the protein-protein interface of the parent domain of the second engineered immunoglobulin chain comprises F170A or comprises F170A and conservative amino acid substitutions thereof, wherein the amino acid position is indicated according to the EU numbering.

In some embodiments the parent domain of the first engineered immunoglobulin chain is a CH1 domain and the parent domain of the second engineered immunoglobulin chain is an IGKC domain, wherein the amino acid residues which are substituted in the protein-protein interface of the parent domain of the first engineered immunoglobulin chain comprises S183Y or S183Y and conservative amino acid substitutions thereof and a further amino acid selected from the group consisting of S124Q, F126Y, K133D, S134E, T139Q, A141S, G143T, H168K, F170T, Q175D, S181F, and V185K or selected from the group consisting of S124Q, F126Y, K133D, S134E, T139Q, A141S, G143T, H168K, F170T, Q175D, S181F, and V185K and conservative amino acid substitutions thereof, and/or wherein the amino acid residues which are substituted in the protein-protein interface of the parent domain of the second engineered immunoglobulin chain comprises S174F and/or S176Y or comprises S174F and/or S176Y and conservative amino acid substitutions thereof, wherein the amino acid position is indicated according to the EU numbering.

In some embodiments the parent domain of the first engineered immunoglobulin chain is a CH1 domain and the parent domain of the second engineered immunoglobulin chain is an IGKC domain, wherein the amino acid residues which are substituted in the protein-protein interface of the parent domain of the first engineered immunoglobulin chain comprises S183Y or S183Y and conservative amino acid substitutions thereof and a further amino acid selected from the group consisting of S124Q, F126Y, K133D, S134E, T139Q, A141S, G143T, H168K, F170T, Q175D, S181F, and V185K or selected from the group consisting of S124Q, F126Y, K133D, S134E, T139Q, A141S, G143T, H168K, F170T, Q175D, S181F, and V185K and conservative amino acid substitutions thereof, and/or wherein the amino acid residues which are substituted in the protein-protein interface of the parent domain of the second engineered immunoglobulin chain comprises S162T or S162T and conservative amino acid substitutions thereof and a further amino acid selected from the group consisting of S114Q, F116Y, F118L, E123D, Q124E, V133T, N137K, Q160K, T164V, S174F, S176Y, and T178K or selected from the group consisting of S114Q, F116Y, F118L, E123D, Q124E, V133T, N137K, Q160K, T164V, S174F, S176Y, and T178K and conservative amino acid substitutions thereof, wherein the amino acid position is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at a position selected from the group consisting of 114, 116, 118, 123, 124, 131, 133, 137, 138, 160, 162, 164, 165, 167, 174, 176, 178, and 180, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue selected from the group consisting of S114E, S114K, S114Q, F116A, F116T, F116Y, F118M, F118L, E123D, Q124E, S131K, S131T, S131N, V133L, V133A, V133T, N137T, N137E, N137K, N138K, N138E, Q160Y, Q160F, Q160K, S162A, S162G, S162D, S162T, T164V, T164M, E165L, D167E, D167S, S174A, S174M, S174N, S174F, S176V, S176F, S176Y, T178W, T178R, T178L, T178K, T180N, T180R, and T180K or comprises an amino acid residue selected from the group consisting of S114E, S114K, S114Q, F116A, F116T, F116Y, F118M, F118L, E123D, Q124E, S131K, S131T, S131N, V133L, V133A, V133T, N137T, N137E, N137K, N138K, N138E, Q160Y, Q160F, Q160K, S162A, S162G, S162D, S162T, T164V, T164M, E165L, D167E, D167S, S174A, S174M, S174N, S174F, S176V, S176F, S176Y, T178W, T178R, T178L, T178K, T180N, T180R, and T180K and conservative amino acid substitutions thereof, wherein the amino acid position of each group member is indicated according to the EU numbering.

In some embodiments the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at a position selected from the group consisting of 124, 126, 128, 133, 134, 139, 141, 143, 147, 148, 168, 170, 173, 175, 181, 183, 185, and 187, wherein the amino acid position of each group member is indicated according to the EU numbering.

In some embodiments the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue selected from the group consisting of S124E, S124K, S124Q, F126A, F126T, F126Y, L128F, L128M, K133D, S134E, T139Q, A141K, A141T, A141N, A141S, G143V, G143A, G143L, G143T, K147T, K147E, D148E, D148K, H168Y, H168F, H168K, F170D, F170A, F170G, F170T, V173L, V173M, Q175E, Q175S, Q175D, S181A, S181N, S181M, S181F, S183V, S183F, S183Y, V185W, V185R, V185L, V185K, T187N, T187K and T187R or comprises an amino acid residue selected from the group consisting of S124E, S124K, S124Q, F126A, F126T, F126Y, L128F, L128M, K133D, S134E, T139Q, A141K, A141T, A141N, A141S, G143V, G143A, G143L, G143T, K147T, K147E, D148E, D148K, H168Y, H168F, H168K, F170D, F170A, F170G, F170T, V173L, V173M, Q175E, Q175S, Q175D, S181A, S181N, S181M, S181F, S183V, S183F, S183Y, V185W, V185R, V185L, V185K, T187N, T187K and T187R and conservative amino acid substitutions thereof, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at a position selected from the group consisting of 131, 137, 160, 176, 178, and 180, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at a position selected from the group consisting of 124, 126, 128, 141, 143, 147, 170, 173, 175, 181, 185, and 187, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at position 178 or comprises T178W or comprises T178W and conservative amino acid substitutions thereof and optionally a further amino acid residue selected from the group consisting of 131, 137, 160, 176, 180, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at position 181 or comprises S181A or comprises S181A and conservative amino acid substitutions thereof and optionally a further amino acid residue selected from the group consisting of 124, 126, 128, 141, 143, 147, 170, 173, 175, 185, and 187, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue selected from the group consisting of S131K, N137T, Q160Y, S176V, T178W, T180N or comprises an amino acid residue selected from the group consisting of S131K, N137T, Q160Y, S176V, T178W, T180N and conservative amino acid substitutions thereof, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue selected from the group consisting of S124E, F126A, L128F, A141T, G143V, K147T, F170D, V173L, Q175E, S181A, V185R, and T187R or are selected from the group consisting of S124E, F126A, L128F, A141T, G143V, K147T, F170D, V173L, Q175E, S181A, V185R, and T187R and conservative amino acid substitutions thereof, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at a position selected from the group consisting of 114, 116, 131, 137, 162, 165, 167, 174, 176, 178, 180, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at a position selected from the group consisting of 141, 143, 147, 168, 183, 185 and 187, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises the amino acid residue at position 174 or comprises 174A or comprises 174A and conservative amino acid substitutions thereof and optionally a further amino acid residue selected from the group consisting of 114, 116, 131, 137, 162, 165, 167, 178, and 180, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at position 185 or comprises V185W or comprises V185W and conservative amino acid substitutions thereof and optionally a further amino acid residue selected from the group consisting of 141, 143, 147, 168, 183, and 187, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue selected from the group consisting of S114E, F116A, S131T, N137T, S162D, E165L, D167E, S174A, T178R, T180R or comprises an amino acid residue selected from the group consisting of S114E, F116A, S131T, N137T, S162D, E165L, D167E, S174A, T178R, T180R and conservative amino acid substitutions thereof, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue selected from the group consisting of A141K, G143V, K147T, H168Y, S183V, V185W, and T187N or comprises an amino acid residue selected from the group consisting of A141K, G143V, K147T, H168Y, S183V, V185W, and T187N and conservative amino acid substitutions thereof, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at a position selected from the group consisting of 114, 116, 131, 133, 137, 138, 162, 164, 174, 176, and 178, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at a position selected from the group consisting of 128, 141, 143, 148, 168, 170, 175, 181, 183, 185, and 187, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises the amino acid residue at position 178 or comprises T178W or comprises T178W and conservative amino acid substitutions thereof and optionally a further amino acid residue selected from the group consisting of 114, 116, 131, 133, 137, 138, 162, 164, 174, and 176, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at position 183 or comprises S183V or comprises S183V and conservative amino acid substitutions thereof and optionally a further amino acid residue selected from the group consisting of 128, 141, 143, 148, 168, 170, 175, 181, 185, and 187, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue selected from the group consisting of S114K, F116T, S131T, V133L, N137E, N138K, S162G, T164M, S174M, S176F, and T178W or comprises an amino acid residue selected from the group consisting of S114K, F116T, S131T, V133L, N137E, N138K, S162G, T164M, S174M, S176F, and T178W and conservative amino acid substitutions thereof, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue selected from the group consisting of L128M, A141N, G143A, D148E, H168F, F170A, Q175S, S181N, S183V, V185L, and T187K or comprises an amino acid residue selected from the group consisting of L128M, A141N, G143A, D148E, H168F, F170A, Q175S, S181N, S183V, V185L, and T187K and conservative amino acid substitutions thereof, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at a position selected from the group consisting of 118, 131, 133, 138, 160, 162, 167, 174, 176, 178, and 180 and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at a position selected from the group consisting of 124, 126, 141, 143, 147, 148, 170, 173, 181, 183 and 185, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises the amino acid residue at position 176 or comprises S176V or comprises S176V and conservative amino acid substitutions thereof and optionally a further amino acid residue selected from the group consisting of 118, 131, 133, 138, 160, 162, 167, 174, 178, 180, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at position 185 or comprises V185W or comprises V185W and conservative amino acid substitutions thereof and optionally a further amino acid residue selected from the group consisting of 124, 126, 141, 143, 147, 148, 170, 173, 181, and 183, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue selected from the group consisting of F118M, S131N, V133A, N138E, Q160F, S162A, D167S, S174N, S176V, and T178L or comprises an amino acid residue selected from the group consisting of F118M, S131N, V133A, N138E, Q160F, S162A, D167S, S174N, S176V, and T178L and conservative amino acid substitutions thereof, and T180K and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue selected from the group consisting of S124K, F126T, A141T, G143L, K147E, D148K, F170G, V173M, S181M, S183F, and V185W or comprises an amino acid residue selected from the group consisting of S124K, F126T, A141T, G143L, K147E, D148K, F170G, V173M, S181M, S183F, and V185W and conservative amino acid substitutions thereof, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue at a position selected from the group consisting of 114, 116, 118, 123, 124, 133, 137, 160, 162, 164, 174, 176, and 178, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue at a position selected from the group consisting of 124, 126, 133, 134, 139, 141, 143, 168, 170, 175, 181, 183, and 185, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises the amino acid residue at position 176 or comprises S176Y or comprises S176Y and conservative amino acid substitutions thereof and optionally a further amino acid residue selected from the group consisting of 114, 116, 118, 123, 124, 133, 137, 160, 162, 164, 174, and 178, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises the amino acid residue at position 183 or comprises S183Y or comprises S183Y and conservative amino acid substitutions thereof and optionally a further amino acid residue selected from the group consisting of 124, 126, 133, 134, 139, 141, 143, 168, 170, 175, 181, and 185, wherein the amino acid position of each group member is indicated according to the EU numbering.

In some embodiments the parent domain of the engineered domain of the third engineered immunoglobulin chain is an IGKC domain and the amino acid residue which is substituted in the protein-protein interface of the parent domain of the engineered domain of the third engineered immunoglobulin chain comprises an amino acid residue selected from the group consisting of S114Q, F116Y, F118L, E123D, Q124E, V133T, N137K, Q160K, S162T, T164V, S174F, S176Y, and T178K or are selected from the group consisting of S114Q, F116Y, F118L, E123D, Q124E, V133T, N137K, Q160K, S162T, T164V, S174F, S176Y, and T178K and conservative amino acid substitutions thereof, and/or the parent domain of the further engineered domain of the first and/or second engineered immunoglobulin chain is a CH1 domain and the amino acid residue which is substituted in the protein-protein interface of the parent domain of the further engineered domain of the first and/or second engineered immunoglobulin chain comprises an amino acid residue selected from the group consisting of S124Q, F126Y, K133D, S134E, T139Q, A141S, G143T, H168K, F170T, Q175D, S181F, S183Y, and V185K or are selected from the group consisting of S124Q, F126Y, K133D, S134E, T139Q, A141S, G143T, H168K, F170T, Q175D, S181F, S183Y, and V185K and conservative amino acid substitutions thereof, wherein the amino acid position of each group member is indicated according to the EU numbering.

In some embodiments the parent domain of the further engineered domain of the first and/or second engineered immunoglobulin chain is a CH1 domain and the parent domain of the engineered domain of the third engineered immunoglobulin chain is a IGKC domain, wherein the amino acid residues which are substituted in the protein-protein interface of the parent domain of the further engineered domain of the first and/or second engineered immunoglobulin chain comprises V185W and S183V or comprises V185W and S183V and conservative amino acid substitutions thereof, and/or the amino acid residues which are substituted in the protein-protein interface of the parent domain of the engineered domain of the third engineered immunoglobulin chain comprises S174A or S174A and conservative amino acid substitutions thereof and/or a further amino acid selected from the group consisting of S114E, F116A, S131T, N137T, S162D, E165L, D167E, T178R, T180R or are selected from the group consisting of S114E, F116A, S131T, N137T, S162D, E165L, D167E, T178R, T180R and conservative amino acid substitutions thereof, wherein the amino acid position is indicated according to the EU numbering.

In some embodiments the parent domain of the engineered domain of the third engineered immunoglobulin chain is an IGKC domain and the parent domain of the further engineered domain of the first and/or second engineered immunoglobulin chain is a CH1 domain, wherein the amino acid residues which are substituted in the protein-protein interface of the parent domain of the engineered domain of the third engineered immunoglobulin chain comprises S176F and/or T178W or comprises S176F and/or T178W and conservative amino acid substitutions thereof, and/or wherein the amino acid residues which are substituted in the protein-protein interface of the parent domain of the further engineered domain of the first and/or second engineered immunoglobulin chain comprises H168F and/or F170A or comprises H168F and/or F170A and conservative amino acid substitutions thereof, wherein the amino acid position is indicated according to the EU numbering.

In some embodiments the parent domain of the engineered domain of the third engineered immunoglobulin chain is an IGKC domain and the parent domain of the further engineered domain of the first and/or second engineered immunoglobulin chain is a CH1 domain, wherein the amino acid residue which is substituted in the protein-protein interface of the parent domain of the engineered domain of the third engineered immunoglobulin chain comprises T178W or comprises T178W and conservative amino acid substitutions thereof, and/or wherein the amino acid residue which is substituted in the protein-protein interface of the parent domain of the further engineered domain of the first and/or second engineered immunoglobulin chain comprises L128M or comprises L128M and conservative amino acid substitutions thereof, wherein the amino acid position is indicated according to the EU numbering.

In some embodiments the parent domain of the engineered domain of the third engineered immunoglobulin chain is an IGKC domain and the parent domain of the further engineered domain of the first and/or second engineered immunoglobulin chain is a CH1 domain, wherein the amino acid residues which are substituted in the protein-protein interface of the parent domain of the engineered domain of the third engineered immunoglobulin chain comprises T178W or comprises T178W and conservative amino acid substitutions thereof, and/or wherein the amino acid residues which are substituted in the protein-protein interface of the parent domain of the further engineered domain of the first and/or second engineered immunoglobulin chain comprises F170A or comprises F170A and conservative amino acid substitutions thereof, wherein the amino acid position is indicated according to the EU numbering.

In some embodiments the parent domain of the further engineered domain of the first and/or second engineered immunoglobulin chain is a CH1 domain and the parent domain of the engineered domain of the third engineered immunoglobulin chain is an IGKC domain, wherein the amino acid residues which are substituted in the protein-protein interface of the parent domain of the further engineered domain of the first and/or second engineered immunoglobulin chain comprises S183Y or comprises S183Y and conservative amino acid substitutions thereof and a further amino acid selected from the group consisting of S124Q, F126Y, K133D, S134E, T139Q, A141S, G143T, H168K, F170T, Q175D, S181F, and V185K or are selected from the group consisting of S124Q, F126Y, K133D, S134E, T139Q, A141S, G143T, H168K, F170T, Q175D, S181F, and V185K and conservative amino acid substitutions thereof, and/or wherein the amino acid residues which are substituted in the protein-protein interface of the parent domain of the engineered domain of the third engineered immunoglobulin chain comprises S174F and/or S176Y or comprises S174F and/or S176Y and conservative amino acid substitutions thereof, wherein the amino acid position is indicated according to the EU numbering.

In some embodiments the parent domain of the further engineered domain of the first and/or second engineered immunoglobulin chain is a CH1 domain and the parent domain of the engineered domain of the third engineered immunoglobulin chain is an IGKC domain, wherein the amino acid residues which are substituted in the protein-protein interface of the parent domain of the further engineered domain of the first and/or second engineered immunoglobulin chain comprises S183Y or comprises S183Y and conservative amino acid substitutions thereof and a further amino acid selected from the group consisting of S124Q, F126Y, K133D, S134E, T139Q, A141S, G143T, H168K, F170T, Q175D, S181F, and V185K or are selected from the group consisting of S124Q, F126Y, K133D, S134E, T139Q, A141S, G143T, H168K, F170T, Q175D, S181F, and V185K and conservative amino acid substitutions thereof, and/or wherein the amino acid residues which are substituted in the protein-protein interface of the parent domain of the engineered domain of the third engineered immunoglobulin chain comprises S162T or comprises S162T and conservative amino acid substitutions thereof and a further amino acid selected from the group consisting of S114Q, F116Y, F118L, E123D, Q124E, V133T, N137K, Q160K, T164V, S174F, S176Y, and T178K or are selected from the group consisting of S114Q, F116Y, F118L, E123D, Q124E, V133T, N137K, Q160K, T164V, S174F, S176Y, and T178K and conservative amino acid substitutions thereof, wherein the amino acid position is indicated according to the EU numbering.

In some embodiments the present disclosure provides a hetero-dimeric immunoglobulin or fragment thereof, wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 88, and optionally a further amino acid residue at a position selected from the group consisting of 3, 5, 7, 20, 22, 26, 27, 79, 81, 84, 84.2, 85.1, 86, and 90 and, wherein the amino acid residue which is substituted in the protein-protein interface of the parent domain of the second engineered immunoglobulin chain comprises the amino acid residue at position 85.1 and/or 86 and optionally a further amino acid residue at a position selected from the group consisting of 3, 5, 7, 20, 22, 26, 27, 79, 81, 84, 84.2, 88, and 90 or at a position selected from the group consisting of 3, 5, 7, 20, 22, 26, 27, 79, 81, 84, 84.2, 85.1, 88, and 90 or at a position selected from the group consisting of 3, 5, 7, 20, 22, 26, 27, 79, 81, 84, 84.2, 86, 88, and 90, wherein the amino acid residue substituted at position 88 in the parent domain of the first engineered immunoglobulin chain is interacting with the amino acid residue substituted at position 85.1 and/or 86 in the parent domain of the second engineered immunoglobulin chain, wherein the amino acid position of each group member is indicated according to the IMGT® numbering.

Positions 3, 5, 7, 20, 22, 26, 27, 79, 81, 84, 84.2, 85.1, 86, 88 and 90 in the protein-protein interface of the CH3 domain as parent domain indicated according to IMGT® numbering correspond in the same order to positions 347, 349, 351, 364, 366, 370, 371, 392, 394, 397, 399, 405, 407, 409 and 411 indicated according to the EU numbering, In some embodiments the parent domain of the first and the second engineered immunoglobulin chain is a CH3 domain.

In some embodiments the parent domains of the first and the second engineered immunoglobulin chain are CH3 domains of different isotypes.

In some embodiments the parent domain of the first engineered immunoglobulin chain is an IgG1 CH3 domain, preferably a human CH3 domain from IGHG1 and the parent domain of the second engineered immunoglobulin chain is an IgG3 CH3 domain, preferably a human CH3 domain from IGHG3 or wherein the parent domain of the first engineered immunoglobulin chain is an IgG3 CH3 domain, preferably a human CH3 domain from IGHG3 and the parent domain of the second engineered immunoglobulin chain is an IgG1 CH3 domain preferably a human CH3 domain from IGHG1.

In some embodiments the amino acid residue which is substituted in the protein-protein interface of the parent domain of the second engineered immunoglobulin chain comprises the amino acid residue at position 85.1 and 86, wherein the amino acid position is indicated according to the IMGT® numbering.

In some embodiments the amino acid residue which is substituted in the protein-protein interface of the parent domain of the first engineered immunoglobulin chain at position 88 is not a charged amino acid, wherein the amino acid position is indicated according to the IMGT® numbering.

In some embodiments the amino acid residue which is substituted in the protein-protein interface of the parent domain of the first engineered immunoglobulin chain at position 88 is not 88I, wherein the amino acid position is indicated according to the IMGT® numbering.

In some embodiments the amino acid residue which is substituted in the protein-protein interface of the parent domain of the first engineered immunoglobulin chain at position 85.1 and/or 86 is not a charged amino acid, wherein the amino acid position is indicated according to the IMGT® numbering.

In some embodiments the amino acid residue which is substituted in the protein-protein interface of the parent domain of the first engineered immunoglobulin chain at position 88 and the amino acid residue which is substituted in the protein-protein interface of the parent domain of the first engineered immunoglobulin chain at position 85.1 and/or 86 are not a charged pair.

In some embodiments the amino acid residue which is substituted in the protein-protein interface of the parent domain of the first engineered immunoglobulin chain at position 88 is 88W or 88W and conservative amino acid substitutions thereof, wherein the amino acid position is indicated according to the IMGT® numbering In some embodiments the CH3 domain is a domain selected from the group consisting of human IgG1 (IGHG1), human IgG2 (IGHG2), human IgG3 (IGHG3) and human IgGP (IGHGP) and the amino acid residue which is substituted in the protein-protein interface of the parent domain of the first engineered immunoglobulin chain is K88W or K88W and conservative amino acid substitutions thereof and optionally a further amino acid residue selected from the group consisting of 3, 5, 7, 20, 22, 26, 27, 79, 81, 84, 84.2, 85.1, 86, and 90, wherein the amino acid position is indicated according to the IMGT® numbering.

In some embodiments the CH3 domain is a human IgA1 (IGHA1) or a IgA2 (IGHA2) CH3 domain and the amino acid residue which is substituted in the protein-protein interface of the parent domain of the first engineered immunoglobulin chain is 188W or 188W and conservative amino acid substitutions thereof and optionally a further amino acid residue selected from the group consisting of 3, 5, 7, 20, 22, 26, 27, 79, 81, 84, 84.2, 85.1, 86, and 90, wherein the amino acid position is indicated according to the IMGT® numbering.

In some embodiments the CH3 domain is a human IgD (IGHD) CH3 domain and the amino acid residue which is substituted in the protein-protein interface of the parent domain of the first engineered immunoglobulin chain is V88W or V88W and conservative amino acid substitutions thereof and optionally a further amino acid residue selected from the group consisting of 3, 5, 7, 20, 22, 26, 27, 79, 81, 84, 84.2, 85.1, 86, and 90, wherein the amino acid position is indicated according to the IMGT® numbering.

In some embodiments the CH3 domain is a human IgE CH3 (IGHE) domain and the amino acid residue which is substituted in the protein-protein interface of the parent domain of the first engineered immunoglobulin chain is T88W or T88W and conservative amino acid substitutions thereof and optionally a further amino acid residue selected from the group consisting of 3, 5, 7, 20, 22, 26, 27, 79, 81, 84, 84.2, 85.1, 86, and 90, wherein the amino acid position is indicated according to the IMGT® numbering.

In some embodiments the CH3 domain is a human IgG4 (IGHG4) CH3 domain and the amino acid residue which is substituted in the protein-protein interface of the parent domain of the first engineered immunoglobulin chain is R88W or R88W and conservative amino acid substitutions thereof and optionally a further amino acid residue selected from the group consisting of 3, 5, 7, 20, 22, 26, 27, 79, 81, 84, 84.2, 85.1, 86, and 90, wherein the amino acid position is indicated according to the IMGT® numbering.

In some embodiments the CH3 domain is a human IgM (IGHM) CH3 domain and the amino acid residue which is substituted in the protein-protein interface of the parent domain of the first engineered immunoglobulin chain is E88W or E88W and conservative amino acid substitutions thereof and optionally a further amino acid residue selected from the group consisting of 3, 5, 7, 20, 22, 26, 27, 79, 81, 84, 84.2, 85.1, 86, and 90, wherein the amino acid position is indicated according to the IMGT® numbering.

In some embodiments the amino acid residue which is substituted in the protein-protein interface of the parent domain of the first engineered immunoglobulin chain at position 88 is selected from the group consisting of 88Q, 88L, 88V, 88R, 88E, 88I, 88T, 88Y, 88K and 88W and/or the further amino acid residue substituted in the protein-protein interface of the parent domain of the first engineered immunoglobulin chain is selected from the group consisting of 20V, 20T, 20A, 20N, 20Q, 20E, 20S, 20K, 20W, 22A, 22G, 22T, 22L, 22I, 22V, 26R, 26Q, 26T, 26K, 26V, 26S, 26N, 26E, 85.1T, 85.1M, 85.1A, 85.1S, 85.1R, 85.1H, 85.1K, 85.1F, 85.1C, 85.1N, 85.1W, 86S, 86I, 86T, 86H, 86Q, 86V, 86W, 86Y and 86F, wherein the amino acid position of each group member is indicated according to the IMGT® numbering.

In some embodiments the amino acid residue which is substituted in the protein-protein interface of the parent domain of the first engineered immunoglobulin chain at position 88 is selected from the group consisting of 88Q, 88L, 88V, 88R, 88E, 88I, 88T, 88Y, and 88W, wherein the amino acid position is indicated according to the IMGT® numbering.

In some embodiments the further amino acid residue substituted in the protein-protein interface of the parent domain of the first engineered immunoglobulin chain is selected from the group consisting of 20V, 20T, 20A, 20N, 20Q, 20E, 20S, 22A, 22G, 22T, 22L, 22I, 22V, 26Q, 26T, 26K, 26V, 26S, 26N, 26E, 85.1T, 85.1M, 85.1A, 85.1S, 85.1R, 85.1H, 85.1K, 85.1F, 85.1C, 85.1N, 86S, 86I, 86T, 86H, 86Q, 86V, and 86F, wherein the amino acid position of each group member is indicated according to the IMGT® numbering.

In some embodiments the further amino acid residue substituted in the protein-protein interface of the parent domain of the first engineered immunoglobulin chain is selected from the group consisting of 20V, 20T, 20A, 20N, 20Q, 20E, 20S, 20K, 22A, 22G, 22T, 22L, 22I, 22V, 26Q, 26T, 26K, 26V, 26S, 26N, 26E, 85.1T, 85.1M, 85.1A, 85.1S, 85.1R, 85.1H, 85.1K, 85.1F, 85.1C, 85.1N, 86S, 86I, 86T, 86H, 86Q, 86V, and 86F, wherein the amino acid position of each group member is indicated according to the IMGT® numbering.

In some embodiments the amino acid residue which is substituted in the protein-protein interface of the parent domain of the first engineered immunoglobulin chain at position 88 is selected from the group consisting of 88Q, 88L, 88V, 88R, 88E, 88T, 88Y, and 88W, wherein the amino acid position is indicated according to the IMGT® numbering.

In some embodiments the further amino acid residue substituted in the protein-protein interface of the parent domain of the first engineered immunoglobulin chain is selected from the group consisting of 20V, 20A, 20N, 20Q, 20E, 20S, 22A, 22G, 22T, 22L, 22I, 22V, 26Q, 26T, 26K, 26V, 26S, 26N, 26E, 85.1T, 85.1M, 85.1S, 85.1R, 85.1H, 85.1K, 85.1F, 85.1C, 85.1N, 86S, 86I, 86H, 86Q, 86V, and 86F, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3E, 3K, 5A, 5T, 7F, 7M, 20K, 20N, 20T, 22A, 22L, 22V, 26E, 26T, 27E, 27K, 79F, 79Y, 81A, 81G, 81D, 84L, 84M, 84.2E, 84.2S, 85.1A, 85.1C, 85.1M, 85.1N, 85.1S, 86F, 86S, 86V, 90K, 90N, and 90R or is selected from the group consisting of 3E, 3K, 5A, 5T, 7F, 7M, 20K, 20N, 20T, 22A, 22L, 22V, 26E, 26T, 27E, 27K, 79F, 79Y, 81A, 81G, 81D, 84L, 84M, 84.2E, 84.2S, 85.1A, 85.1C, 85.1M, 85.1N, 85.1S, 86F, 86S, 86V, 90K, 90N, and 90R and conservative amino acid substitutions thereof, wherein the amino acid position of each group member is indicated according to the IMGT® numbering.

In some embodiments relating to a CH3 domain as parent domain of the first and/or the second engineered immunoglobulin chain the amino acid residue which is substituted in the protein-protein interface of the parent domain of the first engineered immunoglobulin chain is 88I and conservative amino acid substitutions thereof and the optional further amino acid residue which is substituted in the protein-protein interface of the parent domain of the first engineered immunoglobulin chain is 81W and conservative amino acid substitutions thereof, wherein the amino acid position is indicated according to the IMGT® numbering.

In some embodiments relating to a CH3 domain as parent domain of the first and/or the second engineered immunoglobulin chain the amino acid residue which is substituted in the protein-protein interface of the parent domain of the first engineered immunoglobulin chain is 88I and conservative amino acid substitutions thereof and the optional further amino acid residue which is substituted in the protein-protein interface of the parent domain of the first engineered immunoglobulin chain is 81W and conservative amino acid substitutions and/or the optional further amino acid residue or an additional further amino acid residue which is substituted in the protein-protein interface of the parent domain of the second engineered immunoglobulin chain is 86T and conservative amino acid substitutions thereof and/or 84R and conservative amino acid substitutions thereof, wherein the amino acid position is indicated according to the IMGT® numbering.

In some embodiments the amino acid residue which is substituted in the protein-protein interface of the parent domain of the first engineered immunoglobulin chain comprises the amino acid residues at position 88 and at position 20, and optionally a further amino acid residue at a position selected from the group consisting of 3, 5, 7, 22, 26, 27, 79, 81, 84, 84.2, 85.1, 86, and 90, wherein the amino acid position of each group member is indicated according to the IMGT® numbering.

In some embodiments the amino acid residue which is substituted in the protein-protein interface of the parent domain of the second engineered immunoglobulin chain comprises the amino acid residues at position 85.1 and/or 86 and at position 26 and optionally an amino acid residue at a further position, wherein the amino acid position is indicated according to the IMGT® numbering.

In some embodiments the amino acid residue which is substituted at position 85.1 and/or 86 in the protein-protein interface of the parent domain of the second engineered immunoglobulin chain is selected from the group consisting of 85.1A, 85.1S, 85.1C and 85.1N or is selected from the group consisting of 85.1A, 85.1S, 85.1C and 85.1N and conservative amino acid substitutions thereof and/or is selected from the group consisting of 86S and 86V or is selected from the group consisting of 86S and 86V and conservative amino acid substitutions thereof, wherein the amino acid position is indicated according to the IMGT® numbering.

In some embodiments the further amino acid residue which is substituted in the protein-protein interface of the parent domain of the second engineered immunoglobulin chain is at a position selected from the group consisting of 3, 5, 7, 20, 22, 26, 81, 84, 84.2, 88, and 90 or at a position selected from the group consisting of 3, 5, 7, 20, 22, 26, 81, 84, 84.2, 85.1, 88, and 90 or at a position selected from the group consisting of 3, 5, 7, 20, 22, 26, 81, 84, 84.2, 86, 88, and 90, wherein the amino acid position of each group member is indicated according to the IMGT® numbering.

In some embodiments the further amino acid residue which is substituted in the protein-protein interface of the parent domain of the first engineered immunoglobulin chain is at a position selected from the group consisting of 20, 22, 26, 79, 85.1, 86, and 90, and/or the further amino acid residue which is substituted in the protein-protein interface of the parent domain of the second engineered immunoglobulin chain is at position 84 or is 84L or is 84L and conservative amino acid substitutions thereof, and optionally a further amino acid at a position selected from the group consisting of 3, 5, 7, 20, 22, 26, 81, 84.2, 88, and 90 or at a position selected from the group consisting of 3, 5, 7, 20, 22, 26, 81, 84.2, 85.1, 88, and 90 or at a position selected from the group consisting of 3, 5, 7, 20, 22, 26, 81, 84.2, 86, 88, and 90, wherein the amino acid position of each group member is indicated according to the IMGT® numbering.

In some embodiments the further amino acid residue substituted in the protein-protein interface of the parent domain of the first engineered immunoglobulin chain is selected from the group consisting of 20K, 22V, 26T, 79Y, 85.1S, 86V, and 90N or is selected from the group consisting of 20K, 22V, 26T, 79Y, 85.1S, 86V, and 90N and conservative amino acid substitutions thereof and/or the amino acid residue which is substituted in the protein-protein interface of the parent domain of the second engineered immunoglobulin chain comprises the amino acid residues at position 85.1 and 86 or comprises 85.1C and conservative amino acid substitutions thereof and 86S and conservative amino acid substitutions thereof, and the further amino acid residue which is substituted in the protein-protein interface of the parent domain of the second engineered immunoglobulin chain is selected from the group consisting of 3, 5, 7, 20, 22, 26, 81, 84, 84.2, 88, and 90, preferably from the group consisting of 3E, 5A, 7F, 20T, 22V, 26T, 81D, 84L, 84.2E, 88R and 90R or from the group consisting of 3E, 5A, 7F, 20T, 22V, 26T, 81D, 84L, 84.2E, 88R and 90R and conservative amino acid substitutions thereof, wherein the amino acid position of each group member is indicated according to the IMGT® numbering.

In some embodiments the amino acid residue substitution 85.1C is replaced by amino acid residue substitution 85.1A or 85.1S wherein the amino acid position of each group member is indicated according to the IMGT® numbering.

In some embodiments the further amino acid residue substituted in the protein-protein interface of the parent domain of the first engineered immunoglobulin chain is at a position selected from the group consisting of 3, 5, 20, 22, 26, 27, 81, 84, 85.1, and 86, and/or the further amino acid residue which is substituted in the protein-protein interface of the parent domain of the second engineered immunoglobulin chain is at a position selected from the group consisting of 7, 20, 22, 27, 79, 81, 84.2, 88, and 90 or at a position selected from the group consisting of 7, 20, 22, 27, 79, 81, 84.2, 85.1, 88, and 90 or at a position selected from the group consisting of 7, 20, 22, 27, 79, 81, 84.2, 86, 88, and 90, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3K, 5T, 20T, 22L, 26E, 27K, 81G, 84M, 85.1M, 86F or is selected from the group consisting of 3K, 5T, 20T, 22L, 26E, 27K, 81G, 84M, 85.1M, 86F and conservative amino acid substitutions thereof, and/or the further amino acid residue which is substituted in the protein-protein interface of the parent domain of the second engineered immunoglobulin chain is at position 79 or is 79F or is 79F and conservative amino acid substitutions thereof, and optionally a further amino acid residue at a position selected from the group consisting of 7, 20, 22, 27, 81, 84.2, 88, and 90 or at a position selected from the group consisting of 7, 20, 22, 27, 81, 84.2, 85.1, 88, and 90 or at a position selected from the group consisting of 7, 20, 22, 27, 81, 84.2, 86, 88, and 90, wherein the amino acid position of each group member is indicated according to the IMGT® numbering.

In some embodiments the further amino acid residue which is substituted in the protein-protein interface of the parent domain of the first engineered immunoglobulin chain is selected from the group consisting of 3K, 5T, 20T, 22L, 26E, 27K, 81G, 84M, 85.1M, 86F or is selected from the group consisting of 3K, 5T, 20T, 22L, 26E, 27K, 81G, 84M, 85.1M, 86F and conservative amino acid substitutions thereof, and/or the amino acid residue which is substituted in the protein-protein interface of the parent domain of the second engineered immunoglobulin chain comprises the amino acid residues at position 85.1 and 86 or comprises 85.1N and conservative amino acid substitutions thereof and 86V and conservative amino acid substitutions thereof, and the further amino acid residue which is substituted in the protein-protein interface of the parent domain of the second engineered immunoglobulin chain is selected from the group consisting of 7M, 20N, 22A, 27E, 79F, 81A, 84.2S, 88L, and 90K or is selected from the group consisting of 7M, 20N, 22A, 27E, 79F, 81A, 84.2S, 85.1N, 86V, 88L, and 90K and conservative amino acid substitutions thereof, wherein the amino acid position of each group member is indicated according to the IMGT® numbering.

In some embodiments the present disclosure provides a hetero-dimeric immunoglobulin or fragment thereof, wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 84, 84.2, 85.1, 86, 88 and 90 and, wherein the amino acid residues which are substituted in the protein-protein interface of the parent domain of the second engineered immunoglobulin chain comprise the amino acid residue at position 26 and at a further position selected from the group consisting of 3, 22, 27, 79, 81, 84, 85.1, 86, and 88, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In some embodiments the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 84, 84.2, 85.1, 86, 88 and 90 and, the amino acid residues which are substituted in the protein-protein interface of the parent domain of the second engineered immunoglobulin chain comprises the amino acid residues at positions 26 and 86 and optionally at a further position selected from the group consisting of 3, 5, 22, 27, 79, 81, 84, 85.1, 88 and 90, wherein the amino acid position of each group member is indicated according to the IMGT® numbering.

In some embodiments the amino acid residues which are substituted in the protein-protein interface of the parent domain of the first engineered immunoglobulin chain comprise the amino acid residues at positions 20 and 22, and optionally a further amino acid residue at a position selected from the group consisting of 3, 5, 7, 26, 27, 79, 81, 84, 84.2, 85.1, 86, 88 and 90 and, the amino acid residues which are substituted in the protein-protein interface of the parent domain of the second engineered immunoglobulin chain comprise the amino acid residues at positions 26 and at a further position selected from the group consisting of 3, 5, 22, 27, 79, 81, 84, 85.1, 86, 88 and 90, wherein the amino acid position of each group member is indicated according to the IMGT® numbering.

In some embodiments the amino acid residues which are substituted in the protein-protein interface of the parent domain of the first engineered immunoglobulin chain comprise the amino acid residues at positions 20 and 22, and optionally a further amino acid residue at a position selected from the group consisting of 3, 5, 7, 26, 27, 79, 81, 84, 84.2, 85.1, 86, 88 and 90 and, the amino acid residues which are substituted in the protein-protein interface of the parent domain of the second engineered immunoglobulin chain comprise the amino acid residues at positions 26 and 86 and optionally at a further position selected from the group consisting of 3, 5, 22, 27, 79, 81, 84, 85.1, 88 and 90, wherein the amino acid position of each group member is indicated according to the IMGT® numbering.

In some embodiments the amino acid residue which is substituted at position 20 in the protein-protein interface of the parent domain of the first engineered immunoglobulin chain is selected from the group consisting of 20N and 20T, and conservative amino acid substitutions thereof, wherein the amino acid position is indicated according to the IMGT® numbering.

In some embodiments the amino acid residue which is substituted at position 26 in the protein-protein interface of the parent domain of the second engineered immunoglobulin chain is selected from the group consisting of 26T and 26E and conservative amino acid substitutions thereof, wherein the amino acid position is indicated according to the IMGT® numbering.

In some embodiments the amino acid residue which is substituted at position 22 in the protein-protein interface of the parent domain of the first engineered immunoglobulin chain is selected from the group consisting of 22A and 22V, and conservative amino acid substitutions thereof, wherein the amino acid position is indicated according to the IMGT® numbering.

In some embodiments the amino acid residue which is substituted at position 86 in the protein-protein interface of the parent domain of the second engineered immunoglobulin chain is selected from the group consisting of 86V and 86F and conservative amino acid substitutions thereof, wherein the amino acid position is indicated according to the IMGT® numbering.

In some embodiments the amino acid residue which is substituted at position 20 in the protein-protein interface of the parent domain of the first engineered immunoglobulin chain is selected from the group consisting of 20V, 20T, 20A, 20N, 20Q, 20K, 20S, 20W and 20E and/or wherein the further amino acid residue substituted in the protein-protein interface of the parent domain of the first engineered immunoglobulin chain is selected from the group consisting of 22A, 22G, 22L, 22I, 22V, 22T, 26K, 26R, 26Q, 26T, 26V, 26S, 26N, 26E, 85.1W, 85.1F, 85.1T, 85.1M, 85.1A, 85.1S, 85.1R, 85.1H, 85.1K, 85.1C, 85.1N, 86W, 86Y, 86S, 86I, 86H, 86Q, 86V, 86T, 86F, 88Q, 88L, 88V, 88R, 88E, 88T, 88I, 88Y, 88K and 88W, wherein the amino acid position of each group member is indicated according to the IMGT® numbering.

In some embodiments the amino acid residue which is substituted at position 20 in the protein-protein interface of the parent domain of the first engineered immunoglobulin chain is selected from the group consisting of 20V, 20T, 20A, 20N, 20Q, and 20E and/or wherein the further amino acid residue substituted in the protein-protein interface of the parent domain of the first engineered immunoglobulin chain is selected from the group consisting of 22A, 22G, 22L, 22I, 22V, 26Q, 26T, 26V, 26S, 26N, 26E, 85.1T, 85.1M, 85.1A, 85.1S, 85.1R, 85.1H, 85.1K, 85.1C, 85.1N, 86S, 86I, 86T, 86H, 86Q, 86V, 86T, 86F, 88Q, 88L, 88V, 88R, 88E, 88T, 88I, 88Y, and 88W, wherein the amino acid position of each group member is indicated according to the IMGT® numbering.

In some embodiments the amino acid residue which is substituted at position 20 in the protein-protein interface of the parent domain of the first engineered immunoglobulin chain is selected from the group consisting of 20V, 20T, 20A, 20N, 20Q, 20K, 20S and 20E and/or wherein the further amino acid residue substituted in the protein-protein interface of the parent domain of the first engineered immunoglobulin chain is selected from the group consisting of 22A, 22G, 22L, 22I, 22V, 26K, 26Q, 26T, 26V, 26S, 26N, 26E, 85.1T, 85.1M, 85.1A, 85.1S, 85.1R, 85.1H, 85.1K, 85.1C, 85.1N, 86S, 86I, 86H, 86Q, 86V, 86T, 86F, 88Q, 88L, 88V, 88R, 88E, 88T, 88I, 88Y, and 88W, wherein the amino acid position of each group member is indicated according to the IMGT® numbering.

In some embodiments the amino acid residues which are substituted at position 20 and position 22 in the protein-protein interface of the parent domain of the first engineered immunoglobulin chain are selected from the group consisting of 20V, 20T, 20A, 20N, 20Q, 20K, 20S, 20W and 20E and 22A, 22G, 22L, 22I, 22V, 22T and/or wherein the further amino acid residue substituted in the protein-protein interface of the parent domain of the first engineered immunoglobulin chain is selected from the group consisting of 26K, 26R, 26Q, 26T, 26V, 26S, 26N, 26E, 85.1W, 85.1F, 85.1T, 85.1M, 85.1A, 85.1S, 85.1R, 85.1H, 85.1K, 85.1C, 85.1N, 86W, 86Y, 86S, 86I, 86H, 86Q, 86V, 86T, 86F, 88Q, 88L, 88V, 88R, 88E, 88T, 88I, 88Y, 88K and 88W, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3E, 3K, 5A, 5T, 7F, 7M, 22A, 22L, 22V, 26E, 26T, 27E, 27K, 79F, 79Y, 81A, 81G, 81D, 84L, 84M, 84.2E, 84.2S, 85.1A, 85.1C, 85.1M, 85.1N, 85.1S, 86F, 86S, 86V, 88L, 88R, 88W, 90K, 90N, and 90R and conservative amino acid substitutions thereof, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3E, 3K, 5A, 5T, 7F, 7M, 26E, 26T, 27E, 27K, 79F, 79Y, 81A, 81G, 81D, 84L, 84M, 84.2E, 84.2S, 85.1A, 85.1C, 85.1M, 85.1N, 85.1S, 86F, 86S, 86V, 88L, 88R, 88W, 90K, 90N, and 90R and conservative amino acid substitutions thereof, wherein the amino acid position of each group member is indicated according to the IMGT® numbering.

In some embodiments the amino acid residue which is substituted at position 26 in the protein-protein interface of the parent domain of the second engineered immunoglobulin chain is selected from the group consisting of 26K, 26R, 26Q, 26T, 26V, 26S, 26N, 26E and/or wherein the further amino acid residue substituted in the protein-protein interface of the parent domain of the first engineered immunoglobulin chain is selected from the group consisting of 22A, 22G, 22L, 22I, 22V, 22T, 85.1W, 85.1F, 85.1T, 85.1M, 85.1A, 85.1S, 85.1R, 85.1H, 85.1K, 85.1C, 85.1N, 86W, 86Y, 86S, 86I, 86H, 86Q, 86V, 86T, 86F, 88Q, 88L, 88V, 88R, 88E, 88T, 88I, 88Y, 88K and 88W wherein the amino acid position of each group member is indicated according to the IMGT® numbering.

In some embodiments the amino acid residues which are substituted at position 26 and position 86 in the protein-protein interface of the parent domain of the second engineered immunoglobulin chain is selected from the group consisting of 26K, 26R, 26Q, 26T, 26V, 26S, 26N, 26E and 86W, 86Y, 86S, 86I, 86H, 86Q, 86V, 86T, 86F and/or wherein the further amino acid residue substituted in the protein-protein interface of the parent domain of the first engineered immunoglobulin chain is selected from the group consisting of 22A, 22G, 22L, 22I, 22V, 22T, 85.1W, 85.1F, 85.1T, 85.1M, 85.1A, 85.1S, 85.1R, 85.1H, 85.1K, 85.1C, 85.1N, 88Q, 88L, 88V, 88R, 88E, 88T, 88I, 88Y, 88K and 88W, wherein the amino acid position of each group member is indicated according to the IMGT® numbering.

In some embodiments the further amino acid residue substituted in the protein-protein interface of the parent domain of the second engineered immunoglobulin chain is selected from the group consisting of 3E, 3K, 22A, 22L, 22V, 27E, 27K, 79F, 79Y, 81A, 81G, 81D, 84L, 84M, 85.1A, 85.1C, 85.1M, 85.1N, 85.1S, 86F, 86S, 86V, 88L, 88R, and 88W, and conservative amino acid substitutions thereof, wherein the amino acid position of each group member is indicated according to the IMGT® numbering.

In some embodiments the present disclosure provides a hetero-dimeric immunoglobulin or fragment thereof, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 88, and optionally a further amino acid residue at a position selected from the group consisting of 3, 5, 7, 20, 22, 26, 27, 79, 81, 83, 84, 84.2, 84.3, 85.1, 86 and 90 and, wherein the amino acid residue which is substituted in the protein-protein interface of the parent domain of the second engineered immunoglobulin chain comprises the amino acid residue at position 85.1 and/or 86 and optionally a further amino acid residue at a position selected from the group consisting of 3, 5, 7, 20, 22, 26, 27, 79, 81, 83, 84, 84.2, 84.3 and 90 or at a position selected from the group consisting of 3, 5, 7, 20, 22, 26, 27, 79, 81, 83, 84, 84.2, 84.3, 85.1 and 90 or at a position selected from the group consisting of 3, 5, 7, 20, 22, 26, 27, 79, 81, 83, 84, 84.2, 84.3, 86 and 90, wherein the amino acid residue substituted at position 88 in the parent domain of the first engineered immunoglobulin chain is interacting with the amino acid residue substituted at position 85.1 and/or 86 in the parent domain of the second engineered immunoglobulin chain, wherein the amino acid position of each group member is indicated according to the IMGT® numbering. Positions 3, 5, 7, 20, 22, 26, 27, 79, 81, 83, 84, 84.2, 84.3, 85.1, 86 and 90 in the protein-protein interface of the CH2 domain as parent domain indicated according to IMGT® numbering correspond in the same order to positions 239, 241, 243, 258, 260, 264, 265, 288, 290, 292, 293, 295, 296, 301, 303, 305, 307 indicated according to the EU numbering.

In some embodiments the parent domain of the first and the second engineered immunoglobulin chain is a CH2 domain.

In some embodiments the parent domains of the first and the second engineered immunoglobulin chain are CH2 domains of different isotypes.

In some embodiments the parent domain of the first engineered immunoglobulin chain is an IgG1 CH2 domain, preferably a human CH2 domain from IGHG1 and the parent domain of the second engineered immunoglobulin chain is an IgG3 CH2 domain, preferably a human CH2 domain from IGHG3 or wherein the parent domain of the first engineered immunoglobulin chain is an IgG3 CH2 domain, preferably a human CH2 domain from IGHG3 and the parent domain of the second engineered immunoglobulin chain is an IgG1 CH2 domain preferably a human CH2 domain from IGHG1.

In some embodiments the amino acid residue which is substituted in the protein-protein interface of the parent domain of the first engineered immunoglobulin chain at position 88 is 88W or 88W and conservative amino acid substitutions thereof, wherein the amino acid position is indicated according to the IMGT® numbering.

In some embodiments the amino acid residue which is substituted in the protein-protein interface of the parent domain of the second engineered immunoglobulin chain at position 85.1 and/or 86 is selected from the group consisting of 85.1A and 85.1N or is selected from the group consisting of 85.1A and 85.1N and conservative amino acid substitutions thereof, and/or is 86S or 86S and conservative amino acid substitutions thereof, wherein the amino acid position is indicated according to the IMGT® numbering.

In some embodiments the amino acid residue which is substituted in the protein-protein interface of the parent domain of the first engineered immunoglobulin chain at position 88 is selected from the group consisting of 88Q, 88L, 88V, 88R, 88I, 88T, 88K, 88E, 88Y, and 88W and/or wherein the further amino acid residue substituted in the protein-protein interface of the parent domain of the first engineered immunoglobulin chain is selected from the group consisting of 20V, 20T, 20A, 20N, 20K, 20W, 20S, 20E, 20Q, 22A, 22G, 22T, 22L, 22V, 26Q, 26T, 26K, 26V, 26S, 26R, 26N, 26E, 85.1R, 85.1H, 85.1K, 85.1T, 85.1M, 85.1A, 85.1S, 85.1W, 85.1F, 85.1C, 85.1N, 86S, 86I, 86H, 86T, 86W, 86Y, 86V, 86Q and 86F, wherein the amino acid position of each group member is indicated according to the IMGT® numbering.

In some embodiments the amino acid residue which is substituted in the protein-protein interface of the parent domain of the first engineered immunoglobulin chain at position 88 is selected from the group consisting of 88Q, 88L, 88V, 88R, 88I, 88T, 88K, 88E, 88Y, and 88W and/or wherein the further amino acid residue substituted in the protein-protein interface of the parent domain of the first engineered immunoglobulin chain is selected from the group consisting of 20V, 20T, 20A, 20N, 20K, 20W, 20S, 22A, 22G, 22T, 22L, 22V, 26Q, 26T, 26K, 26V, 26S, 26R, 26N, 26E, 85.1T, 85.1M, 85.1A, 85.1S, 85.1W, 85.1F, 85.1C, 85.1N, 86S, 86I, 86H, 86T, 86W, 86Y, 86V, and 86F, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3E, 3K, 5A, 5T, 5Y, 7M, 7L, 20K, 20N, 20T, 20S, 22A, 22L, 22V, 26E, 26T, 27E, 27K, 79F, 79Y, 81A, 81G, 81D, 83M, 83T, 84L, 84.2E, 84.2S, 84.3D, 85.1S, 85.1A, 85.1N, 85.1M, 85.1F, 86S, 86F, 86Y, 90K, 90N, and 90R or is selected from the group consisting of 3E, 3K, 5A, 5T, 5Y, 7M, 7L, 20K, 20N, 20T, 20S, 22A, 22L, 22V, 26E, 26T, 27E, 27K, 79F, 79Y, 81A, 81G, 81D, 83M, 83T, 84L, 84.2E, 84.2S, 84.3D, 85.1S, 85.1A, 85.1N, 85.1M, 85.1F, 86S, 86F, 86Y, 90K, 90N, and 90R and conservative amino acid substitutions thereof, wherein the amino acid position of each group member is indicated according to the IMGT® numbering.

In some embodiments the amino acid residue which is substituted in the protein-protein interface of the parent domain of the first engineered immunoglobulin chain comprises the amino acid residues at position 88 and at position 20, and optionally a further amino acid residue at a position selected from the group consisting of 3, 5, 7, 22, 26, 27, 79, 81, 83, 84, 84.2, 84.3, 85.1, 86 and 90, wherein the amino acid position is indicated according to the IMGT® numbering.

In some embodiments the amino acid residue which is substituted in the protein-protein interface of the parent domain of the second engineered immunoglobulin chain comprises the amino acid residues at position 85.1 and/or 86 and at position 26 and optionally an amino acid residue at a further position, wherein the amino acid position is indicated according to the IMGT® numbering.

In some embodiments the further amino acid residue which is substituted in the protein-protein interface of the parent domain of the first engineered immunoglobulin chain is at a position selected from the group consisting of 20, 22, 26, 79, 85.1, and 90, and/or the further amino acid residue which is substituted in the protein-protein interface of the parent domain of the second engineered immunoglobulin chain is at position 84 or is 84L or is 84L and conservative amino acid substitutions thereof, and optionally a further amino acid at a position selected from the group consisting of 3, 5, 7, 20, 22, 26, 81, 84.2, 88, and 90 or at a position selected from the group consisting of 3, 5, 7, 20, 22, 26, 81, 84.2, 85.1, 88, and 90 or at a position selected from the group consisting of 3, 5, 7, 20, 22, 26, 81, 84.2, 86, 88, and 90, wherein the amino acid position of each group member is indicated according to the IMGT® numbering.

In some embodiments the further amino acid residue substituted in the protein-protein interface of the parent domain of the first engineered immunoglobulin chain is selected from the group consisting of 20K, 22V, 26T, 79Y, 85.1S, and 90N or is selected from the group consisting of 20K, 22V, 26T, 79Y, 85.1S, and 90N and conservative amino acid substitutions thereof and/or the amino acid residue which is substituted in the protein-protein interface of the parent domain of the second engineered immunoglobulin chain at position 85.1 or is 85.1C or is 85.1C and conservative amino acid substitutions thereof, and wherein the amino acid residue which is substituted in the protein-protein interface of the parent domain of the second engineered immunoglobulin chain at position 86 or is 86S or is 86S and conservative amino acid substitutions thereof, and wherein the further amino acid residue which is substituted in the protein-protein interface of the parent domain of the second engineered immunoglobulin chain is selected from the group consisting of 3, 5, 20, 22, 26, 81, 84, 84.2, 88, and 90, preferably from the group consisting of 3E, 5A, 20T, 22V, 26T, 81D, 84L, 84.2E, 88R and 90R or from the group consisting of 3E, 5A, 20T, 22V, 26T, 81D, 84L, 84.2E, 88R and 90R and conservative amino acid substitutions thereof, wherein the amino acid position of each group member is indicated according to the IMGT® numbering.

In some embodiments the amino acid residue substitution 85.1C is replaced by amino acid residue substitution 85.1A or 85.1S wherein the amino acid position of each group member is indicated according to the IMGT® numbering.

In some embodiments the further amino acid residue substituted in the protein-protein interface of the parent domain of the first engineered immunoglobulin chain is at a position selected from the group consisting of 3, 5, 20, 22, 26, 27, 81, 83, 85.1, and 86, and/or the further amino acid residue which is substituted in the protein-protein interface of the parent domain of the second engineered immunoglobulin chain is at a position selected from the group consisting of 7, 20, 22, 27, 79, 81, 84.2, 88, and 90 or at a position selected from the group consisting of 7, 20, 22, 27, 79, 81, 84.2, 85.1, 88, and 90 or at a position selected from the group consisting of 7, 20, 22, 27, 79, 81, 84.2, 86, 88, and 90, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3K, 5T, 20T, 22L, 26E, 27K, 81G, 83M, 85.1M, and 86F or is selected from the group consisting of 3K, 5T, 20T, 22L, 26E, 27K, 81G, 83M, 85.1M, and 86F and conservative amino acid substitutions thereof, and/or
the further amino acid residues which are substituted in the protein-protein interface of the parent domain of the second engineered immunoglobulin chain is at position 79 or is 79F or is 79F and conservative amino acid substitutions thereof, and optionally a further amino acid residue at a position selected from the group consisting of 7, 20, 22, 27, 81, 84.2, 88, and 90 or at a position selected from the group consisting of 7, 20, 22, 27, 81, 84.2, 85.1, 88, and 90, or at a position selected from the group consisting of 7, 20, 22, 27, 81, 84.2, 86, 88, and 90, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3K, 5T, 20T, 22L, 26E, 27K, 81G, 83M, 85.1M, and 86F or is selected from the group consisting of 3K, 5T, 20T, 22L, 26E, 27K, 81G, 83M, 85.1M, and 86F and conservative amino acid substitutions thereof, and/or the amino acid residue which is substituted in the protein-protein interface of the parent domain of the second engineered immunoglobulin chain at position 85.1 is 85.1N or is 85.1N and conservative amino acid substitutions thereof, and wherein the amino acid residue which is substituted in the protein-protein interface of the parent domain of the second engineered immunoglobulin chain at position 22 is 22A or is 22A and conservative amino acid substitutions thereof, and/or wherein the further amino acid residue which is substituted in the protein-protein interface of the parent domain of the second engineered immunoglobulin chain is selected from the group consisting of 7M, 20N, 27E, 79F, 81A, 84.2S, 88L, and 90K or is selected from the group consisting of 7M, 20N, 27E, 79F, 81A, 84.2S, 88L, and 90K and conservative amino acid substitutions thereof, wherein the amino acid position of each group member is indicated according to the IMGT® numbering.

In some embodiments the further amino acid residue substituted in the protein-protein interface of the parent domain of the first engineered immunoglobulin chain is at a position selected from the group consisting of 5, 7, 20, 83, 84.3, 85.1, and 86 and/or the further amino acid residue which is substituted in the protein-protein interface of the parent domain of the second engineered immunoglobulin chain is at a position selected from the group consisting of 5, 7, 20, 83, 84.3, and 88 or at a position selected from the group consisting of 5, 7, 20, 83, 84.3, 85.1, and 88, or at a position selected from the group consisting of 5, 7, 20, 83, 84.3, 86, and 88 wherein the amino acid position of each group member is indicated according to the IMGT® numbering.

In some embodiments the further amino acid residue substituted in the protein-protein interface of the parent domain of the first engineered immunoglobulin chain is selected from the group consisting of 5Y, 7L, 20S, 83T, 84.3D, 85.1F, and 86Y or is selected from the group consisting of 5Y, 7L, 20S, 83T, 84.3D, 85.1F, and 86Y and conservative amino acid substitutions thereof, and/or the further amino acid residues which are substituted in the protein-protein interface of the parent domain of the second engineered immunoglobulin chain is at position 20 or is 20S or is 20S and conservative amino acid substitutions thereof, and optionally a further amino acid residue at a position selected from the group consisting of 5, 7, 83, 84.3, and 88 or at a position selected from the group consisting of 5, 7, 83, 84.3, 85.1 and 88 or at a position selected from the group consisting of 5, 7, 83, 84.3, 86 and 88, wherein the amino acid position of each group member is indicated according to the IMGT® numbering.

In some embodiments the further amino acid residue substituted in the protein-protein interface of the parent domain of the first engineered immunoglobulin chain is selected from the group consisting of 5Y, 7L, 20S, 83T, 84.3D, 85.1F and 86Y or is selected from the group consisting of 5Y, 7L, 20S, 83T, 84.3D, 85.1F and 86Y and conservative amino acid substitutions thereof, and/or the amino acid residue which is substituted in the protein-protein interface of the parent domain of the second engineered immunoglobulin chain is at position 85.1 or is 85.1F or is 85.1F and conservative amino acid substitutions thereof, and wherein the further amino acid residue which is substituted in the protein-protein interface of the parent domain of the second engineered immunoglobulin chain is at position 20 or is 20S or is 20S and conservative amino acid substitutions thereof, and/or wherein a further amino acid residue which is substituted in the protein-protein interface of the parent domain of the second engineered immunoglobulin chain is selected from the group consisting of 5Y, 7L, 83T, 84.3D, 86Y, and 88K or is selected from the group consisting of 5Y, 7L, 83T, 84.3D, 86Y and 88K and conservative amino acid substitutions thereof, wherein the amino acid position of each group member is indicated according to the IMGT® numbering.

In some embodiments the present disclosure provides a hetero-dimeric immunoglobulin or fragment thereof, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 83, 84, 84.2, 84.3, 85.1, 86, 88 and 90 and, wherein the amino acid residue which is substituted in the protein-protein interface of the parent domain of the second engineered immunoglobulin chain comprises the amino acid residue at position 26 and optionally a further amino acid residue at a position selected from the group consisting of 3, 5, 7, 20, 22, 27, 79, 81, 83, 84, 84.2, 84.3, 85.1, 86, 88 and 90, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In some embodiments the present disclosure provides a hetero-dimeric immunoglobulin or fragment thereof, wherein the parent domain of the first and/or the second engineered immunoglobulin chain is a CH2 domain, wherein the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 84, 84.2, 85.1, 86, 88 and 90 and, wherein the amino acid residues which are substituted in the protein-protein interface of the parent domain of the second engineered immunoglobulin chain are at position 26 and at a further position selected from the group consisting of 3, 22, 27, 79, 81, 84, 85.1, 86, and 88, wherein the amino acid residue substituted at position 20 in the parent domain of the first engineered immunoglobulin chain is interacting with the amino acid residue substituted at position 26 in the parent domain of the second engineered immunoglobulin chain, wherein the amino acid position of each group member is indicated according to the IMGT® numbering.

In some embodiments the amino acid residue which is substituted in the protein-protein interface of the parent domain of the first engineered immunoglobulin chain comprises the amino acid residue at position 20, and optionally a further amino acid residue at a position selected from the group consisting of 3, 5, 7, 22, 26, 27, 79, 81, 84, 84.2, 85.1, 86, 88 and 90 and, the amino acid residues which are substituted in the protein-protein interface of the parent domain of the second engineered immunoglobulin chain comprises the amino acid residues at positions 26 and 86 and optionally at a further position selected from the group consisting of 3, 5, 22, 27, 79, 81, 84, 85.1, 88 and 90, wherein the amino acid position of each group member is indicated according to the IMGT® numbering.

In some embodiments the amino acid residues which are substituted in the protein-protein interface of the parent domain of the first engineered immunoglobulin chain comprise the amino acid residues at positions 20 and 22, and optionally a further amino acid residue at a position selected from the group consisting of 3, 5, 7, 26, 27, 79, 81, 84, 84.2, 85.1, 86, 88 and 90 and, the amino acid residues which are substituted in the protein-protein interface of the parent domain of the second engineered immunoglobulin chain comprise the amino acid residues at positions 26 and at a further position selected from the group consisting of 3, 5, 22, 27, 79, 81, 84, 85.1, 86, 88 and 90, wherein the amino acid position of each group member is indicated according to the IMGT® numbering.

In some embodiments the amino acid residues which are substituted in the protein-protein interface of the parent domain of the first engineered immunoglobulin chain comprise the amino acid residues at positions 20 and 22, and optionally a further amino acid residue at a position selected from the group consisting of 3, 5, 7, 26, 27, 79, 81, 84, 84.2, 85.1, 86, 88 and 90 and, the amino acid residues which are substituted in the protein-protein interface of the parent domain of the second engineered immunoglobulin chain comprise the amino acid residues at positions 26 and 86 and optionally at a further position selected from the group consisting of 3, 5, 22, 27, 79, 81, 84, 85.1, 88 and 90, wherein the amino acid position of each group member is indicated according to the IMGT® numbering.

In some embodiments the amino acid residue which is substituted at position 20 in the protein-protein interface of the parent domain of the first engineered immunoglobulin chain is selected from the group consisting of 20N and 20T, and conservative amino acid substitutions thereof, wherein the amino acid position is indicated according to the IMGT® numbering.

In some embodiments the amino acid residue which is substituted at position 26 in the protein-protein interface of the parent domain of the second engineered immunoglobulin chain is selected from the group consisting of 26T and 26E and conservative amino acid substitutions thereof, wherein the amino acid position is indicated according to the IMGT® numbering.

In some embodiments the amino acid residue which is substituted at position 22 in the protein-protein interface of the parent domain of the first engineered immunoglobulin chain is selected from the group consisting of 22A and 22V, and conservative amino acid substitutions thereof, wherein the amino acid position is indicated according to the IMGT® numbering.

In some embodiments the amino acid residue which is substituted at position 86 in the protein-protein interface of the parent domain of the second engineered immunoglobulin chain is selected from the group consisting of 86V and 86F and conservative amino acid substitutions thereof, wherein the amino acid position is indicated according to the IMGT® numbering.

In some embodiments the amino acid residue which is substituted in the protein-protein interface of the parent domain of the first engineered immunoglobulin chain at position 20 is selected from the group consisting of 20V, 20T, 20A, 20N, 20K, 20Q, 20E, 20W and 20S and/or wherein the further amino acid residue substituted in the protein-protein interface of the parent domain of the first engineered immunoglobulin chain is selected from the group consisting of 22A, 22G, 22T, 22L, 22V, 22I, 26Q, 26T, 26K, 26V, 26S, 26R, 26N, 26E, 85.1R, 85.1H, 85.1K, 85.1T, 85.1M, 85.1A, 85.1S, 85.1W, 85.1F, 85.1C, 85.1N, 86Q, 86S, 86I, 86H, 86T, 86W, 86Y, 86V, 86F, 88Q, 88L, 88V, 88R, 88E, 88I, 88T, 88K, 88Y, and 88W, wherein the amino acid position of each group member is indicated according to the IMGT® numbering.

In some embodiments the amino acid residue which is substituted in the protein-protein interface of the parent domain of the first engineered immunoglobulin chain at position 20 is selected from the group consisting of 20V, 20T, 20A, 20N, 20K, 20W and 20S and/or wherein the further amino acid residue substituted in the protein-protein interface of the parent domain of the first engineered immunoglobulin chain is selected from the group consisting of 22A, 22G, 22T, 22L, 22V, 26Q, 26T, 26K, 26V, 26S, 26R, 26N, 26E, 85.1T, 85.1M, 85.1A, 85.1S, 85.1W, 85.1F, 85.1C, 85.1N, 86S, 86I, 86H, 86T, 86W, 86Y, 86V, 86F, 88Q, 88L, 88V, 88R, 88E, 88I, 88T, 88K, 88Y, and 88W, wherein the amino acid position of each group member is indicated according to the IMGT® numbering.

In some embodiments the further amino acid residue substituted in the protein-protein interface of the parent domain of the first engineered immunoglobulin chain is selected from the group consisting of 3E, 3K, 5A, 5T, 5Y, 7M, 7L, 22A, 22L, 22V, 26E, 26T, 27E, 27K, 79F, 79Y, 81A, 81G, 81D, 83M, 83T, 84L, 84.2E, 84.2S, 84.3D, 85.1S, 85.1A, 85.1N, 85.1M, 85.1F, 86S, 86F, 86Y, 88K, 88L, 88R, 88W, 90K, 90N, and 90R or selected from the group consisting of 3E, 3K, 5A, 5T, 5Y, 7M, 7L, 22A, 22L, 22V, 26E, 26T, 27E, 27K, 79F, 79Y, 81A, 81G, 81D, 83M, 83T, 84L, 84.2E, 84.2S, 84.3D, 85.1S, 85.1A, 85.1N, 85.1M, 85.1F, 86S, 86F, 86Y, 88K, 88L, 88R, 88W, 90K, 90N, and 90R and conservative amino acid substitutions thereof, wherein the amino acid position of each group member is indicated according to the IMGT® numbering.

In some embodiments the present disclosure provides a hetero-dimeric immunoglobulin or hetero-dimeric fragment thereof comprising:
(a) a first engineered immunoglobulin chain comprising an engineered domain with a protein-protein interface, wherein at least one amino acid residue of the protein-protein interface of the parent domain of said first engineered immunoglobulin chain is substituted with an amino acid residue at the equivalent 3D structural position from a protein-protein interface of a donor domain of a first member of the naturally occurring immunoglobulin super-family; and
(b) a second engineered immunoglobulin chain comprising an engineered domain with a protein-protein interface, wherein at least one amino acid residue of the protein-protein interface of the parent domain of said second engineered immunoglobulin chain is substituted with an amino acid residue at the equivalent 3D structural position from a protein-protein interface of a donor domain of a second member of the naturally occurring immunoglobulin super-family,
wherein the engineered domain of the first engineered immunoglobulin chain and the engineered domain of the second engineered immunoglobulin chain are not identical and,
wherein the donor domain of the first member of the naturally occurring immunoglobulin super-family and the donor domain of the second member of the naturally occurring immunoglobulin super-family form a naturally occurring hetero-dimer or a naturally occurring homo-dimer and, wherein the parent domain of the first and/or the second engineered immunoglobulin chain is a CH4 domain, wherein the protein-protein interface of the parent domain of the first engineered immunoglobulin chain comprises an amino acid residue substitution at a position selected from the group consisting of 20, 22, 85.1, 86, and 88, and/or wherein the protein-protein interface of the parent domain of the second engineered immunoglobulin chain comprises an amino acid residue substitution at a position selected from the group consisting of 22, 26, 85.1, 86, and 88, wherein the amino acid position of each group member is indicated according to the IMGT® numbering. In some embodiments the parent domain of the first and the second engineered immunoglobulin chain is a naturally occurring CH4 domain.

In some embodiments the amino acid residue which is substituted in the protein-protein interface of the parent domain of the first engineered immunoglobulin chain at position 88 is 88W and conservative amino acid substitutions thereof, wherein the amino acid position is indicated according to the IMGT® numbering.

In some embodiments preferably at least two, more preferably at least three, most preferably at least four, in particular at least five amino acid residues, more particular at least six, even more particular at least seven, most particular all amino acid residues of the protein-protein interface of the parent domain of the first and/or the second engineered immunoglobulin chain are substituted. Equally preferred two, more preferably three, most preferably four, in particular five amino acid residues, more particular six, even more particular seven amino acid residues of the protein-protein interface of the parent domain of the first and/or the second engineered immunoglobulin chain are substituted. Equally preferred less than two, more preferably less than three, most preferably less than four, in particular less than five amino acid residues, more particular less than six, even more particular less than seven amino acid residues of the protein-protein interface of the parent domain of the first and/or the second engineered immunoglobulin chain are substituted.

In some embodiments at least one, preferably at least two, more preferably at least three, most preferably at least four, in particular at least five amino acid residues, more particular at least six, even more particular at least seven, most particular all amino acid residues of the protein-protein interface of the engineered domain of the first engineered immunoglobulin chain is different from the protein-protein interface of the engineered domain of the second engineered immunoglobulin chain In some embodiments the amino acid residues of the protein-protein interface of the parent domain of the first and/or second engineered immunoglobulin chain which are substituted are not adjacent.

In some embodiments the present disclosure provides a hetero-dimeric immunoglobulin or fragment thereof, wherein, at least two, more preferably at least three, most preferably at least four, in particular at least five amino acid residues of the protein-protein interface of the parent domain of the first and/or second engineered immunoglobulin chain which are substituted are not adjacent.

In some embodiments the amino acid sequence of the engineered domains of the first engineered immunoglobulin chain and/or the second engineered immunoglobulin chain do not contain an insertion of one or more amino acid residues compared to the amino acid sequence of the parent domains of the first engineered immunoglobulin chain and/or the second engineered immunoglobulin chain.

In some embodiments the amino acid sequence of the further engineered domain of the first engineered immunoglobulin chain and/or the second engineered immunoglobulin chain do not contain an insertion of one or more amino acid residues compared to the amino acid sequence of the parent domain of the further engineered domain of the first engineered immunoglobulin chain and/or the second engineered immunoglobulin.

In some embodiments the amino acid sequence of the engineered domain of the third engineered immunoglobulin chain do not contain an insertion of one or more amino acid residues compared to the amino acid sequence of the parent domain of the third engineered immunoglobulin chain.

In some embodiments the first engineered immunoglobulin chain and/or the second engineered immunoglobulin chain comprise a further engineered domain with a protein-protein interface, wherein at least one amino acid residue of the protein-protein interface of the parent domain of said further engineered domain of said first engineered immunoglobulin chain and/or said second engineered immunoglobulin chain is substituted with an amino acid residue at the equivalent 3D structural position from a protein-protein interface of a donor domain of a third member of the naturally occurring immunoglobulin super-family, and wherein the protein-protein interface of the further engineered domain of the first engineered immunoglobulin chain and/or the second engineered immunoglobulin chain is interacting with the protein-protein interface of an engineered domain of a third engineered immunoglobulin chain by hetero-dimerization or by homo-dimerization, wherein at least one amino acid residue of the protein-protein interface of the parent domain of said engineered domain of said third engineered immunoglobulin chain is substituted with an amino acid residue at the equivalent 3D structural position from a protein-protein interface of a donor domain of a fourth member of the naturally occurring immunoglobulin super-family, and wherein the donor domain of the third member of the naturally occurring immunoglobulin super-family and the donor domain of the fourth member of the naturally occurring immunoglobulin super-family form a naturally occurring hetero-dimer or a naturally occurring homo-dimer and, wherein the protein-protein interface of the further engineered domain of the first engineered immunoglobulin chain and/or the second engineered immunoglobulin chain and of the engineered domain of the third engineered immunoglobulin chain is different from the protein-protein interface of the engineered domain of the first engineered immunoglobulin chain and of the engineered domain of the second engineered immunoglobulin chain.

Preferably, the further engineered domain of the first engineered immunoglobulin chain and/or the second engineered immunoglobulin chain and the engineered domain of the third engineered immunoglobulin chain are not identical.

Preferably at least two, more preferably at least three, most preferably at least four, in particular at least five amino acid residues, more particular at least six, even more particular at least seven, most particular all amino acid residues of the protein-protein interface of the parent domain of the further engineered domain of the first and/or second engineered immunoglobulin chain and/or the parent domain of the engineered domain of the third engineered immunoglobulin chain are substituted. Equally preferred two, more preferably three, most preferably four, in particular five amino acid residues, more particular six, even more particular seven amino acid residues of the protein-protein interface of the parent domain of the further engineered domain of the first and/or second engineered immunoglobulin chain and/or the parent domain of the engineered domain of the third engineered immunoglobulin chain are substituted. Equally preferred less than two, more preferably less than three, most preferably less than four, in particular less than five amino acid residues, more particular less than six, even more particular less than seven amino acid residues of the protein-protein interface of the parent domain of the further engineered domain of the first and/or second engineered immunoglobulin chain and/or the parent domain of the engineered domain of the third engineered immunoglobulin chain are substituted.

In some embodiments at least one, preferably at least two, more preferably at least three, most preferably at least four, in particular at least five amino acid residues, more particular at least six, even more particular at least seven, most particular all amino acid residues of the protein-protein interface of the parent domain of the further engineered domain of the first and/or second engineered immunoglobulin chain is different from the protein-protein interface of the engineered domain of the third engineered immunoglobulin chain, In some embodiments the present disclosure provides a hetero-dimeric immunoglobulin or fragment thereof, wherein the amino acid residues of the protein-protein interface of the parent domain of the further engineered domain of the first engineered immunoglobulin chain and the parent domain of the engineered domain of the third engineered immunoglobulin chain which are substituted are not adjacent. In some embodiments the present disclosure provides a hetero-dimeric immunoglobulin or fragment thereof, wherein, at least two, more preferably at least three, most preferably at least four, in particular at least five amino acid residues of the protein-protein interface of the parent domain of the further engineered domain of the first engineered immunoglobulin chain and the parent domain of the engineered domain of the third engineered immunoglobulin chain which are substituted are not adjacent.

In some embodiments the third engineered immunoglobulin chain comprises a further engineered domain with a protein-protein interface, wherein at least one amino acid residue of the protein-protein interface of the parent domain of said further engineered domain of said third engineered immunoglobulin chain is substituted with an amino acid residue at the equivalent 3D structural position from a protein-protein interface of a donor domain of a fifth member of the naturally occurring immunoglobulin super-family, and wherein the protein-protein interface of the further engineered domain of the third engineered immunoglobulin chain is interacting with the protein-protein interface of an engineered domain of a fourth engineered immunoglobulin chain by hetero-dimerization or by homo-dimerization, wherein at least one amino acid residue of the protein-protein interface of the parent domain of said engineered domain of said third engineered immunoglobulin chain is substituted with an amino acid residue at the equivalent 3D structural position from a protein-protein interface of a donor domain of a sixth member of the naturally occurring immunoglobulin super-family, and wherein the donor domain of the fifth member of the naturally occurring immunoglobulin super-family and the donor domain of the sixth member of the naturally occurring immunoglobulin super-family form a naturally occurring hetero-dimer or a naturally occurring homo-dimer and, wherein the protein-protein interface of the further engineered domain of the third engineered immunoglobulin chain and of the engineered domain of the fourth engineered immunoglobulin chain is different from the protein-protein interface of the engineered domain of the first engineered immunoglobulin chain and of the engineered domain of the second engineered immunoglobulin chain and from the protein-protein interface of the further engineered domain of the first engineered immunoglobulin chain and/or the second engineered immunoglobulin chain and from the protein-protein interface of the engineered domain of a third engineered immunoglobulin chain.

The parent domains of the further engineered domain of the third engineered immunoglobulin chain and/or of the engineered domain of the fourth engineered immunoglobulin chain is selected from consisting of CH1, CH2, CH3, CH4, IGKC, IGLC1, IGLC2, IGLC3, IGLC6, and IGLC7, wherein the amino acid residues of the protein-protein interface of the further engineered domain of the third engineered immunoglobulin chain and/or of the engineered domain of the fourth engineered immunoglobulin chain which are substituted are e.g. selected from the group of the amino acid residues of the protein-protein interface for the parent domains of the first and/or second engineered immunoglobulin chains as described supra.

The donor domain of the fifth and/or a sixth member of the naturally occurring immunoglobulin super-family are e.g. selected from for the group of donor domain of the first and/or second member of the naturally occurring immunoglobulin super-family as described supra.

In some embodiments the first engineered immunoglobulin chain comprises an engineered domain with a protein-protein interface comprising the amino acid sequence of SEQ ID NO: 13 and/or the second engineered immunoglobulin chain comprises an engineered domain with a protein-protein interface comprising the amino acid sequence selected from the group consisting of SEQ ID NO: 14, SEQ ID NO: 15 and SEQ ID NO: 16, preferably SEQ ID NO: 14 or SEQ ID NO: 15.

In some embodiments the first engineered immunoglobulin chain comprises an engineered domain with a protein-protein interface comprising the amino acid sequence of SEQ ID NO: 13 and/or the second engineered immunoglobulin chain comprises an engineered domain with a protein-protein interface comprising the amino acid sequence of SEQ ID NO: 14.

Thus in a further aspect the present invention provides a hetero-dimeric immunoglobulin or fragment thereof comprising a first engineered immunoglobulin chain comprising an engineered domain with a protein-protein interface comprising the amino acid sequence of SEQ ID NO: 13 and a second engineered immunoglobulin chain comprising an engineered domain with a protein-protein interface.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 13, with the proviso that the amino acid sequence which is at least 80% identical to the amino acid sequence of SEQ ID NO: 13 contains at least two, preferably at least three, more preferably at least four, most preferred at least five, in particular at least six, more particular at least seven, most particular all of the amino acid residues selected from the group consisting of K24, V26, T30, Y52, S65, V67, W69, and N71, wherein the amino acid position of each group member is indicated according to the numbering of the amino acid residues of SEQ ID NO: 13 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 14. In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 14, with the proviso that the amino acid sequence which is at least 80% identical to the amino acid sequence of SEQ ID NO: 14 contains at least one, usually two, preferably at least three, more preferably at least four, most preferred at least five, in particular at least six, more particular at least seven, most particular all of the amino acid residues selected from the group consisting of E7, A9, F11, T24, V26, T30, D54, L57, E59, A65, S67, R69, and R71, wherein the amino acid position of each group member is indicated according to the numbering of the amino acid residues of SEQ ID NO: 14 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 15.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 15, with the proviso that the amino acid sequence which is at least 80% identical to the amino acid sequence of SEQ ID NO: 15 contains at least one, usually two, preferably at least three, more preferably at least four, most preferred at least five, in particular at least six, more particular at least seven, most particular all of the amino acid residues selected from the group consisting of E7, A9, F11, T24, V26, T30, D54, L57, E59, C65, S67, R69, and R71, wherein the amino acid position of each group member is indicated according to the numbering of the amino acid residues of SEQ ID NO: 15 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 16, wherein the protein-protein interface of the engineered domain of the first engineered immunoglobulin chain is interacting with the protein-protein interface of the engineered domain of the second engineered immunoglobulin chain by hetero-dimerization.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 16, with the proviso that the amino acid sequence which is at least 80% identical to the amino acid sequence of SEQ ID NO: 16 contains at least one, usually two, preferably at least three, more preferably at least four, most preferred at least five, in particular at least six, more particular at least seven, most particular all of the amino acid residues selected from the group consisting of E7, A9, F11, T24, V26, T30, D54, L57, E59, S65, S67, R69, and R71, wherein the amino acid position of each group member is indicated according to the numbering of the amino acid residues of SEQ ID NO: 16 in the sequence listing.

In a further aspect the present invention provides a hetero-dimeric immunoglobulin or fragment thereof comprising a first engineered immunoglobulin chain comprising an engineered domain with a protein-protein interface, wherein the first engineered immunoglobulin chain comprises the amino acid sequence of SEQ ID NO: 3 and a second engineered immunoglobulin chain comprising an engineered domain with a protein-protein interface, wherein the protein-protein interface of the engineered domain of the first engineered immunoglobulin chain is interacting with the protein-protein interface of the engineered domain of the second engineered immunoglobulin chain by hetero-dimerization.

In some embodiments the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 3, with the proviso that the amino acid sequence which is at least 80% identical to the amino acid sequence of SEQ ID NO: 3 contains at least one, usually two, preferably at least three, more preferably at least four, most preferred at least five, in particular at least six, more particular at least seven, most particular all of the amino acid residues selected from the group consisting of S144K, T146V, K150T, K172Y, F185S, Y187V, K189W, and T191N, wherein the amino acid position of each group member is indicated according to the numbering of the amino acid residues of SEQ ID NO: 3 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface, wherein the second engineered immunoglobulin chain comprises the amino acid sequence of SEQ ID NO: 4, wherein the protein-protein interface of the engineered domain of the first engineered immunoglobulin chain is interacting with the protein-protein interface of the engineered domain of the second engineered immunoglobulin chain by hetero-dimerization.

In some embodiments the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 4, with the proviso that the amino acid sequence which is at least 80% identical to the amino acid sequence of SEQ ID NO: 4 contains at least one, usually two, preferably at least three, more preferably at least four, most preferred at least five, in particular at least six, more particular at least seven or eight or nine or ten, or eleven or twelve, most particular all of the amino acid residues selected from the group consisting of Q127E, Y129A, L131F, S144T, T146V, K150T, T174D, V177L, D179E, F185C, Y187S, K189R, and T191R, wherein the amino acid position of each group member is indicated according to the numbering of the amino acid residues of SEQ ID NO: 4 in the sequence listing.

In some embodiments the first engineered immunoglobulin chain comprises an engineered domain with a protein-protein interface comprising the amino acid sequence of SEQ ID NO: 35 and/or the second engineered immunoglobulin chain comprises an engineered domain with a protein-protein interface comprising the amino acid sequence of SEQ ID NO: 34.

In a further aspect the present invention provides a hetero-dimeric immunoglobulin or fragment thereof comprising a first engineered immunoglobulin chain comprising an engineered domain with a protein-protein interface comprising the amino acid sequence of SEQ ID NO: 35 and a second engineered immunoglobulin chain comprising an engineered domain with a protein-protein interface.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 35, with the proviso that the amino acid sequence which is at least 80% identical to the amino acid sequence of SEQ ID NO: 35 contains at least one, usually two, preferably at least three, more preferably at least four, most preferred at least five, in particular at least six, more particular at least seven, most particular all of the amino acid residues selected from the group consisting of K127, T129, T144, L146, E150, K151, G174, M177, M185, F187, and W189, wherein the amino acid position of each group member is indicated according to the numbering of the amino acid residues of SEQ ID NO: 35 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 34.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 34, with the proviso that the amino acid sequence which is at least 80% identical to the amino acid sequence of SEQ ID NO: 34 contains at least one, usually two, preferably at least three, more preferably at least four, most preferred at least five, in particular at least six, more particular at least seven, most particular all of the amino acid residues selected from the group consisting of M131, N144, A146, E151, F172, A174, S179, N185, V187, L189, and K191, wherein the amino acid position of each group member is indicated according to the numbering of the amino acid residues of SEQ ID NO: 34 in the sequence listing.

In some embodiments the first engineered immunoglobulin chain comprises an engineered domain with a protein-protein interface comprising the amino acid sequence of SEQ ID NO: 40 and/or the second engineered immunoglobulin chain comprises an engineered domain with a protein-protein interface comprising the amino acid sequence of SEQ ID NO: 39.

In a further aspect the present invention provides a hetero-dimeric immunoglobulin or fragment thereof comprising a first engineered immunoglobulin chain comprising an engineered domain with a protein-protein interface comprising the amino acid sequence of SEQ ID NO: 40 and a second engineered immunoglobulin chain comprising an engineered domain with a protein-protein interface.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 40, with the proviso that the amino acid sequence which is at least 80% identical to the amino acid sequence of SEQ ID NO: 40 contains at least one, usually two, preferably at least three, more preferably at least four, most preferred at least five, in particular at least six, more particular at least seven, most particular all of the amino acid residues selected from the group consisting K7, T9, T24, L26, E30, K31, G55, M57, M67, F69, and W71, wherein the amino acid position of each group member is indicated according to the numbering of the amino acid residues of SEQ ID NO: 40 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 39.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 39, with the proviso that the amino acid sequence which is at least 80% identical to the amino acid sequence of SEQ ID NO: 39 contains at least one, usually two, preferably at least three, more preferably at least four, most preferred at least five, in particular at least six, more particular at least seven, most particular all of the amino acid residues selected from the group consisting of M11, N24, A26, E31, F51, A53, S58, N64, V66, L68, and K70, wherein the amino acid position of each group member is indicated according to the numbering of the amino acid residues of SEQ ID NO: 39 in the sequence listing.

In some embodiments the first engineered immunoglobulin chain comprises an engineered domain with a protein-protein interface comprising the amino acid sequence of SEQ ID NO: 48 and/or the second engineered immunoglobulin chain comprises an engineered domain with a protein-protein interface comprising the amino acid sequence of SEQ ID NO: 49.

In a further aspect the present invention provides a hetero-dimeric immunoglobulin or fragment thereof comprising a first engineered immunoglobulin chain comprising an engineered domain with a protein-protein interface comprising the amino acid sequence of SEQ ID NO: 48 and a second engineered immunoglobulin chain comprising an engineered domain with a protein-protein interface.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 48, with the proviso that the amino acid sequence which is at least 80% identical to the amino acid sequence of SEQ ID NO: 48 contains at least one, usually two, preferably at least three, more preferably at least four, most preferred at least five, in particular at least six, more particular at least seven, most particular all of the amino acid residues selected from the group consisting of Q7, Y9, D16, E17, Q22, S24, T26, K51, T53, D58, F64, Y66, and K68, wherein the amino acid position of each group member is indicated according to the numbering of the amino acid residues of SEQ ID NO: 48 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 49.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 49, with the proviso that the amino acid sequence which is at least 80% identical to the amino acid sequence of SEQ ID NO: 49 contains at least one, usually two, preferably at least three, more preferably at least four, most preferred at least five, in particular at least six, more particular at least seven, most particular all of the amino acid residues selected from the group consisting of Q7, Y9, L11, D16, E17, T26, K30, K53, T55, V57, F67, Y69, and K71, wherein the amino acid position of each group member is indicated according to the numbering of the amino acid residues of SEQ ID NO: 49 in the sequence listing.

In some embodiments the first engineered immunoglobulin chain comprises an engineered domain with a protein-protein interface comprising the amino acid sequence of SEQ ID NO: 76 and/or the second engineered immunoglobulin chain comprises an engineered domain with a protein-protein interface comprising the amino acid sequence of SEQ ID NO: 14.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 76, with the proviso that the amino acid sequence which is at least 80% identical to the amino acid sequence of SEQ ID NO: 76 contains at least one, usually two, preferably at least three, more preferably at least four, most preferred at least five, in particular at least six, more particular at least seven, most particular all of the amino acid residues selected from the group consisting of K24, V26, T30, Y52, S65, V67, W69, and N71, wherein the amino acid position of each group member is indicated according to the numbering of the amino acid residues of SEQ ID NO: 76 in the sequence listing.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 14, with the proviso that the amino acid sequence which is at least 80% identical to the amino acid sequence of SEQ ID NO: 14 contains at least one, usually two, preferably at least three, more preferably at least four, most preferred at least five, in particular at least six, more particular at least seven, most particular all of the amino acid residues selected from the group consisting of E7, A9, F11, T24, V26, T30, D54, L57, E59, A65, S67, R69, and R71, wherein the amino acid position of each group member is indicated according to the numbering of the amino acid residues of SEQ ID NO: 14 in the sequence listing.

In some embodiments the first engineered immunoglobulin chain comprises an engineered domain with a protein-protein interface comprising the amino acid sequence of SEQ ID NO: 78 and/or the second engineered immunoglobulin chain comprises an engineered domain with a protein-protein interface comprising the amino acid sequence of SEQ ID NO: 79. In a further aspect the present invention provides a hetero-dimeric immunoglobulin or fragment thereof comprising a first engineered immunoglobulin chain comprising an engineered domain with a protein-protein interface comprising the amino acid sequence of SEQ ID NO: 78 and a second engineered immunoglobulin chain comprising an engineered domain with a protein-protein interface.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 78, with the proviso that the amino acid sequence which is at least 80% identical to the amino acid sequence of SEQ ID NO: 78 contains at least one, usually two, preferably at least three, more preferably at least four, most preferred at least five, in particular at least six, more particular at least seven, most particular all of the amino acid residues selected from the group consisting of E7, H9, R30, R57, E59, A65, and T67, wherein the amino acid position of each group member is indicated according to the numbering of the amino acid residues of SEQ ID NO: 78 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 79.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 79, with the proviso that the amino acid sequence which is at least 80% identical to the amino acid sequence of SEQ ID NO: 79 contains at least one, usually two, preferably at least three, more preferably at least four, most preferred at least five, in particular at least six, more particular at least seven, most particular all of the amino acid residues selected from the group consisting of T24, L52, W54, I69, and R71, wherein the amino acid position of each group member is indicated according to the numbering of the amino acid residues of SEQ ID NO: 79 in the sequence listing.

In some embodiments the first engineered immunoglobulin chain comprises an engineered domain with a protein-protein interface comprising the amino acid sequence of SEQ ID NO: 84 and/or the second engineered immunoglobulin chain comprises an engineered domain with a protein-protein interface comprising the amino acid sequence of SEQ ID NO: 85.

In a further aspect the present invention provides a hetero-dimeric immunoglobulin or fragment thereof comprising a first engineered immunoglobulin chain comprising an engineered domain with a protein-protein interface comprising the amino acid sequence of SEQ ID NO: 84 and a second engineered immunoglobulin chain comprising an engineered domain with a protein-protein interface.

In some embodiments the engineered domain with a protein-protein interface of the first engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 84, with the proviso that the amino acid sequence which is at least 80% identical to the amino acid sequence of SEQ ID NO: 84 contains at least one, usually two, preferably at least three, more preferably at least four, most preferred at least five, in particular at least six, more particular at least seven, most particular all of the amino acid residues selected from the group consisting of K26, V28, Y56, S71, V73, W75, and N77, wherein the amino acid position of each group member is indicated according to the numbering of the amino acid residues of SEQ ID NO: 84 in the sequence listing.

In a further aspect the present invention provides a hetero-dimeric immunoglobulin or fragment thereof comprising a first engineered immunoglobulin chain comprising an engineered domain with a protein-protein interface and a second engineered immunoglobulin chain comprising an engineered domain with a protein-protein interface comprising the amino acid sequence of SEQ ID NO: 85.

In some embodiments the engineered domain with a protein-protein interface of the second engineered immunoglobulin chain comprises an amino acid sequence which is at least 80%, preferably at least 90%, more preferably at least 95%, most preferred at least 96%, in particular at least 97%, more particular at least 98%, most particular at least 99% identical to the amino acid sequence of SEQ ID NO: 85, with the proviso that the amino acid sequence which is at least 80% identical to the amino acid sequence of SEQ ID NO: 85 contains at least one, usually two, preferably at least three, more preferably at least four, most preferred at least five, in particular at least six, more particular at least seven, most particular all of the amino acid residues selected from the group consisting of E8, A10, F12, V28, D58, L61, A71, S73, R75, and R77, wherein the amino acid position of each group member is indicated according to the numbering of the amino acid residues of SEQ ID NO: 85 in the sequence listing.

In some embodiments the present disclosure provides a hetero-dimeric immunoglobulin or fragment thereof wherein the first engineered immunoglobulin chain comprises the amino acid sequence selected from the group consisting of SEQ ID NOs: 3, 4, 6, 7, 13-29, 34, 35, 36, 39, 40, 41, 42, 48, 49, 50, 51, 59, 61, and 68 and/or the second engineered immunoglobulin chain comprises the amino acid sequence selected from the group consisting of SEQ ID NOs: 3, 4, 6, 7, 13-29, 34, 35, 36, 39, 40, 41, 42, 48, 49, 50, 51, 59, 61, and 68.

In some embodiments the present disclosure provides a hetero-dimeric immunoglobulin or fragment thereof wherein the first engineered immunoglobulin chain comprises the amino acid sequence selected from the group consisting of SEQ ID NOs: 3, 4, 6, 7, 13-29, 34, 35, 36, 39, 40, 41, 42, 48, 49, 50, 51, 59, 61, 68, 73, 78 and 84 and/or the second engineered immunoglobulin chain comprises the amino acid sequence selected from the group consisting of SEQ ID NOs: 3, 4, 6, 7, 13-29, 34, 35, 36, 39, 40, 41, 42, 48, 49, 50, 51, 59, 61, 68, 74, 79 and 85.

In some embodiments the present disclosure provides a hetero-dimeric immunoglobulin or fragment thereof wherein the first engineered immunoglobulin chain comprises the amino acid sequence selected from the group consisting of SEQ ID NOs: 3, 7, 13, 59, and 68 and/or the second engineered immunoglobulin chain comprises the amino acid sequence selected from the group consisting of SEQ ID NOs: 4, 6, 14, 15, 16, 17, 41, 50, and 61.

In some embodiments the present disclosure provides a hetero-dimeric immunoglobulin or fragment thereof wherein the first engineered immunoglobulin chain comprises the amino acid sequence selected from the group consisting of SEQ ID NOs: 3, 7, 13, 59, 68, 73 and 84 and/or the second engineered immunoglobulin chain comprises the amino acid sequence selected from the group consisting of SEQ ID NOs: 4, 6, 14, 15, 16, 17, 41, 50, 61, 74 and 85.

In some embodiments the present disclosure provides a hetero-dimeric immunoglobulin or fragment thereof wherein the first engineered immunoglobulin chain comprises the amino acid sequence selected from the group consisting of SEQ ID NOs: 34, 39, and 41 and/or the second engineered immunoglobulin chain comprises the amino acid sequence selected from the group consisting of SEQ ID NOs: 35, 36, 40, and 42.

In some embodiments the present disclosure provides a hetero-dimeric immunoglobulin or fragment thereof wherein the first engineered immunoglobulin chain comprises the amino acid sequence selected from the group consisting of SEQ ID NOs: 48, 49, 50, and 51 and/or the second engineered immunoglobulin chain comprises the amino acid sequence selected from the group consisting of SEQ ID NOs: 48, 49, 50, and 51. Preferably the first engineered immunoglobulin chain comprises the amino acid sequence selected from the group consisting of SEQ ID NO: 48 and the second engineered immunoglobulin chain comprises the amino acid sequence of SEQ ID NO: 49 or of SEQ ID NO: 51. Equally preferred the first engineered immunoglobulin chain comprises the amino acid sequence selected from the group consisting of SEQ ID NO: 50 and the second engineered immunoglobulin chain comprises the amino acid sequence of SEQ ID NO: 49 or of SEQ ID NO: 51.

In some embodiments the present disclosure provides a hetero-dimeric immunoglobulin or fragment thereof wherein the first engineered immunoglobulin chain comprises the amino acid sequence of SEQ ID NO: 78 and/or the second engineered immunoglobulin chain comprises the amino acid sequence of SEQ ID NO: 79.

In some embodiments the present disclosure provides a hetero-dimeric immunoglobulin or fragment thereof wherein the first and/or second engineered immunoglobulin chain comprises the amino acid sequence selected from the group consisting o SEQ ID NOs: 3, 7, 13, 59, and 68 and the third engineered immunoglobulin chain comprises the amino acid sequence selected from the group consisting of SEQ ID NOs: 4, 6, 14, 15, 16, 17, 41, 50, and 61.

In some embodiments the present disclosure provides a hetero-dimeric immunoglobulin or fragment thereof wherein the first and/or second engineered immunoglobulin chain comprises the amino acid sequence selected from the group consisting of SEQ ID NOs: 34, 39 and 41 and/or the third engineered immunoglobulin chain comprises the amino acid sequence selected from the group consisting of SEQ ID NOs 35, 36, 40, and 42.

In some embodiments the present disclosure provides a hetero-dimeric immunoglobulin or fragment thereof wherein the first and/or second engineered immunoglobulin chain comprises the amino acid sequence selected from the group consisting of SEQ ID NOs: 3, 4, 6, 7, 13-29, 34, 35, 36, 39, 40, 41, 42, 48, 49, 50, 51, 59, 61, 68, 73, 78 and 84 and/or the third engineered immunoglobulin chain comprises the amino acid sequence selected from the group consisting of SEQ ID NOs 3, 4, 6, 7, 13-29, 34, 35, 36, 39, 40, 41, 42, 48, 49, 50, 51, 59, 61, 68, 74, 79 and 85.

In some embodiments the present disclosure provides a hetero-dimeric immunoglobulin or fragment thereof wherein the first and/or second engineered immunoglobulin chain comprises the amino acid sequence of SEQ ID NO: 78 and/or the third engineered immunoglobulin chain comprises the amino acid sequence of SEQ ID NO 79.

In some embodiments the present disclosure provides a hetero-dimeric immunoglobulin or fragment thereof wherein the first and/or second engineered immunoglobulin chain comprises the amino acid sequence selected from the group consisting of SEQ ID NOs: 3, 7, 13, 59, 68 and/or the third engineered immunoglobulin chain comprises the amino acid sequence selected from the group consisting of SEQ ID NOs: 3, 7, 13, 59, 68.

In some embodiments the present disclosure provides a hetero-dimeric immunoglobulin or fragment thereof wherein the first engineered immunoglobulin chain comprises the amino acid sequence of SEQ ID NO: 72, and the second engineered immunoglobulin chain comprises the amino acid sequence of SEQ ID NO: 71 and the third engineered immunoglobulin chain which interacts with the protein-protein interface of the engineered domain of the second engineered immunoglobulin chain comprises the amino acid sequence of SEQ ID NO: 51.

In some embodiments the present disclosure provides a hetero-dimeric immunoglobulin or fragment thereof which comprises a first engineered immunoglobulin chain comprising the amino acid sequence of SEQ ID NO: 72, a second engineered immunoglobulin chain comprising the amino acid sequence of SEQ ID NO: 70, a third engineered immunoglobulin chain with an engineered domain which interacts with the protein-protein interface of the engineered domain of the first engineered immunoglobulin chain comprising the amino acid sequence of SEQ ID NO: 69 and a third engineered immunoglobulin chain with an engineered domain which interacts with the protein-protein interface of the engineered domain of the second engineered immunoglobulin chain comprising the amino acid sequence of SEQ ID NO: 42.

In some embodiments the present disclosure provides a hetero-dimeric immunoglobulin or fragment thereof, wherein the first and second engineered immunoglobulin chains comprise an Fc region. In some embodiments the present disclosure provides a hetero-dimeric immunoglobulin or fragment thereof, wherein the first and/or the second and the third engineered immunoglobulin chains comprise an Fc region. Usually the Fc region is selected from the group consisting of IgA, IgE, IgD, IgG, and IgM Fc region.

In some embodiments the present disclosure provides a hetero-dimeric immunoglobulin or fragment thereof, wherein the first and second engineered immunoglobulin chains comprise an Fc region from the same species, preferably from the same species and isotype, more preferably from the same species, isotype and subclass.

In some embodiments the present disclosure provides a hetero-dimeric immunoglobulin or fragment thereof, wherein the first and/or the second and the third engineered immunoglobulin chains comprise an Fc region from the same species, preferably from the same species and isotype, more preferably from the same species, isotype and subclass.

In some embodiments the present disclosure provides a hetero-dimeric immunoglobulin or fragment thereof, wherein the Fc regions of the first and second engineered immunoglobulin chains are not identical. In some embodiments the present disclosure provides a hetero-dimeric immunoglobulin or fragment thereof, wherein the Fc regions of the first and second engineered immunoglobulin chains have amino acid sequences which are different from each other by one amino acid or by two amino acids or by three amino acids or by four amino acids or by five amino acids or by five to ten amino acids or by ten to thirty amino acids, preferably by at least two amino acids or by at least three amino acids or by at least four amino acids or by at least five amino acids or by at least five to ten amino acids or by at least ten to thirty amino acids.

In some embodiments the present disclosure provides a hetero-dimeric immunoglobulin or fragment thereof which is bispecific.

In some embodiments the present disclosure provides a hetero-dimeric immunoglobulin or fragment thereof, wherein the hetero-dimeric immunoglobulin or fragment thereof is a full-length antibody.

In some embodiments the present disclosure provides a hetero-dimeric immunoglobulin or fragment thereof, wherein the hetero-dimeric immunoglobulin or fragment thereof is a full-length antibody which is bispecific.

In some embodiments the present disclosure provides a hetero-dimeric immunoglobulin or fragment thereof, wherein the bispecific hetero-dimeric immunoglobulin or fragment thereof or the bispecific antibody binds to antigens selected from the group consisting of HER2, EGFR, CD19 and VLA-2. Preferably the bispecific hetero-dimeric immunoglobulin or fragment thereof or the bispecific antibody is specific to HER2 and EGFR. Equally preferably the bispecific hetero-dimeric immunoglobulin or fragment thereof or the bispecific antibody is specific to CD19 and VLA-2.

In some embodiments the present disclosure provides a hetero-dimeric immunoglobulin or fragment thereof which is a Fab, with a first engineered immunoglobulin chain and a second engineered immunoglobulin chain.

In some embodiments the present disclosure provides a hetero-dimeric immunoglobulin or fragment thereof is a F(ab')$_2$ fragment, wherein the first engineered immunoglobulin chain comprises an engineered domain and a further engineered domain, whereas the protein interface of the engineered domain of the first engineered immunoglobulin chain interacts with an engineered domain of a third immunoglobulin chain and the protein interface of the further engineered domain interacts with an engineered domain of a third immunoglobulin chain, wherein the protein interfaces of these engineered domain of these two third immunoglobulin chains are the same or are different form each other.

In some embodiments the present disclosure provides a hetero-dimeric immunoglobulin or fragment thereof, wherein at least one additional polypeptide is fused to the first and/or second engineered immunoglobulin chain. Preferably the one additional polypeptide is fused to the first engineered immunoglobulin chain. Suitably the additional polypeptide is selected from the group consisting of Fab, scFv, diabody, domain antibody, pharmacologically active peptide or protein, receptor extracellular domain, CDR grafted polypeptide and therapeutic engineered protein scaffold. Fusion is usually achieved by genetic engineering as known to the skilled person and may involve amino acid sequence linkers which do not form part of the amino acid sequences to be fused.

In some embodiments the present disclosure provides a multidomain protein comprising at least a first and a second nonidentical engineered domain, each of the first and the second engineered domain containing a protein-protein interface, wherein at least one amino acid residue of the protein-protein interface of the first parent domain are substituted with amino acid residues at the equivalent 3D structural position from a protein-protein interface of a donor domain of a first member of the naturally occurring immunoglobulin super-family and at least one amino acid residue of the protein-protein interface of the second parent domain are substituted with amino acid residues at the equivalent 3D structural position from a protein-protein interface of a donor domain of a second member of the naturally occurring immunoglobulin super-family, wherein the donor domain of the first member of the naturally occurring immunoglobulin super-family and the donor domain of the second member of the naturally occurring immunoglobulin super-family form a hetero-dimer or a homo-dimer.

The multidomain protein comprises preferably a Fc region. Usually the Fc region is selected from the group consisting of IgA, IgE, IgD, IgG, and IgM Fc region.

In some embodiments the present disclosure provides a hetero-dimeric immunoglobulin or fragment thereof or methods of making hetero-dimeric immunoglobulins or fragments thereof as described below wherein the amino acid residue of the protein-protein interface of the parent domain of the parent immunoglobulin chain which is substituted at the equivalent 3D structural position from the protein-protein interface of a donor domain is an amino acid residue in the protein-protein interface of a donor domain which when overlaid on the protein-protein interface of the parent domain by superimposing the carbon alpha traces of both domains, occupies a 3D position within less than a distance of 6 Å to the closest residue of the parent domain, wherein the donor domain is different from the parent domain.

Methods of Making Hetero-Dimeric Immunoglobulins or Fragments Thereof.

In a further aspect the present invention provides a method to produce a hetero-dimeric immunoglobulin or hetero-dimeric fragment thereof comprising:

(a) substituting at least one amino acid residue of the protein-protein interface of a parent domain of a first parent immunoglobulin chain at the equivalent 3D structural position from a protein-protein interface of a donor domain of a first member of the naturally occurring immunoglobulin super-family to obtain a first engineered immunoglobulin chain comprising an engineered domain,
(b) substituting at least one amino acid residue of the protein-protein interface of the parent domain of a second parent immunoglobulin chain at the equivalent 3D structural position from a protein-protein interface of a donor domain of a second member of the naturally occurring immunoglobulin super-family to obtain a second engineered immunoglobulin chain comprising an engineered domain,
(c) culturing a host cell comprising a nucleic acid encoding said engineered immunoglobulin chains, wherein the culturing is such that the nucleic acid is expressed and the engineered immunoglobulin chains produced; and
(d) recovering the hetero-dimeric immunoglobulin or hetero-dimeric fragment thereof from the host cell culture.

In some embodiments the present disclosure provides a method wherein the engineered domain of the first engineered immunoglobulin chain and the engineered domain of the second engineered immunoglobulin chain are not identical.

In some embodiments the present disclosure provides a method wherein the protein-protein interface of the engineered domain of the first engineered immunoglobulin chain is interacting with the protein-protein interface of the engineered domain of the second engineered immunoglobulin chain by hetero-dimerization or by homo-dimerization.

In some embodiments the present disclosure provides a method comprising a parent domain of the first and/or second parent immunoglobulin chain which is selected from the group consisting of CH1, CH2, CH3, CH4, IGKC, IGLC1, IGLC2, IGLC3, IGLC6, and IGLC7. CH1, CH3 can be from IGHA1, IGHA2, IGHD, IGHE, IGHG1, IGHG2, IGHG3, IGHG4, IGHGP and IGHM; CH4 can be from IGHE and IGHM. CH2 can be from IGHA1, IGHA2, IGHD, IGHE, IGHG1, IGHG2, IGHG3, IGHG4, IGHGP and IGHM. In some embodiments the parent domain of the first and/or the second engineered immunoglobulin chain is a domain selected from the group consisting of CH1 domain, CH4 domain, IGKC domain, IGLC1 domain, IGLC2 domain, IGLC3 domain, IGLC6 domain, and IGLC7 domain, preferably from the group consisting of CH1 domain, IGKC domain, IGLC1 domain, IGLC2 domain, IGLC3 domain, IGLC6 domain, and IGLC7 domain.

Usually the parent domain of the first and/or second engineered immunoglobulin chain is from human. Preferably the parent domain of the first and/or second engineered immunoglobulin chain is from human and from the same isotype, species and subclass. The preferred parent domain of the first and/or second engineered immunoglobulin chain, in particular the parent domain of the first and second engineered immunoglobulin chain, is a CH3 domain, more preferably a human CH3 domain, in particular a human CH3 domain from IGHG1.

Equally preferred the parent domain of the first engineered immunoglobulin chain is a CH1 domain and the parent domain of the second engineered immunoglobulin chain is a light chain constant domain such as an IGLC domain or an IGKC domain. Equally, the preferred parent domain of the first engineered immunoglobulin chain is a light chain constant domain such as an IGLC domain or an IGKC domain and the preferred parent domain of the second engineered immunoglobulin chain is a CH1 domain more preferably a human CH1 domain selected from the group consisting of IGHG1, IGHG2, IGHG3, and IGHG4, in particular a human CH1 domain from IGHG1.

In some embodiments the present disclosure provides a method, wherein the parent domains of the first and the second engineered immunoglobulin chain form a naturally occurring homo-dimer. In some embodiments the present disclosure provides a method, wherein the parent domains of the first and the second engineered immunoglobulin chain form a naturally occurring hetero-dimer.

In some embodiments the present disclosure provides a method, wherein the donor domain of the first member of the naturally occurring immunoglobulin super-family and the donor domain of the second member of the naturally occurring immunoglobulin super-family form a naturally occurring hetero-dimer or a naturally occurring homo-dimer and/or wherein the protein-protein interface of the engineered domain of the first engineered immunoglobulin chain is interacting with the protein-protein interface of the engineered domain of the second engineered immunoglobulin chain by hetero-dimerization or by homo-dimerization. Preferably the donor domain of the first member of the naturally occurring immunoglobulin super-family and the donor domain of the second member of the naturally occurring immunoglobulin super-family form a naturally occurring hetero-dimer.

In some embodiments the present disclosure provides a method, wherein the amino acid residues from the protein-protein interface of the donor domain of the first and second member of the naturally occurring immunoglobulin super-family are amino acids non essential to the core integrity of the domain.

In some embodiments the present disclosure provides a method, wherein the first and the second member of the naturally occurring immunoglobulin super-family are selected from the TCR constant domain family. Preferably the donor domain of the first member of the naturally occurring immunoglobulin super-family is the TCR constant domain alpha (SEQ ID NO: 1) and the donor domain of the second member of the naturally occurring immunoglobulin super-family is the TCR constant domain beta (SEQ ID NO: 2). Equally the donor domain of the first member of the naturally occurring immunoglobulin super-family can be the TCR constant domain beta (SEQ ID NO: 2) and the donor domain of the second member of the naturally occurring immunoglobulin super-family can be the TCR constant domain alpha (SEQ ID NO: 1). In a further embodiment the present disclosure provides a method, wherein the donor domain of the first member of the naturally occurring immunoglobulin super-family is the TCR constant domain alpha (SEQ ID NO: 1) and the donor domain of the second member of the naturally occurring immunoglobulin super-family is the TCR constant domain beta (SEQ ID NO: 2), wherein the cysteine (C) at amino acid position 75 in SEQ ID NO: 2 is substituted with alanine (A) or serine (S), preferably with alanine (A).

In a further embodiment the present disclosure provides a method, wherein the donor domain of the first member of the naturally occurring immunoglobulin super-family is the TCR constant domain gamma (SEQ ID NO: 33) and the donor domain of the second member of the naturally occurring immunoglobulin super-family is the TCR constant domain delta (SEQ ID NO: 32) or wherein the donor domain of the first member of the naturally occurring immunoglobulin super-family is the TCR constant domain delta (SEQ ID NO: 32) and the donor domain of the second member of the naturally occurring immunoglobulin super-family is the TCR constant domain gamma (SEQ ID NO: 33).

In some embodiments the present disclosure provides a method, wherein the donor domain of the first member of the naturally occurring immunoglobulin super-family is the TCR constant domain alpha (SEQ ID NO: 1), the donor domain of the second member of the naturally occurring immunoglobulin super-family is the TCR constant domain beta (SEQ ID NO: 2), the donor domain of the third member of the naturally occurring immunoglobulin super-family is the TCR constant domain delta (SEQ ID NO: 32) and the donor domain of the fourth member of the naturally occurring immunoglobulin super-family is the TCR constant domain gamma (SEQ ID NO: 33).

In some embodiments the present disclosure provides a method, wherein the donor domain of the first member of the naturally occurring immunoglobulin super-family is the TCR constant domain delta (SEQ ID NO: 32), the donor domain of the second member of the naturally occurring immunoglobulin super-family is the TCR constant domain gamma (SEQ ID NO: 33), the donor domain of the third member of the naturally occurring immunoglobulin super-family is the TCR constant domain alpha (SEQ ID NO: 1) and the donor domain of the fourth member of the naturally occurring immunoglobulin super-family is the TCR constant domain beta (SEQ ID NO: 2).

In some embodiments the present disclosure provides a method, wherein the donor domain of the first member of the naturally occurring immunoglobulin super-family is the TCR constant domain alpha (SEQ ID NO: 1) or the TCR constant domain delta (SEQ ID NO: 32), the donor domain of the second member of the naturally occurring immunoglobulin super-family is the TCR constant domain beta (SEQ ID NO: 2) or the TCR constant domain gamma (SEQ ID NO: 33), the donor domain of the third and the fourth member of the naturally occurring immunoglobulin super-family is the IgG1 CH3 domain (SEQ ID NO: 47), with the proviso that if the donor domain of the first member of the naturally occurring immunoglobulin super-family is the TCR constant domain alpha (SEQ ID NO: 1), the donor domain of the second member of the naturally occurring immunoglobulin super-family is the TCR constant domain beta (SEQ ID NO: 2) and if the donor domain of the first member of the naturally occurring immunoglobulin super-family is the TCR constant domain delta (SEQ ID NO: 32), the donor domain of the second member of the naturally occurring immunoglobulin super-family is the TCR constant domain gamma (SEQ ID NO: 33).

In a further embodiment the present disclosure provides a method, wherein the first engineered immunoglobulin chain and/or the second engineered immunoglobulin chain comprise a further engineered domain with a protein-protein interface, wherein at least one amino acid residue of the protein-protein interface of the parent domain of said further engineered domain of said first engineered immunoglobulin chain and/or said second engineered immunoglobulin chain is substituted with an amino acid residue at the equivalent 3D structural position from a protein-protein interface of a donor domain of a third member of the naturally occurring immunoglobulin super-family, and
wherein the protein-protein interface of the further engineered domain of the first engineered immunoglobulin chain and/or the second engineered immunoglobulin chain is interacting with the protein-protein interface of an engineered domain of a third engineered immunoglobulin chain by hetero-dimerization or by homo-dimerization, wherein at least one amino acid residue of the protein-protein interface of the parent domain of said engineered domain of said third engineered immunoglobulin chain is substituted with an amino acid residue at the equivalent 3D structural position from a protein-protein interface of a donor domain of a fourth member of the naturally occurring immunoglobulin super-family and,
wherein the protein-protein interface of the further engineered domain of the first engineered immunoglobulin chain and/or the second engineered immunoglobulin chain and of the engineered domain of the third engineered immunoglobulin chain is different from the protein-protein interface of the engineered domain of the first engineered immunoglobulin chain and of the engineered domain of the second engineered immunoglobulin chain.

In some embodiments the present disclosure provides a method, wherein the further engineered domain of the first engineered immunoglobulin chain and/or the second engineered immunoglobulin chain and the engineered domain of the third engineered immunoglobulin chain are not identical.

In some embodiments the parent domain of the first and/or second engineered immunoglobulin chain, in particular the parent domain of the first and second engineered immunoglobulin chain is a CH3 domain, preferably a CH3 domain of the same species, isotype and subclass, and the parent domain of the further engineered domain of the first engineered immunoglobulin chain and/or the second engineered immunoglobulin is a CH1 domain and the parent domain of the engineered domain of the third engineered immunoglobulin chain is a light chain constant domain such as an IGLC domain or an IGKC domain.

In some embodiments the parent domain of the first engineered immunoglobulin chain is a light chain constant domain such as an IGLC domain or an IGKC domain and the parent domain of the engineered domain of the second engineered immunoglobulin chain is a CH1 domain and the parent domain of the further engineered domain of the first engineered immunoglobulin chain and/or the second engineered immunoglobulin and the parent domain of the engineered domain of the third engineered immunoglobulin chain is a CH3 domain, preferably a CH3 domain of the same species, isotype and subclass.

In some embodiments the present disclosure provides a method, wherein the amino acid residues of the protein-protein interface of the parent domain of the first and/or second parent immunoglobulin chain which are substituted are not adjacent.

In some embodiments the present disclosure provides a method, wherein the amino acid residues of the protein-protein interface of the parent domain of the further engineered domain of the first engineered immunoglobulin chain and/or the second engineered immunoglobulin and/or the parent domain of the engineered domain of the third engineered immunoglobulin chain which are substituted are not adjacent.

In some embodiments the present disclosure provides a method, wherein, preferably at least two, more preferably at least three, most preferably at least four, in particular at least five amino acid residues of the protein-protein interface of the parent domain of the first and/or second engineered immunoglobulin chain which are substituted are not adjacent.

In some embodiments the present disclosure provides a method, wherein, preferably at least two, more preferably at least three, most preferably at least four, in particular at least five amino acid residues of the protein-protein interface of the parent domain of the further engineered domain of the first engineered immunoglobulin chain and/or the second engineered immunoglobulin and/or the parent domain of the engineered domain of the third engineered immunoglobulin chain which are substituted are not adjacent.

In some embodiments the present disclosure provides a method, wherein preferably at least two, more preferably at least three, most preferably at least four, in particular at least five more particular at least six, most particular at least seven amino acid residues of the protein-protein interface of the parent domain of the first and/or second parent immunoglobulin chain are substituted.

In some embodiments the present disclosure provides a method, wherein preferably at least two, more preferably at least three, most preferably at least four, in particular at least five more particular at least six, most particular at least seven amino acid residues of the protein-protein interface of the parent domain of the further engineered domain of the first engineered immunoglobulin chain and/or the second engineered immunoglobulin and/or the parent domain of the engineered domain of the third engineered immunoglobulin chain are substituted.

In some embodiments the present disclosure provides a method, wherein the amino acid sequence of the engineered domains of the first engineered immunoglobulin chain and/or the second engineered immunoglobulin chain do not contain an insertion of one or more amino acid residues compared to the amino acid sequence of the parent domains of the first engineered immunoglobulin chain and/or the second engineered immunoglobulin chain.

In some embodiments the present disclosure provides a method, wherein at least one 3D structural position of the protein-protein interface of the engineered domain of the first engineered immunoglobulin chain is different in amino acid residue compared to the identical 3D structural position of the protein-protein interface of the engineered domain of the second engineered immunoglobulin chain.

In some embodiments the present disclosure provides a method, wherein the first and second engineered immunoglobulin chains have parent domains from the same species, preferably from the same species and isotype, more preferably from the same species, isotype and subclass. In some embodiments the present disclosure provides a method, wherein the first and second engineered immunoglobulin chains have identical parent domains, i.e. parent domains which have the identical amino acid sequence.

In some embodiments the present disclosure provides a method, wherein the first and second engineered immunoglobulin chains have parent domains from IgG1, preferably human IgG1.

In some embodiments the present disclosure provides a method, wherein the first and second engineered immunoglobulin chains have parent domains which are not identical. In some embodiments the present disclosure provides a method, wherein the first and second engineered immunoglobulin chains have parent domains which have amino acid sequences which are different from each other by one amino acid or by two amino acids or by three amino acids or by four amino acids or by five amino acids or by five to ten amino acids or by ten to thirty amino acids In some embodiments the present disclosure provides a method, wherein the first and second engineered immunoglobulin chains comprise an Fc region. In some embodiments the present disclosure provides a method, wherein the first and/or the second and the third engineered immunoglobulin chains comprise an Fc region. Usually the Fc region is selected from the group consisting of IgA, IgE, IgD, IgG, and IgM Fc region.

In some embodiments the present disclosure provides a method, wherein the first and second engineered immunoglobulin chains comprise an Fc region from the same species, preferably from the same species and isotype, more preferably from the same species, isotype and subclass.

In some embodiments the present disclosure provides a method, wherein the first and/or the second and the third engineered immunoglobulin chains comprise an Fc region from the same species, preferably from the same species and isotype, more preferably from the same species, isotype and subclass.

In some embodiments the present disclosure provides a method, wherein the Fc regions of the first and second engineered immunoglobulin chains are not identical. In some embodiments the present disclosure provides a method, wherein the Fc regions of the first and second engineered immunoglobulin chains have amino acid sequences which are different from each other by one amino acid or by two amino acids or by three amino acids or by four amino acids or by five amino acids or by five to ten amino acids or by ten to thirty amino acids In some embodiments the present disclosure provides a method, wherein the hetero-dimeric immunoglobulin or fragment thereof is a full-length antibody.

In some embodiments the present disclosure provides a method, wherein the hetero-dimeric immunoglobulin or fragment thereof is a full-length antibody which is bispecific.

In some embodiments the present disclosure provides a bispecific hetero-dimeric immunoglobulin or fragment thereof or a bispecific full-length antibody which binds to antigens selected from the group consisting of HER2, EGFR, CD19 and VLA-2. Preferably the bispecific hetero-dimeric immunoglobulin or fragment thereof or the bispecific antibody is specific to HER2 and EGFR. Equally preferably the bispecific hetero-dimeric immunoglobulin or fragment thereof or the bispecific antibody is specific to CD19 and VLA-2.

In some embodiments the present disclosure provides a method, wherein at least one additional polypeptide is fused to the first and/or second engineered immunoglobulin chain. Preferably the additional domain is fused to the first engineered immunoglobulin chain. Optionally the additional domain can be fused to the first and/or second parent immunoglobulin chain before engineering the parent domain. Suitably the additional domain is selected from the group consisting of FAB, scFv, diabody, domain antibody, pharmacologically active peptide or protein, receptor extracellular domain, CDR grafted polypeptide and therapeutic engineered protein scaffold.

In a further aspect the present invention provides a method to engineer a protein-protein interface of a domain of a multidomain protein comprising:
(a) providing a multidomain protein comprising a domain with a protein-protein interface;
(b) selecting as a donor domain a naturally occurring immunoglobulin super-family member comprising a domain with a protein-protein interface which is different from the domain of (a);
(c) overlaying 3D structures of the domain with the protein-protein interface of (a) and the donor domain with the protein-protein interface of (b);
(d) identifying exposed protein-protein interface residues in the overlayed 3D structures of the domain with the protein-protein interface of (a) and the donor domain with the protein-protein interface of (b);

e) substituting at least one amino acid residue of the identified exposed protein-protein interface amino acid residues of the domain with the protein-protein interface of (a) with amino acid residues at the equivalent 3D structural position from the identified exposed protein-protein interface amino acid residues from the donor domain with the protein-protein interface of (b).

In some embodiments the present disclosure provides a method, wherein the naturally occurring immunoglobulin super-family member is a naturally occurring homo-dimer In some embodiments the present disclosure provides a method, wherein the naturally occurring immunoglobulin super-family member is a naturally occurring hetero-dimer. Usually at least two, preferably at least three, more preferably at least four, most preferred at least five, in particular at least six, more particular at least seven amino acid residues are substituted. Preferably the domain with a protein-protein interface of the multidomain protein of (a) is capable to form a homo-dimer, preferably a naturally occurring homo-dimer, with another domain. Preferably the domain with a protein-protein interface of the multidomain protein of (a) is capable to form a hetero-dimer, preferably a naturally occurring hetero-dimer, with another domain. Preferably, the exposed interface residues identified in the immunoglobulin chain and in the selected immunoglobulin super-family members are non essential to the domain core integrity. Preferably, the naturally occurring immunoglobulin super-family member is selected from the TCR constant domain family. More preferably, the donor domain is the TCR constant domain alpha (SEQ ID NO: 1) or the TCR constant domain beta (SEQ ID NO: 2), whereas in an alternative embodiment the cysteine (C) at amino acid position 75 in SEQ ID NO: 2 is substituted with alanine (A) or serine (S). As well preferred as donor domain is a CH3 domain, more preferably a human CH3 domain, in particular a human CH3 domain from IGHG1.

In a further embodiment the present disclosure provides a method, wherein the donor domain is the TCR constant domain gamma (SEQ ID NO: 33) or the TCR constant domain delta (SEQ ID NO: 32).

In some embodiments the present disclosure provides a method, wherein the amino acid residues of the protein-protein interface of the parent domain of the first and/or second parent immunoglobulin chain which are substituted are not adjacent.

Preferably, the identified exposed protein-protein interface amino acid residues of the donor domain with the protein-protein interface of (b) which are used for substituting at least one amino acid residue of the identified exposed protein-protein interface amino acid residues of the domain with the protein-protein interface of (a) are selected from the group consisting of K20, V22, T26, Y43, S61, V63, W65 and N67 wherein the amino acid position of each group member corresponds to the amino acid position in SEQ ID NO: 1. Alternatively preferred, the identified exposed protein-protein interface amino acid residues of the donor domain with the protein-protein interface of (b) which are used for substituting at least one amino acid residue of the identified exposed protein-protein interface amino acid residues of the domain with the protein-protein interface of (a) are selected from the group consisting of E10, A12, F14, T28, V30, T34, D59, L63, E65, C75, S77, R79 and R81 wherein the amino acid position of each group member corresponds to the amino acid position in SEQ ID NO: 2.

Preferably, the identified exposed protein-protein interface amino acid residues of the donor domain with the protein-protein interface of (b) which are used for substituting at least one amino acid residue of the identified exposed protein-protein interface amino acid residues of the domain with the protein-protein interface of (a) are selected from the group consisting of K4, T6, T22, L24, E28, K29, G53, M56, M63, F65, W67, wherein the amino acid position of each group member corresponds to the amino acid position in SEQ ID NO: 33 Alternatively preferred, the identified exposed protein-protein interface amino acid residues of the donor domain with the protein-protein interface of (b) which are used for substituting at least one amino acid residue of the identified exposed protein-protein interface amino acid residues of the domain with the protein-protein interface of (a) are selected from the group consisting of M13, N18, A20, E25, F44, A47, S51, N57, V59, L61, K63, wherein the amino acid position of each group member corresponds to the amino acid position in SEQ ID NO: 32.

Preferably, the identified exposed protein-protein interface amino acid residues of the donor domain with the protein-protein interface of (b) which are used for substituting at least one amino acid residue of the identified exposed protein-protein interface amino acid residues of the domain with the protein-protein interface of (a) are selected from the group consisting of Q127, Y129, L131, D136, E137, Q142, S144, T146, K150, K172, T174, V177, D179, F185, Y187, K189, wherein the amino acid position of each group member corresponds to the amino acid position in SEQ ID NO: 12.

In a further aspect the present invention provides the use of a donor domain of a first and a second member of the naturally occurring immunoglobulin super-family to engineer a hetero-dimeric immunoglobulin or hetero-dimeric fragment thereof comprising a first engineered immunoglobulin chain comprising at least one engineered domain which has a protein-protein interface which is substituted with at least one amino acid residue from the protein-protein interface of the donor domain of the first member of the naturally occurring immunoglobulin super-family and a second engineered immunoglobulin chain comprising at least one engineered domain which has a protein-protein interface which is substituted with at least one amino acid residue from the protein-protein interface of the donor domain of the second member of the naturally occurring immunoglobulin super-family.

Usually, the donor domain of the first member of the naturally occurring immunoglobulin super-family and the donor domain of the second member of the naturally occurring immunoglobulin super-family form a naturally occurring hetero-dimer or a naturally occurring homo-dimer, preferably a naturally occurring hetero-dimer. Preferably the first and the second member of the naturally occurring immunoglobulin super-family are selected from T cell receptor chains.

More preferably the donor domain of the first member of the naturally occurring immunoglobulin super-family is the TCR constant domain alpha (SEQ ID NO: 1) and the donor domain of the second member of the naturally occurring immunoglobulin super-family is the TCR constant domain beta (SEQ ID NO: 2).

Equally more preferred, the donor domain of the first member of the naturally occurring immunoglobulin super-family is the TCR constant domain delta (SEQ ID NO: 32) and the donor domain of the second member of the naturally occurring immunoglobulin super-family is the TCR constant domain gamma (SEQ ID NO: 33). Equally more preferred, the donor domain of the first and the second member of the naturally occurring immunoglobulin super-family is a CH3 domain.

EXAMPLES

Example 1

Construction of an Immunoglobulin Fc Hetero-Dimer Having a CH3-CH3 Protein-Protein Interface Based on the Human α/β T Cell Receptor Constant Domains This example demonstrates that two human IGHG1 Fc chains (each chain consisting of human hinge (γ1), CH2 and CH3 constant domains; EU residues 221-447) having mutations in the protein-protein interface of their CH3 domains (EU residues 341-447) carefully selected from a subset of the protein-protein interface residues from the human T-cell receptor (TCR) constant domain alpha (GenBank database accession number AA072258.1 [residues 135-225]; SEQ ID NO: 1; IMGT® reference TRAC [complete sequence], the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005); Kaas Q et al., *Briefings in Functional Genomics & Proteomics*, 6(4):253-64 (2007)) for one chain and the human TCR constant domain beta (GenBank database accession number AAA61026.1 [residues 134-261], SEQ ID NO: 2; IMGT® reference TRBC2 [IMGT® residues 1.8-124]) for the second chain, assemble into a hetero-dimeric Fc molecule with at least 76% efficacy. TRBC2 is one of two naturally occurring allotypes for the human TCR constant domain beta. Both TRBC1 and TRBC2 can be equivalently used for the purpose to mutate the CH3 domain of IGHG1 Fc chains since there is no difference in the amino acid sequence of their protein-protein interfaces.

Mutations were derived from the analysis of an overlay of the crystal structure of the LC13 TCR molecule (Kjer-Nielsen L et al., *Structure*, 10(11):1521-32 (2002)) with the crystal structure of the Fc fragment from human IGHG1 (Krapp S et al., *J Mol Biol*, 325(5):979-89 (2003)). Both TCR and IGHG1 Fc 3D structures were retrieved from the Protein Data Bank (PDB codes 1KGC and 1H3Y for TRBC2 (SEQ ID NO: 2) and human IGHG1, respectively; www.p-db.org; Bernstein F C et al., *Eur J Biochem*, 80(2):319-24 (1977)), overlaid with the Coot software (Emsley P and Cowtan K, *Acta Crystallogr D Biol Crystallogr*, 60(Pt 12 Pt 1):2126-32 (2004)) and further visualized with the Discovery-Studio software from Accelrys (Cambridge, UK). Examination of the protein-protein interface of the overlaid 3D structures of the TCR hetero-dimeric constant domains and the CH3 homo-dimer was used as a starting point for rational design. Several parameters were considered; these included but were not limited to: preservation of the prolines residues, and preservation of amino acid positions involved in the integrity of the domain cores as well as some of the electrostatic contacts from the IGHG1 CH3 homo-dimer; abrogating specific hydrophobic contacts found in the IGHG1 CH3 homo-dimer, and replacing those with selected hydrophobic contacts found in the TCR constant domain hetero-dimer. This analysis led to the design of two subsets of amino acid substitutions, one subset originating from equivalent 3D positions between the protein-protein interface of one subunit of the CH3 homo-dimer and the protein-protein interface of the TCR constant domain alpha, and a second subset originating from equivalent 3D positions between the protein-protein interface of the second subunit of the CH3 homo-dimer and the protein-protein interface of the TCR constant domain beta; each subset creating two new and unique CH3 engineered domain sequences which can hetero-dimerize.

The engineered human IGHG1 Fc chain thereof having mutations derived from the protein-protein interface of the human TCR constant domain alpha in the protein-protein interface of its CH3 domain is designated "BT alpha chain" (FIG. 1), while the engineered human IGHG1 Fc chain thereof having mutations derived from the protein-protein interface of the human TCR constant domain beta in the protein-protein interface of its CH3 domain is designated "BT beta chain" (FIG. 1). More specifically, the BT alpha chain consists of an immunoglobulin Fc chain from human IGHG1 having an engineered CH3 domain with the following substitutions: S364K, T366V, K370T, K392Y, F405S, Y407V, K409W, and T411N (SEQ ID NO: 3) (EU numbering); and accordingly, the "BT beta chain" consists of an immunoglobulin Fc chain from human IGHG1 having an engineered CH3 domain with the following substitutions: Q347E, Y349A, L351F, S364T, T366V, K370T, T394D, V397L, D399E, F405C, Y407S, K409R, and T411R (SEQ ID NO: 4) (EU numbering).

Figure 2:
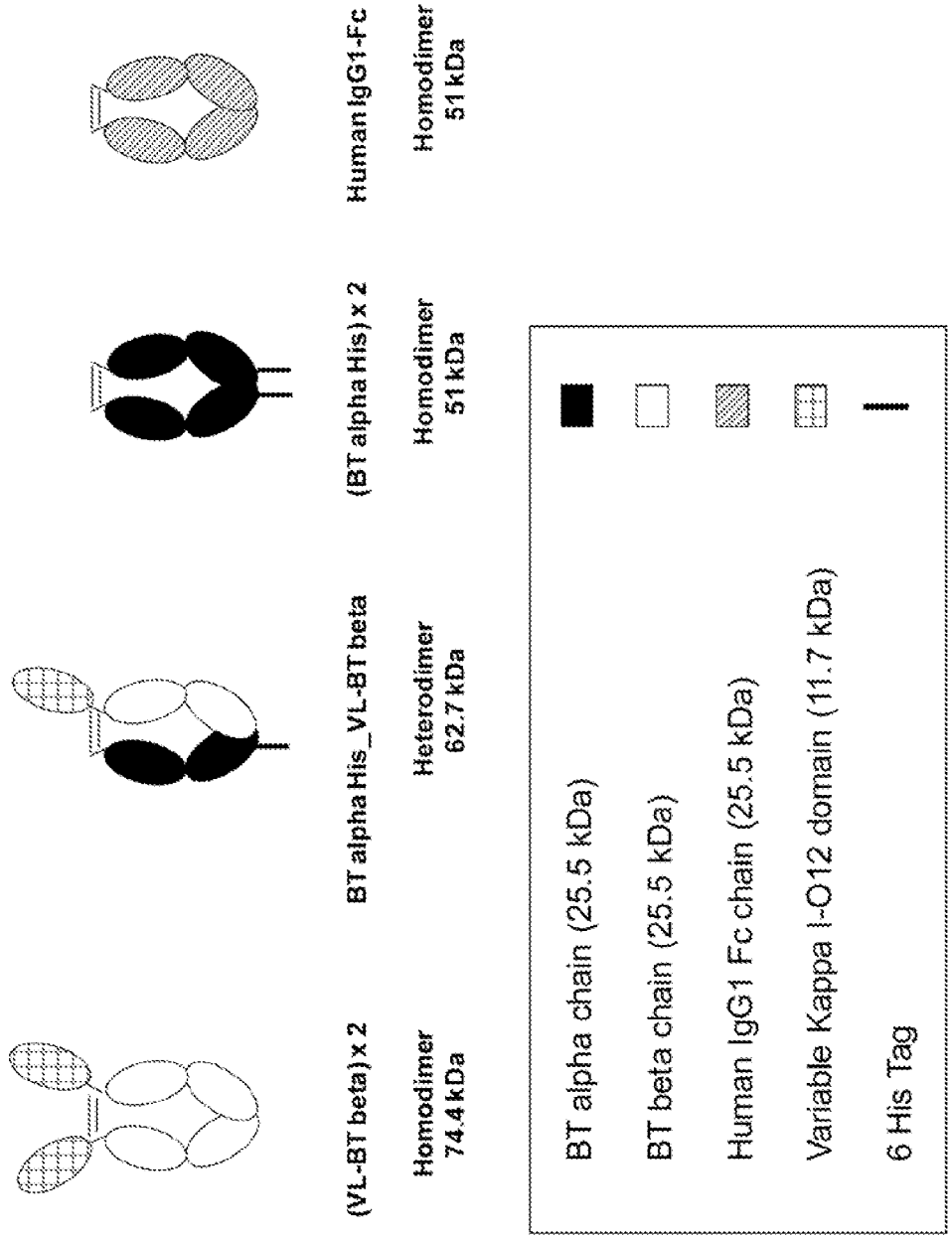
FIG. 2: Schematic diagram of the various pairings of the BT alpha His and VL-BT beta chains. The BT alpha chain has a pol alpha His homo-dimer (E) VL-BT beta F405A monomer.

The formation of the hetero-dimer Fc can be assessed by SDS-PAGE analysis of samples under non-reducing and reducing conditions. Because the BT alpha chain and the BT beta chain have similar molecular weights, the BT beta chain was fused to a variable light-chain Kappa domain antibody (abbreviated VL, a subfamily KappaI-O12 member derived from the VBASE2 humIGKV115 sequence with the IGKJ1*01 junction, SEQ ID NO: 5; Retter I et al., *Nucleic Acids Res*, 33(Database issue):D671-4 (2005)), to generate a difference in SDS-PAGE mobility and consequently facilitate the identification of hetero-dimer formation (SEQ ID NO: 6) (FIG. 2). Furthermore, to enable confirmation of the presence of the BT alpha chain in the hetero-dimer, a series of six histidine residues was included at its C-terminus (SEQ ID NO: 7). This hetero-dimeric construct is abbreviated BT alpha His_VL-BT beta.

To create the BT alpha His and the VL-BT beta chain cDNA coding sequences, a cDNA coding the engineered CH3 domain of the BT alpha chain (SEQ ID NO: 8) and the engineered CH3 domain of the BT beta chain were synthesized by GENEART AG (Regensburg, Germany). The BT beta chain was originally synthesized with the F405A mutation, which was later converted to F405C (SEQ ID NO: 9) by standard mutagenesis. Using PCR assembly techniques, each chain had their respective engineered CH3 domain cDNA coding sequence fused downstream of a synthetic cDNA encoding for the human IGHG1 hinge (DKTHTCP-PCP) and IGHG1 CH2 constant domain (separately synthesized by GENEART AG). The polyhistidine sequence located at the C-terminus of the BT alpha His chain was included in the anti-sense oligonucleotide during PCR amplification; while the variable Kappa domain antibody located at the N-terminus of the VL-BT beta chain was engineered by fusing the domain cDNA (separately synthesized by GENEART AG) upstream of the BT beta chain cDNA coding sequence using PCR assembly techniques. Finally, the BT alpha His chain and VL-BT beta chain coding DNA sequences (SEQ ID NOs: 10, and 11, respectively) were ligated in independent vectors which are based on a modified pREP4 (Invitrogen, CA, USA) vector carrying CMV promoter and Bovine Growth Hormone poly-adenylation signal. In both chain expression-vectors, secretion was driven by the murine VJ2C leader peptide.

For transient expression of the BT alpha His_VL-BT beta hetero-dimer, equal quantities of each engineered chains vectors were co-transfected into suspension-adapted HEK-EBNA cells (ATCC-CRL-10852) using Polyethyleneimine (PEI). Typically, 100 ml of cells in suspension at a density of 0.8-1.2 million cells per ml is transfected with a DNA-PEI mixture containing 50 µg of expression vector encoding the BT alpha His chain and 50 µg expression vector encoding the VL-BT beta chain. When recombinant expression vectors encoding each engineered chain genes are introduced into the host cells, the hetero-dimeric construct is produced by further culturing the cells for a period of 4 to 5 days to allow for secretion into the culture medium (EX-CELL 293, HEK293-serum-free medium (Sigma, Buchs, Switzerland), supplemented with 0.1% pluronic acid, 4 mM glutamine, and 0.25 µg/ml geneticin). The hetero-dimeric construct was then purified from cell-free supernatant using recombinant Streamline rProtein A media (GE Healthcare Europe GmbH, Glattbrugg, Switzerland), and used for further analysis.

Figure 3:
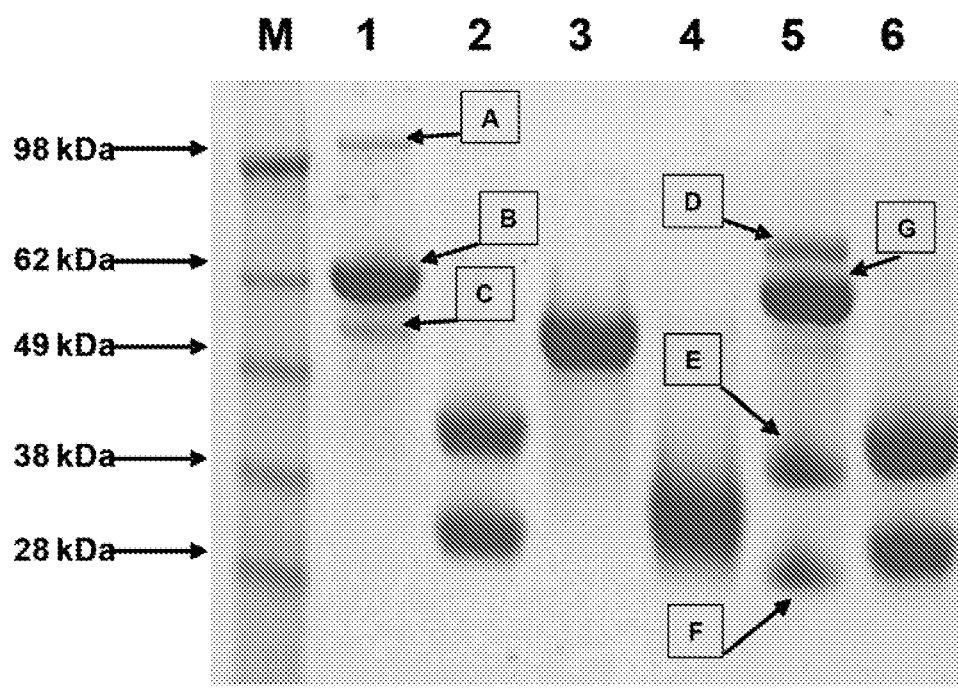
Figure 4A:
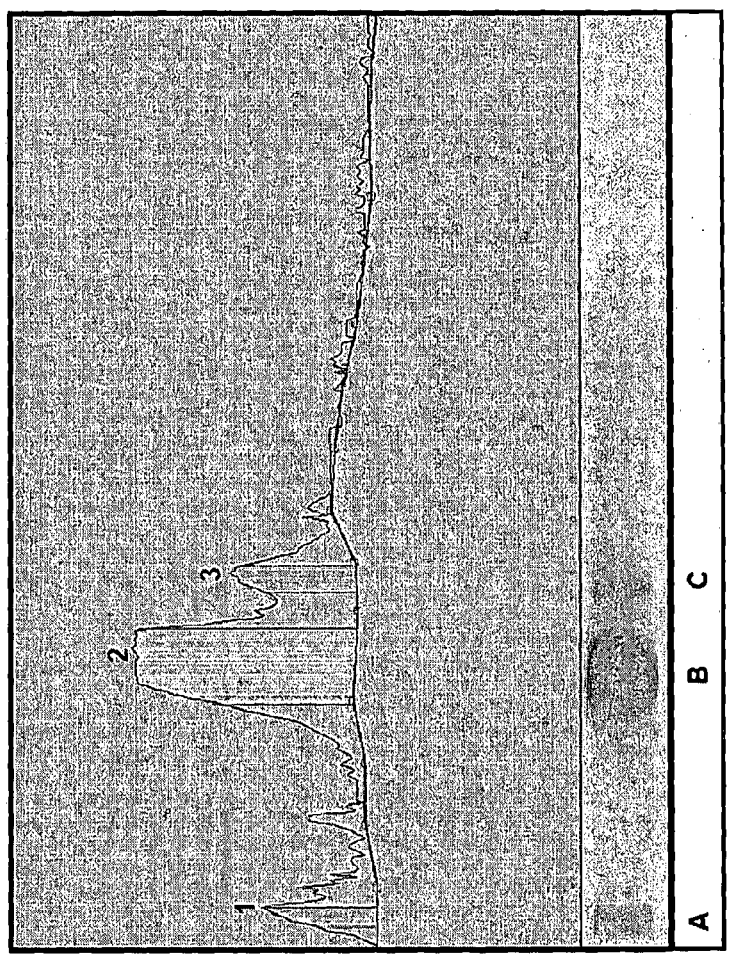
Figure 4B:
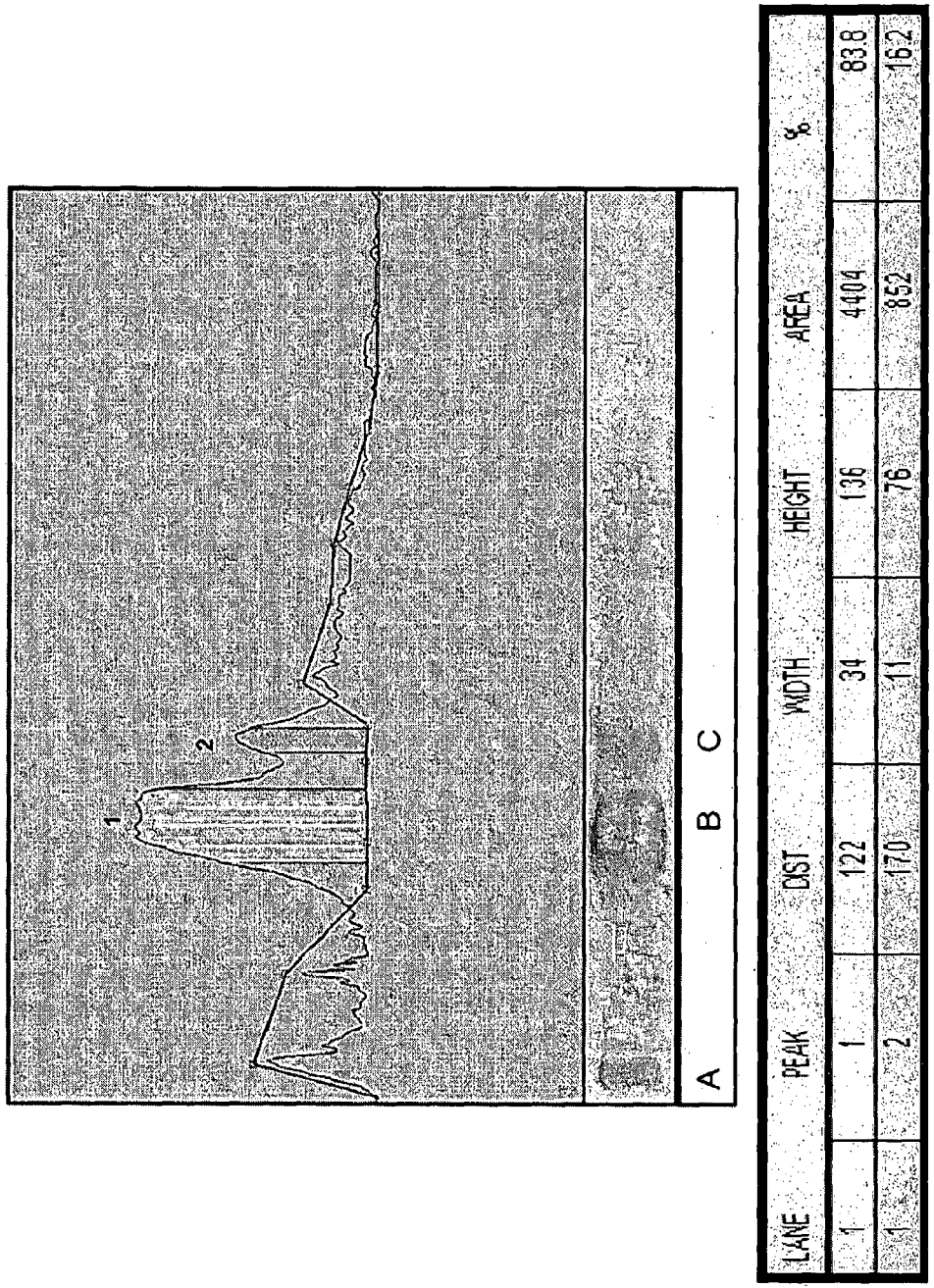
Figure 5:
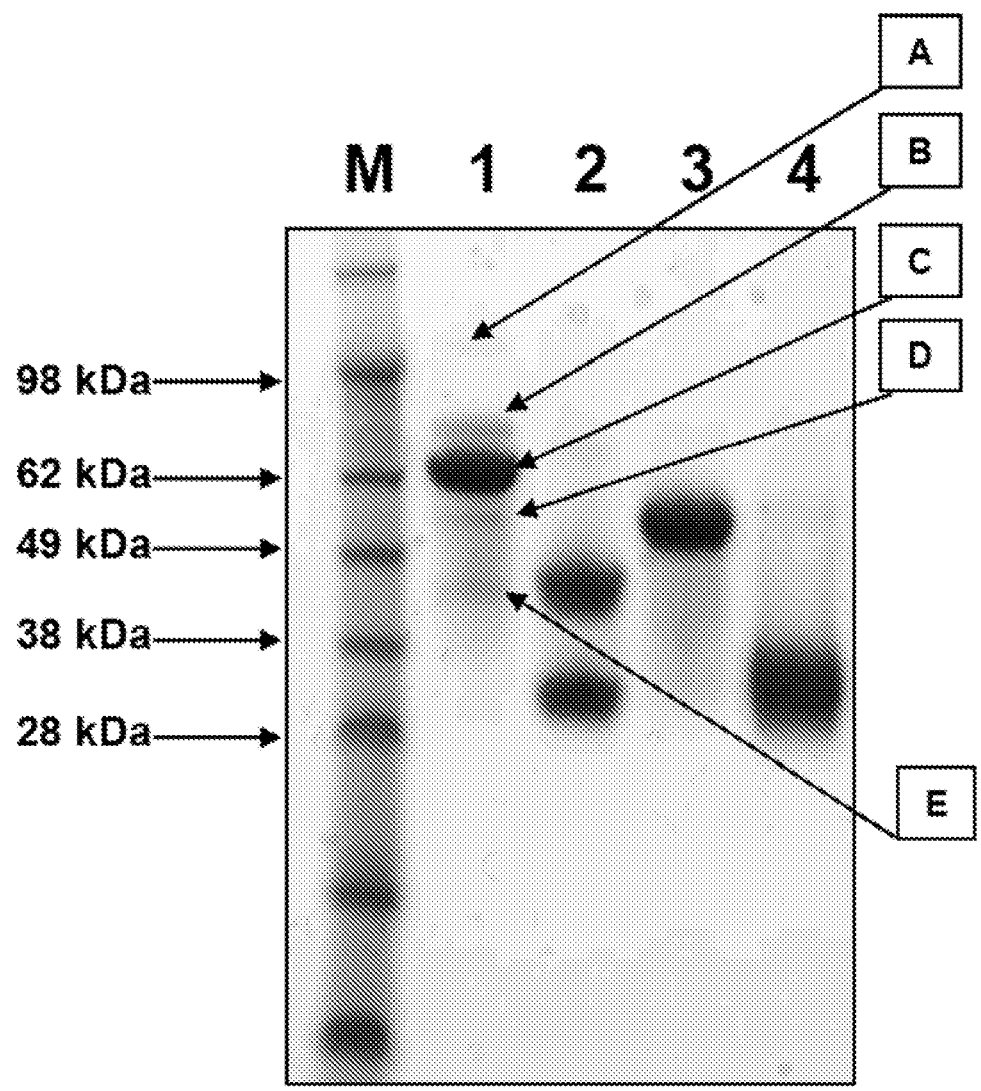
Figure 6:
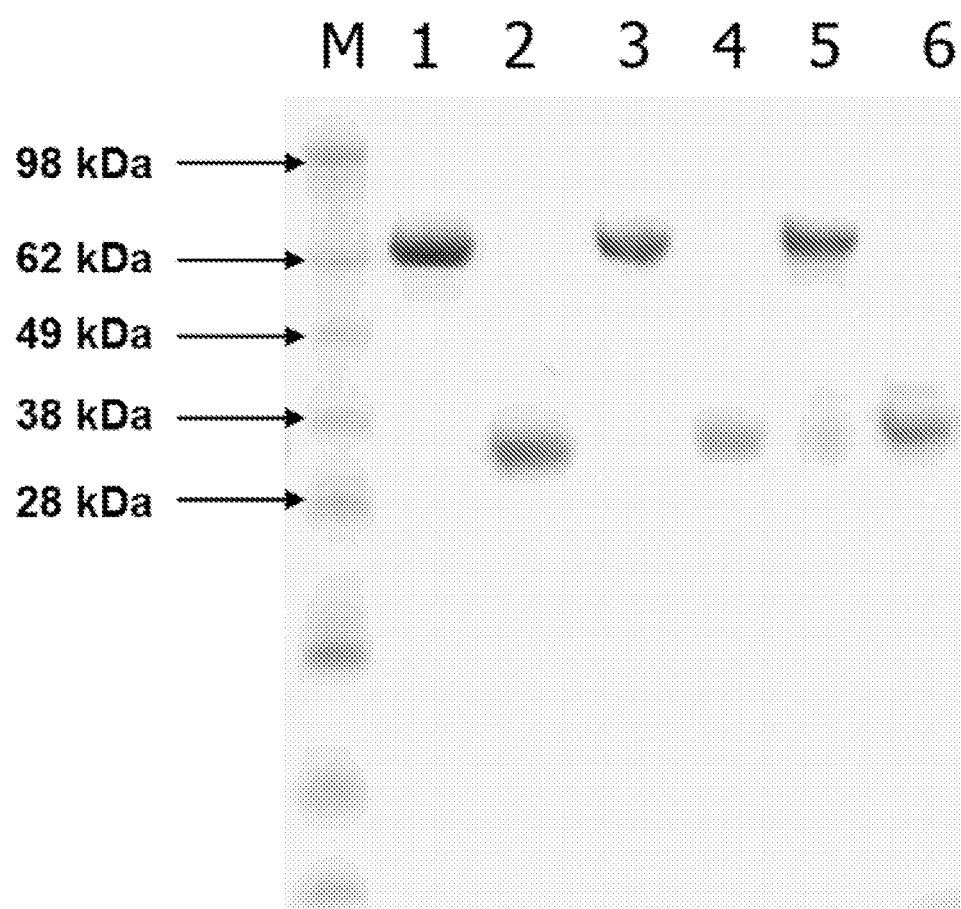
Figure 7A:
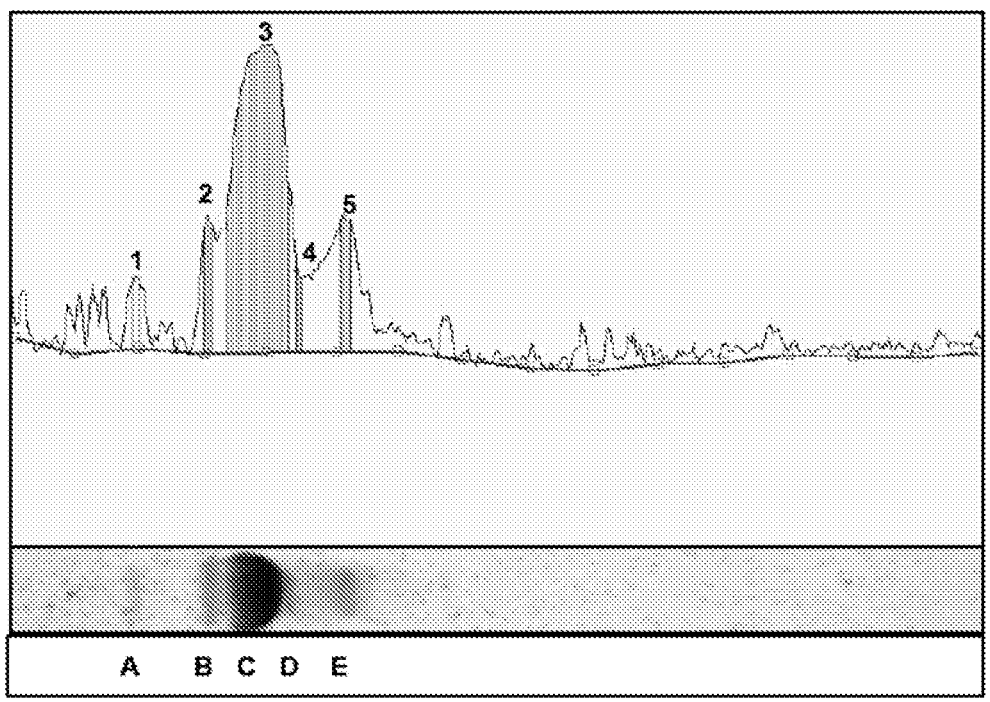
FIG. 7B: scanning densitometry analysis assessing the relative proportion of the BT alpha His_VL-BT beta F405A hetero-dimer to homo-dimers after protein-A purification when omitting the aggregates (4-12% SDS Tris-glycine polyacrylamide gel, non-reducing conditions). (A) undefined aggregates. (B) VL-BT beta F405A homo-dimer (C) BT alpha His_VL-BT beta F405A hetero-dimer (D) BT alpha His homo-dimer (E) VL-BT beta F405A monomer.
FIG. 7C: DSC thermogram of the hetero-dimeric BT alpha His_BT beta (F405A) HA hetero-dimer
Figure 7B:
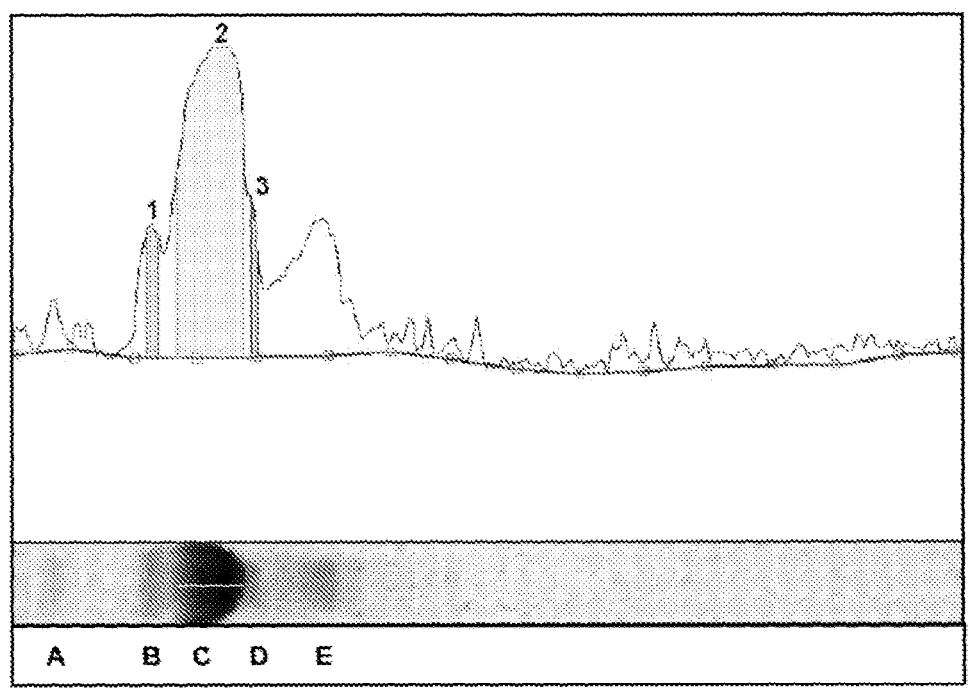
Figure 7C:
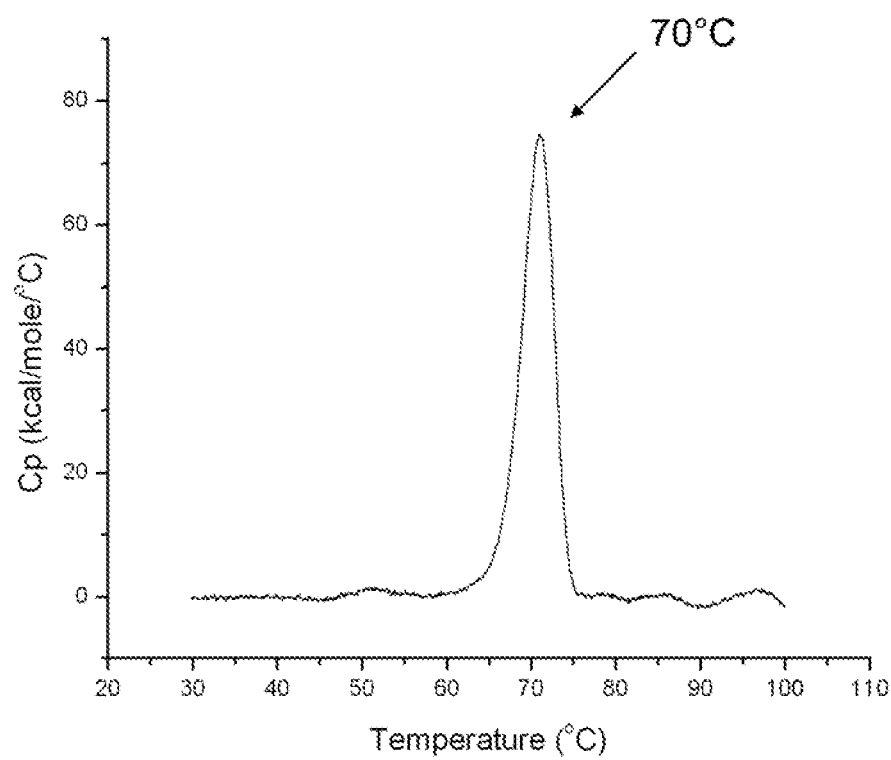

Transient transfection production yields were above 20 mg/l. The results of a typical SDS-PAGE analysis are shown in FIG. 3. Post protein-A purification the BT alpha His_VL-BT beta hetero-dimer is the main species produced with little homo-dimeric species present (lane 1). Of particular interest is the comparison with the SDS-PAGE mobility of a standard homo-dimeric human IGHG1 Fc (GenBank database accession number AAC82527.1 residues 103-329; SEQ ID NO: 12 (lane 3)), under reducing conditions, the BT alpha His_VL-BT beta hetero-dimer breaks down into the two expected molecular weight bands for the BT alpha His chain and the VL-BT beta chain (lane 2; 25.5 kDa, and 37.2 kDa, respectively; an additional 3 kDa needs to be added to each of these molecular weights to account for chain N-glycosylation at Asn 297) whereas the standard homo-dimeric human IGHG1 Fc (lane 4) collapses into one unique molecular weight band having a similar mobility to the BT alpha His chain. Accordingly, under non-reducing condition, comparison with a standard homo-dimeric human IGHG1 Fc allows identification of traces of BT alpha His homo-dimer present at a very low abundance. Finally aggregates can be also detected at a very low abundance.

It is possible to assess the proportion of hetero-dimer to homo-dimer in the protein-A purified preparation by scanning densitometry analysis of the non-reduced SDS-polyacrylamide (4-12%) gel bands. Relative ratios of the different species mentioned above were quantified using a FluorChem SP imaging system (Witec AG, Littau, Switzerland) following the protocol provided by the manufacturer. The BT alpha chain His_VL-BT beta chain hetero-dimer represents overall at least 76.1% of the protein-A purified material (FIG. 4A); when omitting traces of aggregates in the relative ratio measurements, the BT alpha chain His_VL-BT beta chain hetero-dimer represents overall at least 83.8% of the protein-A purified material (FIG. 4B).

Example 2

Construction of Immunoglobulin Fc Hetero-Dimer Variants Having a CH3-CH3 Protein-Protein Interface Based on the Human α/β T Cell Receptor Constant Domains T-cell receptor domains are very prone to aggregation and misassociation during folding, and this is often compounded by incorrect disulfide bond formation (Pecorari F et al., *J Mol Biol,* 285(4):1831-43 (1999)). Mutation of the unpaired cysteine in the TCR constant domain beta has been shown to facilitate the production of TCR molecules in *E. coli* (Willcox B E et al., *Protein Sci,* 8(11):2418-23 (1999)). In addition, this unpaired cysteine has been mutated in several TCR molecule crystal structures. Mutations of C405A and C405S in the BT beta chain coding DNA sequences were derived from the analysis of an overlay of the crystal structure of the Fc fragment from human IGHG1 (Krapp S et al., *J Mol Biol,* 325(5):979-89 (2003)) with the crystal structure of the CD1d-α-GalCer-specific TCR molecule 5E (PDB code 2CDF, Gadola S D et al., *J Exp Med,* 203(3):699-710 (2006)) and the crystal structure of the T cell receptor (TCR) HA1.7 (PDB code 1J8H, Hennecke J and Wiley D C, *J Exp Med,* 195(5):571-81 (2002)). Since the engineered CH3 domain of the BT beta chain was originally synthesized with the F405A mutation, this construct was directly used to build a new VL-BT beta chain identical to the VL-BT beta chain described in example 1 except for the introduction of the F405A mutation. The VL-BT beta chain having the F405A mutation was then modified to create a second VL-BT beta chain having the F405S mutation using standard mutagenesis techniques. These two new chains identical to the VL-BT beta chain described in example 1 expect for their F405A and F405S mutations respectively, are referred herein as "VL-BT beta F405A chain" or "VL-BT beta F405A" and "VL-BT beta F405S chain" or "VL-BT beta F405S".

Transient expression of the BT alpha His_VL-BT beta F405S hetero-dimer and BT alpha His_VL-BT beta F405A hetero-dimer were performed as described in example 1. Production yields for the BT alpha His_VL-BT beta F405A hetero-dimer were similar to the BT alpha His_VL-BT beta hetero-dimer (22 mg/l each). For the BT alpha His_VL-BT beta F405S hetero-dimer production yields of 37 mg/l were obtained. To assess the quality of the BT alpha His_VL-BT beta F405S hetero-dimer formation over the BT alpha His_VL-BT beta hetero-dimer described in example 1, both BT hetero-dimers were run on the same SDS-PAGE gel (FIG. 3, lane 1 (BT alpha His_VL-BT beta) and 5 (BT alpha His_VL-BT beta F405S)). Post protein-A purification the BT alpha His_VL-BT beta F405S hetero-dimer is the main species produced, however when compared to the BT alpha His_VL-BT beta hetero-dimer described in example 1, significantly higher amounts of monomeric species as well as VL-BT beta F405S homo-dimer species were observed, indicating a higher hetero-dimeric assembly efficacy of the naturally occurring F405C substitution over the mutated F405S substitution. Similarly to the BT alpha His_VL-BT beta hetero-dimer, under reducing conditions, the BT alpha His_VL-BT beta F405S hetero-dimer breaks down into the two expected molecular weight bands for the BT alpha His chain and the VL-BT beta F405S chain (lane 6).

The results of a typical SDS-PAGE analysis for the BT alpha His_VL-BT beta F405A hetero-dimer are shown in FIG. 5. Post protein-A purification the BT alpha His_VL-BT beta F405A hetero-dimer is the main species produced with little homo-dimeric species present (lane 1). Similarly to the BT alpha His_VL-BT beta hetero-dimer, under reducing conditions, the BT alpha His_VL-BT beta F405A hetero-dimer breaks down into the two expected molecular weight bands for the BT alpha His chain and the VL-BT beta F405A chain (lane 2). Accordingly, under non-reducing condition, comparison with a standard homo-dimeric human IGHG1 Fc (lane 3: non-reducing conditions, lane 4: reducing conditions) allows identification of traces of BT alpha His homo-dimer present at a very low abundance. Finally traces of VL-BT beta F405A homo-dimer and monomer as well as aggregates can be also detected at a very low abundance.

To further demonstrate the identity of BT alpha His_VL-BT beta F405A hetero-dimer, the protein-A purified material was loaded on Ni$^{2+}$ affinity sepharose (GE Healthcare Europe GmbH, Glattbrugg, Switzerland), a chromatographic step which is specific for species containing the BT alpha His chain due to its polyhistidine sequence. After a wash step, bound and eluted fractions from the Ni$^{2+}$ affinity step were pooled and loaded onto protein-L affinity agarose (GenScript USA Inc., Piscataway, N.J., USA), a superantigen affinity resin which specifically select for species having the variable light-chain Kappa domain antibody, i.e. the VL-BT beta F405A chain. Outputs of the above purification steps were then assessed by Western blotting with an antibody against the polyhistidine sequence labeled with horseradish peroxidase, thereby detecting the BT alpha His chain. The blot was stained using Sigma Fast 3,3'-Diaminobenzidine precipitating substrate (Sigma, Buchs, Switzerland). FIG. 6 shows that the BT alpha His chain is consistently detected before, and after $Ni^{2+}$ sepharose but also and more importantly after protein-L agarose chromatography, demonstrating the identity of the hetero-dimer It is possible to assess the proportion of hetero-dimer to homo-dimer in the protein-A purified preparation by scanning densitometry analysis of the non-reduced SDS-polyacrylamide (4-12%) gel bands. Relative ratios of the different species mentioned above were quantified using a FluorChem SP imaging system (Witec AG, Littau, Switzerland) following the protocol provided by the manufacturer. The BT alpha chain His_VL-BT beta chain hetero-dimer represents overall at least 80.7% of the protein-A purified material (FIG. 7A); when omitting traces of aggregates and VL-BT beta F405A chain monomer in the relative ratio measurements, the BT alpha chain His_VL-BT beta F405A chain hetero-dimer represents overall at least 86.9% of the protein-A purified material (FIG. 7B).

Protein stability is a crucial issue for the development of recombinant antibody therapeutics. A poor stability can affect the ability of an antibody to fold when expressed in various cell types (Garber E and Demarest S J, *Biochem Biophys Res Commun,* 355(3):751-7 (2007)), and lead to a fraction of the clinical material to be misfolded, non functional and/or prone to aggregate, and thus potentially immunogenic (Chirino A J et al., *Drug Discov Today,* 9(2):82-90 (2004)). To assess the intrinsic stability of the hetero-dimeric Fc fragment without any interference from an additional protein domain, a BT beta chain without variable kappa domain (this chain was engineered similarly to the other BT beta chains but had a C-terminal HA tag (YPYDVPDYA) and no VL domain, abbreviated BT beta (F405A) HA chain; SEQ ID NO: 17) was co-expressed with a BT alpha His chain. The resulting hetero-dimeric molecule: BT alpha His_BT beta (F405A) HA was purified as above and analyzed using differential scanning calorimetry (DSC). The calorimetric measurements were carried out on a VP-DSC differential scanning microcalorimeter (GE Healthcare Europe GmbH, Glattbrugg, Switzerland). The cell volume was 0.128 ml, the heating rate was 1° C./min, and the excess pressure was kept at 64 p.s.i. The protein was used at a concentration of 2 mg/ml in PBS (pH 7.4). The molar heat capacity of the protein was estimated by comparison with duplicate samples containing identical buffer from which the protein had been omitted. The partial molar heat capacities and melting curves were analyzed using standard procedures. Thermograms were baseline corrected and concentration normalized before being further analyzed using a Non-Two State model in the Origin (v7.0) software (Origin-Lab Corporation, Northampton, Mass., USA; provided by GE Healthcare Europe GmbH, Glattbrugg, Switzerland).

The expected melting profiles for the human IgG subclasses are known (Garber E and Demarest S J, *Biochem Biophys Res Commun,* 355(3):751-7 (2007)), and all profiles have been shown to contain three unfolding transitions corresponding to the independent unfolding of the CH2, CH3, and FAB domains. Of the four human IgG subclasses, IGHG1 has the most stable CH3 domain (~85° C.); while other subclasses CH3 domains are less stable, although none are known to melt below 70° C. Similarly, all subclasses are known to have a melting temperature of ~70° C. for the CH2 domain (Garber E and Demarest S J, *Biochem Biophys Res Commun,* 355(3):751-7 (2007)). Overall no melting transition is expected to be lower than 70° C. for a stable antibody Fc fragment (hinge-CH2-CH3). FIG. 7C shows a thermogram of the BT alpha His_BT beta (F405A) HA hetero-dimer exhibiting a single sharp transition at 70° C., accounting for the melting transitions of both the CH2 domain and the engineered CH3 domain. It is important to note that no sharp decrease after the heat absorption peak was recorded, indicating that no precipitation or aggregate formation occurred after thermal unfolding as expected for a stable antibody Fc fragment (Liu H et al., *Immunol Lett,* 106(2):144-53 (2006)). Furthermore, the hetero-dimeric Fc fragment has stability similar to the naturally occurring Fc fragments since the melting transitions of its domains are similar to the ones observed for the human IGHG4 Fc fragment where both the CH2 domain and the CH3 domain melt at approximately 70° C. (Garber E and Demarest S J, *Biochem Biophys Res Commun,* 355(3):751-7 (2007)). In conclusion, this thermal unfolding study shows that the hetero-dimeric Fc fragment with engineered protein-protein interfaces based on the TCR alpha and beta constant domains is stable and suitable for building further therapeutic hetero-dimeric immunoglobulins.

Example 3

Construction of Immunoglobulin Fc Hetero-Dimer Variants Having a CH3-CH3 Protein-Protein Interface Based on the Human α/β T Cell Receptor Constant Domains with Minimal Substitutions To identify pairs of BT alpha and beta chains that will form hetero-dimers over the formation of possible homo-dimers with a reduced number of amino acid substitutions originating from the key protein-protein interface residues from the human T-cell receptor (TCR) constant domain alpha (GenBank database accession number AA072258.1, residues 135-225; SEQ ID NO: 1; IMGT® reference TRAC [complete sequence], the international ImMunoGeneTics information System®; Lefranc M P et al., *Nucleic Acids Res,* 27(1):209-12 (1999); Ruiz M et al., *Nucleic Acids Res,* 28(1):219-21 (2000); Lefranc M P, *Nucleic Acids Res,* 29(1):207-9 (2001); Lefranc M P, *Nucleic Acids Res,* 31(1):307-10 (2003); Lefranc M P et al., *Dev Comp Immunol,* 29(3):185-203 (2005); Kaas Q et al., *Briefings in Functional Genomics & Proteomics,* 6(4):253-64 (2007)) for one chain and the human TCR constant domain beta (GenBank database accession number AAA61026.1 [residues 134-261], SEQ ID NO: 2; IMGT® reference TRBC2 [IMGT® residues 1.8-124]) for the second chain, two or more of the substitutions described in example 1 and 2 were gradually introduced in each chain.

There are multiple subsets of amino acid substitutions originating from the key protein-protein interface residues from the human TCR constant domain alpha and beta that can be chosen to alternate between the TCR constant domain sequence and the human IGHG1 Fc sequence in the BT alpha and beta chains, respectively. The choice of residues for each considered subset is based on structural considerations, for example, protein-protein surface interaction calculations. All substitution subsets were engineered by mutating the human IGHG1 Fc DNA coding sequence (SEQ ID NO: 12) using standard molecular biology techniques (example 1). The resulting variants were then ligated independently into the modified pREP4 vector mentioned previously and co-transfected into HEK293-EBNA cells as described in example 1. Protein production was also according to example 1. Each subset of substitutions was assessed for its rate of hetero-dimerization using a combination of SDS-PAGE analysis of samples under non-reducing and reducing conditions, and scanning densitometry (as stated in example 1).

Because the engineered chains have close molecular weights, similarly to example 1, the BT beta chain variants were fused to a variable light-chain kappa domain antibody (abbreviated VL, a subfamily Kappa I-O12 member derived from the VBASE2 humIGKV115 sequence with the IGKJ1*01 junction, SEQ ID NO: 5; Retter I. et al, 2005, Nucleic Acids Res., 33, Database issue D671-D674) to generate a difference in SDS-PAGE mobility and consequently facilitate the identification of hetero-dimer formation. To differentiate these chains from example 1, and since these BT chains have identical amino acid sequence to the human IGHG1 Fc sequence except for the specific TCR alpha and beta constant domain based substitutions which have been introduced by site-directed mutagenesis, the BT alpha and VL-BT beta chains are herein abbreviated Fc (BTA) chain and VL-Fc (BTB) chain, respectively. For each chain, the specific substitutions which have been introduced into the human IGHG1 Fc sequence are indicated using the EU numbering. The result of these expression experiments, in terms of yield and hetero-dimerization rate are summarized in Table 1. Two to six substitutions were made in each chain.

Figure 8:
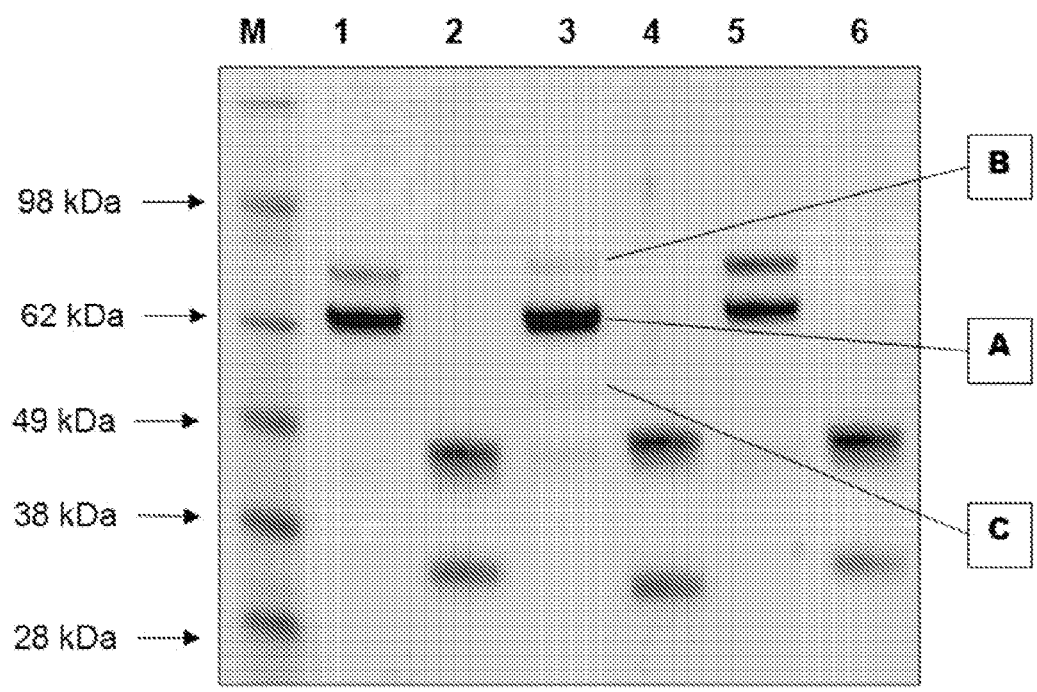
FIG. 8: SDS-PAGE analysis demonstrating production of the hetero-dimer Fc (BTA)-S364K-T366

The results of a typical SDS-PAGE analysis are shown in FIG. 8. Post protein-A purification the hetero-dimer is the main species produced with little homo-dimeric species present (lane1). Under reducing conditions the hetero-dimer breaks down into the two expected molecular weight bands for the engineered Fc (BTA) chain and the other engineered VL-Fc (BTB) chain (lane 2; ~25 kDa and ~37 kDa, respectively). Transient transfection production yields were up to 50 mg/l while the best hetero-dimerization rate was 90%.

Figure 9:
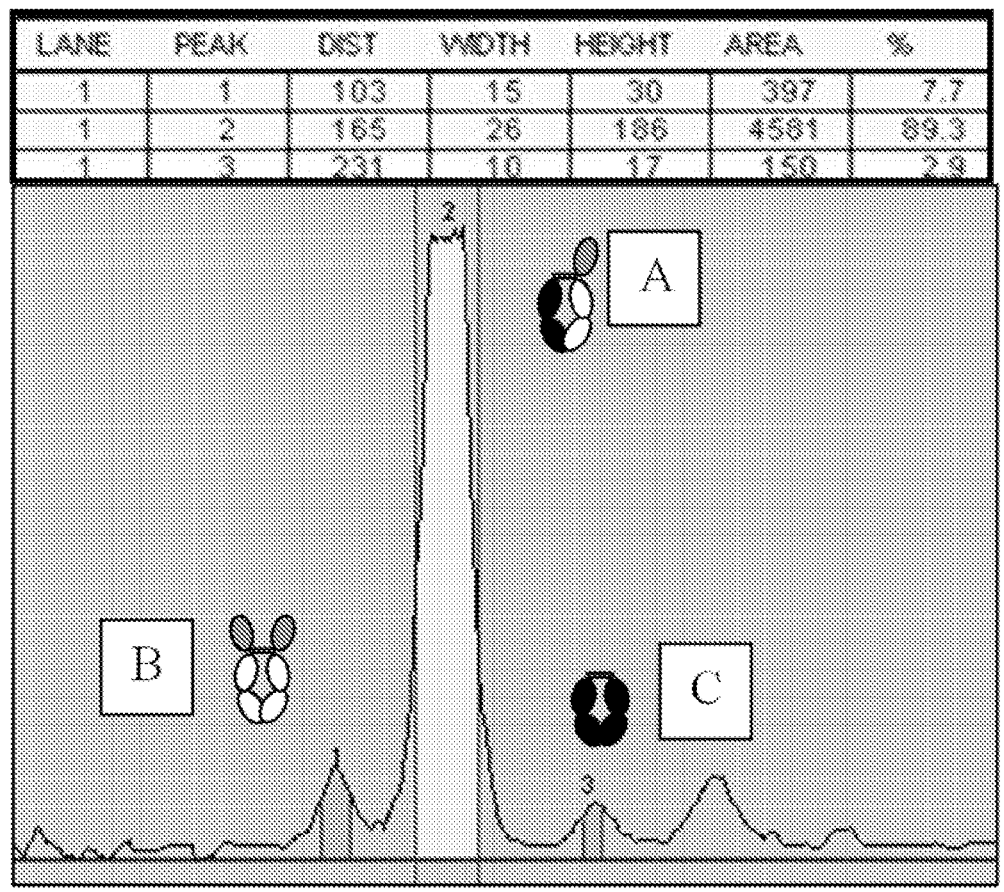

The best combination of substitution subsets was: Fc (BTA)-S364K-T366V-K370T-K392Y-K409W-T411N_VL-Fc (BTB)-F405A-Y407S (SEQ ID NOs: 23 and 24) with a 90% hetero-dimerization rate (FIG. 9) and a transient transfection yield of 30 mg/l. The minimal number of substitutions tested in each chain was two with a 64% hetero-dimerization rate and a transient transfection yield of 35 mg/l. To compare the hetero-dimerization technology described herein with existing methods, a "knob-into-hole" Fc variant (Merchant A M et al., *Nat Biotechnol*, 16(7):677-81 (1998)) with the portion encompassing the "hole" fused to a variable light-chain kappa domain antibody (VL, SEQ ID NO: 5) was created (abbreviated Fc-T366W_VL-Fc-T3665-L368A-Y407V; EU numbering; SEQ ID NOs: 30 and 31). In side by side expression experiments, the "knob-into-hole" based molecule had only a 66% hetero-dimerization rate (data not shown).

TABLE 1

Production yields of minimal BT chains. Hetero-dimer formation percentage is indicated in brackets and represents the percentage of hetero-dimer in the protein-A purified material when omitting impurities in the relative ratio measurements.

| Fc (BTA) chain | VL-Fc (BTB) chain | | | | | |
|---|---|---|---|---|---|---|
| | F405A Y407S SEQ ID NO: 24 | F405A K409R SEQ ID NO: 25 | Y407S K409R SEQ ID NO: 26 | K409R T411R SEQ ID NO: 27 | F405A Y407S K409R SEQ ID NO: 28 | F405A Y407S K409R T411R SEQ ID NO: 29 |
| Y407V K409W SEQ ID NO: 18 | 35 mg/l (64) | 11 mg/l (32) | 39 mg/l (30) | 41 mg/l (36) | 45 mg/l (47) | 28 mg/l (36) |
| K392Y K409W SEQ ID NO: 19 | 35 mg/l (52) | 46 mg/l (46) | 30 mg/l (46) | 18 mg/l (14) | 35 mg/l (50) | 29 mg/l (30) |
| T366V K409W SEQ ID NO: 20 | 51 mg/l (57) | 50 mg/l (46) | 27 mg/l (49) | 26 mg/l (26) | 26 mg/l (49) | 26 mg/l (34) |
| Y407V K409W T411N SEQ ID NO: 21 | 18 mg/l (50) | 20 mg/l (25) | 5 mg/l (25) | 25 mg/l (not quantifiable) | 4 mg/l (52) | 21 mg/l (53) |
| F405S Y407V K409W T411N SEQ ID NO: 22 | 8 mg/l (7) | 7 mg/l (4) | 8 mg/l (5) | 12 mg/l (not quantifiable) | 4 mg/l (15) | 29 mg/l (9) |
| S364K T366V K370T K392Y K409W T411N SEQ ID NO: 23 | 30 mg/l (90) | 5 mg/l (60) | 7 mg/l (74) | 9 mg/l (32) | 10 mg/l (72) | 42 mg/l (88) |

Example 4

Construction of an Immunoglobulin Fc Hetero-Dimer Having a CH3-CH3 Protein-Protein Interface Based on the Human δ/γ T Cell Receptor Constant Domains This example demonstrates that two human IGHG1 Fc chains (each chain consisting of human hinge (γ1), CH2 and CH3 constant domains; EU residues 221-447) having mutations in the protein-protein interface of their CH3 domains (EU residues 341-447) carefully selected from a subset of the protein-protein interface residues from the human T-cell receptor (TCR) constant domain delta (GenBank database accession number AAA61125.1 [residues 135-221]; SEQ ID NO: 32; IMGT® reference TRDC [IMGT® residues 1.7-120], the international ImMunoGeneTics information System®; Lefranc M P et al., Nucleic Acids Res, 27(1):209-12 (1999); Ruiz M et al., Nucleic Acids Res, 28(1):219-21 (2000); Lefranc M P, Nucleic Acids Res, 29(1):207-9 (2001); Lefranc M P, Nucleic Acids Res, 31(1):307-10 (2003); Lefranc M P et al., Dev Comp Immunol, 29(3):185-203 (2005); Kaas Q et al., Briefings in Functional Genomics & Proteomics, 6(4):253-64 (2007)) for one chain and the human TCR constant domain gamma (GenBank database accession number AAA61110.1 [residues 145-245], SEQ ID NO: 33; IMGT® reference TRGC1 [IMGT® residues 1.1-124]) for the second chain, assemble into a hetero-dimeric Fc molecule with at least 52% efficacy. TRGC1 and TRDC are naturally occurring isotypes. TRGC1 is one of two naturally occurring allotypes for the human TCR constant domain gamma. Both TRGC1 and TRGC2 (termed 2× or 3×) can be equivalently used for the purpose to mutate the CH3 domain of IGHG1 Fc chains since there is no difference in the amino acid sequence of their protein-protein interfaces.

Mutations were derived from the analysis of an overlay of the crystal structure of the G115 γδTCR molecule (Allison T J et al., Nature, 411(6839):820-4 (2001)) with the crystal structure of the Fc fragment from human IGHG1 (Krapp S et al., J Mol Biol, 325(5):979-89 (2003)). Both TCR and IGHG1 Fc 3D structures were retrieved from the Protein Data Bank (PDB codes 1HXM and 1H3Y for human TCR and human IGHG1, respectively; www.pdb.org; Bernstein F C et al., Eur J Biochem, 80(2):319-24 (1977)), overlaid with the Coot software (Emsley P and Cowtan K, Acta Crystallogr D Biol Crystallogr, 60(Pt 12 Pt 1):2126-32 (2004)) and further visualized with the Discovery-Studio software from Accelrys (Cambridge, UK). Examination of the protein-protein interfaces of the overlaid 3D structures of the TCR hetero-dimeric constant domains and the CH3 homo-dimer was used as a starting point for rational design. Several parameters were considered; these included but were not limited to: the preservation of the prolines residues and the preservation of amino acid positions involved in the integrity of the domain cores as well as some of the electrostatic contacts from the IGHG1 CH3 homo-dimer; abrogating specific hydrophobic contacts found in the IGHG1 CH3 homo-dimer, and replacing those with selected hydrophobic contacts found in the TCR constant domain hetero-dimer. This analysis led to the design of two subsets of amino acid substitutions, one subset originating from equivalent 3D positions between the protein-protein interface of one subunit of the CH3 homo-dimer and the protein-protein interface of the TCR constant domain delta, and a second subset originating from equivalent 3D positions between the protein-protein interface of the second subunit of the CH3 homo-dimer and the protein-protein interface of the TCR constant domain gamma; each subset creating two new and unique CH3 engineered domain sequences which can hetero-dimerize.

The engineered human IGHG1 Fc chain thereof having mutations derived from the protein-protein interface of the human TCR constant domain delta in the protein-protein interface of its CH3 domain is designated "BT delta chain", while the engineered human IGHG1 Fc chain thereof having mutations derived from the protein-protein interface of the human TCR constant domain gamma in the protein-protein interface of its CH3 domain is designated "BT gamma chain". More specifically, the BT delta chain consists of an immunoglobulin Fc chain from human IGHG1 having an engineered CH3 domain with the following substitutions: L351M, S364N, T366A, G371E, K392F, T394A, D399S, F405N, Y407V, K409L, and T411K (SEQ ID NO: 34) (EU numbering); and accordingly, the "BT gamma chain" consists of an immunoglobulin Fc chain from human IGHG1 having an engineered CH3 domains with the following substitutions: Q347K, Y349T, S364T, T366L, K370E, G371K, T394G, V397M, F405M, Y407F, K409W (SEQ ID NO: 35) (EU numbering).

The formation of the Fc hetero-dimer can be assessed by SDS-PAGE analysis of samples under non-reducing and reducing conditions. Because the BT delta chain and the BT gamma chain have similar molecular weights, the BT gamma chain was fused to a variable light-chain kappa domain antibody (abbreviated VL, a subfamily Kappa I-O12 member derived from the VBASE2 humIGKV115 sequence with the IGKJ1*01 junction, SEQ ID NO: 5; Retter I et al., Nucleic Acids Res, 33(Database issue):D671-4 (2005)) (VL-BT gamma, SEQ ID NO: 36), to generate a difference in SDS-PAGE mobility and consequently facilitate the identification of hetero-dimer formation. The resulting hetero-dimeric construct is abbreviated BT delta_VL-BT gamma.

To create the BT delta and the VL-BT gamma chain cDNA coding sequences, a cDNA coding the engineered CH3 domain of the BT delta chain (SEQ ID NO: 37) and the engineered CH3 domain of the BT gamma chain (SEQ ID NO: 38) were synthesized by GENEART AG (Regensburg, Germany). Using PCR assembly techniques, each chain had their respective engineered CH3 domain cDNA coding sequence fused downstream of a synthetic cDNA coding for the human hinge IGHG1 (DKTHTCPPCP) and CH2 constant domain (separately synthesized by GENEART AG). The variable kappa domain antibody located at the N-terminus of the VL-BT gamma chain was engineered by fusing the domain cDNA (separately synthesized by GENEART AG) upstream of the BT gamma chain cDNA coding sequence using PCR assembly techniques.

Figure 10:
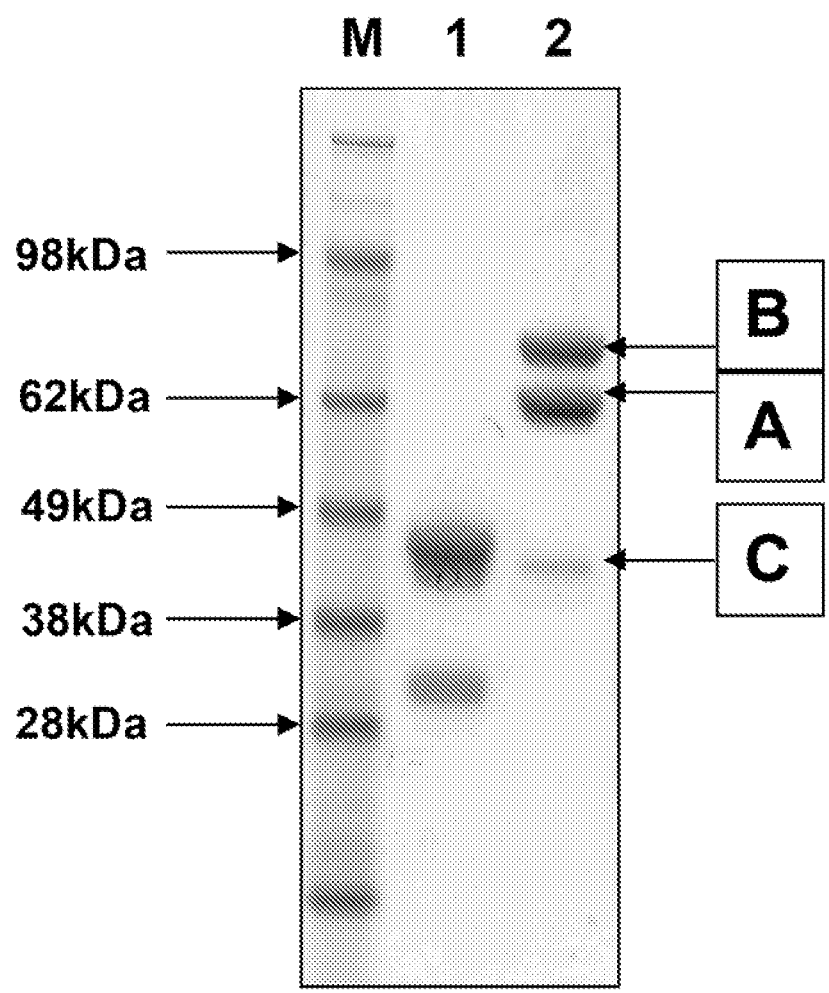

The resulting variants were then ligated independently into the modified pREP4 vector mentioned previously and co-transfected into HEK293-EBNA cells as described in example 1. Protein production was also according to example 1. Transient transfection yields were up to 60 mg/l. The results of a typical SDS-PAGE analysis are shown in FIG. 10.

Figure 11A:
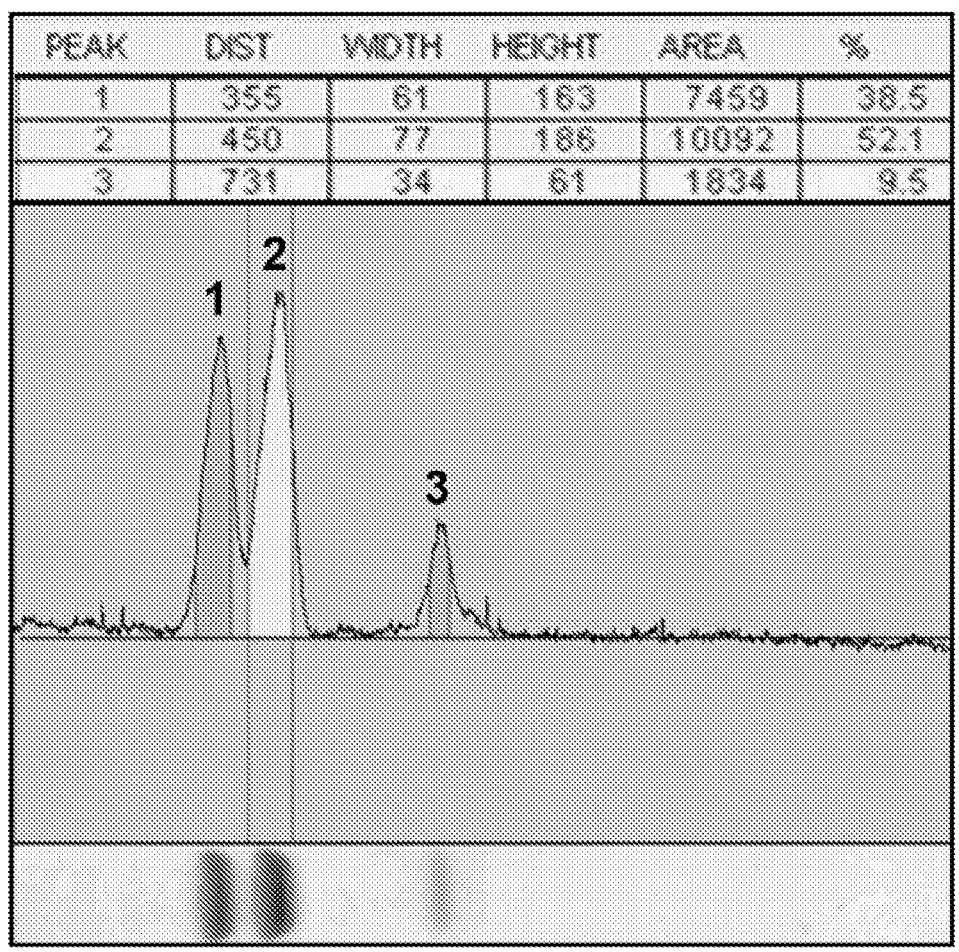
Figure 11B:
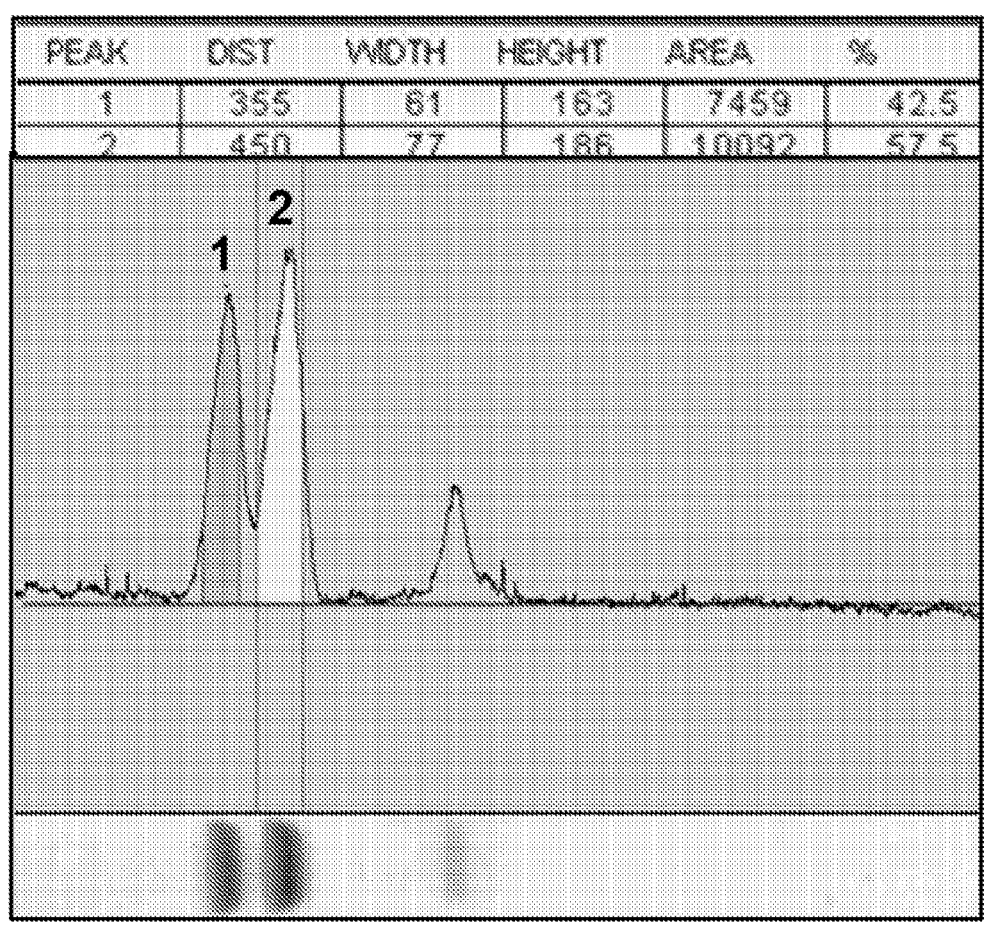

To assess the proportion of hetero-dimer to homo-dimer in the protein-A purified material, the relative ratios of the different species were quantified by scanning densitometry analysis of the non-reduced SDS-polyacrylamide (4-12%) gel bands according to the procedure described in example 1. The BT delta_VL-BT gamma hetero-dimer represents at least 52.1% of the protein-A purified material (FIG. 11A); when omitting traces of aggregates and monomer in the relative ratio measurements, the BT delta_VL-BT gamma hetero-dimer represents at least 57.5% of the protein-A purified material (FIG. 11B).

Example 5

Construction of a Monovalent Immunoglobulin with a Hetero-Dimeric Fc Having a CH3-CH3 Protein-Protein Interface Based on the Human α/β T Cell Receptor Constant Domains, and a FAB Fragment Having a CH1-CK Protein-Protein Interface Based on the Hetero-Dimeric δ/γ T Cell Receptor Constant Domains This example demonstrates that at least three human immunoglobulin chains: one chain consisting of a heavy chain variable domain fused to the human heavy chain constant domains CH1 (γ1), hinge (γ1), CH2 (γ1) and engineered CH3 domain from the BT alpha or BT beta chain, one BT alpha or one BT beta chain, and one chain consisting of a light chain variable domain fused to the human CK light chain constant domain wherein the protein-protein interface of the CH1 (γ1) (IGHG1, EU residues 118-215) and CK(IGKC, EU residues 108-214) domains have been carefully substituted at selected positions with a subset of the protein-protein interface residues from the naturally occurring human TCR constant domain delta (GenBank database accession number AAA61125.1 [residues 135-221]; SEQ ID NO: 32; IMGT® reference TRDC [IMGT® residues 1.7-120], the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1): 307-10 (2003); Lefranc M P et al., *Dev Comp Immunol*, 29(3):185-203 (2005); Kaas Q et al., *Briefings in Functional Genomics & Proteomics*, 6(4):253-64 (2007)), and the naturally occurring human TCR constant domain gamma (GenBank database accession number AAA61110.1 [residues 145-245]; SEQ ID NO: 33; IMGT® reference TRGC1 [IMGT® residues 1.1-124]) respectively, assemble into a FAB engineered hetero-dimeric immunoglobulin molecule with at least 50% efficacy.

Mutations were derived from the analysis of an overlay of the crystal structure of the TCR molecule with the crystal structure of a human FAB (γ1) fragment. Both TCR and human FAB (γ1) fragment 3D structures were retrieved from the Protein Data Bank (PDB code 1HXM, and 1VGE, respectively; Allison T J et al., *Nature*, 411(6839):820-4 (2001); Chacko S et al., *J Biol Chem*, 271(21):12191-8 (1996)), overlaid with the Coot software (Emsley P and Cowtan K, *Acta Crystallogr D Biol Crystallogr*, 60(Pt 12 Pt 1):2126-32 (2004)) and further visualized with the Discovery-Studio software from Accelrys (Cambridge, UK). Examination of the protein-protein interfaces of the overlaid 3D structures of the δ/γ TCR hetero-dimeric constant domains and the CH1 (γ1)-CK hetero-dimer was used as a starting point for rational design. Several parameters were considered; these included but were not limited to: the preservation of the proline residues and the preservation of amino acid positions involved in the integrity of the domain cores as well as some of the electrostatic contacts between the CH1 (γ1), and the CK domains; abrogating specific hydrophobic contacts found in the CH1 (γ1)-CK heterodimer, and replacing those with selected hydrophobic contacts found in the TCR constant domain gamma-delta hetero-dimer. This analysis led to the design of two subsets of amino acid substitutions, one subset originating from equivalent 3D positions between the protein-protein interface of the CH1 (γ1) domain and the protein-protein interface of the TCR constant domain delta, and a second subset originating from equivalent 3D positions between the protein-protein interface of the CK domain and the protein-protein interface of the TCR constant domain gamma; thereby creating two engineered, novel and unique domains which can still hetero-dimerize but differently from the naturally occurring CH1 (γ1)-CK hetero-dimeric domain pair.

Figure 12:
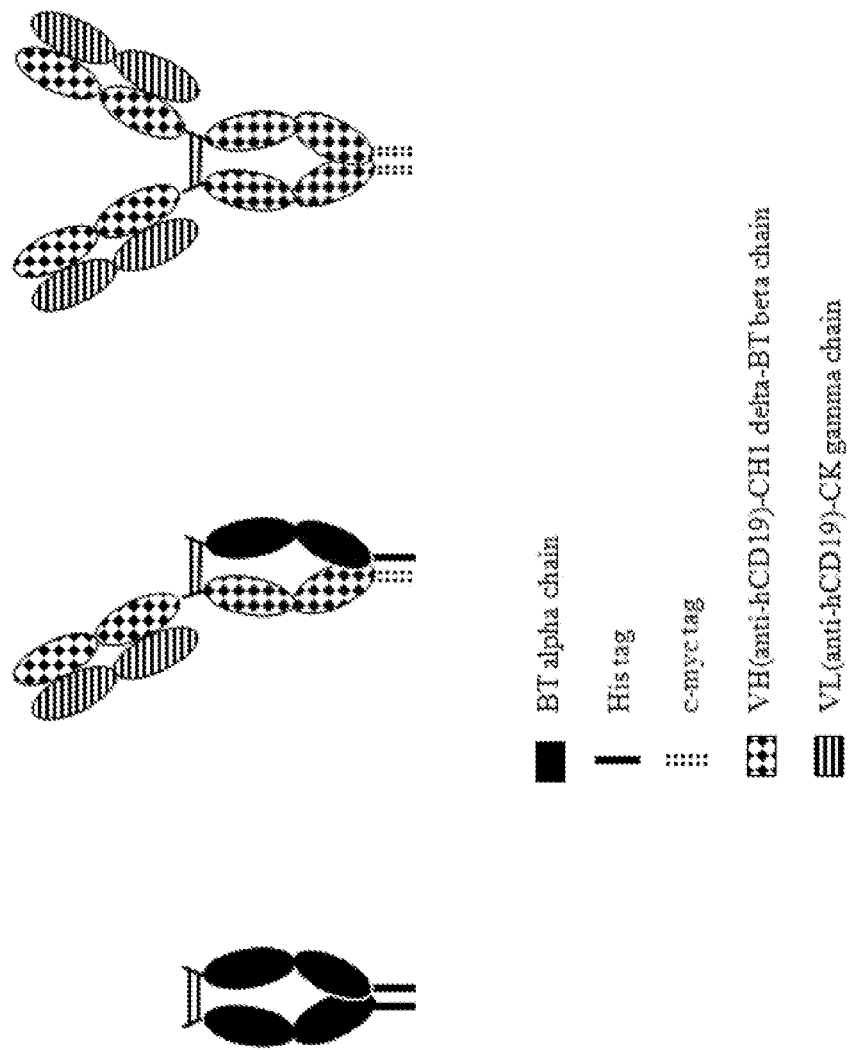

An engineered heavy chain of a FAB fragment comprising a variable heavy chain domain, and a human CH1 (γ1) domain having mutations derived from the protein-protein interface of the human TCR constant domain delta in its protein-protein interface is designated "VH-CH1 delta" (FIG. 12), while an engineered kappa light chain comprising a variable light chain domain, and a human CK domain having mutations derived from the protein-protein interface of the human TCR constant domain gamma in its protein-protein interface is designated "VL-CK gamma" (FIG. 12). More specifically, a VH-CH1 delta consists of an engineered heavy chain FAB fragment having an engineered CH1 (γ1) domain with the following substitutions: L128M, A141N, G143A, D148E, H168F, F170A, Q175S, S181N, S183V, V185L, T187K (SEQ ID NO: 39) (EU numbering); and accordingly, a VL-CK gamma consists of an engineered kappa light chain having an engineered CK domain with the following substitutions: S114K, F116T, S131T, V133L, N137E, N138K, S162G, T164M, S174M, S176F, T178W (SEQ ID NO: 40) (EU numbering).

In this example, the variable heavy chain and light chain domains from a humanized anti human CD19 antibody disclosed in the PCT Publication NO: WO 2010/095031 (abbreviated VH(anti-hCD19), and VL(anti-hCD19)) were used as inputs to build the VH-CH1 delta and the VL-CK gamma chains, respectively. The combination of a VH-CH1 delta chain fused upstream of a previously described BT beta chain (examples 1-3) (note that in this example, the chain had a C-terminal c-myc tag (EQKLISEEDLN), abbreviated BT beta c-myc chain) results in a newly engineered immunoglobulin heavy chain which once co-expressed with the newly engineered VL-CK gamma light chain described above, and a BT alpha His chain described in examples 1-3, creates a new type of hetero-dimeric monovalent (i.e. having one specificity for one antigen) immunoglobulin molecule having a novel FAB fragment wherein the CH1 (γ1) and CK constant domains have novel protein-protein interfaces based on the TCR delta and TCR gamma constant domain protein-protein interfaces, respectively, and a Fc fragment with hetero-dimeric engineered CH3 domains based on the TCR alpha and beta constant domains (examples 1-3). This novel immunoglobulin molecule is abbreviated VH(anti-hCD19)-CH1 delta-BT beta c-myc_BT alpha His_VL(anti-hCD19)-CK gamma (SEQ ID NOs: 41, 7, and 42).

To create the VH(anti-hCD19)-CH1 delta-BT beta c-myc chain and the VL(anti-hCD19)-CK gamma chain cDNA coding sequences (SEQ ID NOs: 43 and 44, respectively), a unique cDNA encompassing both the CH1 delta domain sequence (SEQ ID NO: 45) and the CK gamma domain sequence (SEQ ID NO: 46) was synthesized by GENEART AG (Regensburg, Germany). Using PCR, each chain was amplified individually, and the respective engineered constant domain cDNA coding sequences were fused downstream of a synthetic cDNA coding for their respective variable domains (separately synthesized by GENEART AG). The resulting VH(anti-hCD19)-CH1 delta cDNA fragment was then further fused upstream of a BT beta F405A chain having a C-terminal c-myc tag to generate the final VH(anti-hCD19)-CH1 delta-BT beta c-myc chain. Subsequently, the two chains were then ligated independently in the modified pREP4 vector described in example 1. The BT alpha His chain originated from example 1 (SEQ ID NO: 10).

For transient expression of the VH(anti-hCD19)-CH1 delta-BT beta c-myc_BT alpha His_VL(anti-hCD19)-CK gamma molecule, equal quantities of three engineered chain vectors were co-transfected into suspension-adapted HEK293-EBNA cells as described previously (example 1). The FAB engineered hetero-dimeric construct was then purified from the cell-free supernatant using protein-A affinity chromatography and used for further analysis (procedure according to example 1). The correct assembly of the FAB engineered hetero-dimer can be assessed by SDS-PAGE analysis of samples under non-reducing conditions, since the correctly assembled molecule is expected to have a different SDS-PAGE mobility from the possible homo-dimeric species.

Figure 13:
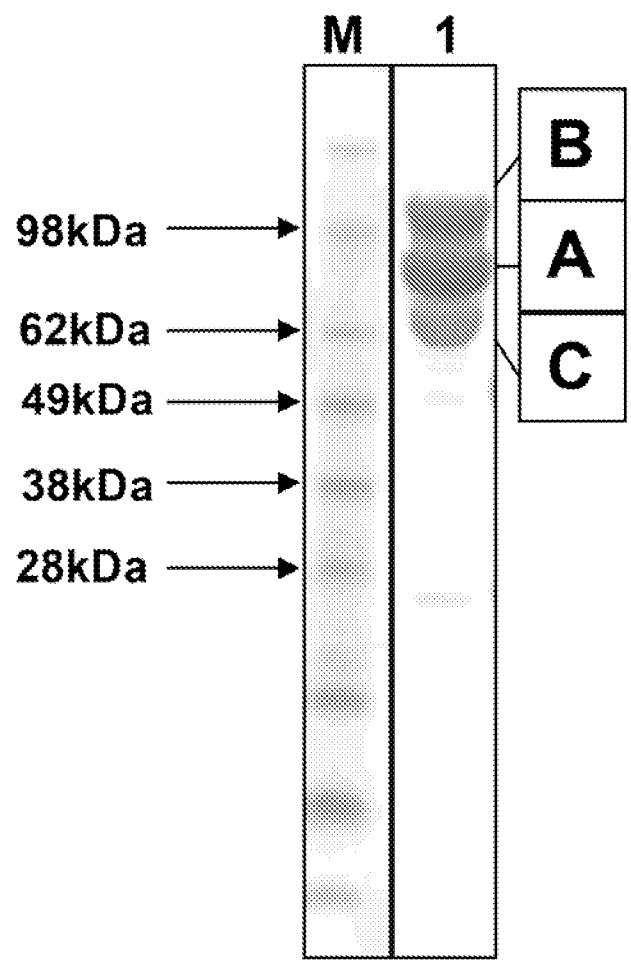

Transient transfection yields were above 16 mg/l. The results of a typical SDS-PAGE analysis are shown in FIG. 13. Post protein-A purification the VH(anti-hCD19)-CH1 delta-BT beta c-myc_BT alpha His_VL(anti-hCD19)-CK gamma molecule (lane1) is the main species produced (A) with some homo-dimeric species (B) and some half-molecules (C) present.

Figure 14:
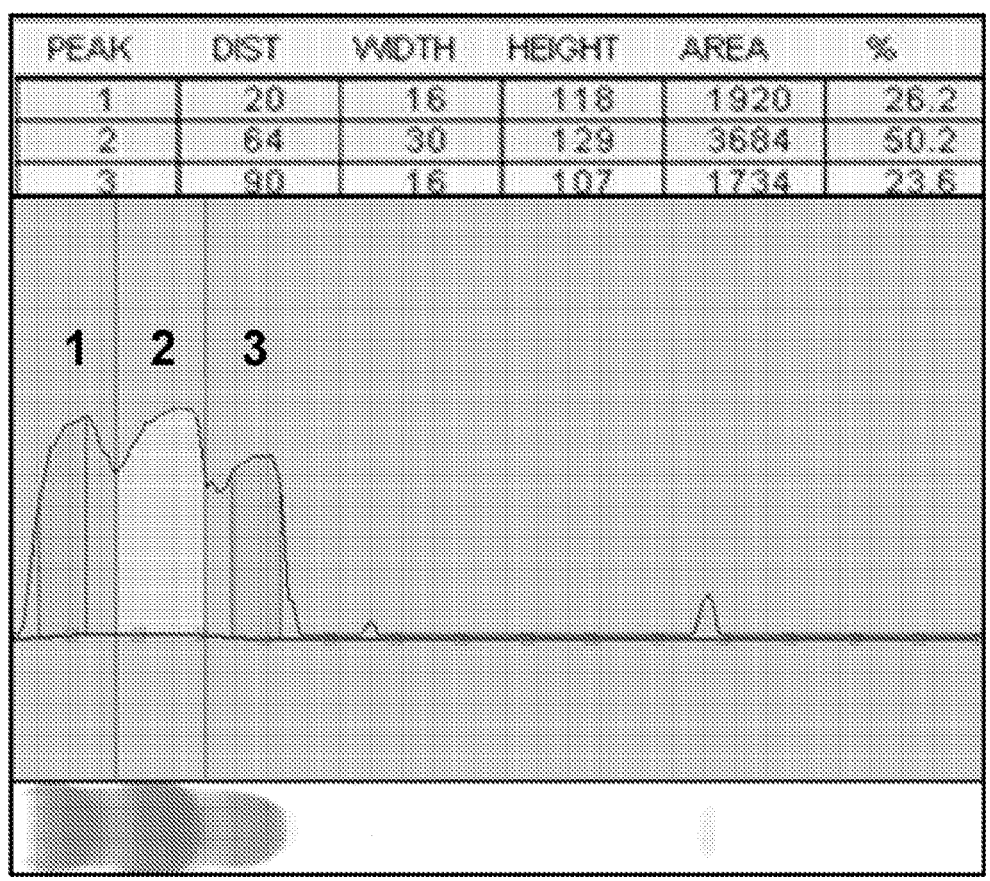

It is possible to assess the proportion of hetero-dimer to homo-dimer in the protein-A purified preparation by scanning densitometry analysis of the non-reduced SDS-polyacrylamide (4-12%) gel bands (procedure according to example 1). FIG. 14 shows that the VH(anti-hCD19)-CH1 delta-BT beta c-myc_BT alpha His_VL(anti-hCD19)-CK gamma molecule represents at least 50% of the protein-A purified material.

Figure 15:
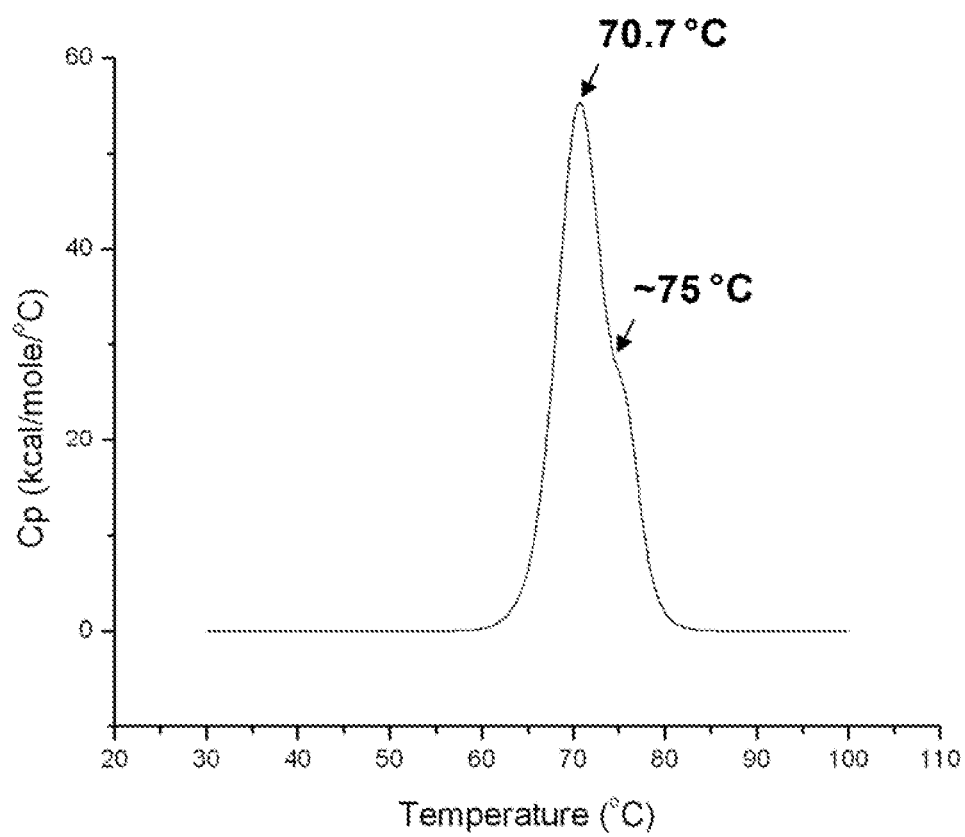

The thermal stability of the VH(anti-hCD19)-CH1 delta-BT beta c-myc_BT alpha His_VL(anti-hCD19)-CK gamma molecule was assessed using calorimetric measurements (DSC) (see example 2 for methods). Monoclonal antibodies have melting profiles which are characteristic of their isotypes, and which usually combine transitions for the FAB fragment, the CH2 and the CH3 domains (see example 2); within an antibody melting profile, the specific transition for the FAB fragment can easily be identified (Garber E and Demarest S J, *Biochem Biophys Res Commun,* 355(3):751-7 (2007)). FIG. 15 shows an example of a thermal unfolding experiment for the VH(anti-hCD19)-CH1 delta-BT beta c-myc_BT alpha His_VL(anti-hCD19)-CK gamma molecule: two overlapping sharp transitions at 70.7° C. and ~75° C. are observed, accounting for the melting transitions of the engineered FAB fragment, the CH2 domains, and the engineered CH3 domains. Since the BT alpha His_BT beta (F405A) HA hetero-dimeric Fc displayed a single sharp melting transition at 70° C. in previous measurements (example 2), it is possible to conclude that the melting transition of the engineered FAB fragment of the VH(anti-hCD19)-CH1 delta-BT beta c-myc_BT alpha His gamma molecule has a mid-point of ~75° C. It is important to note that no sharp decrease after the heat absorption peak was recorded, indicating that no precipitation or aggregate formation occurred after thermal unfolding (Liu H et al., *Immunol Lett,* 106(2):144-53 (2006)). In conclusion, this thermal denaturation study shows that the novel FAB fragment with engineered protein-protein interfaces based on the TCR delta and gamma constant domains is stable and suitable for building further therapeutic hetero-dimeric immunoglobulins; more precisely, immunoglobulin molecules comprising two novel hetero-dimeric pairs of constant domains, one pair having engineered protein-protein interfaces based on the human T-cell receptor constant domain alpha and beta, and the other pair having engineered protein-protein interfaces based on the human T-cell receptor constant domain delta and gamma.

Example 6

Construction of a Monovalent Immunoglobulin with a Hetero-Dimeric Fc Having a CH3-CH3 Protein-Protein Interface Based on the Human α/β T Cell Receptor Constant Domains, and a FAB Fragment Having a CH1-CK Protein-Protein Interface Based on the Homo-Dimeric IGHG1 CH3 Constant Domains This example demonstrates that at least three human immunoglobulin chains: one chain consisting of a heavy chain variable domain fused to the human heavy chain constant domains CH1 (γ1), hinge (γ1), CH2 (γ1) and engineered CH3 domain from the BT alpha or BT beta chain, one BT alpha or one BT beta chain, and one chain consisting of a light chain variable domain fused to the human CK light chain constant domain wherein the protein-protein interface of the CH1 (γ1) (IGHG1, EU residues 118-215) and CK (IGKC, EU residues 108-214) domains have been carefully substituted at selected positions with a subset of the protein-protein interface residues from the human CH3 (γ1) constant domain (IGHG1, EU residues 341-447; SEQ ID NO: 47), assemble into a FAB engineered hetero-dimeric immunoglobulin molecule with at least 51.9% efficacy.

Mutations were derived from the analysis of an overlay of the crystal structure of a Fc (γ1) fragment with the crystal structure of a human FAB (γ1) fragment. Both Fc (γ1) fragment and human FAB (γ1) fragment 3D structures were retrieved from the Protein Data Bank (PDB code 1H3U, and 1VGE, respectively; Krapp S et al., *J Mol Biol,* 325(5):979-89 (2003), Chacko S et al., *J Biol Chem,* 271(21):12191-8 (1996)), overlaid with the Coot software (Emsley P and Cowtan K, *Acta Crystallogr D Biol Crystallogr,* 60(Pt 12 Pt 1):2126-32 (2004)) and further visualized with the Discovery-Studio software from Accelrys (Cambridge, UK). Examination of the protein-protein interfaces of the overlaid 3D structures of the homo-dimeric CH3 (γ1) constant domain pair and the CH1 (γ1)-CK hetero-dimer was used as a starting point for rational design. Several parameters were considered; these included but were not limited to: the preservation of the proline residues and the preservation of amino acid positions involved in the integrity of the domain cores as well as some of the electrostatic contacts from the CH1 (γ1)-CK hetero-dimer, abrogating specific hydrophobic contacts found in the CH1 (γ1)-CK hetero-dimer, and replacing those with selected hydrophobic contacts found in the homo-dimeric CH3 constant domain pair. This analysis led to the design of two subsets of amino acid substitutions, one subset originating from equivalent 3D positions between the protein-protein interface of the CH1 (γ1) constant domain and the protein-protein interface of the human CH3 (γ1) constant domain, and a second subset originating from equivalent 3D positions between the protein-protein interface of the CK domain and the protein-protein interface of the human CH3 (γ1) constant domain; thereby creating two engineered, novel and unique domains which can still hetero-dimerize but differently from the naturally occurring CH1 (γ1)-Cκ hetero-dimeric domain pair.

Figure 16:
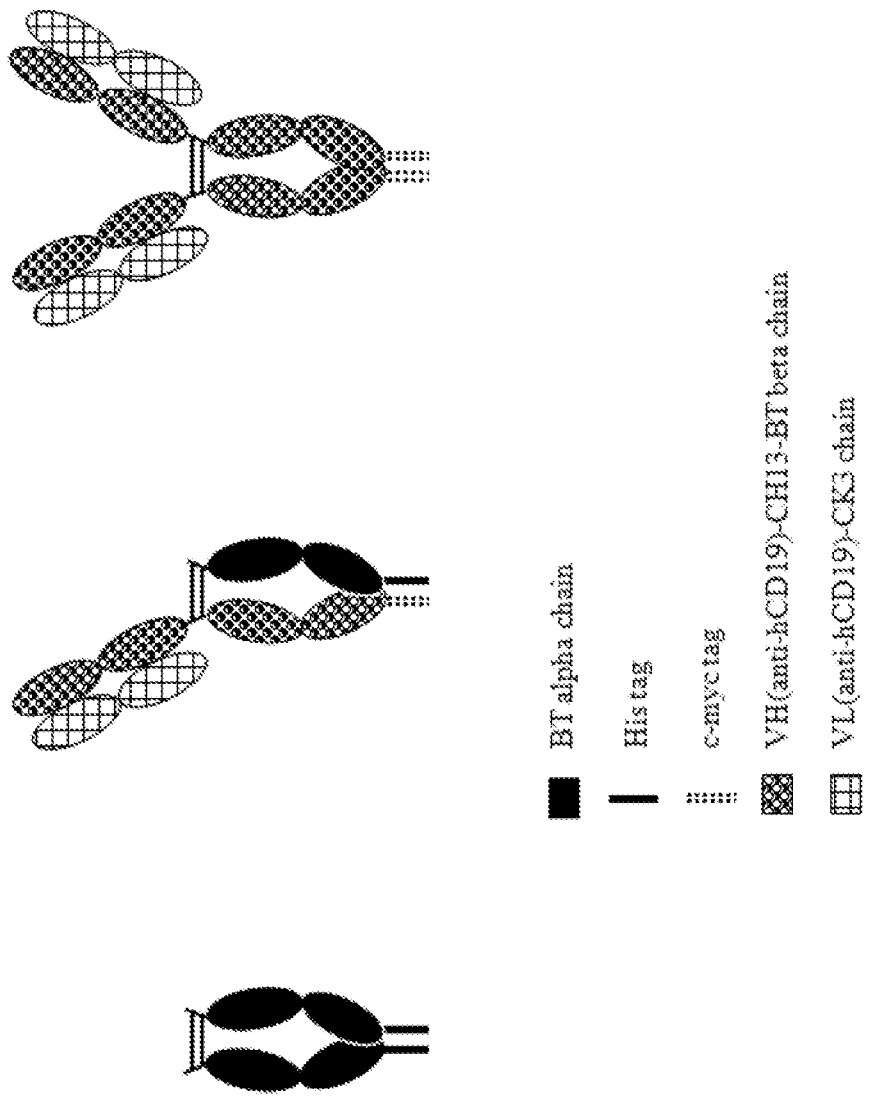

An engineered heavy chain of a FAB fragment comprising a variable heavy chain domain, and a human CH1 (γ1) domain having mutations derived from the protein-protein interface of the CH3 (γ1) constant domain in its protein-protein interface is designated "VH-CH13" (FIG. 16), while an engineered kappa light chain comprising a variable light chain domain, and an engineered human Cκ constant domain having mutations derived from the protein-protein interface of the CH3 (γ1) constant domain in its protein-protein interface is designated "VL-CK3" (FIG. 16). More specifically, a VH-CH13 chain consists of an engineered heavy chain FAB fragment having an engineered CH1 (γ1) domain with the following substitutions: S124Q, F126Y, K133D, S134E, T139Q, A141S, G143T, H168K, F170T, Q175D, S181F, S183Y, V185K (SEQ ID NO: 48) (EU numbering); and accordingly, a VL-CK3 domain consists of an engineered light chain FAB fragment having an engineered Cκ domain with the following substitutions: S114Q, F116Y, F118L, E123D, Q124E, V133T, N137K, Q160K, S162T, T164V, S174F, S176Y, T178K (SEQ ID NO: 49) (EU numbering).

In this example, the variable heavy chain and light chain domains from a humanized anti human CD19 antibody disclosed in the PCT Publication NO: WO 2010/095031 (abbreviated VH(anti-hCD19), and VL(anti-hCD19)) were used as inputs to build the VH-CH13 and the VL-CK3 chains, respectively. The combination of a VH-CH13 chain fused upstream of a previously described BT beta chain (note that in this example, the chain had a C-terminal c-myc tag (EQKLISEEDLN), abbreviated BT beta c-myc chain), results in a newly engineered immunoglobulin heavy chain which once co-expressed with the newly engineered VL-CK3 light chain described above, and a BT alpha His chain described in examples 1-3, creates a new type of hetero-dimeric monovalent (i.e. having one specificity for one antigen) immunoglobulin molecule having a novel FAB fragment wherein the CH1 (γ1) and CK constant domains have novel protein-protein interfaces based on the CH3 (γ1) constant domain homo-dimeric protein-protein interface, and a Fc fragment with hetero-dimeric engineered CH3 domains based on the TCR alpha and beta constant domains (see examples 1-3). This novel immunoglobulin molecule is abbreviated VH(anti-hCD19)-CH13-BT beta c-myc_BT alpha His_VL(anti-hCD19)-CK3 (SEQ ID NOs: 50, 7, and 51).

To create the VH(anti-hCD19)-CH13-BT beta c-myc chain and the VL(anti-hCD19)-CK3 chain cDNA coding sequences (SEQ ID NOs: 52 and 53, respectively), a unique cDNA encompassing both the CH13 domain sequence (SEQ ID NO: 54) and the CK3 domain sequence (SEQ ID NO: 55) was synthesized by GENEART AG (Regensburg, Germany). Using PCR, each chain was amplified individually, and the respective engineered constant domain cDNA coding sequences were fused downstream of a synthetic cDNA coding for their respective variable domains (separately synthesized by GENEART AG). The resulting VH(anti-hCD19)-CH13 DNA fragment was further fused upstream of a BT beta F405A chain having a C-terminal c-myc tag to generate the final VH(anti-hCD19)-CH13-BT beta c-myc chain. Subsequently, the two chains were ligated independently in the modified pREP4 vector described in example 1. The BT alpha His chain originated from example 1 (SEQ ID NO: 10).

For transient expression of the VH(anti-hCD19)-CH13-BT beta c-myc_BT alpha His_VL(anti-hCD19)-CK3 molecule, equal quantities of the three engineered chain vectors were co-transfected into suspension-adapted HEK293-EBNA cells as described previously (example 1). The FAB engineered hetero-dimeric construct was then purified from the cell-free supernatant using protein-A affinity chromatography and used for further analysis (procedure according to example 1). The correct assembly of the FAB engineered hetero-dimer can be assessed by SDS-PAGE analysis of samples under non-reducing conditions, since the correctly assembled molecule is expected to have a different SDS-PAGE mobility from the possible homo-dimeric species.

Figure 17:
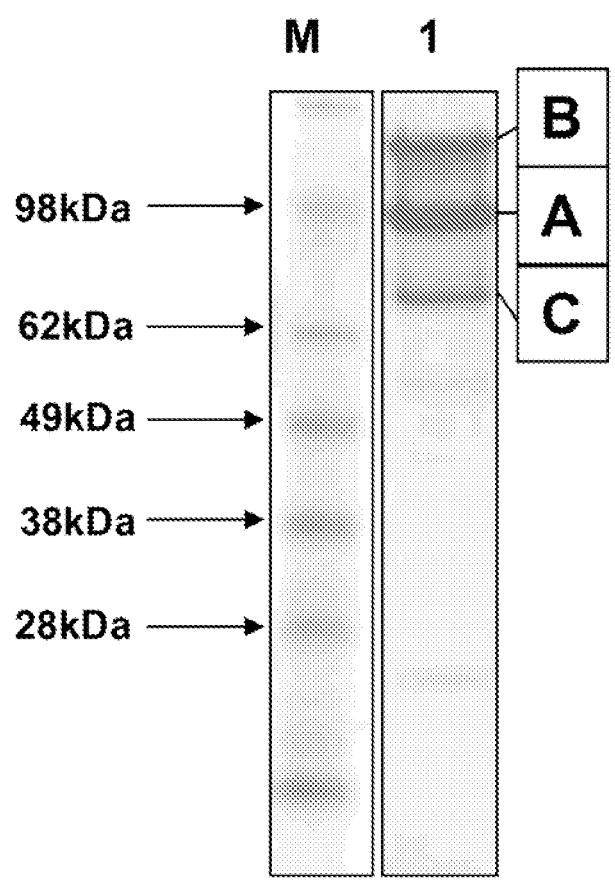

Transient transfection yields were 50 mg/l. The results of a typical SDS-PAGE analysis are shown in FIG. 17. Post protein-A purification the VH(anti-hCD19)-CH13-BT beta c-myc_BT alpha His_VL(anti-hCD19)-CK3 molecule (lane1) is the main species produced (A) with some homo-dimeric species (B) and some half-molecule (C) present.

Figure 18:
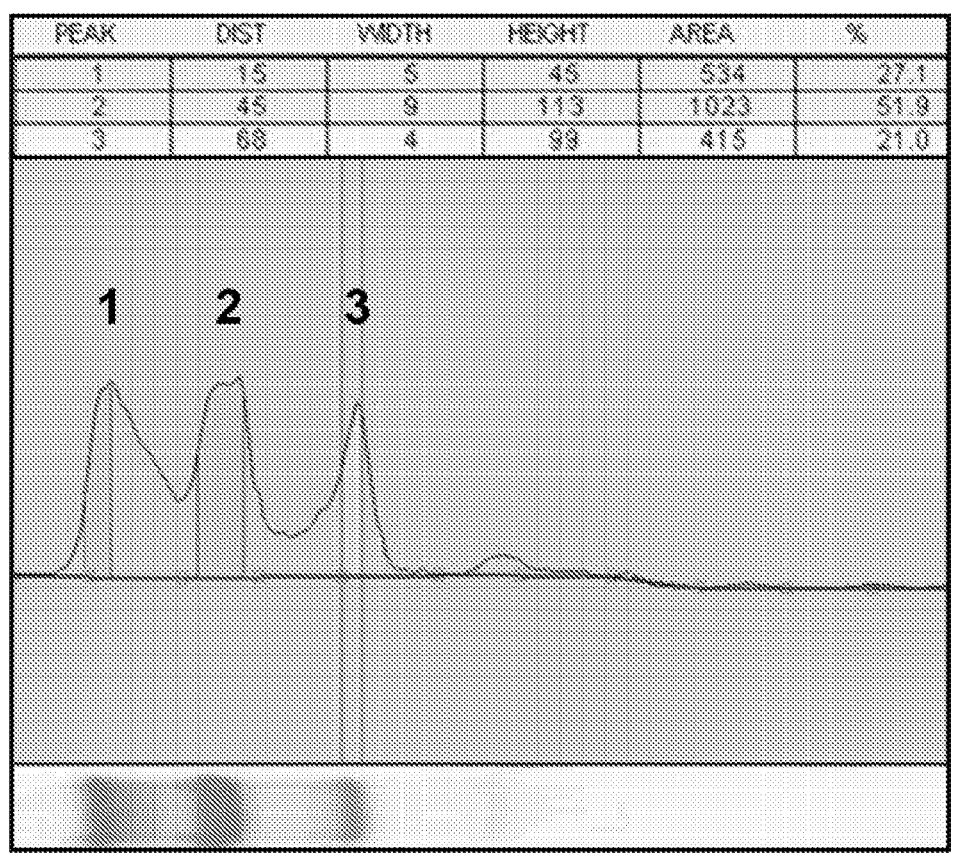

It is possible to assess the proportion of hetero-dimer to homo-dimer in the protein-A purified preparation by scanning densitometry analysis of the non-reduced SDS-polyacrylamide (4-12%) gel bands (procedure according to example 1). FIG. 18 shows that the VH(anti-hCD19)-CH13-BT beta c-myc_BT alpha His_VL(anti-hCD19)-CK3 molecule represents at least 51.9% of the protein-A purified material.

In conclusion, this example shows that the novel FAB fragment with engineered protein-protein interfaces based on the protein-protein interface of the homo-dimeric CH3 (γ1) constant domain is suitable for building further therapeutic hetero-dimeric immunoglobulins; more precisely, immunoglobulin molecules comprising two novel hetero-dimeric pairs of constant domains, one pair having engineered protein-protein interfaces based on the human T-cell receptor constant domain alpha and beta, and the other pair having engineered protein-protein interfaces based on the homo-dimeric CH3 (γ1) constant domain.

Example 7

Immunoglobulin Domains with Engineered Protein-Protein Interfaces Derived from Naturally Occurring Homo-Dimeric or Hetero-Dimeric Immunoglobulin Super-Family Members This present example provides various set of mutations in human immunoglobulin domains to create novel protein-protein interfaces in acceptor domains and allow for one engineered domain to interact by hetero-dimerization or homo-dimerization with another engineered domain.

The mutations can be derived from naturally occurring dimeric immunoglobulin super-family members for example from the naturally occurring homo-dimeric human IGHG1 CH3 domain or from a naturally occurring hetero-dimers such as the human TCRα (IMGT® reference TRAC, the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005); Kaas Q et al., *Briefings in Functional Genomics & Proteomics*, 6(4):253-64 (2007)), TCRβ (IMGT® reference TRBC1 and TRBC2), TCRγ (IMGT® reference TRGC1, TRGC2(2×), and TRGC2(3×)), and TCRδ (IMGT® reference TRDC) constant domains and introduced into the human heavy chain immunoglobulin constant domains of the γ1, γ2, γ3, γ4, α1, α2, ε, and μ isotypes (IMGT® reference IGHG1, IGHG2, IGHG3, IGHG4, IGHA1, IGHA2, IGHE, IGHM, respectively) or into the human immunoglobulin light chain constant domain κ (IMGT® reference IGKC) or into the human immunoglobulin light chain constant domains λ1, λ2, λ3, λ6, and λ7 (IMGT® reference IGLC1, IGLC2, IGLC3, IGLC6, and IGLC7, respectively).

In this example, amino acid substitutions were derived from the analysis of overlays of 3D structures of TCR domains (PDB codes: 1KGC or 1J8H (TCRα-TCRβ) and 1HXM (TCRδ-TCRγ)) with 3D structures of human IgG domains which were either retrieved form public databases (see Table 2) or modelled depending on availability (CH1 domains of α1, α2, ε; CH2 domains of γ2, γ3, α2, μ; CH3 domains of γ2, γ3, α2, μ and CH4 domain of μ). In addition, amino acid substitutions were derived from the analysis of overlays of 3D structures of human IgG domains in a pair wise fashion; for example, the human IGHG1 CH3 homo-dimeric pair of domains was overlaid onto the human IGHG1 CH1-Cκ hetero-dimer Models were calculated using the structure homology-modelling server SWISS-MODEL (Arnold K et al., Bioinformatics, 22(2):195-201 (2006); http://swissmodel.expasy.org) in the automated mode with the following inputs: the protein domain amino acid sequence retrieved from the IMGT® database with specific amino acid substitutions depending on the project requirements (the international ImMunoGeneTics information System®; Lefranc M P et al., Nucleic Acids Res, 27(1):209-12 (1999); Ruiz M et al., Nucleic Acids Res, 28(1):219-21 (2000); Lefranc M P, Nucleic Acids Res, 29(1):207-9 (2001); Lefranc M P, Nucleic Acids Res, 31(1):307-10 (2003); Lefranc M P et al., Dev Comp Immunol, 29(3):185-203 (2005); Kaas Q et al., Briefings in Functional Genomics & Proteomics, 6(4):253-64 (2007)), and a 3D structure template consisting of an experimentally solved 3D structure from a related protein domain automatically identified by the SWISS-MODEL software. All experimentally solved 3D structures were retrieved from the RCSB Protein Data Bank (www.pdb.org; Berman H M et al., Nucleic Acids Res, 28(1):235-42 (2000)). Overlays were performed using the Coot software (Emsley P and Cowtan K, Acta Crystallogr D Biol Crystallogr, 60(Pt 12 Pt 1):2126-32 (2004)). Visualization for analysis was done in the Discovery-Studio software from Accelrys (Cambridge, UK). The selection of each subset of mutations followed similar criteria to the ones described in example 1.

Examples of homo-dimeric or hetero-dimeric immunoglobulin domains to be used as donor domains or parent domain are selected from the group consisting of human IGHA1 CH1, IGHA1 CH2, IGHA1 CH3, IGHA2 CH1, IGHA2 CH2, IGHA2 CH3, IGHD CH1, IGHD CH2, IGHD CH3, IGHG1 CH1, IGHG1 CH2, IGHG1 CH3, IGHG2 CH1, IGHG2 CH2, IGHG2 CH3, IGHG3 CH1, IGHG3 CH2, IGHG3 CH3, IGHG4 CH1, IGHG4 CH2, IGHG4 CH3, IGHGP CH1, IGHGP CH2, IGHGP CH3, IGHE CH1, IGHE CH2, IGHE CH3, IGHE CH4, IGHM CH1, IGHM CH2, IGHM CH3, IGHM CH4, IGKC, IGLC1, IGLC2, IGLC3, IGLC6, IGLC7, TRAC, TRBC1, TRBC2, TRDC, TRGC1, TRGC2 (2x), and TRGC2 (3x).

TABLE 2

PDB codes used for the overlay analysis of human IgG molecules.

| Isotype | CH1 | CH2—CH3 | CH4 | Cκ | Cλ |
|---------|------|---------|------|------|------|
| γ1 | 1VGE | 1H3U | | 1VGE | 7FAB |
| γ2 | 3KYM | | | | |
| γ3 | 1Q1J | | | | |
| γ4 | 3NAA | 1ADQ | | | |
| μ | 1QLR | | | | |
| α1 | | 1OW0 | | | |
| ε | | 2WQR | 2WQR | | |

Details of the amino acid variations for the CH1-CH3 domains between the human IGHG1, IGHG2, IGHG3, and IGHG4 isotypes can be found in FIG. 19.

Complete lists of the substitutions derived from the protein-protein interface of the human TCR constant domains (TRAC, TRBC2, TRDC, and TRGC1) or the human IGHG1 CH3 domain that can be introduced in the human IGHG1-G4 CH1, IGHG1-G4 CH2, IGHG1-G4 CH3, IHGE CH4, IGHM CH4, IGKC, and IGLC (IGLC1, IGLC2, IGLC3, IGLC6, and IGLC7) protein-protein interfaces are provided in FIG. 20-23 which corresponds to IMGT® numbering as referenced in the IMGT® database (http://imgt.cines.fr/, the international ImMunoGeneTics information System®; Lefranc M P et al., Nucleic Acids Res, 27(1):209-12 (1999); Ruiz M et al., Nucleic Acids Res, 28(1):219-21 (2000); Lefranc M P, Nucleic Acids Res, 29(1):207-9 (2001); Lefranc M P, Nucleic Acids Res, 31(1):307-10 (2003); Lefranc M P et al., Dev Comp Immunol, 29(3):185-203 (2005); Kaas Q et al., Briefings in Functional Genomics & Proteomics, 6(4):253-64 (2007)).

A complete overview of the preferred positions considered for substitution with key amino acid residues derived from the protein-protein interface of the TCR constant domains (α, β, δ, γ) or the CH3 domain of IGHG1 is also provided below. Since the IMGT® numbering is based on the comparative analysis of the 3D structures of the immunoglobulin super-family domains, it defines the 3D equivalent positions of the substitutions between donor and acceptor (parent) domains.

7.1 Examples of Molecular Modelling.

7.1.1 Modelling Hetero-Dimeric Domain Pairs Based on the Human TCRα-TCRβ Constant Domain Protein-Protein Interface.

a. TCRα Based Substitutions.

The amino acid sequence positions from the protein-protein interface of the human TCRα constant domain (donor domain) which are used to substitute the 3D equivalent amino acid sequence positions from the protein-protein interface of the parent immunoglobulin domain are listed below:

The donor positions from human TCRα are as follows: 20, 22, 26, 79, 85.1, 86, 88, and 90 (having the following amino acids: K20, V22, T26, Y79, S85.1, V86, W88, and N90), wherein the amino acid position of each group member is indicated according to the IMGT® numbering (the international ImMunoGeneTics information System®; Lefranc M P et al., Nucleic Acids Res, 27(1):209-12 (1999); Ruiz M et al., Nucleic Acids Res, 28(1):219-21 (2000); Lefranc M P, Nucleic Acids Res, 29(1):207-9 (2001); Lefranc M P, Nucleic Acids Res, 31(1):307-10 (2003); Lefranc M P et al., Dev Comp Immunol, 29(3):185-203 (2005); Kaas Q et al., Briefings in Functional Genomics & Proteomics, 6(4): 253-64 (2007)).

The acceptor positions in all human immunoglobulin domains are as follows: 20, 22, 26, 79, 85.1, 86, 88, and 90; except for position 79 in α1: CH2 (78), α2: CH2 (78), ε: CH2 (81) and ε: CH3 (80), wherein the amino acid position of each group member is indicated according to the IMGT® numbering.

b. TCRβ Based Substitutions.

The amino acid sequence positions from the protein-protein interface of the human TCRβ constant domain (donor domain) which are used to substitute the 3D equivalent amino acid sequence positions from the protein-protein interface of the parent immunoglobulin domain are listed below:

The donor positions from the human TCR beta are as follows: 3, 5, 7, 20, 22, 26, 81, 84.1, 84.3, 85.1, 86, 88, and 90 (having the following amino acids: E3, A5, F7, T20, V22, T26, D81, L84.1, E84.3, C85.1 or A85.1 or S85.1, S86, R88, and R90), wherein the amino acid position of each group member is indicated according to the IMGT® numbering.

The acceptor positions in all human immunoglobulin domains are as follows: 3, 5, 7, 20, 22, 26, 81, 84, 84.2, 85.1, 86, 88, and 90; except for position 81 in α1: CH2 (80), α2: CH2 (80), ε: CH2 (83); except for position 84 in α1: CH2 (83), α2: CH2 (83); except for position 84.2 in α1: CH2 (84), α2: CH2 (84), wherein the amino acid position of each group member is indicated according to the IMGT® numbering.

c. Modelling the Human TCRα-TCRβ Constant Domain Protein-Protein Interface on the Human IGHG1 CH3 Homo-Dimer.

To model a novel hetero-dimer based on the human IGHG1 CH3 homo-dimer with protein-protein interfaces derived from the human TCRα/β constant domains, two models of a human IGHG1 CH3 monomer substituted in its protein-protein interface with selected amino acids were calculated (see above for methods). One monomer was substituted at selected equivalent 3D positions in its protein-protein interface with amino acids from the protein-protein interface of the human TCRα constant domain, and a second monomer was substituted at selected equivalent 3D positions in its protein-protein interface with amino acids from the protein-protein interface of the human TCRβ constant domain. The Cα traces of the resulting models for the two engineered protein domains were further overlaid on the experimentally solved parental CH3 homo-dimer 3D structure (PDB code 1H3U) for visual inspection. In addition, a computational analysis of the protein-protein interface of the engineered domains was performed using the online PIC web server (http://crick.mbu.iisc.ernet.in/~PIC/, Tina K G et al., Nucleic Acids Res, 35(Web Server issue):W473-6 (2007)). Tables 3 and 4 list the interacting residues in the protein-protein interface of the engineered hetero-dimer identified from computational analysis, and direct measurements; the amino acid position of each group member is indicated according to the IMGT® numbering. From the modelling of a large number of immunoglobulin domain pairs engineered in their protein-protein interface with substitutions derived from naturally occurring homo-dimeric and hetero-dimeric protein-protein interface residues, the residues 20, 22, 26, 85.1, 86 and 88, in particular the residues 22, 85.1, 86 and 88 (numbering according to IMGT®) were repeatedly found to provide the most important contacts between the protein-protein interfaces of the engineered domains. More generally, by visual inspection and calculation of protein-protein interactions (using the online PIC web server (http://crick.mbu.iisc.ernet.in/~PIC/, Tina K G et al., Nucleic Acids Res, 35(Web Server issue): W473-6 (2007) or other protein-protein interaction programs known in the art), the residues 20, 22, 26, 85.1, 86 and 88, in particular the residues 22, 85.1, 86 and 88 were found to mediate the most important interactions for the hetero-dimerization or homo-dimerization of all engineered domains.

Without being bound by theory, the analysis of the newly engineered domain protein-protein interfaces identified four important subsets of interacting residues: residue 88 in the first engineered immunoglobulin (BT alpha) interacts with residue 85.1 and 86 in the second engineered immunoglobulin (BT beta), residue 85.1 in the first engineered immunoglobulin (BT alpha) interacts with residue 86 in the second engineered immunoglobulin (BT beta), residue 22 in the first engineered immunoglobulin (BT alpha) interacts with residue 22 and residue 86 in the second engineered immunoglobulin (BT beta), and residue 20 in the first engineered immunoglobulin (BT alpha) interacts with residue 26 in the second engineered immunoglobulin (BT beta). Conversely, residue 88 in the second engineered immunoglobulin (BT beta) interacts with residue 85.1 and 86 in the first engineered immunoglobulin (BT alpha), residue 85.1 in the second engineered immunoglobulin (BT beta) interacts with residue 86 in the first engineered immunoglobulin (BT alpha), residue 22 in the second engineered immunoglobulin (BT beta) interacts with residue 22 and residue 86 in the first engineered immunoglobulin (BT alpha), and residue 20 in the second engineered immunoglobulin (BT beta) interacts with residue 26 in the first engineered immunoglobulin (BT alpha).

TABLE 3

Interactions between positions from the protein-protein interface of the TCRα—CH3 monomer to the protein-protein interface of TCRβ—CH3 monomer in the newly engineered CH3 hetero-dimer. The IMGT ® numbering is used.

| TCRα—CH3 (BT alpha) | TCRβ—CH3 (BT beta) |
|---|---|
| 20 | 3, 5, 7, 26, 84.2, 85.1, 86 |
| 22 | 5, 7, 22, 86, 88 |
| 26 | 20, 88, 90 |
| 79 | 26, 81, 84, 85.1, 86 |
| 85.1 | 20, 81, 86, 88, 90 |
| 86 | 22, 81, 84, 86, 88 |
| 88 | 26, 81, 84, 84.2, 85.1, 86 |
| 90 | 26, 84.2, 85.1 |

TABLE 4

Interactions between positions from the protein-protein interface of the TCRβ—CH3 monomer to the protein-protein interface of TCRα—CH3 monomer in the newly engineered CH3 hetero-dimer. The IMGT ® numbering is used.

| TCRβ—CH3 (BT beta) | TCRα—CH3 (BT alpha) |
|---|---|
| 3 | 20 |
| 5 | 20, 22 |
| 7 | 20, 22 |
| 20 | 26, 85.1, 86 |
| 22 | 22, 86 |
| 26 | 20, 79, 88, 90 |
| 81 | 79, 85.1, 86, 88 |

TABLE 4-continued

Interactions between positions from the protein-protein interface of the TCRβ—CH3 monomer to the protein-protein interface of TCRα—CH3 monomer in the newly engineered CH3 hetero-dimer. The IMGT ® numbering is used.

| TCRβ—CH3 (BT beta) | TCRα—CH3 (BT alpha) |
| --- | --- |
| 84 | 79, 86, 88 |
| 84.2 | 20, 79, 88, 90 |
| 85.1 | 20, 79, 86, 88, 90 |
| 86 | 20, 22, 79, 85.1, 86 |
| 88 | 22, 26, 85.1, 86 |
| 90 | 26, 85.1 |

7.1.2 Modelling Hetero-Dimeric Domain Pairs Based on the Human TCRδ-TCRγ Constant Domain Protein-Protein Interface.

a. TCRδ Based Substitutions.

The amino acid sequence positions from the protein-protein interface of the human TCR constant domain (donor domain) which are used to substitute the 3D equivalent amino acid sequence positions from the protein-protein interface of the parent immunoglobulin domain are listed below:

The donor positions from the human TCR delta are as follows: 7, 20, 22, 27, 79, 82, 84.2, 85.1, 86, 88, and 90 (having the following amino acids: M7, N20, A22, E27, F79, A82, S84.2, N85.1, V86, L88, and K90), wherein the amino acid position of each group member is indicated according to the IMGT® numbering.

The acceptor positions in all human immunoglobulin domains are as follows: 7, 20, 22, 27, 79, 81, 84.2, 85.1, 86, 88, 90; except for position 79 in α1: CH2 (78), α2: CH2 (78), ε: CH2 (81) and ε: CH3 (80); except for position 81 in α1: CH2 (80), α2: CH2 (80), ε: CH2 (83) and ε: CH3 (82); except for position 84.2 in α1: CH2 (84), α2: CH2 (84), ε: CH2 (84.4), wherein the amino acid position of each group member is indicated according to the IMGT® numbering.

b. TCRγ Based Substitutions.

The amino acid sequence positions from the protein-protein interface of the human TCRγ constant domain (donor domain) which are used to substitute the 3D equivalent amino acid sequence positions from the protein-protein interface of the parent immunoglobulin domain are listed below:

The donor positions from the human TCR gamma are as follows: 3, 5, 20, 22, 26, 27, 81, 84, 85.1, 86, and 88 (having the following amino acids: K3, T5, T20, L22, E26, K27, G81, M84, M85.1, F86, and W88), wherein the amino acid position of each group member is indicated according to the IMGT® numbering.

The acceptor positions in all human immunoglobulin domains are as follows: 3, 5, 20, 22, 26, 27, 81, 84, 85.1, 86, 88; except for position 81 in α1: CH2 (80), α2: CH2 (80), ε: CH2 (83); except for position 84 in γ1, γ2, γ3, γ3: CH2 (for all 83), α1: CH2 (83), α2: CH2 (83), ε: CH2 (84.1), μ: CH2 (83) and μ: CH3 (83), wherein the amino acid position of each group member is indicated according to the IMGT® numbering.

c. Modelling the Human TCRδ-TCRγ Constant Domain Protein-Protein Interface on the Human IGHG1 CH3 Homo-Dimer.

To model a novel hetero-dimer based on the human IGHG1 CH3 homo-dimer with protein-protein interfaces derived from the human TCRδ/γ constant domains, two models of a human IGHG1 CH3 monomer substituted in its protein-protein interface with selected amino acids were calculated (see above for methods). One monomer was substituted at selected equivalent 3D positions in its protein-protein interface with amino acids from the protein-protein interface of the human TCRδ constant domain, and a second monomer was substituted at selected equivalent 3D positions in its protein-protein interface with amino acids from the protein-protein interface of the human TCRγ constant domain. The Cα traces of the resulting models for the two engineered protein domains were further overlaid on the experimentally solved parental CH3 homo-dimer 3D structure (PDB code 1H3U) for visual inspection. In addition, a computational analysis of the protein-protein interface of the engineered domains was performed using the online PIC web server (http://crick.mbu.iisc.ernet.in/~PIC/, Tina K G et al., Nucleic Acids Res, 35(Web Server issue):W473-6 (2007)). Tables 5 and 6 list the interacting residues in the protein-protein interface of the engineered hetero-dimer identified from computational analysis, and direct measurements; the amino acid position of each group member is indicated according to the IMGT® numbering. From the modelling of a large number of immunoglobulin domain pairs engineered in their protein-protein interface with substitutions derived from naturally occurring homo-dimeric and hetero-dimeric protein-protein interface residues, the residues 20, 22, 26, 85.1, 86 and 88, in particular the residues 22, 85.1, 86 and 88 (numbering according to IMGT®) were repeatedly found to provide the most important contacts between the protein-protein interfaces of the engineered domains. More generally, by visual inspection and calculation of protein-protein interactions (using the online PIC web server (http://crick.mbu.iisc.ernet.in/~PIC/, Tina K G et al., Nucleic Acids Res, 35(Web Server issue): W473-6 (2007) or other protein-protein interaction programs known in the art), the residues 20, 22, 26, 85.1, 86 and 88, in particular the residues 22, 85.1, 86 and 88 were found to mediate the most important interactions for the hetero-dimerization or homo-dimerization of all engineered domains.

Without being bound by theory, the analysis of the newly engineered domain protein-protein interfaces identified four important subsets of interacting residues: residue 88 in the first engineered immunoglobulin (BT delta) interacts with residue 85.1 and 86 in the second engineered immunoglobulin (BT gamma), residue 85.1 in the first engineered immunoglobulin (BT delta) interacts with residue 86 in the second engineered immunoglobulin (BT gamma), residue 22 in the first engineered immunoglobulin (BT delta) interacts with residue 22 and residue 86 in the second engineered immunoglobulin (BT gamma), and residue 20 in the first engineered immunoglobulin (BT delta) interacts with residue 26 in the second engineered immunoglobulin (BT gamma). Conversely, residue 88 in the second engineered immunoglobulin (BT gamma) interacts with residue 85.1 and 86 in the first engineered immunoglobulin (BT delta), residue 85.1 in the second engineered immunoglobulin (BT gamma) interacts with residue 86 in the first engineered immunoglobulin (BT delta), residue 22 in the second engineered immunoglobulin (BT gamma) interacts with residue 22 and residue 86 in the first engineered immunoglobulin (BT delta), and residue 20 in the second engineered immunoglobulin (BT gamma) interacts with residue 26 in the first engineered immunoglobulin (BT delta).

TABLE 5

Interactions between positions from the protein-protein interface of the TCRδ—CH3 monomer to the protein-protein interface of TCRγ—CH3 monomer in the newly engineered CH3 hetero-dimer. The IMGT ® numbering is used.

| TCRδ—CH3 (BT delta) | TCRγ—CH3 (BT gamma) |
|---|---|
| 7 | 20, 22 |
| 20 | 3, 5, 26, 27, 85.1, 86 |
| 22 | 5, 22, 26, 86 |
| 26 | 20, 88 |
| 27 | 13 |
| 79 | 26, 81, 84, 85.1, 86 |
| 81 | 81, 84, 85.1, 86 |
| 84.2 | 20, 81, 88 |
| 85.1 | 20, 81, 86, 88 |
| 86 | 20, 22, 84, 86, 88 |
| 88 | 26, 81, 84, 85.1, 86 |
| 90 | 26, 27, 85.1, 90 |

TABLE 6

Interactions between positions from the protein-protein interface of the TCRγ—CH3 monomer to the protein-protein interface of TCRδ—CH3 monomer in the newly engineered CH3 hetero-dimer. The IMGT ® numbering is used.

| TCRγ-CH3 (BT gamma) | TCRδ—CH3 (BT delta) |
|---|---|
| 3 | 20 |
| 5 | 20, 22 |
| 20 | 7, 26, 84.2, 85.1, 86 |
| 22 | 7, 22, 79, 86 |
| 26 | 20, 79, 88, 90 |
| 27 | 20, 90 |
| 81 | 81, 84.2, 85.1, 88 |
| 84 | 79, 81, 86, 88 |
| 85.1 | 20, 79, 81, 86, 88, 90 |
| 86 | 20, 22, 79, 81, 85.1, 86, 88 |
| 88 | 84.2, 85.1, 86 |

7.1.3 Modelling Hetero-Dimeric Domain Pairs Based on the Human IGHG1 CH3 Constant Domain Pair Protein-Protein Interface.

The amino acid sequence positions from the protein-protein interface of the human IGHG1 CH3 constant domain (donor domain) which are used to substitute the 3D equivalent amino acid sequence positions from the protein-protein interface of the parent immunoglobulin domain are listed below:
 a. A first set of donor positions from the human CH3 of IGHG1 comprises the following positions: 3, 5, 12, 13, 18, 20, 22, 79, 81, 84.2, 85.1, 86, and 88 (having the following amino acids: Q3, Y5, D12, E13, Q18, S20, T22, K79, T81, D84.2, F85.1, Y86, and K88), wherein the amino acid position of each group member is indicated according to the IMGT® numbering.
  The acceptor positions for the first set in all human immunoglobulin domains except for all human immunoglobulin light chain domains are as follows: 3, 5, 12, 13, 18, 20, 22, 79, 81, 84.2, 85.1, 86, and 88, except for position 81 in γ1, γ2, γ3, γ3: CH2 (for all 83), except for position 84.2 in γ1, γ2, γ3, γ3: CH2 (for all 84.3), wherein the amino acid position of each group member is indicated according to the IMGT® numbering.
 b. A second set of donor positions from the human CH3 of IGHG1 comprises the following positions: 3, 5, 7, 12, 13, 22, 26, 79, 81, 84, 85.1, 86, and 88 (having the following amino acids: Q3, Y5, L7, D12, E13, T22, K26, K79, T81, V84, F85.1, Y86, and K88), wherein the amino acid position of each group member is indicated according to the IMGT® numbering.
  The acceptor positions for the second set in all human immunoglobulin light chain domains are as follows: 3, 5, 7, 12, 13, 22, 26, 79, 81, 83, 85.1, 86, and 88, except for a human IGLC domain where the second set in is as follows: 3, 5, 7, 11, 12, 22, 26, 79, 81, 83, 85.1, 86, and 88, wherein the amino acid position of each group member is indicated according to the IMGT® numbering.

c. Modelling the Human IGHG1 CH3 Homo-Dimer Protein-Protein Interface on the Human CH1-CK Hetero-Dimer Protein-Protein Interface.

A model for the human IGHG1 CH1 domain substituted in its protein-protein interface with amino acids at equivalent 3D positions derived from the protein-protein interface of a human IGHG1 CH3 constant domain (CH13), and a model for the human Cκ domain substituted in its protein-protein interface with amino acids at equivalent 3D positions derived from the protein-protein interface of a human IGHG1 CH3 constant domain (CK3) were calculated (see above for methods). The Cα traces of the resulting models for the two engineered protein domains were further overlaid on the experimentally solved parental human IGHG1 CH1-Cκ hetero-dimer 3D structure (PDB code 1VGE) for visual inspection. In addition, a computational analysis of the protein-protein interface of the engineered domains was performed using the online PIC web server (http://crick.mbu.iisc.ernet.in/~PIC/, Tina K G et al., Nucleic Acids Res, 35(Web Server issue):W473-6 (2007)). Tables 7 and 8 list the interacting residues in the protein-protein interface of the engineered hetero-dimer identified from computational analysis, and direct measurements; the amino acid position of each group member is indicated according to the IMGT® numbering. From the modelling of a large number of immunoglobulin domain pairs engineered in their protein-protein interface with substitutions derived from naturally occurring homo-dimeric and hetero-dimeric protein-protein interface residues, the residues 20, 22, 26, 85.1, 86 and 88, in particular the residues 22, 85.1, 86 and 88 (numbering according to IMGT®) were repeatedly found to provide the most important contacts between the protein-protein interfaces of the engineered domains. More generally, by visual inspection and calculation of protein-protein interactions (using the online PIC web server (http://crick.mbu.iisc.ernet.in/~PIC/, Tina K G et al., Nucleic Acids Res, 35(Web Server issue):W473-6 (2007) or other protein-protein interaction programs known in the art), the residues 20, 22, 26, 85.1, 86 and 88, in particular the residues 22, 85.1, 86 and 88 were found to mediate the most important interactions for the hetero-dimerization or homo-dimerization of all engineered domains.

Without being bound by theory, the analysis of the newly engineered domain protein-protein interfaces identified four important subsets of interacting residues: residue 88 in the first engineered immunoglobulin (CH13) interacts with residue 85.1 and 86 in the second engineered immunoglobulin (CK3), residue 85.1 in the first engineered immunoglobulin (CH13) interacts with residue 86 in the second engineered immunoglobulin (CK3), residue 22 in the first engineered immunoglobulin (CH13) interacts with residue 22 and residue 86 in the second engineered immunoglobulin (CK3), and residue 20 in the first engineered immunoglobulin (CH13) interacts with residue 26 in the second engineered immunoglobulin (CK3). Conversely, residue 88 in the second engineered immunoglobulin (CK3) interacts with residue 85.1 and 86 in the first engineered immunoglobulin (CH13), residue 85.1 in the second engineered immunoglobulin (CK3) interacts with residue 86 in the first engineered immunoglobulin (CH13), residue 22 in the second engineered immunoglobulin (CK3) interacts with residue 22 and residue 86 in the first engineered immunoglobulin (CH13), and residue 20 in the second engineered immunoglobulin (CK3) interacts with residue 26 in the first engineered immunoglobulin (CH13).

TABLE 7

Interactions between positions from the protein-protein interface of the CH13 monomer to the protein-protein interface of CK3 monomer in the newly engineered CH1—CK hetero-dimer. The IMGT ® numbering is used.

| CH13 | CK3 |
|---|---|
| 3 | 13 |
| 5 | 12, 13 |
| 12 | 79, 88 |
| 13 | 3, 5, 7 |
| 18 | 3, 5, 26 |
| 20 | 3, 5, 7, 26, 85.1, 86 |
| 22 | 7, 22, 86 |
| 26 | 20 |
| 79 | 26, 81, 83, 85.1, 86 |
| 81 | 79, 81, 83, 85.1, 86 |
| 84.2 | 79, 88 |
| 85.1 | 79, 81, 86, 88 |
| 86 | 79, 81, 83, 85.1, 86 |
| 88 | 26, 81, 83, 85.1, 86 |

TABLE 8

Interactions between positions from the protein-protein interface of the CK3 monomer to the protein-protein interface of CH13 monomer in the newly engineered CH1—CK hetero-dimer. The IMGT ® numbering is used.

| CK3 | CH13 |
|---|---|
| 3 | 13, 18, 20 |
| 5 | 13, 18, 20 |
| 7 | 13, 20, 22 |
| 12 | 5 |
| 13 | 3, 5 |
| 20 | 26 |
| 22 | 22, 86 |
| 26 | 20, 79, 88 |
| 79 | 12, 81, 84.2, 85.1, 86 |
| 81 | 79, 81, 85.1, 86, 88 |
| 83 | 79, 81, 86, 88 |
| 85.1 | 20, 79, 81, 86, 88 |
| 86 | 20, 22, 79, 81, 86, 88 |
| 88 | 12, 84.2, 85.1, 86 |

7.2 Summary of Donor Positions Derived from Human TCR Constant Domains (TRAC, TRBC2, TRDC, TRGC1) and IGHG1 CH3.

A summary of the donor positions derived from the human TRAC (TCRα, abbreviated ALPHA), TRBC2 (TCRβ, abbreviated BETA), TRDC (TCRδ, abbreviated DELTA), TRGC1 (TCRγ, abbreviated GAMMA) and IGHG1 CH3 (abbreviated CH3) is found in Table 9. The amino acid position of each group member is indicated according to the IMGT® numbering Amino acid positions for CH3 (set i) are donor positions for substituting all human immunoglobulin domains except for light chain domains Amino acid positions for CH3 (set ii) are donor positions for substituting all human immunoglobulin light chain domains.

TABLE 9

Donor positions derived from the human TRAC, TRBC2, TRDC, TRGC1 and IGHG1 CH3. The IMGT ® numbering is used.

| IMGT ® | 3 | 5 | 7 | 12 | 13 | 18 | 20 | 22 | 26 | 27 | 79 |
|---|---|---|---|---|---|---|---|---|---|---|---|
| ALPHA  |   |   |   |    |    |    | K  | V  | T  |    | Y |
| BETA   | E | A | F |    |    |    | T  | V  | T  |    |   |
| DELTA  |   |   |   |    | M  |    | N  | A  |    | E  | F |
| GAMMA  | K | T |   |    |    |    | T  | L  | E  | K  |   |
| CH3 set i  | Q | Y |   | D | E | Q | S | T |   |   | K |
| CH3 set ii | Q | Y | L | D | E |   |   | T | K |   | K |

| IMGT ® | 81 | 82 | 84 | 84.1 | 84.2 | 84.3 | 85.1 | 86 | 88 | 90 |
|---|---|---|---|---|---|---|---|---|---|---|
| ALPHA  |   |   |   |     |     |     | S  | V | W | N |
| BETA   | D |   |   | L   |     | E   | C* | S | R | R |
| DELTA  |   | A |   |     | S   |     | N  | V | L | K |
| GAMMA  | G |   | M |     |     |     | M  | F | W |   |
| CH3 set i  | T |   |   |     | D   |     | F  | Y | K |   |
| CH3 set ii | T |   | V |     |     |     | F  | Y | K |   |

(* or C or S)

7.3 Basis for Additional Substitutions.

In a more general approach, the protein-protein interface residues from naturally occurring dimeric protein domains of the immunoglobulin super-family selected from the group consisting of 3, 5, 7, 12, 13, 18, 20, 22, 26, 27, 79, 81, 82, 84, 84.1, 84.2, 84.3, 85.1, 86, 88, and 90, can be used as donor residues to create new dimers, wherein the amino acid position of each group member is indicated according to the IMGT® numbering. Table 10 shows the amino acid residues of selected positions 20, 22, 26, 85.1, 86, and 88 from the hetero-dimeric donor domain CH1, and homo-dimeric domains CH2, CH3 and CH4 originating from different isotypes which can be used to substitute amino acids at the same positions in parent domains. Table 11 shows the amino acid residues of selected positions 20, 22, 26, 85.1, 86, and 88 from various hetero-dimeric human immunoglobulin superfamily members which can be used to substitute amino acids at the same positions in parent domains.

TABLE 10

Amino acid residues of selected positions 20, 22, 26, 85.1, 86, and 88 of the hetero-dimeric donor domain CH1, and homo-dimeric CH2, CH3 and CH4 domains. The IMGT ® numbering is used.

|  | 20 | 22 | 26 | 85.1 | 86 | 88 |
|---|---|---|---|---|---|---|
| CH1 | | | | | | |
| IGHA1 | V | A | Q | T | S | Q |
| IGHA2 | V | A | Q | T | S | Q |
| IGHD  | V | A | T | M | S | Q |
| IGHE  | T | G | T | A | I | L |
| IGHG1 | A | G | K | S | S | V |
| IGHG2 | A | G | K | S | S | V |
| IGHG3 | A | G | K | S | S | V |
| IGHG4 | A | G | K | S | S | V |
| IGHGP | A | G | K | S | S | V |
| IGHM  | A | G | Q | A | T | Q |
| CH2 | | | | | | |
| IGHA1 | N | T | T | S | S | V |
| IGHA2 | N | T | T | S | S | V |
| IGHD  | T | T | V | S | H | R |

TABLE 10-continued

Amino acid residues of selected positions 20, 22, 26, 85.1, 86, and 88 of the hetero-dimeric donor domain CH1, and homo-dimeric CH2, CH3 and CH4 domains. The IMGT ® numbering is used.

| | 20 | 22 | 26 | 85.1 | 86 | 88 |
|---|---|---|---|---|---|---|
| IGHE | Q | L | S | S | Q | E |
| IGHG1 | E | T | V | R | V | V |
| IGHG2 | E | T | V | R | V | V |
| IGHG3 | E | T | V | R | V | V |
| IGHG4 | E | T | V | R | V | V |
| IGHGP | E | T | V | H | V | V |
| IGHM | K | I | T | K | T | T |
| CH3 | | | | | | |
| IGHA1 | T | T | R | A | T | I |
| IGHA2 | T | T | R | A | T | I |
| IGHD | W | L | S | W | W | V |
| IGHE | T | T | V | T | T | T |
| IGHG1 | S | T | K | F | Y | K |
| IGHG2 | S | T | K | F | Y | K |
| IGHG3 | S | T | K | F | Y | K |
| IGHG4 | S | T | K | F | Y | R |
| IGHGP | T | T | K | F | Y | K |
| IGHM | K | T | T | S | V | E |
| CH4 | | | | | | |
| IGHE | T | A | Q | F | F | R |
| IGHM | T | T | T | F | H | I |

TABLE 11

Amino acid residues of selected positions 20, 22, 26, 85.1, 86, and 88 of various hetero-dimeric human immunoglobulin superfamily members. The IMGT ® numbering is used.

| | 20 | 22 | 26 | 85.1 | 86 | 88 |
|---|---|---|---|---|---|---|
| Human IGKC | S | V | N | S | S | T |
| Human IGLC1-IGLC7 | T | V | S | A | S | Y |
| Human TRAC | K | V | T | S | V | W |
| Human TRBC1, TRBC2 | T | V | T | C | S | R |
| Human TRDC | N | A | K | N | V | L |
| Human TRGC1, TRGC2 (2x, 3x) | T | L | E | M | F | W |

7.4 Correspondence Between the IMGT® Unique Numbering, the EU Numbering, and the Kabat Numbering.

The correspondence between the IMGT® unique numbering and the EU numbering for most of the human heavy chain constant domains cited above is found in Table 12. The correspondence between the IMGT® unique numbering and the EU numbering for the human kappa constant light chain domain, and the correspondence between the IMGT® unique numbering and the Kabat numbering for the human lambda constant light chain domains are both found in Table 13.

A complete correspondence for the human IGHG1 CH1-CH3, IGKC, and IGLC domains is found in FIGS. 19A, 19B, 19C, 19D, 22, 23A, and 23B and alternatively at the IMGT® database (the international ImMunoGeneTics information System®; Lefranc M P et al., *Nucleic Acids Res*, 27(1):209-12 (1999); Ruiz M et al., *Nucleic Acids Res*, 28(1):219-21 (2000); Lefranc M P, *Nucleic Acids Res*, 29(1):207-9 (2001); Lefranc M P, *Nucleic Acids Res*, 31(1):307-10 (2003); Lefranc M P et al., *Dev Comp Immunol*, 29(3):185-203 (2005); Kaas Q et al., *Briefings in Functional Genomics & Proteomics*, 6(4):253-64 (2007)), more specifically from the pages found at:

http://imgt.cines.fr/textes/IMGTScientificChart/Numbering/Hu_IGHGnber.html;
http://imgt.cines.fr/textes/IMGTScientificChart/Numbering/Hu_IGKCnber.html;
http://imgt.cines.fr/textes/IMGTScientificChart/Numbering/Hu_IGLCnber.html.

TABLE 12

Correspondence between the IMGT ® unique numbering and the EU numbering for the CH1, CH2, and CH3 domains of human IGHG1, IGHG2, IGHG3, and IGHG4.

| IMGT ® | 3 | 5 | 7 | 12 | 13 | 18 | 20 | 22 | 26 | 27 | 79 |
|---|---|---|---|---|---|---|---|---|---|---|---|
| CH1 EU | 124 | 126 | 128 | 133 | 134 | 139 | 141 | 143 | 147 | 148 | 168 |
| CH2 EU | 239 | 241 | 243 | 248 | 249 | 256 | 258 | 260 | 264 | 265 | 288 |
| CH3 EU | 347 | 349 | 351 | 356 | 357 | 362 | 364 | 366 | 370 | 371 | 392 |

| IMGT ® | 81 | 83 | 84 | 84.2 | 85.1 | 86 | 88 | 90 |
|---|---|---|---|---|---|---|---|---|
| CH1 EU | 170 | 172 | 173 | 175 | 181 | 183 | 185 | 187 |
| CH2 EU | 290 | 292 | 293 | 295 | 301 | 303 | 305 | 307 |
| CH3 EU | 394 | 396 | 397 | 399 | 405 | 407 | 409 | 411 |

TABLE 13

Correspondence between the IMGT ® unique numbering and the EU numbering for human IGKC, and correspondence between the IMGT ® unique numbering and the Kabat numbering for human IGLC (IGLC1, IGLC2, IGLC3, IGLC6, and IGLC7 domains).

| IMGT ® | 3 | 5 | 7 | 12 | 13 | 18 | 20 | 22 | 26 | 27 | 79 |
|---|---|---|---|---|---|---|---|---|---|---|---|
| IGKC EU | 114 | 116 | 118 | 123 | 124 | 129 | 131 | 133 | 137 | 138 | 160 |
| IGLC Kabat | 114 | 116 | 118 | 123 | 124 | 129 | 131 | 133 | 137 | 138 | 160 |

| IMGT ® | 81 | 83 | 84 | 84.2 | 85.1 | 86 | 88 | 90 |
|---|---|---|---|---|---|---|---|---|
| IGKC EU | 162 | 164 | 165 | 167 | 174 | 176 | 178 | 180 |
| IGLC Kabat | 162 | 164 | 165 | 167 | 174 | 176 | 178 | 180 |

Example 8

Construction of a Bispecific Hetero-Dimeric Immunoglobulin Having a CH3-CH3 Protein-Protein Interface Based on the Human α/β T Cell Receptor Constant Domains The HER family of receptor tyrosine kinases are important mediators of cell growth, differentiation, and survival (Earp H S et al., Breast Cancer Res Treat, 35(1):115-32 (1995)); the receptor family includes four distinct members: epidermal growth factor receptor EGFR (ErbB1, or HER1), HER2 (ErbB2 or p185$^{neu}$) HER3 (ErbB3) and HER4 (ErbB4 or tyro2) which are generally found in various combinations in cells (Rowinsky E K, Annu Rev Med, 55:433-57 (2004); Hynes N E and Lane H A, Nat Rev Cancer, 5(5):341-54 (2005)). Receptor dimerization is an essential requirement for ErbB function and for the signaling activity of these receptors (Baselga J and Swain S M, Nat Rev Cancer, 9(7):463-75 (2009)); more specifically, receptor hetero-dimerization is thought to increase the diversity of cellular responses to various HER ligands. Therapeutics that target a single receptor from the HER family are presently in use in treating diseases such as breast cancer, non-small cell lung cancer, colorectal cancer, head and neck cancer and pancreatic cancer (Engelman J A and Janne P A, Clin Cancer Res, 14(10):2895-9 (2008); Baselga J and Swain S M, Nat Rev Cancer, 9(7):463-75 (2009)). Although these therapies had some success, issues related to native and induced resistance and toxicity are currently limiting their efficacies (Robert C et al., Lancet Oncol, 6(7):491-500 (2005); Jones K L and Buzdar A U, Lancet Oncol, 10(12):1179-87 (2009)). Therapeutics that could target multiple receptors from the HER family may offer improved clinical efficacy and lower toxicity.

Figure 24:
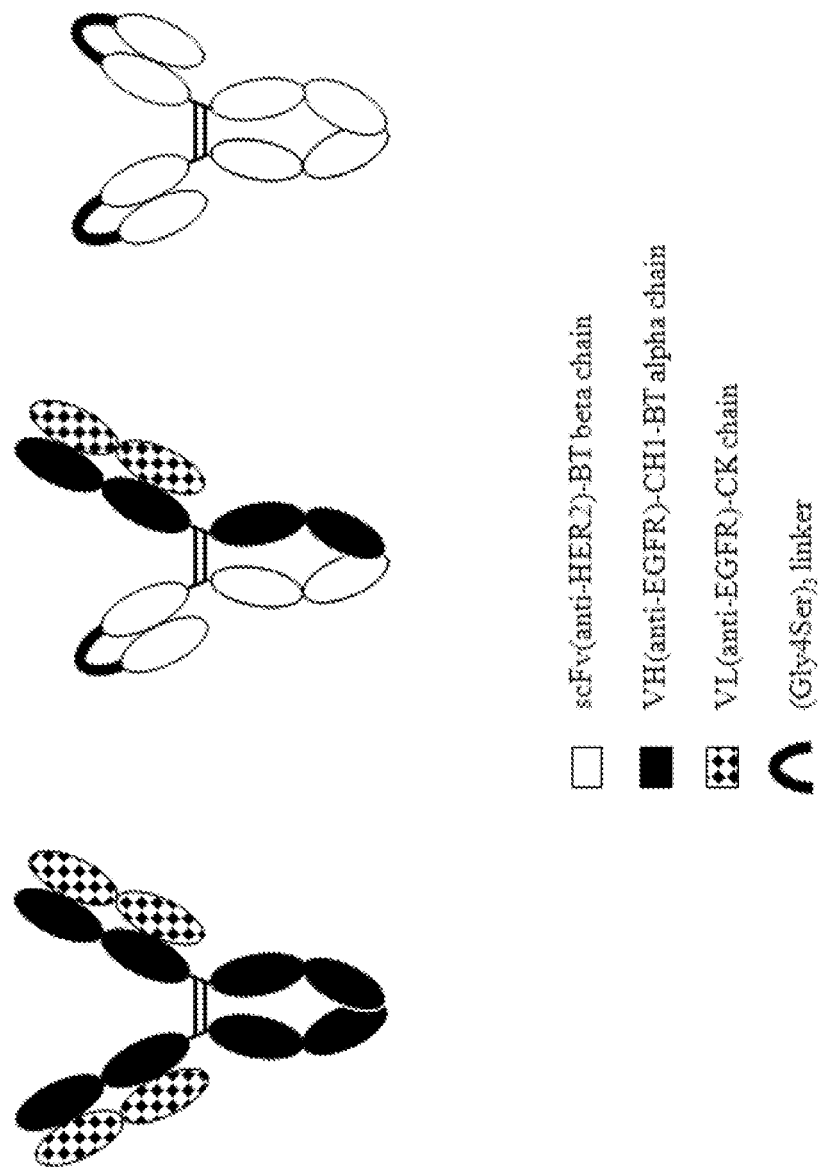
FIG. 24: Schematic diagram of possible modified heavy chain pairings when expressing the Erbitux FAB-BT alpha_Herceptin scFv-BT beta hetero-dimer

To produce a bispecific molecule that could specifically bind to at least two HER receptors (FIG. 24), the antigen binding sites derived from the recombinant humanized anti-HER2 antibody 4D5 (rhuMAbHER2, huMAB4D5-8, Trastuzumab or Herceptin®; U.S. Pat. No. 5,821,337), and the recombinant chimeric anti-EGFR antibody C225 (IMC-C225, Cetuximab or Erbitux®; PCT Publication NO: WO 96/40210) were selected as inputs for gene synthesis at GENEART AG (Regensburg, Germany). For both antibodies, the heavy chain variable sequence (VH) and the light chain variable sequence (VL) were synthesized and reformatted into a scFv fragment (VH and VL domains were fused with a 15 amino acid GlySer linker: (Gly$_4$Ser)$_3$) and a chimeric FAB fragment (i.e., a murine VH-human CH1 (γ1) chain assembled with a murine VL-human CK chain) for the anti-HER2 antibody 4D5 and the anti-EGFR antibody C225, respectively. All DNA manipulations followed standard molecular biology techniques and primarily involved PCR amplification, and PCR fragment assembly methods. To create the anti-EGFR portion of the bispecific molecule, the anti-EGFR antibody C225 murine VH-human CH1 (γ1) chain was fused upstream of a BT alpha chain described in example 1 (abbreviated VH(anti-EGFR)-CH1-BT alpha chain, SEQ ID NO: 56), while the anti-EGFR antibody C225 murine VL was fused upstream of a human Kappa constant domain (abbreviated VL(anti-EGFR)-CK chain, SEQ ID NO: 57). To create the anti-HER2 portion of the bispecific molecule, the anti-HER2 scFv was fused upstream of a BT beta F405A chain described in example 2 with a short GlySer amino acid linker (GGGS) between the two sequences (abbreviated scFv(anti-HER2)-BT beta chain, SEQ ID NO: 58). All three resulting chains were further ligated independently into the modified pREP4 vector mentioned in example 1 and co-transfected into HEK293-EBNA cells as described in example 1. Protein production was also according to the procedure described in example 1.

The expected bispecific molecule consisting of one VH(anti-EGFR)-CH1-BT alpha chain, one VL(anti-EGFR)-CK chain, and one scFv(anti-HER2)-BT beta chain (SEQ ID NOs: 59, 60, and 61), is designated "Erbitux FAB-BT alpha_Herceptin scFv-BT beta".

Figure 25:
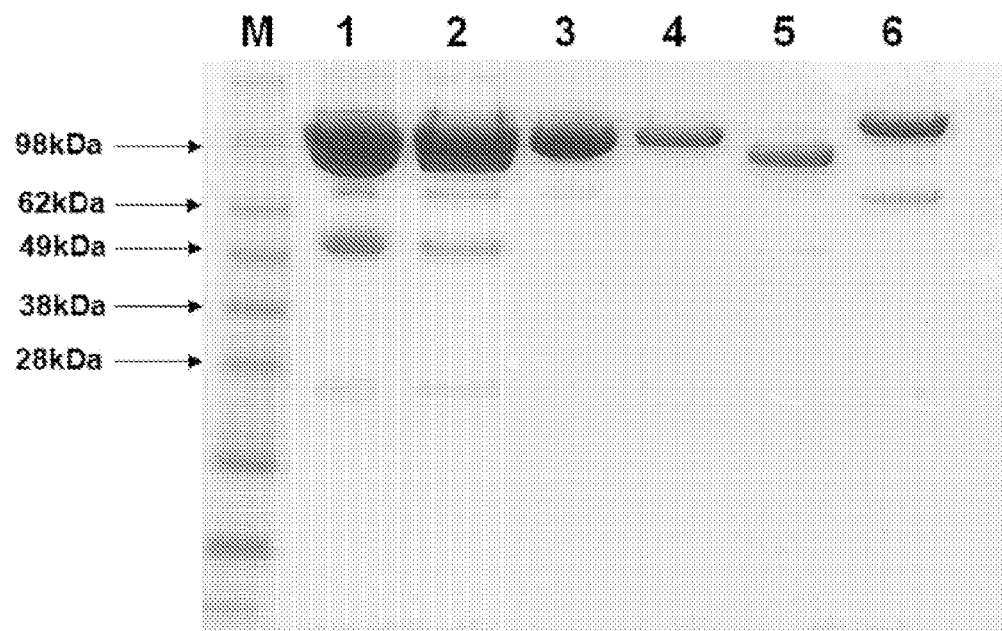
FIG. 25: SDS-PAGE demonstrating production of the Erbitux FAB-BT alpha_Herceptin scFv-BT beta. Samples of protein pools after each purification step are shown (4-12% SDS Tris-glycine polyacrylamide gel, non-reducing conditions). (M) Molecular weight marker as indicated. (1) after protein-A chromatography. (2) after anion IEX. (3) after cation IEX. (4) after size-exclusion chromatography. (5) control: scFv-Fc fusion protein. (6) control: monoclonal antibody.
Figure 26:
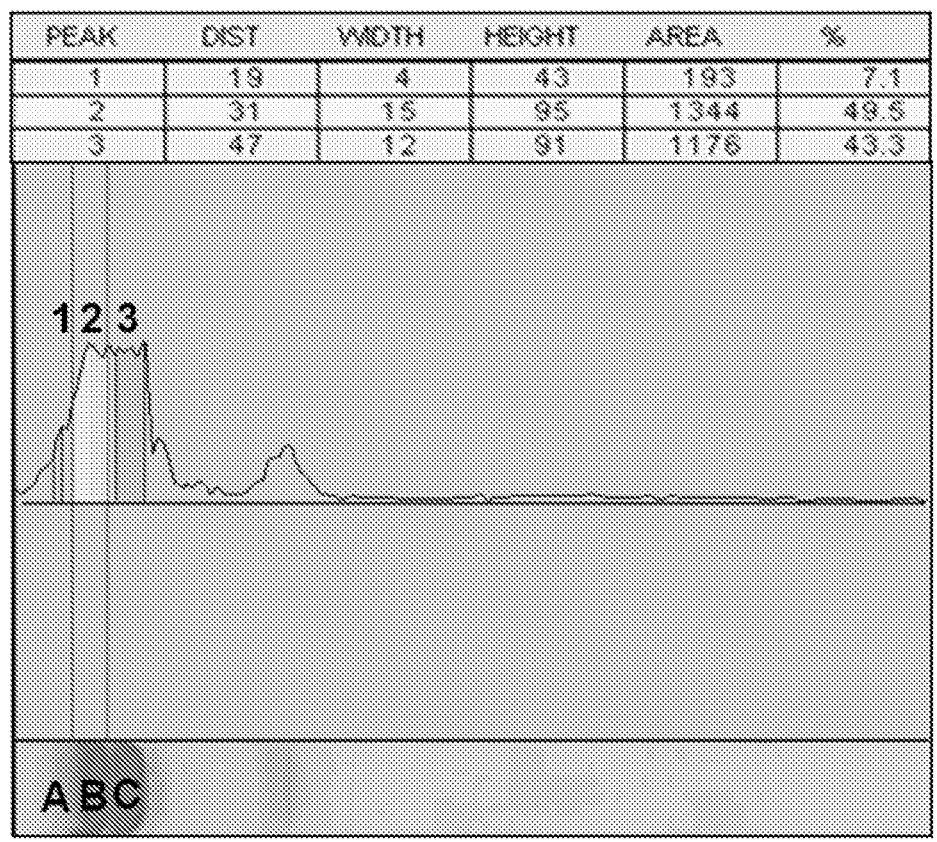
FIG. 26: Scanning densitometry analysis assessing the relative proportion of the Erbitux FAB-BT alpha_Herceptin scFv-BT beta hetero-dimer after protein-A purification (4-12% SDS Tris-glycine polyacrylamide gel, non-reducing conditions). (A) VH(anti-EGFR) CH1-BT alpha_VL(anti-EGFR)-CK homo-dimer (B) Erbitux FAB-BT alpha_Herceptin scFv-BT beta hetero-dimer (C) scFv(anti-HER2)-BT beta homo-dimer. Impurities have been omitted from measurement.

To isolate the Erbitux FAB-BT alpha_Herceptin scFv-BT beta hetero-dimer from homo-dimers, ion-exchange chromatography (IEX) steps were performed post protein-A purification (procedure according to example 1). First, an anion-IEX step was performed: the protein-A eluate was buffer exchanged (into 50 mM Tris-HCl pH 9.0) and loaded on a 4 ml SourceQ 30 packed column operated on an ÄKTA Purifier (both from GE Healthcare Europe GmbH, Glattbrugg, Switzerland). The Erbitux FAB-BT alpha_Herceptin scFv-BT beta was then eluted with a shallow pH gradient ranging from pH 9.0 to pH 5.0 (final buffer condition was 50 mM sodium acetate pH 5.0). Following SDS-PAGE analysis, the fractions containing the majority of the Erbitux FAB-BT alpha_Herceptin scFv-BT beta hetero-dimer were pooled and rebuffered to 50 mM sodium acetate pH 5.0. In a second step, cation IEX was performed by loading the rebuffered fractions from the anion IEX step on a 1 ml MonoS column (GE Healthcare Europe GmbH, Glattbrugg, Switzerland) and running a shallow gradient from 50 mM sodium acetate pH 5.0 to 50 mM Tris-HCl pH 9.0. Fractions containing the Erbitux FAB-BT alpha_Herceptin scFv-BT beta hetero-dimer were selected by SDS-PAGE analysis. Finally the purified the Erbitux FAB-BT alpha_Herceptin scFv-BT beta hetero-dimer was polished on a size-exclusion chromatography column (Superdex 200 HR16/60, GE Healthcare Europe GmbH, Glattbrugg, Switzerland) to remove traces of aggregates and buffer exchange the final bispecific molecule into PBS. FIG. 25 shows a polyacrylamide SDS gel profile after each purification step as well as two control molecules: a scFv-Fc fusion protein and a monoclonal antibody. The production yields from transient transfections were up to 30 mg/l with a hetero-dimerization rate of 49.5% as judged by scanning densitometry analysis of non-reduced SDS-polyacrylamide (4-12%) gel bands (see example 1 for methods) (FIG. 26).

Figure 27:
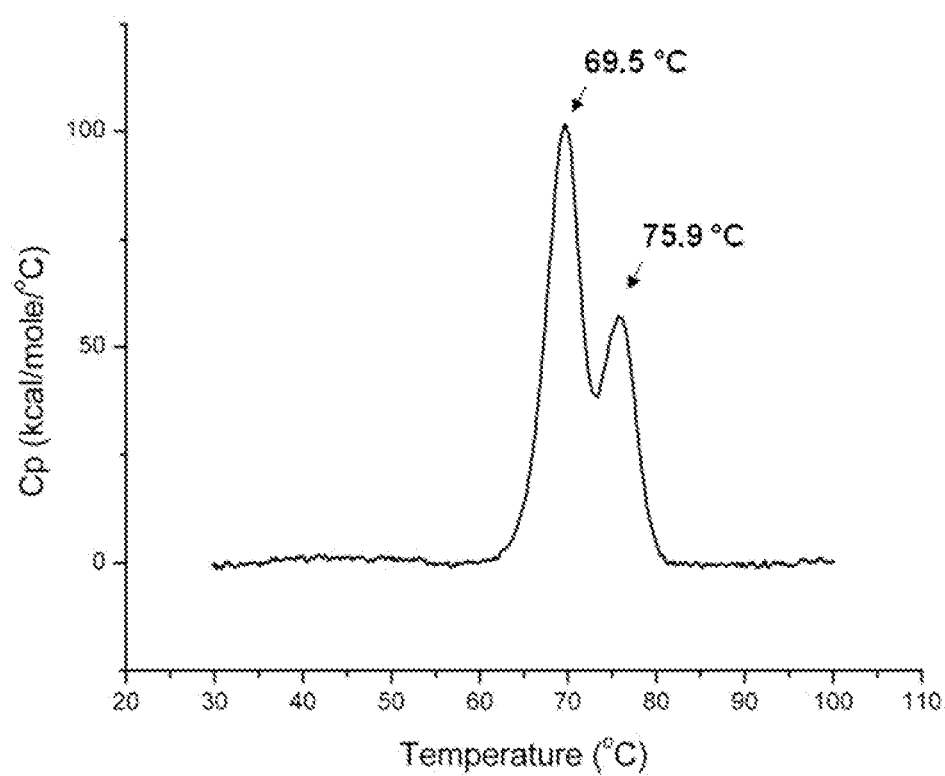
FIG. 27: DSC thermogram of the Erbitux FAB-BT alpha_Herceptin scFv-BT beta hetero-dimer.

To assess the stability of Erbitux FAB-BT alpha_Herceptin scFv-BT beta hetero-dimer, the purified material was analysed using differential scanning calorimetry (DSC). The calorimetric measurements were carried out on a VP-DSC differential scanning microcalorimeter (GE Healthcare Europe GmbH, Glattbrugg, Switzerland) as described in example 2. The cell volume was 0.128 ml, the heating rate was 1° C./min, and the excess pressure was kept at 64 p.s.i. The protein was used at a concentration of 0.95 mg/ml in PBS (pH 7.4). FIG. 27 shows a thermogram of the Erbitux FAB-BT alpha_Herceptin scFv-BT beta hetero-dimer exhibiting two thermal transitions at 69.5 and 75.9° C. It is important to note that no sharp decrease after the heat absorption peak was recorded, indicating that no precipitation or aggregate formation occurred after thermal unfolding (Liu H et al., *Immunol Lett,* 106(2):144-53 (2006)). Hence, the melting transitions observed for the Erbitux FAB-BT alpha_Herceptin scFv-BT beta hetero-dimer are similar to the ones observed for a human IGHG4 Fc fragment CH2 and CH3 domains, and similar to the melting transitions generally observed for stable human FAB fragments (Garber E and Demarest S J, *Biochem Biophys Res Commun,* 355(3): 751-7 (2007)). In conclusion, this thermal unfolding study shows that the Erbitux FAB-BT alpha_Herceptin scFv-BT beta hetero-dimer with engineered protein-protein interface based on the TCR alpha and beta constant domains has similar thermo-stability to naturally occurring immunoglobulins.

Figure 28A:
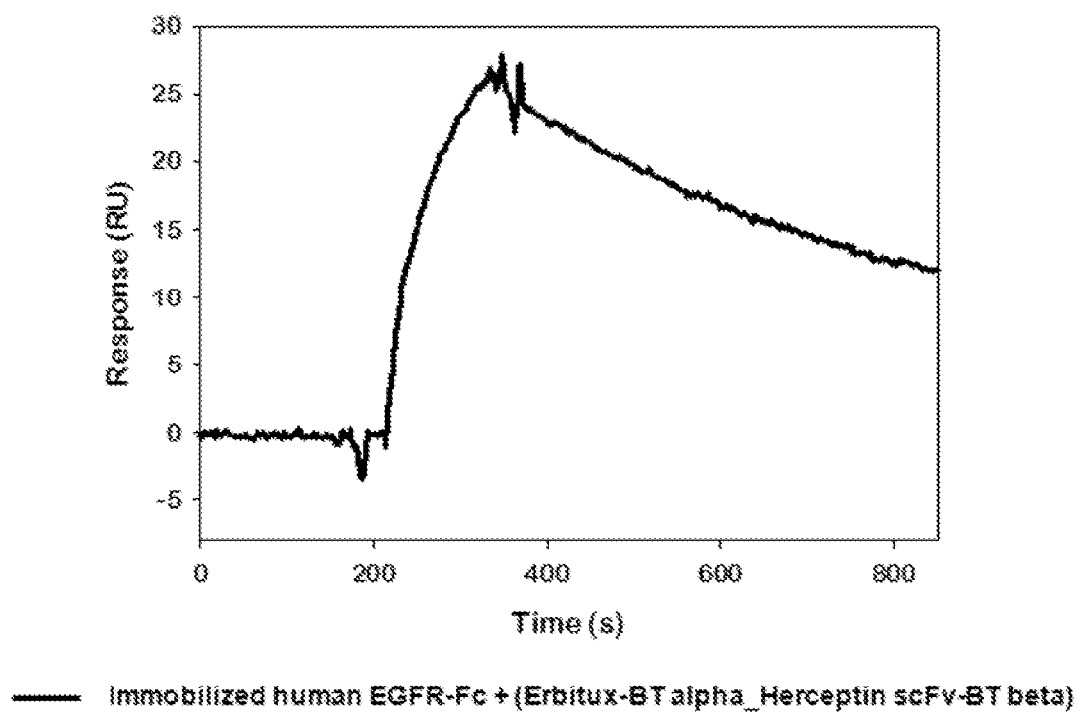
FIG. 28A: BIAcore sensorgram showing the binding and dissociation of the Erbitux FAB-BT alpha_Herceptin scFv-BT beta hetero-dimer to/from immobilized human EGFR-Fc.
Figure 28B:
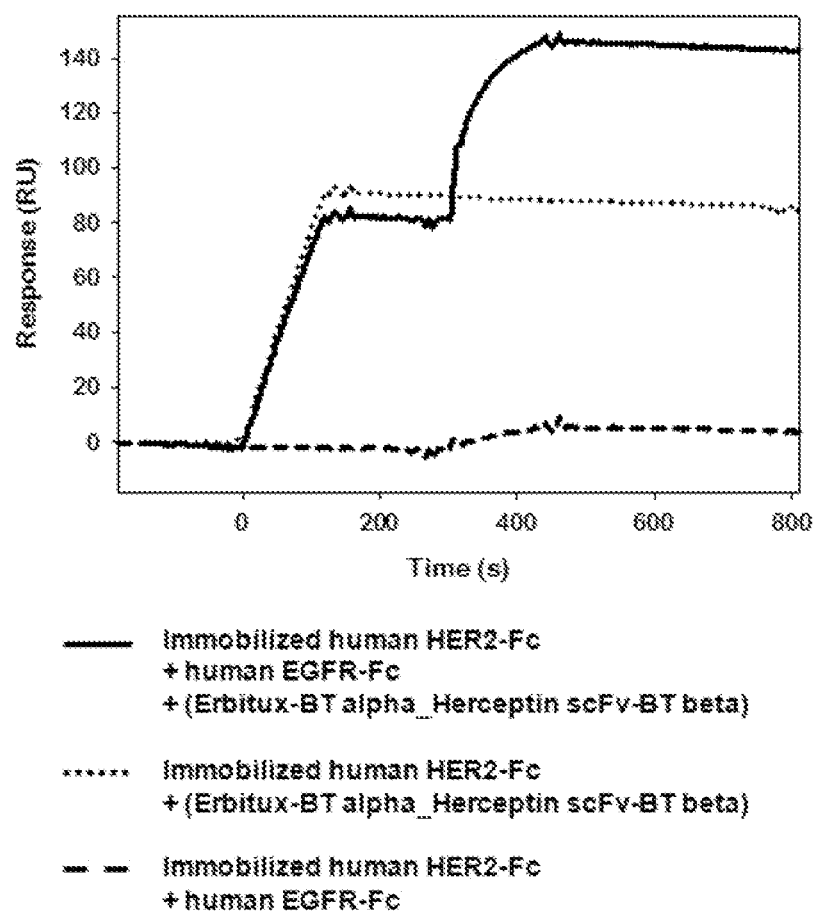
FIG. 28B: Demonstration of simultaneous binding of the bispecific Erbitux FAB-BT alpha_Herceptin scFv-BT beta hetero-dimer to both antigens using SPR technology. The Erbitux FAB-BT alpha_Herceptin scFv-BT beta hetero-dimer and the human EGFR-Fc were injected sequentially on immobilized human HER2-Fc (solid line). Controls: (dotted line) binding of the Erbitux FAB-BT alpha_Herceptin scFv-BT beta hetero-dimer to the immobilized human HER2-Fc, (dashed line) absence of binding of the human EGFR-Fc to the immobilized human HER2-Fc.

The ability of the Erbitux FAB-BT alpha_Herceptin scFv-BT beta hetero-dimer to bind simultaneously to both of its cognate antigens (human EGFR and human HER2) was tested by surface plasmon resonance (SPR) on a BIAcore 2000 instrument (GE Healthcare Europe GmbH, Glattbrugg, Switzerland). In the present example, the recombinant extracellular domains from the human EGFR and HER2 receptors were individually fused upstream of a human Fc (γ1) fragment (abbreviated EGFR-Fc and HER2-Fc, SEQ ID NO: 62 and 63, respectively). Briefly, the extracellular domains of the human EGFR and HER2 were amplified by PCR from the imaGenes clone NO: EX-A0275-M02 and Ex-BOO17-M10 (imaGenes GmbH, campus Berlin-Buch, Berlin, Germany), respectively. PCR products were then fused upstream of a human Fc (γ1) portion using PCR assembly methods (SEQ ID NO: 64 and 65, respectively) and independently cloned into a mammalian cell expression vector based on the pcDNA3.1 vector DNA from Invitrogen (Invitrogen AG, Basel, Switzerland). Finally each recombinant vector was transfected into HEK293 cells; after 4-5 days post transfection, supernatants were harvested and recombinant proteins were purified to homogeneity by protein-A affinity chromatography. SPR experiments were performed at 25° C. in 1×HBS-EP buffer (GE Healthcare Europe GmbH, Glattbrugg, Switzerland) at a flow rate of 30 µl/min. The purified Fc-fused antigens were immobilized on a research-grade CM5 chip (GE Healthcare Europe GmbH, Glattbrugg, Switzerland) via amine coupling using a standard protocol provided by the manufacturer. EFGR-Fc and HER2-Fc, which were immobilized on different channels of the chip led to a signal of 410 and 880 response units (RU), respectively. A channel lacking immobilized antigens was used as reference channel. Responses from this channel were subtracted from measurements. For the binding and co-binding experiments, the Erbitux FAB-BT alpha_Herceptin scFv-BT beta hetero-dimer and the EGFR-Fc were diluted in 1×HBS-EP buffer (Healthcare Europe GmbH, Glattbrugg, Switzerland) to a final concentration of 25 and 100 nM, respectively. For all analytes the injections were limited to two minutes. FIG. 28A shows the binding and dissociation between the Erbitux FAB-BT alpha_Herceptin scFv-BT beta hetero-dimer and the immobilized EGFR-Fc. Co-binding of the Erbitux FAB-BT alpha_Herceptin scFv-BT beta and the EGFR-Fc as analytes to the immobilized HER2-Fc is shown in FIG. 28B. In this binding experiment, the Erbitux FAB-BT alpha_Herceptin scFv-BT beta hetero-dimer was first injected on the channel with immobilized HER2-Fc, showing the binding of Erbitux FAB-BT alpha_Herceptin scFv-BT beta hetero-dimer to the antigen. Three minutes after this first injection, EGFR-Fc was injected, resulting in a co-binding event with the Erbitux FAB-BT alpha_Herceptin scFv-BT beta hetero-dimer; to verify that the observed response was a true co-binding event and not an interaction between both antigens, the EGFR-Fc was injected on the immobilized HER2-Fc and no significant response was recorded (FIG. 28B).

Example 9

Construction of a Bispecific Hetero-Dimeric Immunoglobulin Having a CH3-CH3 Protein-Protein Interface Based on the Human α/β T Cell Receptor Constant Domains, and a FAB Fragment Having a CH1-CK Protein-Protein Interface Based on the Hetero-Dimeric δ/γ T Cell Receptor Constant Domains Example 5 provides a novel set of modified CH1 (γ1) and Cκ constant domains based on the protein-protein interfaces of the human TCR constant domains delta and gamma. This new pair of FAB constant domains offers the opportunity to create human bispecific antibodies without having to compromise in using a common light chain.

Figure 29:
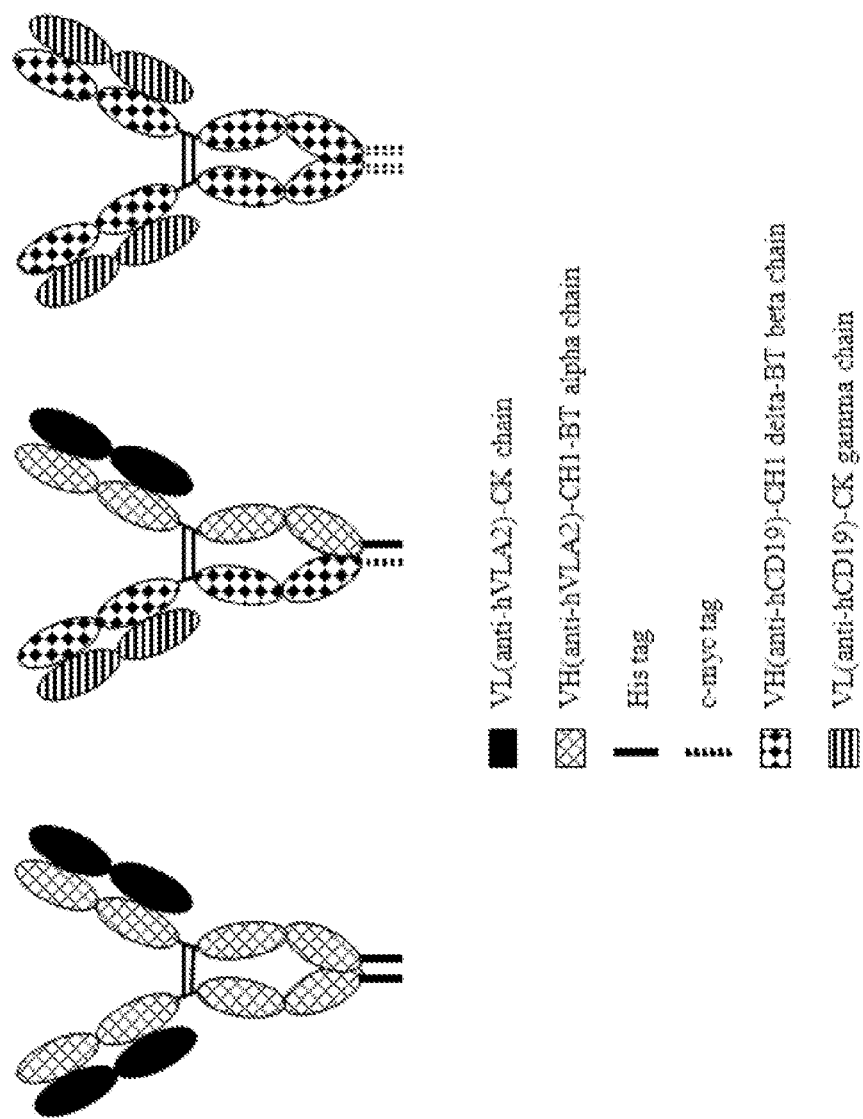
FIG. 29: Schematic diagram of possible modified heavy chain pairings when expressing the anti-hCD19_anti-hVLA2 bispecific antibody. Both heavy chains, VH(anti-hVLA2)-CH1-BT alpha and VH(anti-hCD19)-BT delta-BT beta are C-terminally fused to the His and c-myc tag respectively.

This novel type of bispecific antibody will be based on two distinct heavy chains having different variable domains, and two distinct light chains having different variable domains. The correct assembly of the four distinct chains of the bispecific antibody is based on two principles: (1) to force the two different antibody heavy chains to hetero-dimerize, the novel pair of engineered hetero-dimeric CH3 domains described in example 1-3 will be used, (2) to circumvent any potential light chain mispairing, the novel set of CH1 (γ1) and CK constant domains described in example 5 will be introduced in one of the two FAB arms of the bispecific antibody. Hence, the bispecific antibody will encompass at least three different protein-protein interfaces in three different portions: the first FAB arm having the naturally occurring hetero-dimeric pair of CH1 (γ1) and CK constant domains, the second FAB arm having the novel hetero-dimeric pair of CH1 (γ1) and CK constant domains with protein-protein interfaces originating from the heterodimeric pair of TCR delta and TCR gamma constant domains, and one Fc fragment having the novel heterodimeric pair of engineered CH3 (γ1) constant domains with protein-protein interfaces originating from the hetero-dimeric TCR alpha and TCR beta constant domains (FIG. 29).

To produce a full and correctly assembled bispecific antibody that could specifically bind to at least two antigens, the variable heavy chain and variable light chain domains from a humanized anti human CD19 antibody (abbreviated VH(anti-hCD19) and VL(anti-hCD19) respectively, disclosed in the PCT Publication NO: WO 2010/095031), and the variable heavy chain and variable light chain domains from a humanized anti alpha 2 subunit of the human VLA-2 receptor (VLA2) antibody (abbreviated VH(anti-hVLA2) and VL(anti-hVLA2) respectively, disclosed in the PCT Publication NO: WO 2007/056858), were selected as inputs for expression and functional studies. The coding cDNAs for VH(anti-hVLA2) and VL(anti-hVLA2) domains were available from studies described in the PCT Publication NO: WO 2007/056858.

To create the four distinct chains of the bispecific antibody, two new immunoglobulin chains were created using PCR techniques: a first chain consisting of the variable heavy chain VH(anti-hVLA2) fused upstream of a human CH1(γ1)-BT alpha His chain (example 1 and 2) (abbreviated VH(anti-hVLA2)-CH1-BT alpha His, SEQ ID NO: 66), and a second chain consisting of the variable light chain VL(hVLA2) fused upstream of the naturally occurring human CK constant domain (abbreviated VL(anti-hVLA2)-CK, SEQ ID NO: 67). Following PCR assembly, both chain cDNAs were ligated independently into the modified pREP4 vector described example 1. The final two immunoglobulin chains needed to produce the complete bispecific antibody originated from example 5: a third chain consisting of the VH(anti-hCD19)-CH1 delta-BT beta c-myc chain (SEQ ID NO: 43), and a fourth chain consisting of the VL(anti-hCD19)-CK gamma chain (SEQ ID NO: 44). The resulting bispecific antibody having all the four distinct chains is abbreviated anti-hCD19_anti-hVLA2 bispecific antibody (SEQ ID NOs: 68, 69, 41, and 42).

All four vectors carrying the recombinant immunoglobulin chains were co-transfected into HEK293-EBNA cells and protein production was performed according to the procedure described in example 1. Small quantities of antibody species having a single specificity towards either the human VLA2 antigen (abbreviated anti-hVLA2 antibody) or the human CD19 antigen (abbreviated hCD19 antibody) were obtained by co-transfection of chain "one" with chain "two", and chain "three" with chain "four", respectively. These antibodies were later used as controls in FACS experiments (see below).

The production yields of transient transfections were about 18 mg/l post protein A purification (procedure according to example 1). To isolate fully assembled bispecific molecules from traces of homo-dimeric species, two affinity chromatographic steps were sequentially implemented. The first step was based on protein L affinity chromatography (Protein L resin from GenScript, Piscataway, N.J. USA; used according to the manufacturer's protocol), and made use of the specificity of protein-L towards the light chain variable domains originating from Kappa subgroup κ1 and κ3, but not K2 (Nilson B H et al., *J Biol Chem*, 267(4):2234-9 (1992)). Since the variable VL(anti-hVLA2) light chain domain belongs to the κ2 subclass, and the variable VL(anti-hCD19) light chain domain belongs to the κ1 subclass, this step allowed for the removal of any homo-dimeric antibody species lacking the variable VL(anti-hCD19) domain (see above, chain "four"). For the second step, the protein pool after protein L purification was buffer-exchanged into 50 mM Tris-HCl pH 9.0, 200 mM NaCl and loaded on a 1 ml HisTrap $Ni^{2+}$-NTA affinity chromatography column operated on an ÄKTA Purifier (both from GE Healthcare Europe GmbH, Glattbrugg, Switzerland) at a flow rate of 0.6 ml/min. This step allowed for the removal of any homo-dimeric antibody species lacking the BT alpha chain (see above, chain "one").

Figure 30:
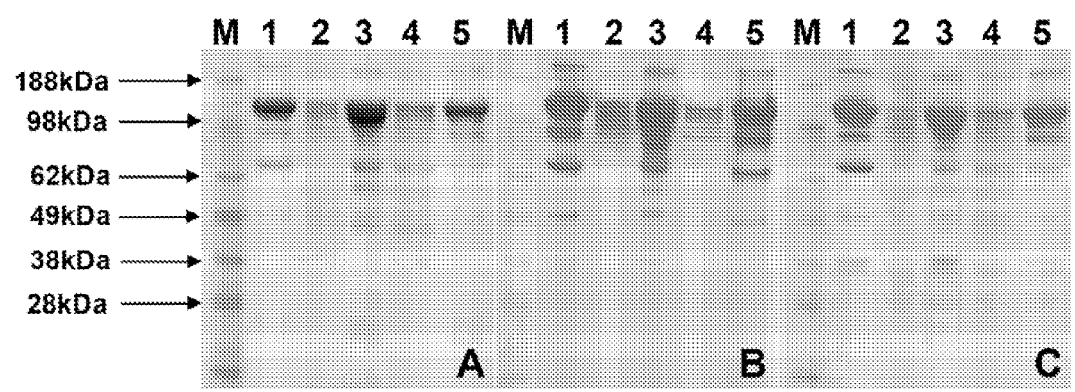
FIG. 30: SDS-PAGE and Western blot analysis of the anti-hCD19_anti-hVLA2 bispecific antibody. Samples were taken after each purification step (4-12% SDS Tris-glycine polyacrylamide gels under non-reducing conditions); both eluate and unbound pools are shown. (M) Molecular weight marker as indicated. (1) eluate pool from protein-A chromatography. (2) unbound pool from protein-L chromatography. (3) eluate pool from protein-L chromatography. (4) unbound pool from $Ni^{2+-}NTA$ chromatography. (5) eluate pool from $Ni^{2+-}NTA$ chromatography. (A) SDS-PAGE. (B) Western blot detected with an anti His tag antibody. (C) Western blot detected with an anti c-myc tag antibody.

To confirm the presence of the anti-hCD19_anti-hVLA2 bispecific antibody, a Western blot analysis was performed on sample aliquots isolated at different steps of the purification process. For detection, a horse radish peroxidase conjugated anti His tag (Sigma, Buchs, Switzerland) and anti c-myc tag (Roche Diagnostics (Schweiz) AG, Rotkreuz, Switzerland) antibodies were used. For staining, the peroxidase substrate SIGMA FAST 3,3'-Diaminobenzidine (Sigma, Buchs, Switzerland) was used. Comparison of two Western blots, one detected with the anti His tag antibody and one detected with the anti c-myc antibody confirmed the presence of the anti-hCD19_anti-hVLA2 bispecific antibody after the two purification steps (FIG. 30, lane 5 in panels B and C).

Figure 31:
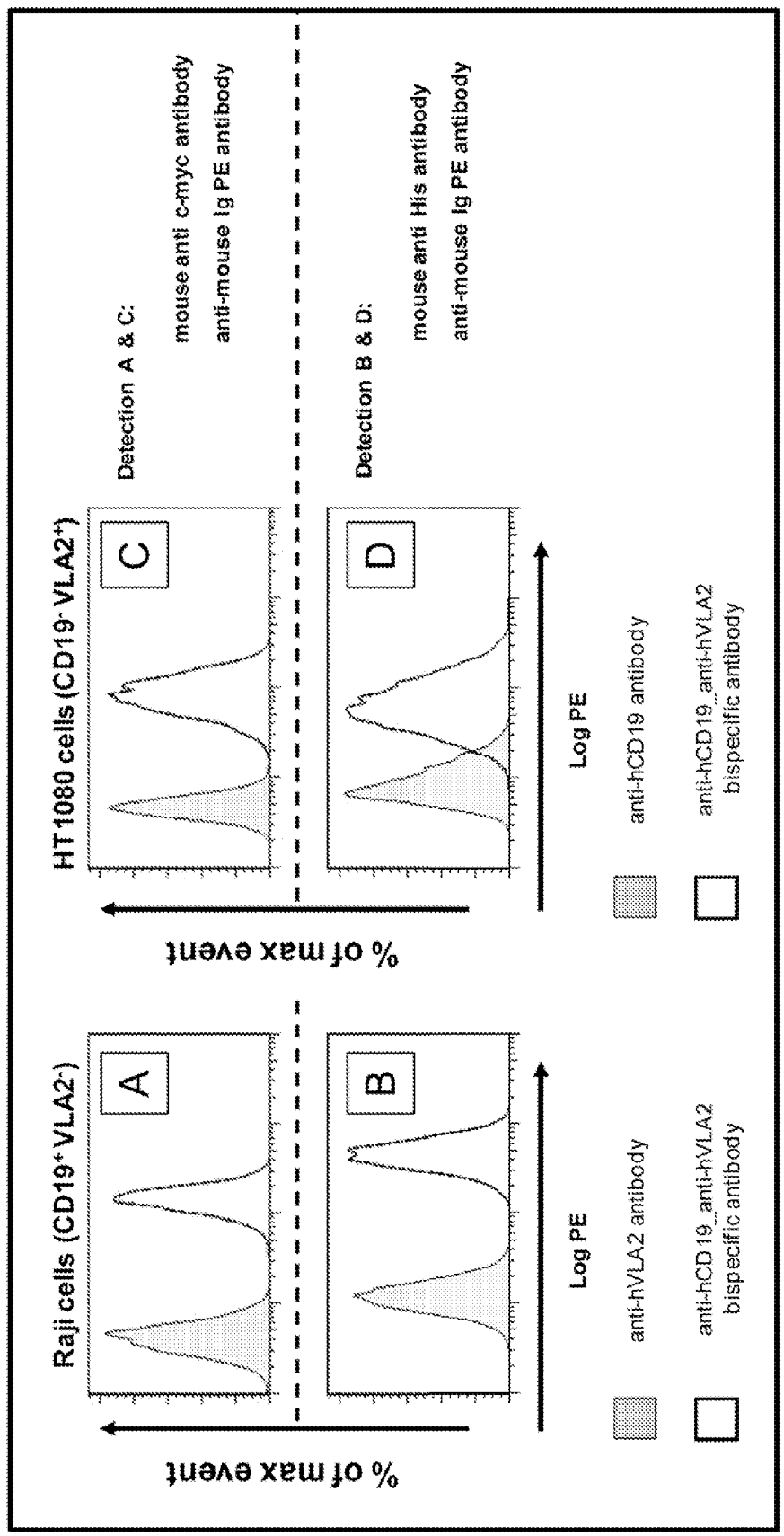
FIG. 31: Flow cytometry detection of the anti-hCD19_anti-hVLA2 bispecific antibody binding to $CD19^+$ $VLA2^-$ and $CD19^-$ $VLA2^+$ cells. Stained cells were acquired on a FACS CyAn™ ADP flow cytometer. Histograms display the normalized % of maximal event (Y axis) according to Phycoerythrin (PE) fluorescence intensity (X-axis) for each staining A and B: Raji cells were stained with the anti-hVLA2 antibody (grey histogram) as an isotype control or the anti-hCD19_anti-VLA2 bispecific antibody (white histogram). Binding of the primary antibodies was revealed by (A) a mouse anti c-myc tag antibody or (B) a mouse anti His tag antibody and stained with a PE-labelled anti-mouse Ig antibody.

To confirm the dual specificity of the anti-hCD19_anti-hVLA2 bispecific antibody, two independent FACS binding experiments were designed. In both experiments, the bispecific antibody was tested for binding to one of its two cognate antigens displayed at the cell-surface of target cells while detecting with the affinity tag present on the chain having the second specificity. Since the anti-hCD19_anti-hVLA2 bispecific antibody specificities are towards both the human CD19 cell-surface protein and the alpha 2 subunit of the human VLA-2 receptor, the Raji cell line (a human Burkitt's lymphoma cell line, DSMZ clone NO: ACC319), and the HT1080 cell-line (human fibrosarcoma cell line, ATCC clone NO: CCL-121) were selected as target cells, respectively. Raji cells are strictly $CD19^+$ and $VLA2^-$, while HT1080 cells are $VLA2^+$ and $CD19^-$ (data not shown), thereby preventing any false positives. Both cell lines were harvested from standard culture conditions and counted (viability >90% according to trypan blue exclusion). Cells were washed once in staining buffer: a PBS solution supplemented with 2.5% FBS from PAA (PAA Laboratories, Pasching, Austria; catalogue NO: A15-101) and 10% versene from GIBCO-Invitrogen AG (Basel, Switzerland, catalogue NO: 15040) prior to the staining procedure. Staining was performed on $2 \times 10^5$ cells per condition, in V-bottom 96-well plates, on ice. Each incubation step was done in 50 ml of staining buffer supplemented with 10 µg/ml of anti-hCD19_anti-hVLA2 bispecific antibody and further incubated for 20 min. Cells were then washed twice with cold staining buffer and incubated 20 min with either a mouse anti His tag antibody (Sigma, Buchs, Switzerland; catalogue NO: A7058-1VL), or a mouse anti c-myc tag antibody (Roche Diagnostics (Schweiz) AG, Rotkreuz, Switzerland; catalogue NO: 11667149001), both at a concentration of 10 µg/ml in staining buffer. A control sample with cells kept only in staining buffer was also made for both cell lines. For detection, cells were washed twice with staining buffer and incubated 20 min with a Phycoerythrin-conjugated mouse-anti-Human Ig Fc fragment specific antibody (eBioscience, San Diego, USA; distributor: eBioscience CBI Medicals PV, Baar, Switzerland; catalogue NO: 12-4998-82) used at a 1:200 dilution in staining buffer. Finally, cells were washed once with staining buffer and resuspended in 300 ml of cold staining buffer and promptly analyzed by flow cytometry (CyAn™ ADP, Beckman Coulter International S.A., Nyon, Switzerland). Data were processed using the Flowjo® software (Tree Star, Inc., Ashland, Oreg., USA); histograms were plotted on live cells based on Forward and Side Scatter parameter gating. FIG. 31A shows the binding of the anti-hCD19_anti-hVLA2 bispecific antibody to Raji cells detected with a mouse-anti c-myc tag antibody, in this experiment the anti-hVLA2 antibody lacking the c-myc tag is used as a negative control. FIG. 31B shows the binding of the anti-hCD19_anti-hVLA2 bispecific antibody to Raji cells detected with a mouse-anti His tag antibody, in this experiment the anti-hVLA2 antibody is also used as a negative control, since it lacks the hCD19 specificity in spite of having the polyhistidine tag sequence. FIG. 31C shows the binding of the anti-hCD19_anti-hVLA2 bispecific antibody to HT1080 cells detected with a mouse-anti c-myc tag antibody, in this experiment the anti-hCD19 antibody is used as a negative control since it lacks the hVLA2 specificity in spite of having the c-myc tag sequence. FIG. 31D shows the binding of the anti-hCD19_anti-hVLA2 bispecific antibody to HT1080 cells detected with a mouse-anti His tag antibody, in this experiment the anti-hCD19 antibody lacking the polyhistidine tag sequence is used as a negative control. When taken together these four independent binding experiments show that when engaging target cells with one FAB arm, the anti-hCD19_anti-hVLA2 bispecific antibody is always detectable via the tag located on the opposite Fc subunit (carrying the other FAB arm, see FIGS. 31B and 31C). This demonstrates the identity of the anti-hCD19_anti-hVLA2 as being a full bispecific antibody consisting of four different chains correctly assembled into two distinct FAB fragments each having a unique specificity brought together by a hetero-dimeric Fc region.

The thermal stability of the anti-hCD19_anti-hVLA2 bispecific antibody was assessed using calorimetric measurements (DSC) (see example 2 for methods; the protein was used at a concentration of 0.57 mg/ml in PBS). FIG. 32 shows a thermogram of the anti-hCD19_anti-hVLA2 bispecific antibody exhibiting three sharp transitions at 70.9, 76.6 and 82.8° C., none of which are below 70° C. thereby implying a stable immunoglobulin molecule (example 2). It is important to note that no sharp decrease after the heat absorption peak was recorded, indicating that no precipitation or aggregate formation occurred after thermal unfolding (Liu H et al., *Immunol Lett*, 106(2):144-53 (2006)). Since the BT alpha His_BT beta hetero-dimeric Fc fragment from example 2 displayed a single sharp melting transition at 70° C., it is possible to conclude that the melting transitions for both FAB arms have a mid-point superior to 75° C. as expected for a properly assembled and stable FAB fragments (Garber E and Demarest S J, *Biochem Biophys Res Commun*, 355(3):751-7 (2007)). In conclusion, this thermal unfolding study shows that the anti-hCD19_anti-hVLA2 bispecific antibody is stable.

This example also shows that when combined, two or more novel hetero-dimeric pairs of constant domains having engineered protein-protein interfaces derived form the human T-cell receptor constant domains can be used as building blocks to create novel bispecific antibodies which are stable and suitable for therapeutic use in humans.

Example 10

Construction of Immunoglobulin Fc Hetero-Dimer Variants with Mixed Gamma Immunoglobulin Isotype Backgrounds This example demonstrates that two human CH3 domains, one domain derived from IGHG1 and the second domain derived from IGHG3 having mutations in the protein-protein interface of their CH3 domains carefully selected from the T-cell receptor (TCR) constant domain alpha and beta (as described in example 1) assemble into a hetero-dimeric Fc molecule.

Mutations were derived from the analysis of an overlay of the crystal structure of the human LC13 TCR molecule (PDB code 1KGC; Bernstein F C et al., *Eur J Biochem*, 80(2):319-24 (1977)) with the crystal structure of the Fc fragment from human IGHG1 (PDB code 1H3Y) as described in example 1. Since human IGHG1 and IGHG3 CH3 domains only differ at position 384, 392, 397, 422, 435, and 436 (EU numbering), their protein-protein interfaces are identical excepting for the residue at position 392, and allow for the design of a mixed isotype hetero-dimeric immunoglobulin based on the 3D equivalent positions described in example 1.

The hetero-dimeric immunoglobulin described in this example consists of the assembly of two Fc chain variants: one chain from human IGHG3 origin having mutations in the protein-protein interface of its CH3 domain carefully selected from the TCR constant domain alpha protein-protein interface (referred as BT alpha IGHG3 chain) (SEQ ID NO: 73), and one chain from human IGHG1 origin having mutations in the protein-protein interface of its CH3 domain carefully selected from the TCR constant domain beta protein-protein interface (referred as BT beta F405A chain) (SEQ ID NO: 74). To generate a difference in SDS-PAGE mobility, the latter Fc chain variant was fused to a variable light-chain kappa domain antibody (abbreviated VL) resulting in an engineered immunoglobulin chain referred as VL-BT beta F405A chain (SEQ ID NO: 75). The engineered CH3 domain from IGHG3 origin described herein is abbreviated CH3-BT alpha IGHG3 domain, and has SEQ ID NO: 76. The VL-BT beta F405A chain encompasses the CH3-BT beta F405A domain described in example 2 (SEQ ID NO: 14). The hetero-dimeric immunoglobulin consisting of the assembly of the two aforementioned chains is abbreviated BT alpha IGHG3_VL-BT beta F405A hetero-dimer.

cDNA encoding the VL-BT beta F405A chain was built as described in example 2. cDNA encoding the BT alpha IGHG3 chain encompassed the CH3-BT alpha IGHG3 domain coding sequence (SEQ ID NO: 77) which was originally synthesized by GENEART AG (Regensburg, Germany) Human IGHG1 hinge and CH2 domain coding sequences were subsequently added upstream to this synthesized fragment using standard PCR assembly methods. Each chain encoding PCR product was digested, purified, and ligated independently into the modified pREP4 vector mentioned previously (example 1). The two resulting sequence-verified recombinant vectors were then co-transfected into HEK293-EBNA cells as described in example 1. Protein production and purification were also according to example 1. For the BT alpha IGHG3_VL-BT beta F405A hetero-dimer, a production yield of 10 mg/l was obtained.

To assess the proportion of hetero-dimer to homo-dimer in the protein-A purified material, the relative ratios of the different species were quantified by scanning densitometry analysis of the non-reduced SDS-polyacrylamide (4-12%) gel bands according to the procedure described in example 1. Post protein-A purification the BT alpha IGHG3_VL-BT beta F405A hetero-dimer is the main species produced, followed by the VL-BT beta F405A VL-BT beta F405A homo-dimer, and the VL-BT beta F405A chain (half molecule) (FIG. 33; lane 1). Under reducing conditions, the BT alpha IGHG3_VL-BT beta F405A hetero-dimer breaks down into the two expected molecular weight bands for the BT alpha IGHG3 and the VL-BT beta F405A chains (half molecules) (FIG. 33; lane 2). FIG. 34 shows that BT alpha IGHG3_VL-BT beta F405A hetero-dimer represents at least 91% of the protein-A purified material.

Example 11

Construction of Immunoglobulin Fc Hetero-Dimer Variants with Mixed Immunoglobulin Class Backgrounds This example demonstrates that two human Fc chains, derived from IGHG1 having mutations in the protein-protein interface of their CH3 domains carefully selected from the protein-protein interface of the CH3 domains from IGHA1 or IGHA2, assemble into a hetero-dimeric Fc molecule, thereby demonstrating that protein-protein interfaces from two different pairs of homo-dimeric immunoglobulin domains can be combined to create a novel hetero-dimeric protein-protein interface pair which upon grafting onto a naturally occurring pair of homo-dimeric immunoglobulin domains induce domain hetero-dimerization. Note that the scope of the method described herein is not limited to IGHA1, but has broad application using all type of homo-dimeric immunoglobulin domains. IGHA1 and IGHA2 have identical CH3 domain amino acid sequences, and IGHA1 CH3 amino acid sequence (SEQ ID NO: 96) used herein is fully interchangeable with IGHA2 CH3 amino acid sequence (SEQ ID NO: 97).

Mutations were derived from the analysis of the CH3 domain protein-protein interface interactions of the crystal structure of human IGHG1 and IGHA1 Fc fragments (Krapp S et al., *J Mol Biol*, 325(5):979-89 (2003) and Herr A B et al., *Nature*, 423(6940):614-20 (2003), respectively). The IGHG1 and IGHA1 Fc 3D structures were retrieved from the Protein Data Bank (PDB code 1H3Y and 1OW0 respectively; www.pdb.org; Bernstein F C et al., *Eur J Biochem*, 80(2):319-24 (1977)) and further analyzed as described in example 1.

The hetero-dimeric immunoglobulin described in this example consists of the assembly of two Fc chain variants: one human IGHG1 Fc chain thereof having mutations in the protein-protein interface of its CH3 domain derived from a selected group of 3D equivalent positions found in the protein-protein interface of the naturally occurring human IGHA1 CH3 constant domain pair (designated "Fc IGHAG" chain), and a second engineered human IGHG1 Fc chain thereof having mutations in the protein-protein interface of its CH3 domain derived from a selected group of 3D equivalent positions found in the protein-protein interface of the naturally occurring human IGHA1 CH3 constant domain pair (designated "Fc IGHGA" chain), wherein the selected group of 3D equivalent positions found in the protein-protein interface of the naturally occurring human IGHA1 CH3 constant domain pair is different in each engineered CH3 domain. More specifically, the "Fc IGHAG" chain consists of an immunoglobulin Fc chain from human IGHG1 having a CH3 domain with the following substitutions (abbreviated CH3 IGHAG domain; SEQ ID NO: 78): Q347E, Y349H, K370R, V397R, D399E, F405A, and Y407T (EU numbering); and conversely, the "Fc IGHGA" consists of an immunoglobulin Fc chain from human IGHG1 having a CH3 domain with the following substitutions (abbreviated CH3 IGHGA domain; SEQ ID NO: 79): S364T, K392L, T394W, K409I, and T411R (EU numbering). To generate a difference in SDS-PAGE mobility, one Fc chain variant was fused to a variable light-chain kappa domain antibody (abbreviated VL). The different PCR steps gave two final chains: the Fc IGHAG chain (SEQ ID NO: 80), and the VL-Fc IGHGA chain (SEQ ID NO: 81). The hetero-dimeric immunoglobulin construct described herein resulting from the assembly of these two chains is designated Fc IGHAG_VL-Fc IGHGA hetero-dimer.

cDNA coding sequences for the CH3 IGHGA and CH3 IGHAG domains (SEQ ID NO: 82 and 83, respectively) were synthesized by GENEART AG (Regensburg, Germany), and used to create their respective engineered chains by PCR assembly methods. Each chain encoding PCR product was digested, purified, and ligated independently into the modified pREP4 vector mentioned previously (example 1). The two resulting sequence-verified recombinant vectors were then co-transfected into HEK293-EBNA cells as described in example 1. Protein production and purification were also according to example 1. For the Fc IGHAG_VL-Fc IGHGA hetero-dimer, a production yield of 12 mg/l was obtained.

To assess the proportion of hetero-dimer to homo-dimer in the protein-A purified material, the relative ratios of the different species were quantified by scanning densitometry analysis of the non-reduced SDS-polyacrylamide (4-12%) gel bands according to the procedure described in example 1. Post protein-A purification, the Fc IGHAG_VL-Fc IGHGA hetero-dimer is the main species produced followed by the VL-Fc IGHGA_VL-Fc IGHGA homo-dimer and single chains (Fc IGHAG chain and VL-Fc IGHGA chains, i.e. half molecules) (FIG. 35, lane 1). Under reducing conditions, the Fc IGHAG_VL-Fc IGHGA hetero-dimer breaks down into the two expected molecular weight bands for the Fc IGHAG and the VL-Fc IGHGA chains (FIG. 35, lane 2). FIG. 36 shows that the Fc IGHAG_VL-Fc IGHGA hetero-dimer represents at least 54% of the protein-A purified material.

Example 12

Construction of Immunoglobulin Fc Hetero-Dimer Variants with Different Immunoglobulin Class Backgrounds 12.1 Construction of a Hetero-Dimer Variant with a Chimeric IGHG1-IGHM Immunoglobulin Class Background This example demonstrates that two chains, each consisting of a human IGHG1 hinge, a human IGHG1 CH2 domain and an engineered human IGHM CH4 domain, wherein one chain has mutations in the protein-protein interface of its IGHM CH4 domain carefully selected from 3D equivalent positions of the protein-protein interface of the T-cell receptor (TCR) constant domain alpha and the second chain has mutations in the protein-protein interface of its IGHM CH4 domain carefully selected from 3D equivalent positions of the protein-protein interface of the TCR constant domain beta, assemble into a hetero-dimeric immunoglobulin; the 3D equivalent positions are identical to the ones described in example 1.

Specifically, the hetero-dimeric immunoglobulin described in this example consists of the assembly of two Fc chain variants: one engineered chain comprising an engineered IGHM CH4 domain wherein its protein-protein interface is substituted with a selected group of 3D equivalent positions found in the protein-protein interface of the naturally occurring human TCR constant domain alpha (designated "BT alpha IGHM-4" chain), and a second engineered chain comprising an engineered IGHM CH4 domain wherein its protein-protein interface is substituted with a selected group of 3D equivalent positions found in the protein-protein interface of the naturally occurring human TCR constant domain beta (designated "BT beta IGHM-4" chain). More specifically, the BT alpha IGHM-4 chain encompasses a CH4 domain from human IGHM with the following substitutions (abbreviated IGHM CH4 alpha domain; SEQ ID NO: 84): T20K, T22V, V79Y, F85.1S, H86V, 188W, and T90N (IMGT numbering); and conversely, the BT beta IGHM-4 chain encompasses of a CH4 domain from human IGHM with the following substitutions (abbreviated IGHM CH4 beta domain; SEQ ID NO: 85): D3E, Y5A, L7F, T22V, S81D, M84L, F85.1A, H86S, 188R, and T90R (IMGT numbering).

cDNA coding sequences for the IGHM CH4 alpha domain and IGHM CH4 beta domain (SEQ ID NO: 86 and 87, respectively) were synthesized by GENEART AG (Regensburg, Germany), and used to create their respective engineered chains by PCR assembly methods. A short stretch of six histidine residues was appended at the C-terminus of the BT alpha IGHM-4 chain (abbreviated His) by including a polyhistidine coding sequence in the PCR antisense oligonucleotide. To generate a difference in SDS-PAGE mobility, one Fc chain variant was fused to a variable light-chain kappa domain antibody (abbreviated VL). The different PCR steps gave two final chains: the BT alpha IGHM-4 His chain (SEQ ID NO: 88), and the VL-BT beta IGHM-4 chain (SEQ ID NO: 89) (FIG. 37 labelled A and FIG. 37 labelled B). The hetero-dimeric immunoglobulin construct described herein resulting from the assembly of these two chains is designated BT alpha IGHM-4 His_VL-BT IGHM-4 beta hetero-dimer.

Each chain encoding PCR product was digested, purified, and ligated independently into the modified pREP4 vector mentioned previously. The two resulting sequence-verified recombinant vectors were subsequently co-transfected into HEK293-EBNA cells as described in example 1. Protein expression was also according to example 1. Purification was performed using protein-L affinity agarose (GenScript USA Inc., Piscataway, N.J., USA). The proportion of hetero-dimer to homo-dimer in the cell-culture supernatants and protein-L purified preparations were assessed by scanning densitometry analysis of the non-reduced SDS-polyacrylamide (4-12%) gel bands (procedure according to example 1).

Post protein-L purification, the BT alpha IGHM-4 His_VL-BT IGHM-4 beta hetero-dimer is isolated without any contaminants (FIG. 38, lane 3, labelled as A), representing 100% of the protein-L eluted material as measured by scanning densitometry analysis of the non-reduced SDS-PAGE band (FIG. 39). Under reducing conditions, the BT alpha IGHM-4 His_VL-BT beta IGHM-4 hetero-dimer band breaks down into the two expected molecular weight bands for the BT alpha IGHM-4 His and VL-BT beta IGHM-4 chains (half molecules) (FIG. 38, lane 4).

12.2 Construction of a Hetero-Dimer with a Chimeric IGHG1-IGHE Immunoglobulin Class Background This example demonstrates that two chains, each consisting of a human IGHG1 hinge, a human IGHG1 CH2 domain and an engineered human IGHE CH4 domain, wherein one chain has mutations in the protein-protein interface of its IGHE CH4 domain carefully selected from 3D equivalent positions of the protein-protein interface of the T-cell receptor (TCR) constant domain alpha and the second chain has mutations in the protein-protein interface of its IGHE CH4 domain carefully selected from 3D equivalent positions of the protein-protein interface of the TCR constant domain beta, assemble into a hetero-dimeric immunoglobulin; the 3D equivalent positions are identical to the ones described in example 1.

Specifically, the hetero-dimeric immunoglobulin described in this example consists of the assembly of two Fc chain variants: one engineered chain comprising an engineered IGHE CH4 domain wherein its protein-protein interface is substituted with a selected group of 3D equivalent positions found in the protein-protein interface of the naturally occurring human TCR constant domain alpha (designated "BT alpha IGHE-4" chain), and a second engineered chain comprising an engineered IGHE CH4 domain wherein its protein-protein interface is substituted with a selected group of 3D equivalent positions found in the protein-protein interface of the naturally occurring human TCR constant domain beta (designated "BT beta IGHE-4" chain). More specifically, the BT alpha IGHE-4 chain encompasses a CH4 domain from human IGHE with the following substitutions (abbreviated IGHE CH4 alpha domain; SEQ ID NO: 90): T20K, A22V, Q26T, S79Y, F85.1S, F86V, R88W, and E90N (IMGT numbering); and conversely, the BT beta IGHGE4 chain encompasses a CH4 domain from human IGHE with the following substitutions (abbreviated IGHE CH4 beta domain; SEQ ID NO: 91): Y5A, A22V, Q26T, T81D, R84L, T84.2E, F85.1A, F86S, and E90R (IMGT numbering).

Similarly to example 12.1, cDNA coding sequences for the IGHE CH4 alpha and IGHE CH4 beta domains (SEQ ID NO: 92 and 93, respectively) were synthesized by GENEART AG (Regensburg, Germany), and used to create their respective engineered chains by PCR assembly methods. A short stretch of six histidine residues was appended at the C-terminus of the BT alpha IGHE-4 chain (abbreviated His) by including a polyhistidine coding sequence in the PCR anti-sense oligonucleotide. To generate a difference in SDS-PAGE mobility, one Fc chain variant was fused to a variable light-chain kappa domain antibody (abbreviated VL). The different PCR steps gave two final chains: the BT alpha IGHE-4 His chain (SEQ ID NO: 94), and the VL-BT IGHE-4 beta chain (SEQ ID NO: 95) (FIG. 37 labelled C and FIG. 37 labelled D). The hetero-dimeric immunoglobulin construct described herein resulting from the assembly of these two chains is designated BT alpha IGHE-4 His_VL-BT IGHE-4 beta hetero-dimer Each chain encoding PCR product was digested, purified, and ligated independently into the modified pREP4 vector mentioned previously. The two resulting sequence-verified recombinant vectors were subsequently co-transfected into HEK293-EBNA cells as described in example 1. Protein production and purification were also according to example 1. The proportion of hetero-dimer to homo-dimer in the protein-A purified preparations were assessed by scanning densitometry analysis of the non-reduced SDS-polyacrylamide (4-12%) gel bands (procedure according to example 1).

Post protein-A purification, the hetero-dimer is isolated (FIG. 40, lane 1, labelled as A) with a hetero-dimerization rate of 10% (FIG. 41, peak 2), and bands corresponding to the BT alpha IGHE-4 His homo-dimer (FIG. 40, lane 1, labelled as B), the VL-BT beta IGHE-4 chain (half molecule) (FIG. 40, lane 1, labelled as C), and the BT alpha IGHE-4 His chain (half molecule) (FIG. 40, lane 1, labelled as D) are observed. Under reducing conditions, the BT alpha IGHE-4 His_VL-BT beta IGHE-4 hetero-dimer breaks down into the two expected molecular weight bands for the BT alpha IGHE-4 His and VL-BT beta IGHE-4 chains (half molecules) (FIG. 40, lane 2).

The invention claimed is:

1. A hetero-dimeric immunoglobulin or hetero-dimeric fragment thereof comprising:
   (a) a first engineered immunoglobulin chain comprising an engineered parent domain having a protein-protein interface, wherein at least one amino acid residue of the protein-protein interface of the parent domain of said first engineered immunoglobulin chain is substituted with an amino acid residue from a protein-protein interface of a first donor domain; and
   (b) a second engineered immunoglobulin chain comprising an engineered parent domain having a protein-protein interface, wherein at least one amino acid residue of the protein-protein interface of the parent domain of said second engineered immunoglobulin chain is substituted with an amino acid residue from a protein-protein interface of a second donor domain,
   wherein the engineered parent domain of the first engineered immunoglobulin chain and the engineered parent domain of the second engineered immunoglobulin chain are not identical and,
   wherein the first donor domain and the second donor domain form a naturally occurring TCR constant domain hetero-dimer or a naturally occurring TCR constant domain homo-dimer and,
   wherein the parent domain of the first and/or the second engineered immunoglobulin chain is a CH3 domain, wherein the amino acid residue which is substituted in the protein-protein interface of the parent domain of the first engineered immunoglobulin chain comprises the amino acid residue at position 88, and,
   wherein the amino acid residue which is substituted in the protein-protein interface of the parent domain of the second engineered immunoglobulin chain comprises the amino acid residue at position 85.1 and/or 86, and
   wherein the amino acid residue substituted at position 88 in the parent domain of the first engineered immunoglobulin chain is interacting with the amino acid residue substituted at position 85.1 and/or 86 in the parent domain of the second engineered immunoglobulin chain,
   wherein the amino acid position of each group member is indicated according to the IMGT® numbering.

2. The hetero-dimeric immunoglobulin or hetero-dimeric fragment thereof of claim 1, wherein the parent domain of the first and/or the second engineered immunoglobulin chain is a naturally occurring CH3 domain.

3. The hetero-dimeric immunoglobulin or hetero-dimeric fragment thereof of claim 1, wherein the first engineered immunoglobulin chain and/or the second engineered immunoglobulin chain comprise a third engineered domain with a protein-protein interface, wherein at least one amino acid residue of the protein-protein interface of the parent domain of said further engineered domain of said first engineered immunoglobulin chain and/or said second engineered immunoglobulin chain is substituted with an amino acid residue from a protein-protein interface of a third donor domain, and
   wherein the protein-protein interface of the further engineered domain of the first engineered immunoglobulin chain and/or the second engineered immunoglobulin chain is interacting with the protein-protein interface of an engineered domain of a third engineered immunoglobulin chain by hetero-dimerization or by homo-dimerization,
   wherein at least one amino acid residue of the protein-protein interface of the parent domain of said engineered domain of said third engineered immunoglobulin chain is substituted with an amino acid residue from a protein-protein interface of a fourth donor domain, and
   wherein the third donor domain and the fourth donor domain form a naturally occurring TCR constant domain hetero-dimer or a naturally occurring TCR constant domain homo-dimer and, wherein the protein-protein interface of the further engineered domain of the first engineered immunoglobulin chain and/or the second engineered immunoglobulin chain and of the engineered domain of the third engineered immunoglobulin chain is different from the protein-protein interface of the engineered domain of the first engineered immunoglobulin chain and of the engineered domain of the second engineered immunoglobulin chain.

4. The hetero-dimeric immunoglobulin or hetero-dimeric fragment thereof of claim 1, wherein the first and second engineered immunoglobulin chains comprise an Fc region.

5. The hetero-dimeric immunoglobulin or hetero-dimeric fragment thereof of claim 3, wherein at least two amino acid residues of the protein-protein interface of the parent domain of the further engineered domain of the first engineered immunoglobulin chain and/or the second engineered immunoglobulin chain and/or of the parent domain of the engineered domain of the third engineered immunoglobulin chain are substituted.

6. The hetero-dimeric immunoglobulin or hetero-dimeric fragment thereof of claim 3, wherein the hetero-dimeric immunoglobulin or hetero-dimeric fragment thereof or the full-length antibody is bispecific.

7. The hetero-dimeric immunoglobulin or hetero-dimeric fragment thereof of claim 6, wherein the bispecific hetero-dimeric immunoglobulin or hetero-dimeric fragment thereof or the bispecific full-length antibody binds to antigens selected from the group consisting of HER2, EGFR, CD19, and VLA-2.

8. The hetero-dimeric immunoglobulin or hetero-dimeric fragment thereof of claim 1, wherein at least one additional polypeptide is fused to the first and/or second engineered immunoglobulin chain.

9. The hetero-dimeric immunoglobulin or hetero-dimeric fragment thereof of claim 8, wherein said additional polypeptide is selected from the group consisting of Fab, scFv, diabody, domain antibody, pharmacologically active peptide or protein, receptor extracellular domain, CDR grafted polypeptide, and therapeutic engineered protein scaffold.

10. The hetero-dimeric immunoglobulin or hetero-dimeric fragment thereof of claim 1, wherein the amino acid residues of the protein-protein interface of the parent domain of the first and/or second engineered immunoglobulin chain which are substituted are not adjacent.

11. The hetero-dimeric immunoglobulin or hetero-dimeric fragment thereof claim 1, wherein at least two amino acid residues of the protein-protein interface of the parent domain of the first and/or second engineered immunoglobulin chain are substituted.

12. The hetero-dimeric immunoglobulin or hetero-dimeric fragment thereof claim 1, wherein the parent domain of the first engineered immunoglobulin chain is an IgG1 CH3 domain and the parent domain of the second engineered immunoglobulin chain is an IgG3 CH3 domain or wherein the parent domain of the first engineered immunoglobulin chain is an IgG3 CH3 domain and the parent domain of the second engineered immunoglobulin chain is an IgG1 CH3 domain.

13. The hetero-dimeric immunoglobulin or hetero-dimeric fragment thereof of claim 1, wherein the amino acid sequence of the engineered domains of the first engineered immunoglobulin chain and/or the second engineered immunoglobulin chain do not contain an insertion of one or more amino acid residues compared to the amino acid sequence of the parent domains of the first engineered immunoglobulin chain and/or the second engineered immunoglobulin chain.

14. The hetero-dimeric immunoglobulin or hetero-dimeric fragment thereof of claim 1, wherein a further amino acid residue at a position selected from the group consisting of 3, 5, 7, 20, 22, 26, 27, 79, 81, 84, 84.2, 85.1, 86, and 90 is substituted in the protein-protein interface of the parent domain of the first engineered immunoglobulin chain.

15. The hetero-dimeric immunoglobulin or hetero-dimeric fragment thereof of claim 1, wherein a further amino acid residue at a position selected from the group consisting of 3, 5, 7, 20, 22, 26, 27, 79, 81, 84, 84.2, 85.1, 86, 88, and 90 is substituted in the protein-protein interface of the parent domain of the second engineered immunoglobulin chain.

16. The hetero-dimeric immunoglobulin or hetero-dimeric fragment thereof of claim 14 or claim 15, wherein:
  a) the amino acid residue which is substituted in the protein-protein interface of the parent domain of the first engineered immunoglobulin chain at position 88 is 88W and conservative amino acid substitutions thereof, wherein the amino acid position is indicated according to the IMGT® numbering;
  b) the amino acid residue which is substituted at position 85 and/or 86 in the protein-protein interface of the parent domain of the second engineered immunoglobulin chain is selected from the group consisting of 85.1A, 85.1S, 85.1C and 85.1N and conservative amino acid substitutions thereof and/or is selected from the group consisting of 86S and 86V and conservative amino acid substitutions thereof, wherein the amino acid position is indicated according to the IMGT® numbering;
  c) the amino acid residue which is substituted in the protein-protein interface of the parent domain of the first engineered immunoglobulin chain at position 88 is selected from the group consisting of 88Q, 88L, 88V, 88R, 88E, 88I, 88T, 88Y, 88K and 88W and/or wherein the further amino acid residue substituted in the protein-protein interface of the parent domain of the first engineered immunoglobulin chain is selected from the group consisting of 20V, 20T, 20A, 20N, 20Q, 20E, 20S, 20K, 20W, 22A, 22G, 22T, 22L, 22I, 22V, 26R, 26Q, 26T, 26K, 26V, 26S, 26N, 26E, 85.1T, 85.1M, 85.1A, 85.1S, 85.1R, 85.1H, 85.1K, 85.1F, 85.1C, 85.1N, 85.1W, 86S, 86I, 86T, 86H, 86Q, 86V, 86W, 86Y and 86F, wherein the amino acid position of each group member is indicated according to the IMGT® numbering;
  d) the amino acid residue which is substituted in the protein-protein interface of the parent domain of the first engineered immunoglobulin chain at position 88 is selected from the group consisting of 88Q, 88L, 88V, 88R, 88E, 88I, 88T, 88Y, and 88W and/or wherein the further amino acid residue substituted in the protein-protein interface of the parent domain of the first engineered immunoglobulin chain is selected from the group consisting of 20V, 20T, 20A, 20N, 20Q, 20E, 20S, 20K, 22A, 22G, 22T, 22L, 22I, 22V, 26Q, 26T, 26K, 26V, 26S, 26N, 26E, 85.1T, 85.1M, 85.1A, 85.1S, 85.1R, 85.1H, 85.1K, 85.1F, 85.1C, 85.1N, 86S, 86I, 86T, 86H, 86Q, 86V, and 86F, wherein the amino acid position of each group member is indicated according to the IMGT® numbering;
  e) the amino acid residue which is substituted in the protein-protein interface of the parent domain of the first engineered immunoglobulin chain comprises the amino acid residues at position 88 and at position 20, and optionally a further amino acid residue at a position selected from the group consisting of 3, 5, 7, 22, 26, 27, 79, 81, 84, 84.2, 85.1, 86, and 90, wherein the amino acid position of each group member is indicated according to the IMGT® numbering;
f) the amino acid residue which is substituted in the protein-protein interface of the parent domain of the second engineered immunoglobulin chain comprises the amino acid residues at position 85.1 and/or 86 and at position 26 and optionally an amino acid residue at a further position, wherein the amino acid position is indicated according to the IMGT® numbering;
g) the amino acid residue which is substituted in the protein-protein interface of the parent domain of the second engineered immunoglobulin chain comprises the amino acid residues at position 85.1 and 86 or comprises 85.1C and conservative amino acid substitutions thereof and 86S and conservative amino acid substitutions thereof, and wherein the further amino acid residue which is substituted in the protein-protein interface of the parent domain of the second engineered immunoglobulin chain is selected from the group consisting of 3E, 5A, 7F, 20T, 22V, 26T, 81D, 84L, 84.2E, 88R and 90R and conservative amino acid substitutions of any of these thereof, wherein the amino acid position of each group member is indicated according to the IMGT® numbering;
h) the amino acid residue which is substituted in the protein-protein interface of the parent domain of the second engineered immunoglobulin chain comprises the amino acid residues at position 85.1 and 86 or comprises 85.1N and conservative amino acid substitutions thereof and 86V and conservative amino acid substitutions thereof, and wherein the further amino acid residue which is substituted in the protein-protein interface of the parent domain of the second engineered immunoglobulin chain is selected from the group consisting of 7M, 20N, 22A, 27E, 79F, 81A, 84.2S, 85.1N, 86V, 88L, and 90K and conservative amino acid substitutions of any of these thereof, wherein the amino acid position of each group member is indicated according to the IMGT® numbering; or
i) the amino acid residue which is substituted in the protein-protein interface of the parent domain of the first engineered immunoglobulin chain is 88I and conservative amino acid substitutions thereof and the optional further amino acid residue which is substituted in the protein-protein interface of the parent domain of the first engineered immunoglobulin chain is 81W and conservative amino acid substitutions thereof, wherein the amino acid position of each group member is indicated according to the IMGT® numbering.

17. The hetero-dimeric immunoglobulin or hetero-dimeric fragment thereof of claim 14 or claim 15, wherein:
a) the further amino acid residue which is substituted in the protein-protein interface of the parent domain of the first engineered immunoglobulin chain is selected from the group consisting of 3E, 3K, 5A, 5T, 7F, 7M, 20K, 20N, 20T, 22A, 22L, 22V, 26E, 26T, 27E, 27K, 79F, 79Y, 81A, 81G, 81D, 84L, 84M, 84.2E, 84.2S, 85.1A, 85.1C, 85.1M, 85.1N, 85.1S, 86F, 86S, 86V, 90K, 90N, and 90R and conservative amino acid substitutions of any of these thereof, wherein the amino acid position of each group member is indicated according to the IMGT® numbering;
b) wherein the further amino acid residue which is substituted in the protein-protein interface of the parent domain of the first engineered immunoglobulin chain is at a position selected from the group consisting of 20, 22, 26, 79, 85.1, 86, and 90, wherein the amino acid position of each group member is indicated according to the IMGT® numbering;
c) the further amino acid residue which is substituted in the protein-protein interface of the parent domain of the first engineered immunoglobulin chain is selected from the group consisting of 20K, 22V, 26T, 79Y, 85.1S, 86V, and 90N and conservative amino acid substitutions of any of these thereof, wherein the amino acid position of each group member is indicated according to the IMGT® numbering;
d) the further amino acid residue which is substituted in the protein-protein interface of the parent domain of the second engineered immunoglobulin chain is at position 84 or is 84L and conservative amino acid substitutions thereof, and optionally a further amino acid at a position selected from the group consisting of 3, 5, 7, 20, 22, 26, 81, 84.2, 85.1, 86, 88, and 90, wherein the amino acid position of each group member is indicated according to the IMGT® numbering;
e) the further amino acid residue which is substituted in the protein-protein interface of the parent domain of the second engineered immunoglobulin chain is at a position selected from the group consisting of 3, 5, 7, 20, 22, 26, 81, 84, 84.2, 85.1, 86, 88, and 90, wherein the amino acid position of each group member is indicated according to the IMGT® numbering;
f) wherein the further amino acid residue which is substituted in the protein-protein interface of the parent domain of the first engineered immunoglobulin chain is at a position selected from the group consisting of 3, 5, 20, 22, 26, 27, 81, 84, 85.1, and 86, wherein the amino acid position of each group member is indicated according to the IMGT® numbering;
g) the further amino acid residue which is substituted in the protein-protein interface of the parent domain of the first engineered immunoglobulin chain is selected from the group consisting of 3K, 5T, 20T, 22L, 26E, 27K, 81G, 84M, 85.1M, 86F and conservative amino acid substitutions of any of these thereof, wherein the amino acid position of each group member is indicated according to the IMGT® numbering;
h) the further amino acid residue which is substituted in the protein-protein interface of the parent domain of the second engineered immunoglobulin chain is at a position selected from the group consisting of 7, 20, 22, 27, 79, 81, 84.2, 85.1, 86, 88, and 90, wherein the amino acid position of each group member is indicated according to the IMGT® numbering; or
i) the further amino acid residue which is substituted in the protein-protein interface of the parent domain of the second engineered immunoglobulin chain is at position 79 or is 79F and conservative amino acid substitutions thereof, and optionally a further amino acid residue at a position selected from the group consisting of 7, 20, 22, 27, 81, 84.2, 85.1, 86, 88, and 90, wherein the amino acid position of each group member is indicated according to the IMGT® numbering.

18. The hetero-dimeric immunoglobulin or hetero-dimeric fragment thereof of claim 17, wherein the amino acid residue substitution 85.1C is replaced by amino acid residue substitution 85.1A or 85.1S, wherein the amino acid position of each group member is indicated according to the IMGT® numbering.

19. A method of producing a hetero-dimeric immunoglobulin or hetero-dimeric fragment thereof of claim 1, the method comprising:
(a) substituting at least one amino acid residue of the protein-protein interface of a parent domain of a first parent immunoglobulin chain with a residue from a protein-protein interface of a first donor domain to obtain a first engineered immunoglobulin chain comprising an engineered domain;
(b) substituting at least one amino acid residue of the protein-protein interface of the parent domain of a second parent immunoglobulin chain with a residue from a protein-protein interface of a second donor domain to obtain a second engineered immunoglobulin chain comprising an engineered domain;
(c) culturing a host cell comprising a nucleic acid encoding said engineered immunoglobulin chains, wherein the culturing is such that the nucleic acid is expressed and the engineered immunoglobulin chains produced; and
(d) recovering the hetero-dimeric immunoglobulin or hetero-dimeric fragment thereof from the host cell culture.

20. The method of claim 19, wherein:
a) the first donor domain is the TCR constant domain alpha (SEQ ID NO: 1) and the second donor domain is the TCR constant domain beta (SEQ ID NO: 2);
b) the first donor domain is the TCR constant domain alpha (SEQ ID NO: 1) and the second donor domain is the TCR constant domain beta (SEQ ID NO: 2), wherein the cysteine (C) at amino acid position 75 in SEQ ID NO: 2 is substituted with alanine (A) or serine (S); or
c) the first donor domain is the TCR constant domain gamma (SEQ ID NO: 33) and second donor domain is the TCR constant domain delta (SEQ ID NO: 32).

21. The method of claim 19, wherein the first engineered immunoglobulin chain and/or the second engineered immunoglobulin chain comprise a further engineered domain with a protein-protein interface, wherein at least one amino acid residue of the protein-protein interface of the parent domain of said further engineered domain of said first engineered immunoglobulin chain and/or said second engineered immunoglobulin chain is substituted with an amino acid residue from a protein-protein interface of a third donor domain, and
wherein the protein-protein interface of the further engineered domain of the first engineered immunoglobulin chain and/or the second engineered immunoglobulin chain is interacting with the protein-protein interface of an engineered domain of a third engineered immunoglobulin chain by hetero-dimerization or by homo-dimerization, wherein at least one amino acid residue of the protein-protein interface of the parent domain of said engineered domain of said third engineered immunoglobulin chain is substituted with an amino acid residue from a protein-protein interface of a fourth donor domain and,
wherein the protein-protein interface of the further engineered domain of the first engineered immunoglobulin chain and/or the second engineered immunoglobulin chain and of the engineered domain of the third engineered immunoglobulin chain is different from the protein-protein interface of the engineered domain of the first engineered immunoglobulin chain and of the engineered domain of the second engineered immunoglobulin chain.

* * * * *

SEQUENCE LISTING

<160> NUMBER OF SEQ ID NOS: 124

<210> SEQ ID NO 1
<211> LENGTH: 91
<212> TYPE: PRT
<213> ORGANISM: Homo sapiens
<220> FEATURE:
<221> NAME/KEY: MISC_FEATURE
<222> LOCATION: (1)..(91)
<223> OTHER INFORMATION: T cell receptor constant domain alpha

<400> SEQUENCE: 1

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro
                85                  90

<210> SEQ ID NO 2
<211> LENGTH: 128
<212> TYPE: PRT
<213> ORGANISM: Homo sapiens
<220> FEATURE:
<221> NAME/KEY: MISC_FEATURE
<222> LOCATION: (1)..(128)
<223> OTHER INFORMATION: T cell receptor constant domain beta (Homo
      sapiens)

<400> SEQUENCE: 2

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

<210> SEQ ID NO 3
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Lys
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Tyr Thr Thr Pro Pro
                165                 170                 175

Val Leu Asp Ser Asp Gly Ser Phe Ser Leu Val Ser Trp Leu Asn Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

```
Ala Thr Phe Pro Pro Ser Arg Asp Glu Leu Thr Lys Asn Gln Val Thr
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Asp Gly Ser Phe Cys Leu Ser Ser Arg Leu Arg Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 5
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105

<210> SEQ ID NO 6
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95
```

```
Thr Phe Gly Gln Gly Thr Lys Val Glu Ile Lys Arg Asp Lys Thr His
                100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Ala Thr Phe Pro
225                 230                 235                 240

Pro Ser Arg Asp Glu Leu Thr Lys Asn Gln Val Thr Leu Val Cys Leu
                245                 250                 255

Val Thr Gly Phe Tyr Pro Ser Asp Ile Ala Val Glu Trp Glu Ser Asn
            260                 265                 270

Gly Gln Pro Glu Asn Asn Tyr Lys Thr Asp Pro Pro Leu Leu Glu Ser
        275                 280                 285

Asp Gly Ser Phe Cys Leu Ser Ser Arg Leu Arg Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 7
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

Tyr Thr Leu Pro Pro Ser Arg Asp Glu Leu Thr Lys Asn Gln Val Lys
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Tyr Thr Thr Pro Pro
                165                 170                 175

Val Leu Asp Ser Asp Gly Ser Phe Ser Leu Val Ser Trp Leu Asn Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys His His His His His His
225                 230

<210> SEQ ID NO 8
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 8
ggccagccca gagaacccca ggtgtacacc ctgccccca gcagagatga gctgaccaag     60
aaccaggtca gctcgtgtg cctggtcacc ggcttctacc ccagcgatat cgccgtggag    120
tgggagagca acggccagcc tgaaaacaac tactacacca ccccccctgt gctggacagc    180
gacggcagct tcagcctggt gtcctggctg aacgtggaca gagccggtg gcagcagggc    240 aacgtgttca gctgcagcgt gatgcacgag gccctgcaca accactacac ccagaagtcc    300
ctgagcctgt ctcctggcaa g    321

<210> SEQ ID NO 9
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 9
ggacagccca gggaacctga ggtggccaca ttcccaccta gccgggacga gctgacaaaa     60
aatcaggtca ccctcgtctg tctcgtgacc ggcttttacc cttccgacat tgccgtggaa    120
tgggaatcca atgggcagcc cgagaacaat acaagacag accccccct gctggaatcc    180 gatggcagct tctgcctgag cagccggctg cgggtggaca gtccagatg gcagcagggg    240 aatgtctttt cctgctccgt catgcatgaa gccctccaca atcattata acagaaaagc    300 ctgagcctga gccccggcaa g    321

<210> SEQ ID NO 10
<211> LENGTH: 699
<212> TYPE: DNA
<213> ORGANISM: Artificial Sequence
<220> FEATURE:
<223> OTHER INFORMATION: Synthetic polynucleotide

<400> SEQUENCE: 10
gacaaaactc acacatgccc ccctgccct gccctgagc tgctgggcgg acctccgtg     60 ttcctgttcc cccccaagcc caaggacacc ctgatgatca gccggacccc cgaggtgacc    120

```
tgcgtggtgg tggacgtgag ccacgaggac cctgaggtga agttcaattg gtacgtggac      180
ggcgtggagg tgcacaacgc caagaccaag ccccgggagg aacagtacaa cagcacctac      240
cgggtggtgt ccgtgctgac cgtgctgcac caggactggc tgaacggcaa ggaatacaag      300
tgcaaggtct ccaacaaggc cctgcctgcc cccatcgaga aaaccatctc caaagccaaa      360
ggccagccca gagaacccca ggtgtacacc ctgcccccca gcagagatga gctgaccaag      420
aaccaggtca gcctcgtgtg cctggtcacc ggcttctacc ccagcgatat cgccgtggag      480
tgggagagca acggccagcc tgaaaacaac tactacacca cccccctgt gctggacagc       540 gacggcagct tcagcctggt gtcctggctg aacgtggaca gagccggtg gcagcagggc       600 aacgtgttca gctgcagcgt gatgcacgag gccctgcaca accactacac ccagaagtcc      660
ctgagcctgt ctcctggcaa gcatcaccat caccatcac                             699

<210> SEQ ID NO 11
<211> LENGTH: 1005
<212> TYPE: DNA
<213> ORGANISM: Artificial Sequence
<220> FEATURE:
<223> OTHER INFORMATION: Synthetic polynucleotide

<400> SEQUENCE: 11
gacatccaga tgacccagag cccccagcagc ctgagcgcca gcgtgggcga ccgggtgacc      60
atcacctgcc gggccagcca gagcatcagc tcctacctga actggtatca gcagaagccc      120
ggcaaggccc ccaagctgct gatctatgct gcctcctctc tccagagcgg cgtgcccagc      180
cggttttccg ggtctgggtc cgggacagat ttcaccctga ccatcagcag cctccagccc      240
gaggatttcg ccacctacta ctgccagcag agctacagca cccccaacac cttcggccag      300
ggaacaaagg tggagatcaa agcgggacaaa actcacactt gcccaccgtg cccagcacct      360
gaactcctgg ggggaccgtc agtcttcctc ttccccccaa aacccaagga caccctcatg      420
atctcccgga cccctgaggt cacctgcgtg gtggtggacg tgagccacga ggaccctgag      480
gtgaagttca attggtacgt ggacggcgtg gaggtgcaca acgccaagac caagccccgg      540
gaggaacagt acaacagcac ctaccgggtg gtgtccgtgc tgaccgtgct gcaccaggac      600
tggctgaacg gcaaggaata caagtgcaag gtctccaaca aggccctgcc tgccccatc      660 gaaaagacca tcagcaaggc caaggacag cccaggaac ctgaggtggc acattccca       720 cctagccggg acgagctgac aaaaaatcag gtcaccctcg tctgtctcgt gaccggcttt      780 taccccttccg acattgccgt ggaatgggaa tccaatgggc agcccgagaa caattacaag      840
acagaccccc cctgctgga tccgatggc agcttctgcc tgagcagccg gctgcgggtg      900
gacaagtcca gatggcagca ggggaatgtc ttttcctgct ccgtcatgca tgaagccctc      960
cacaatcatt atacacagaa aagcctgagc ctgagccccg gcaag                      1005

<210> SEQ ID NO 12
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 12

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
```

-continued

```
                20                  25                  30
Ile Ser Arg Thr Pro Glu Val Thr Cys Val Val Asp Val Ser His
            35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 13
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 13

Gly Gln Pro Arg Glu Pro Gln Val Tyr Thr Leu Pro Pro Ser Arg Asp
 1               5                  10                  15
Glu Leu Thr Lys Asn Gln Val Lys Leu Val Cys Leu Val Thr Gly Phe
                20                  25                  30
Tyr Pro Ser Asp Ile Ala Val Glu Trp Glu Ser Asn Gly Gln Pro Glu
            35                  40                  45
Asn Asn Tyr Tyr Thr Thr Pro Pro Val Leu Asp Ser Asp Gly Ser Phe
 50                  55                  60
Ser Leu Val Ser Trp Leu Asn Val Asp Lys Ser Arg Trp Gln Gln Gly
 65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Synthetic polypeptide
```

<400> SEQUENCE: 14

```
Gly Gln Pro Arg Glu Pro Glu Val Ala Thr Phe Pro Pro Ser Arg Asp
1               5                   10                  15

Glu Leu Thr Lys Asn Gln Val Thr Leu Val Cys Leu Val Thr Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Asp Pro Pro Leu Leu Glu Ser Asp Gly Ser Phe
    50                  55                  60

Ala Leu Ser Ser Arg Leu Arg Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 15
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 15

```
Gly Gln Pro Arg Glu Pro Glu Val Ala Thr Phe Pro Pro Ser Arg Asp
1               5                   10                  15

Glu Leu Thr Lys Asn Gln Val Thr Leu Val Cys Leu Val Thr Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Asp Pro Pro Leu Leu Glu Ser Asp Gly Ser Phe
    50                  55                  60

Cys Leu Ser Ser Arg Leu Arg Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 16
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 16

```
Gly Gln Pro Arg Glu Pro Glu Val Ala Thr Phe Pro Pro Ser Arg Asp
1               5                   10                  15

Glu Leu Thr Lys Asn Gln Val Thr Leu Val Cys Leu Val Thr Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Asp Pro Pro Leu Leu Glu Ser Asp Gly Ser Phe
    50                  55                  60

Ser Leu Ser Ser Arg Leu Arg Val Asp Lys Ser Arg Trp Gln Gln Gly
65                  70                  75                  80
```

Asn Val Phe Ser Cys Ser Val Met His Glu Ala Leu His Asn His Tyr
             85                 90                 95

Thr Gln Lys Ser Leu Ser Leu Ser Pro Gly Lys
          100              105

<210> SEQ ID NO 17
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 17

Asp Lys Thr His Thr Cys Pro Pro Cys Pro Ala Pro Glu Leu Leu Gly
1               5                 10               15

Gly Pro Ser Val Phe Leu Phe Pro Pro Lys Pro Lys Asp Thr Leu Met
          20              25              30

Ile Ser Arg Thr Pro Glu Val Thr Cys Val Val Val Asp Val Ser His
         35               40              45

Glu Asp Pro Glu Val Lys Phe Asn Trp Tyr Val Asp Gly Val Glu Val
 50               55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
         85               90              95

Lys Glu Tyr Lys Cys Lys Val Ser Asn Lys Ala Leu Pro Ala Pro Ile
         100            105           110

Glu Lys Thr Ile Ser Lys Ala Lys Gly Gln Pro Arg Glu Pro Glu Val
        115           120           125

Ala Thr Phe Pro Pro Ser Arg Asp Glu Leu Thr Lys Asn Gln Val Thr
   130               135              140

Leu Val Cys Leu Val Thr Gly Phe Tyr Pro Ser Asp Ile Ala Val Glu
145             150             155           160

Trp Glu Ser Asn Gly Gln Pro Glu Asn Asn Tyr Lys Thr Asp Pro Pro
        165           170           175

Leu Leu Glu Ser Asp Gly Ser Phe Ala Leu Ser Ser Arg Leu Arg Val
   180               185              190

Asp Lys Ser Arg Trp Gln Gln Gly Asn Val Phe Ser Cys Ser Val Met
        195           200           205

His Glu Ala Leu His Asn His Tyr Thr Gln Lys Ser Leu Ser Leu Ser
   210               215              220

Pro Gly Lys Tyr Pro Tyr Asp Val Pro Asp Tyr Ala
225             230             235

<210> SEQ ID NO 18
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 18

Asp Lys Thr His Thr Cys Pro Pro Cys Pro Ala Pro Glu Leu Leu Gly
1               5                 10               15

Gly Pro Ser Val Phe Leu Phe Pro Pro Lys Pro Lys Asp Thr Leu Met
          20              25              30

Ile Ser Arg Thr Pro Glu Val Thr Cys Val Val Val Asp Val Ser His

```
                35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
                130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Trp Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
                210                 215                 220
Pro Gly Lys
225

<210> SEQ ID NO 19
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 19

Asp Lys Thr His Thr Cys Pro Pro Cys Pro Ala Pro Glu Leu Leu Gly
 1                   5                  10                  15
Gly Pro Ser Val Phe Leu Phe Pro Pro Lys Pro Lys Asp Thr Leu Met
                 20                  25                  30
Ile Ser Arg Thr Pro Glu Val Thr Cys Val Val Val Asp Val Ser His
                 35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
                130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Tyr Thr Thr Pro Pro
```

165                 170                 175
Val Leu Asp Ser Asp Gly Ser Phe Phe Leu Tyr Ser Trp Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 20
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 20

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Val Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Trp Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 21
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 21

-continued

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Trp Leu Asn Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 22
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Ser Leu Val Ser Trp Leu Asn Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 23
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Lys
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Tyr Thr Thr Pro Pro
                165                 170                 175

Val Leu Asp Ser Asp Gly Ser Phe Phe Leu Tyr Ser Trp Leu Asn Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 24
<211> LENGTH: 335
```

```
<212> TYPE: PRT
<213> ORGANISM: Artificial Sequence
<220> FEATURE:
<223> OTHER INFORMATION: Synthetic polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Ala Leu Ser Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 25
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 25
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Ala Leu Tyr Ser Arg Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 26
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Asn
                 85                  90                  95

Thr Phe Gly Gln Gly Thr Lys Val Glu Ile Lys Arg Asp Lys Thr His
                100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Ser Arg Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 27
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Asn
                 85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Arg Leu Arg Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 28
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 28

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Asn
                 85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Ala Leu Ser Ser Arg Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 29
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
            115                 120                 125

```
Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Ser Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Ala Leu Ser Ser Arg Leu Arg Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 30
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160
```

-continued

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 31
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Ser Cys Ala
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285
```

-continued

```
Asp Gly Ser Phe Phe Leu Val Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 32
<211> LENGTH: 87
<212> TYPE: PRT
<213> ORGANISM: Artificial Sequence
<220> FEATURE:
<223> OTHER INFORMATION: Synthetic polypeptide

<400> SEQUENCE: 32

Arg Ser Gln Pro His Thr Lys Pro Ser Val Phe Val Met Lys Asn Gly
1               5                   10                  15

Thr Asn Val Ala Cys Leu Val Lys Glu Phe Tyr Pro Lys Asp Ile Arg
            20                  25                  30

Ile Asn Leu Val Ser Ser Lys Lys Ile Thr Glu Phe Asp Pro Ala Ile
        35                  40                  45

Val Ile Ser Pro Ser Gly Lys Tyr Asn Ala Val Lys Leu Gly Lys Tyr
    50                  55                  60

Glu Asp Ser Asn Ser Val Thr Cys Ser Val Gln His Asp Asn Lys Thr
65                  70                  75                  80

Val His Ser Thr Asp Phe Glu
                85

<210> SEQ ID NO 33
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 33

Val Ser Pro Lys Pro Thr Ile Phe Leu Pro Ser Ile Ala Glu Thr Lys
1               5                   10                  15

Leu Gln Lys Ala Gly Thr Tyr Leu Cys Leu Leu Glu Lys Phe Phe Pro
            20                  25                  30

Asp Val Ile Lys Ile His Trp Glu Glu Lys Lys Ser Asn Thr Ile Leu
        35                  40                  45

Gly Ser Gln Glu Gly Asn Thr Met Lys Thr Asn Asp Thr Tyr Met Lys
    50                  55                  60

Phe Ser Trp Leu Thr Val Pro Glu Lys Ser Leu Asp Lys Glu His Arg
65                  70                  75                  80

Cys Ile Val Arg His Glu Asn Asn Lys Asn Gly Val Asp Gln Glu Ile
                85                  90                  95

Ile Phe Pro Pro Ile
            100

<210> SEQ ID NO 34
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 34
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Met Pro Pro Ser Arg Asp Glu Leu Thr Lys Asn Gln Val Asn
    130                 135                 140

Leu Ala Cys Leu Val Lys Glu Phe Tyr Pro Ser Asp Ile Ala Val Glu
145                 150                 155                 160

Trp Glu Ser Asn Gly Gln Pro Glu Asn Asn Tyr Phe Thr Ala Pro Pro
                165                 170                 175

Val Leu Ser Ser Asp Gly Ser Phe Asn Leu Val Ser Leu Leu Lys Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 35
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 35

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Lys Val
        115                 120                 125

```
Thr Thr Leu Pro Pro Ser Arg Asp Glu Leu Thr Lys Asn Gln Val Thr
    130                 135                 140

Leu Leu Cys Leu Val Glu Lys Phe Tyr Pro Ser Asp Ile Ala Val Glu
145                 150                 155                 160

Trp Glu Ser Asn Gly Gln Pro Glu Asn Asn Tyr Lys Thr Gly Pro Pro
                165                 170                 175

Met Leu Asp Ser Asp Gly Ser Phe Met Leu Phe Ser Trp Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 36
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Lys Val Thr Thr Leu Pro
225                 230                 235                 240

Pro Ser Arg Asp Glu Leu Thr Lys Asn Gln Val Thr Leu Leu Cys Leu
                245                 250                 255
```

```
Val Glu Lys Phe Tyr Pro Ser Asp Ile Ala Val Glu Trp Glu Ser Asn
            260                 265                 270

Gly Gln Pro Glu Asn Asn Tyr Lys Thr Gly Pro Pro Met Leu Asp Ser
        275                 280                 285

Asp Gly Ser Phe Met Leu Phe Ser Trp Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 37
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 37
ggccagccca gagaacccca ggtgtacacc atgcccccca gcagggacga gctgaccaag      60
aaccaggtca acctggcctg cctggtcaaa gagttctacc ccagcgatat cgccgtggaa     120
tgggagagca acggccagcc tgagaacaac tacttcaccg cccctcccgt gctgagcagc     180
gacggcagct tcaacctggt gtccctgctg aaggtggaca gagccggtgc agcagggc      240 aacgtgttca gctgcagcgt gatgcacgag gccctgcaca ccactacac ccagaagtcc      300 ctgagcctga gccccggaaa g                                              321

<210> SEQ ID NO 38
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 38
ggccagcccc gcgagcccaa agtgacaacc ctgcccccca gccgggacga gctgaccaag      60
aatcaggtca cactgctgtg cctggtggaa aagttctacc ccagcgatat cgccgtggaa     120
tgggagagca acggccagcc cgagaacaac tacaagaccg ccctcccat gctggacagc      180 gacggcagct tcatgctgtt cagctggctg accgtggaca gagccggtgc agcagggc      240 aacgtgttca gctgcagcgt gatgcacgag gccctgcaca ccactacac ccagaagtcc      300 ctgagcctga gccccggaaa g                                              321

<210> SEQ ID NO 39
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 39

Ala Ser Thr Lys Gly Pro Ser Val Phe Pro Met Ala Pro Ser Ser Lys
1               5                   10                  15

Ser Thr Ser Gly Gly Thr Ala Asn Leu Ala Cys Leu Val Lys Glu Tyr
            20                  25                  30

Phe Pro Glu Pro Val Thr Val Ser Trp Asn Ser Gly Ala Leu Thr Ser
        35                  40                  45

Gly Val Phe Thr Ala Pro Ala Val Leu Ser Ser Ser Gly Leu Tyr Asn
```

```
                    50                  55                  60
Leu Val Ser Leu Val Lys Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val

<210> SEQ ID NO 40
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 40

Arg Thr Val Ala Ala Pro Lys Val Thr Ile Phe Pro Pro Ser Asp Glu
  1               5                  10                  15

Gln Leu Lys Ser Gly Thr Ala Thr Val Leu Cys Leu Leu Glu Lys Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Gly Val Met Glu Gln Asp Ser Lys Asp Ser
 50                  55                  60

Thr Tyr Met Leu Phe Ser Trp Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 41
<211> LENGTH: 461
<212> TYPE: PRT
<213> ORGANISM: Artificial Sequence
<220> FEATURE:
<223> OTHER INFORMATION: Synthetic polypeptide

<400> SEQUENCE: 41

Gln Val Gln Leu Val Gln Ser Gly Gly Gly Val Val Gln Pro Gly Arg
  1               5                  10                  15

Ser Leu Arg Leu Ser Cys Ala Ala Ser Gly Val Ser Leu Pro Asp Tyr
                 20                  25                  30

Gly Val Ser Trp Val Arg Gln Ala Pro Gly Lys Gly Leu Glu Trp Val
             35                  40                  45

Ala Val Ile Trp Gly Ser Glu Thr Thr Tyr Tyr Asn Ser Ala Leu Lys
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Met Ala Pro Ser Ser Lys Ser Thr Ser Gly Gly Thr Ala Asn
        130                 135                 140

Leu Ala Cys Leu Val Lys Glu Tyr Phe Pro Glu Pro Val Thr Val Ser
```

```
            145                 150                 155                 160
Trp Asn Ser Gly Ala Leu Thr Ser Gly Val Phe Thr Ala Pro Ala Val
                165                 170                 175

Leu Ser Ser Ser Gly Leu Tyr Asn Leu Val Ser Leu Val Lys Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Glu Val Ala
                340                 345                 350

Thr Phe Pro Pro Ser Arg Asp Glu Leu Thr Lys Asn Gln Val Thr Leu
                355                 360                 365

Val Cys Leu Val Thr Gly Phe Tyr Pro Ser Asp Ile Ala Val Glu Trp
                370                 375                 380

Glu Ser Asn Gly Gln Pro Glu Asn Asn Tyr Lys Thr Asp Pro Pro Leu
385                 390                 395                 400

Leu Glu Ser Asp Gly Ser Phe Ala Leu Ser Ser Arg Leu Arg Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys Glu Gln Lys Leu Ile Ser Glu Glu Asp Leu Asn
    450                 455                 460

<210> SEQ ID NO 42
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Ile Lys Leu Leu Ile
            35                  40                  45

Tyr His Thr Ser Arg Leu His Ser Gly Val Pro Ser Arg Phe Ser Gly
```

```
                  50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Thr Leu Pro Tyr
                 85                  90                  95

Thr Phe Gly Pro Gly Thr Lys Val Asp Ile Lys Arg Thr Val Ala Ala
            100                 105                 110

Pro Lys Val Thr Ile Phe Pro Pro Ser Asp Glu Gln Leu Lys Ser Gly
            115                 120                 125

Thr Ala Thr Val Leu Cys Leu Leu Glu Lys Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Gly Val Met Glu Gln Asp Ser Lys Asp Ser Thr Tyr Met Leu Phe
                165                 170                 175

Ser Trp Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 43
<211> LENGTH: 1383
<212> TYPE: DNA
<213> ORGANISM: Artificial Sequence
<220> FEATURE:
<223> OTHER INFORMATION: Synthetic polynucleotide

<400> SEQUENCE: 43
caggtccagc tggtgcagtc tggggggaggc gtggtccagc ctggggaggtc cctgagactc       60 tcctgtgcag cctctggcgt gagcctgccc gactacggcg tgagctgggt ccgccaggct      120
ccaggcaagg ggctggagtg ggtggcagtg atctggggct ccgagacaac ctactacaac      180
agcgccctga gagccgatt caccatctcc agagacaatt ccaagaacac gctgtatttg      240
caaatgaaca gcctgagagc cgaggacacg gccgtgtatt actgtgcgaa gcactactac      300
tacgccggca gctacgccat ggactactgg ggccagggaa ccctggtcac cgtctcctca      360
gcgtcgacca agggcccag cgtgttcccg atggcccca gcagcaagag caccagcggc      420
ggcacagcca acctggcctg cctggtgaag gagtacttcc ccgagcccgt gaccgtgtcc      480
tggaactctg gagccctgac ctccggcgtg ttcaccgccc ccgccgtgct ctccagcagc      540
ggcctgtaca acctggtgag cctcgtgaag gtgcccagca gcctgggga acccagacc       600 tacatctgca acgtgaacca caagcccagc aacaccaagg tggacaagaa ggtggagccc      660
aagagctgcg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag gacagcccag ggaacctgag gtggccacat ccccacctag ccgggacgag     1080
ctgacaaaaa atcaggtcac cctcgtctgt ctcgtgaccg gcttttaccc ttccgacatt     1140
```

```
gccgtggaat gggaatccaa tgggcagccc gagaacaatt acaagacaga ccccccctg    1200 ctggaatccg atggcagctt cgccctgagc agccggctgc gggtggacaa gtccagatgg    1260
cagcagggga atgtcttttc ctgctccgtc atgcatgaag ccctccacaa tcattataca    1320
cagaaaagcc tgagcctgtc tcctggcaag gaacaaaaac tcatctcaga agaggatctg    1380
aat                                                                  1383
```

<210> SEQ ID NO 44
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 44

```
gatattcaga tgacccagtc tccatcctcc ctgtctgcat ctgtaggaga cagagtcacc     60
atcacttgcc gggccagcca ggacatcagc aagtacctga actggtatca gcagaaacca    120
gggaaagcca tcaagctcct gatctatcac accagccggc tgcacagcgg ggtcccatca    180
aggttcagtg gcagtggatc tgggacagat ttcactctca ccatcagcag tctgcaacct    240
gaagattttg caacttacta ctgtcagcaa ggcgccacac tgccctacac cttcggccct    300
gggaccaaag tggatatcaa acgtacggtg gccgctccca agtgaccat cttcccccc     360 agcgacgagc agctgaagag cggcaccgcc accgtgctgt gcctgctgga agttctac     420 ccccgggagg ccaaggtgca gtggaaggtg acaacgccc tccagagcgg caacagccag    480
gaaggcgtca tggagcagga cagcaaggac tccacctaca tgctgttcag ctggctgacc    540
ctgagcaagg ccgactacga aagcacaag gtgtacgcct gcgaggtgac ccaccagggc    600
ctgtccagcc ccgtgaccaa gagcttcaac cggggcgagt gc                      642
```

<210> SEQ ID NO 45
<211> LENGTH: 294
<212> TYPE: DNA
<213> ORGANISM: Artificial Sequence
<220> FEATURE:
<223> OTHER INFORMATION: Synthetic polynucleotide

<400> SEQUENCE: 45

```
gcgtcgacca agggcccag cgtgttcccg atggccccca gcagcaagag caccagcggc     60
ggcacagcca acctggcctg cctggtgaag gagtacttcc ccgagcccgt gaccgtgtcc    120
tggaactctg gagccctgac ctccggcgtg ttcaccgccc ccgccgtgct ctccagcagc    180
ggcctgtaca acctggtgag cctcgtgaag gtgcccagca gcctgggg aacccagacc     240 tacatctgca acgtgaacca caagcccagc aacaccaagg tggacaagaa ggtg          294
```

<210> SEQ ID NO 46
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 46

```
cgtacggtgg ccgctcccaa ggtgaccatc ttcccccca gcgacgagca gctgaagagc     60
ggcaccgcca ccgtgctgtg cctgctggag aagttctacc ccggaggc caaggtgcag     120 tggaaggtgg acaacgccct ccagagcggc aacagccagg aaggcgtcat ggagcaggac    180
```

```
agcaaggact ccacctacat gctgttcagc tggctgaccc tgagcaaggc cgactacgag      240
aagcacaagg tgtacgcctg cgaggtgacc caccagggcc tgtccagccc cgtgaccaag      300
agcttcaacc ggggcgagtg c                                                321
```

<210> SEQ ID NO 47
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 47

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 48
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 48

```
Ala Ser Thr Lys Gly Pro Gln Val Tyr Pro Leu Ala Pro Ser Ser Asp
1               5                   10                  15

Glu Thr Ser Gly Gly Gln Ala Ser Leu Thr Cys Leu Val Lys Asp Tyr
            20                  25                  30

Phe Pro Glu Pro Val Thr Val Ser Trp Asn Ser Gly Ala Leu Thr Ser
        35                  40                  45

Gly Val Lys Thr Thr Pro Ala Val Leu Asp Ser Ser Gly Leu Tyr Phe
    50                  55                  60

Leu Tyr Ser Lys Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 49
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 49

```
Arg Thr Val Ala Ala Pro Gln Val Tyr Ile Leu Pro Pro Ser Asp Asp
1               5                   10                  15
```

```
Glu Leu Lys Ser Gly Thr Ala Ser Val Thr Cys Leu Leu Lys Asn Phe
             20                  25                  30

Tyr Pro Arg Glu Ala Lys Val Gln Trp Lys Val Asp Asn Ala Leu Gln
         35                  40                  45

Ser Gly Asn Ser Lys Glu Thr Val Val Glu Gln Asp Ser Lys Asp Ser
 50                  55                  60

Thr Tyr Phe Leu Tyr Ser Lys Leu Thr Leu Ser Lys Ala Asp Tyr Glu
 65                  70                  75                  80

Lys His Lys Val Tyr Ala Cys Glu Val Thr His Gln Gly Leu Ser Ser
             85                  90                  95

Pro Val Thr Lys Ser Phe Asn Arg Gly Glu Cys
            100                 105

<210> SEQ ID NO 50
<211> LENGTH: 461
<212> TYPE: PRT
<213> ORGANISM: Artificial Sequence
<220> FEATURE:
<223> OTHER INFORMATION: Synthetic polypeptide

<400> SEQUENCE: 50

Gln Val Gln Leu Val Gln Ser Gly Gly Gly Val Val Gln Pro Gly Arg
 1               5                  10                  15

Ser Leu Arg Leu Ser Cys Ala Ala Ser Gly Val Ser Leu Pro Asp Tyr
             20                  25                  30

Gly Val Ser Trp Val Arg Gln Ala Pro Gly Lys Gly Leu Glu Trp Val
         35                  40                  45

Ala Val Ile Trp Gly Ser Glu Thr Thr Tyr Tyr Asn Ser Ala Leu Lys
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Gln Val
            115                 120                 125

Tyr Pro Leu Ala Pro Ser Ser Asp Glu Thr Ser Gly Gly Gln Ala Ser
        130                 135                 140

Leu Thr Cys Leu Val Lys Asp Tyr Phe Pro Glu Pro Val Thr Val Ser
145                 150                 155                 160

Trp Asn Ser Gly Ala Leu Thr Ser Gly Val Lys Thr Thr Pro Ala Val
                165                 170                 175

Leu Asp Ser Ser Gly Leu Tyr Phe Leu Tyr Ser Lys Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Ala
            340                 345                 350

Thr Phe Pro Pro Ser Arg Asp Glu Leu Thr Lys Asn Gln Val Thr Leu
        355                 360                 365

Val Cys Leu Val Thr Gly Phe Tyr Pro Ser Asp Ile Ala Val Glu Trp
370                 375                 380

Glu Ser Asn Gly Gln Pro Glu Asn Asn Tyr Lys Thr Asp Pro Pro Leu
385                 390                 395                 400

Leu Glu Ser Asp Gly Ser Phe Ala Leu Ser Ser Arg Leu Arg Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Glu Gln Lys Leu Ile Ser Glu Glu Asp Leu Asn
        450                 455                 460

<210> SEQ ID NO 51
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys Arg Thr Val Ala Ala
            100                 105                 110

Pro Gln Val Tyr Ile Leu Pro Pro Ser Asp Asp Glu Leu Lys Ser Gly
        115                 120                 125

Thr Ala Ser Val Thr Cys Leu Leu Lys Asn Phe Tyr Pro Arg Glu Ala
    130                 135                 140

Lys Val Gln Trp Lys Val Asp Asn Ala Leu Gln Ser Gly Asn Ser Lys
145                 150                 155                 160

Glu Thr Val Val Glu Gln Asp Ser Lys Asp Ser Thr Tyr Phe Leu Tyr
                165                 170                 175

Ser Lys Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 1383
<212> TYPE: DNA
<213> ORGANISM: Artificial Sequence
<220> FEATURE:
<223> OTHER INFORMATION: Synthetic polynucleotide

<400> SEQUENCE: 52
caggtccagc tggtgcagtc tggggggaggc gtggtccagc ctggggaggtc cctgagactc      60 tcctgtgcag cctctggcgt gagcctgccc gactacggcg tgagctgggt ccgccaggct     120
ccaggcaagg ggctggagtg ggtggcagtg atctggggct ccgagacaac ctactacaac     180
agcgccctga gagccgatt caccatctcc agagacaatt ccaagaacac gctgtatttg     240
caaatgaaca gcctgagagc cgaggacacg gccgtgtatt actgtgcgaa gcactactac     300
tacggcggca gctacgccat ggactactgg ggcagggaa ccctggtcac cgtctcctca     360
gccagcacca agggccccca ggtgtaccct ctggccccca gcagcgacga gacaagcgga     420
ggccaggcca gcctgacctg cctggtgaaa gactacttcc ccgagcccgt gaccgtgtcc     480
tggaactctg gcgccctgac cagcggcgtg aaaaccaccc tgctgtgct ggacagcagc     540 ggcctgtact cctgtacag caaagtgacc gtgcctagca gcagcctggg cacccagacc     600
tacatctgca acgtgaacca caagcccagc aacaccaagg tggacaagaa agtggaaccg     660
aaaagctgcg acaaaactca cacatgccca ccgtgcccag cacctgaact cctgggggga     720
ccgtcagtct tcctcttccc cccaaaaccc aaggacaccc tcatgatctc ccggaccct     780 gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gacagcccag ggaacctgag gtggccacat tcccacctag ccgggacgag    1080
ctgacaaaaa atcaggtcac cctcgtctgt ctcgtgaccg gcttttaccc ttccgacatt    1140
gccgtggaat gggaatccaa tgggcagccc gagaacaatt acaagacaga ccccccctg    1200 ctggaatccg atggcagctt cgccctgagc agccggctgc gggtggacaa gtccagatgg    1260
cagcagggga atgtctttc ctgctccgtc atgcatgaag ccctccacaa tcattataca    1320
cagaaaagcc tgagcctgtc tcctggcaag gaacaaaaac tcatctcaga agaggatctg    1380
aat                                                                  1383

<210> SEQ ID NO 53
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 53
gatattcaga tgacccagtc tccatcctcc ctgtctgcat ctgtaggaga cagagtcacc      60

```
atcacttgcc gggccagcca ggacatcagc aagtacctga actggtatca gcagaaacca    120
gggaaagcca tcaagctcct gatctatcac accagccggc tgcacagcgg ggtcccatca    180
aggttcagtg gcagtggatc tgggacagat ttcactctca ccatcagcag tctgcaacct    240
gaagattttg caacttacta ctgtcagcaa ggcgccacac tgcccacac cttcggccct     300 gggaccaaag tggatatcaa aagaaccgtg ctgctcctc aggtgtacat cctgcctccc     360
agcgacgatg agctgaagtc tggcaccgcc agcgtgacat gtctgctgaa gaacttctac    420
ccccgcgagg ccaaggtgca gtggaaagtg gacaacgccc tgcagagcgg caacagcaaa    480
gaaaccgtgg tggaacagga cagcaaggac tccacctact ttctgtactc caagctgacc    540
ctgagcaagg ccgactacga aagcacaag gtgtacgcct gcgaagtgac ccaccagggc     600
ctgagcagcc ccgtgaccaa gagcttcaac cggggcgagt gc                       642
```

<210> SEQ ID NO 54
<211> LENGTH: 294
<212> TYPE: DNA
<213> ORGANISM: Artificial Sequence
<220> FEATURE:
<223> OTHER INFORMATION: Synthetic polynucleotide

<400> SEQUENCE: 54

```
gccagcacca agggccccca ggtgtaccct ctggccccca gcagcgacga gacaagcgga     60
ggccaggcca gcctgacctg cctggtgaaa gactacttcc ccgagcccgt gaccgtgtcc    120
tggaactctg gcgccctgac cagcggcgtg aaaaccaccc tgctgtgtgct ggacagcagc   180 ggcctgtact tcctgtacag caaagtgacc gtgcctagca gcagcctggg cacccagacc    240
tacatctgca acgtgaacca caagcccagc aacaccaagg tggacaagaa agtg          294
```

<210> SEQ ID NO 55
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 55

```
agaaccgtgg ctgctcctca ggtgtacatc ctgcctccca gcgacgatga gctgaagtct     60
ggcaccgcca gcgtgacatg tctgctgaag aacttctacc cccgcgaggc caaggtgcag    120
tggaaagtgg acaacgccct gcagagcggc aacagcaaag aaaccgtggt ggaacaggac    180
agcaaggact ccacctactt tctgtactcc aagctgaccc tgagcaaggc cgactacgag    240
aagcacaagg tgtacgcctg cgaagtgacc caccagggcc tgagcagccc cgtgaccaag    300
agcttcaacc ggggcgagtg c                                               321
```

<210> SEQ ID NO 56
<211> LENGTH: 1347
<212> TYPE: DNA
<213> ORGANISM: Artificial Sequence
<220> FEATURE:
<223> OTHER INFORMATION: Synthetic polynucleotide

<400> SEQUENCE: 56

```
caggtccagc tgaagcagag cggcccaggc ctcgtgcagc cctctcagtc tctcagcatc     60
acctgcaccg tgtccggctt cagcctgacc aactacggcg tgcactgggt ccgccagagc    120
cccggcaagg gcctggaatg gctgggcgtg atctggtccg gcggcaacac cgactacaac    180
```

| | |
|---|---:|
| acccccttca ccagcaggct gtccatcaac aaggacaaca gcaagagcca ggtgttcttc | 240 |
| aagatgaaca gcctgcagag caacgacacc gccatctact actgcgccag ggctctgacc | 300 |
| tactacgact acgagttcgc ctactgggga cagggcaccc tggtcactgt ctccgccgcc | 360 |
| agcaccaagg gcccagcgt gttcccctg gccccagca gcaagagcac ctctggcggc | 420 |
| acagccgccc tgggctgcct ggtcaaggac tacttccccg agcccgtgac agtgtcctgg | 480 |
| aacagcggag ccctgacctc cggcgtccac accttccccg ccgtgctgca gagcagcggc | 540 |
| ctgtacagcc tgagcagcgt ggtcacagtg ccctctagca gcctcggcac ccagacctac | 600 |
| atctgcaacg tgaaccacaa gcccagcaac accaaggtgg acaagaaggt ggagcccaag | 660 |
| agctgcgaca aaactcacac atgccccccc tgccctgccc ctgagctgct gggcggaccc | 720 |
| tccgtgttcc tgttcccccc caagcccaag gacaccctga tgatcagccg gacccccgag | 780 |
| gtgacctgcg tggtggtgga cgtgagccac gaggaccctg aggtgaagtt caattggtac | 840 |
| gtggacggcg tggaggtgca caacgccaag accaagcccc gggaggaaca gtacaacagc | 900 |
| acctaccggg tggtgtccgt gctgaccgtg ctgcaccagg actggctgaa cggcaaggaa | 960 |
| tacaagtgca aggtctccaa caaggccctg cctgccccca tcgagaaaac catctccaaa | 1020 |
| gccaaaggcc agcccagaga accccaggtg tacaccctgc cccccagcag agatgagctg | 1080 |
| accaagaacc aggtcaagct cgtgtgcctg gtcaccggct tctacccag cgatatcgcc | 1140 |
| gtggagtggg agagcaacgg ccagcctgaa aacaactact acaccacccc ccctgtgctg | 1200 |
| gacagcgacg gcagcttcag cctggtgtcc tggctgaacg tggacaagag ccggtggcag | 1260 |
| cagggcaacg tgttcagctg cagcgtgatg cacgaggccc tgcacaacca ctacacccag | 1320 |
| aagtccctga gcctgtctcc tggcaag | 1347 |

<210> SEQ ID NO 57
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 57

| | |
|---|---:|
| gacatcctgc tgacccagag ccccgtgatc ctgagcgtgt ccccaggcga gagggtgtcc | 60 |
| ttcagctgca gagccagcca gagcatcggc accaacatcc actggtatca gcagaggacc | 120 |
| aacggcagcc ccaggctgct gatcaagtac gccagcgagt ccatcagcgg catccccagc | 180 |
| aggttcagcg gcagcggctc cggcaccgac ttcaccctga gcatcaacag cgtggagagc | 240 |
| gaggacatcg ccgactacta ctgccagcag aacaacaact ggcccaccac cttcggagcc | 300 |
| ggcaccaagc tggaactgaa gaggaccgtg gctgccccca gcgtgttcat cttcccccc | 360 |
| agcgacgagc agctgaagtc cggcaccgcc agcgtggtct gcctgctgaa caacttctac | 420 |
| ccccgggagg ccaaggtgca gtggaaggtg gacaacgccc tgcagagcgg caacagccag | 480 |
| gaaagcgtca ccgagcagga cagcaaggac tccacctaca gcctgagcag cacccctgacc | 540 |
| ctgagcaagg ccgactacga gaagcacaag gtgtacgcct gcgaggtcac ccaccagggc | 600 |
| ctgtccagcc ccgtgaccaa gagcttcaac aggggcgagt gc | 642 |

<210> SEQ ID NO 58
<211> LENGTH: 1422
<212> TYPE: DNA
<213> ORGANISM: Artificial Sequence
<220> FEATURE:
<223> OTHER INFORMATION: Synthetic polynucleotide

<400> SEQUENCE: 58

```
gaggtgcagc tggtcgagtc tggcggcgga ctggtgcagc ctggcggctc cctgcggctg      60
tcctgcgccg cctccggctt caacatcaag gacacctaca tccactgggt gcggcaggcc     120
cctggcaagg gcctggagtg ggtggcccgg atctacccta ccaacggcta caccagatac     180
gccgactccg tgaagggccg gttcaccatc tccgccgaca cctccaagaa caccgcctac     240
ctgcagatga actccctgcg ggccgaggac accgccgtgt actactgctc agatggggga     300
ggagatggct tctacgccat ggactactgg ggccagggca ccctggtgac cgtgtcctcc     360
ggtggcggtg gcagcggcgg tggtggttcc ggaggcggcg gttctgacat ccagatgacc     420
cagtccccct ccagcctgtc tgcctccgtg ggcgaccggg tgaccatcac ctgccgggcc     480
tcccaggacg tgaacaccgc cgtggcctgg tatcagcaga agcctggcaa ggcccctaag     540
ctgctgatct actccgcctc cttcctgtac tccggcgtgc cttccggtt ctccggctcc     600
cggtccggca ccgacttcac cctgaccatc tcctccctgc agcctgagga cttcgccacc     660
tactactgcc agcagcacta caccaccccct cctaccttcg gccagggcac caaggtggag     720
atcaagggag gaggagggtc agacaaaact cacacttgcc caccgtgccc agcacctgaa     780
ctcctggggg gaccgtcagt cttcctcttc cccccaaaac ccaaggacac cctcatgatc     840
tcccggaccc ctgaggtcac ctgcgtggtg gtggacgtga gccacgagga ccctgaggtg     900
aagttcaatt ggtacgtgga cggcgtggag gtgcacaacg ccaagaccaa gccccgggag     960
gaacagtaca acagcaccta ccgggtggtg tccgtgctga ccgtgctgca ccaggactgg    1020
ctgaacggca aggaatacaa gtgcaaggtc tccaacaagg ccctgcctgc ccccatcgaa    1080
aagaccatca gcaaggccaa gggacagccc agggaacctg aggtggccac attcccacct    1140
agccgggacg agctgacaaa aaatcaggtc accctcgtct gtctcgtgac cggcttttac    1200
ccttccgaca ttgccgtgga atgggaatcc aatgggcagc ccgagaacaa ttacaagaca    1260
gacccccccc tgctggaatc cgatggcagc ttctgcctga gcagccggct gcgggtggac    1320
aagtccagat ggcagcaggg gaatgtcttt tcctgctccg tcatgcatga agccctccac    1380
aatcattata cacagaaaag cctgagcctg agccccggca ag                       1422
```

<210> SEQ ID NO 59
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 59

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95
```

-continued

```
Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Lys Leu Val
        355                 360                 365

Cys Leu Val Thr Gly Phe Tyr Pro Ser Asp Ile Ala Val Glu Trp Glu
370                 375                 380

Ser Asn Gly Gln Pro Glu Asn Asn Tyr Tyr Thr Thr Pro Pro Val Leu
385                 390                 395                 400

Asp Ser Asp Gly Ser Phe Ser Leu Val Ser Trp Leu Asn Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 60
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 60

Asp Ile Leu Leu Thr Gln Ser Pro Val Ile Leu Ser Val Ser Pro Gly

```
1               5                   10                  15
Glu Arg Val Ser Phe Ser Cys Arg Ala Ser Gln Ser Ile Gly Thr Asn
                20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 61
<211> LENGTH: 474
<212> TYPE: PRT
<213> ORGANISM: Artificial Sequence
<220> FEATURE:
<223> OTHER INFORMATION: Synthetic polypeptide

<400> SEQUENCE: 61

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
                20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Gly Gly Gly Gly Ser Gly Gly Gly
            115                 120                 125
Gly Ser Gly Gly Gly Gly Ser Asp Ile Gln Met Thr Gln Ser Pro Ser
            130                 135                 140
Ser Leu Ser Ala Ser Val Gly Asp Arg Val Thr Ile Thr Cys Arg Ala
```

```
                145                 150                 155                 160
        Ser Gln Asp Val Asn Thr Ala Val Ala Trp Tyr Gln Lys Pro Gly
                        165                 170                 175

Lys Ala Pro Lys Leu Leu Ile Tyr Ser Ala Ser Phe Leu Tyr Ser Gly
                        180                 185                 190

Val Pro Ser Arg Phe Ser Gly Ser Arg Ser Gly Thr Asp Phe Thr Leu
                        195                 200                 205

Thr Ile Ser Ser Leu Gln Pro Glu Asp Phe Ala Thr Tyr Tyr Cys Gln
                    210                 215                 220

Gln His Tyr Thr Thr Pro Pro Thr Phe Gly Gln Gly Thr Lys Val Glu
        225                 230                 235                 240

Ile Lys Gly Gly Gly Gly Ser Asp Lys Thr His Thr Cys Pro Pro Cys
                        245                 250                 255

Pro Ala Pro Glu Leu Leu Gly Gly Pro Ser Val Phe Leu Phe Pro Pro
                    260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
        305                 310                 315                 320

Glu Gln Tyr Asn Ser Thr Tyr Arg Val Val Ser Val Leu Thr Val Leu
                        325                 330                 335

His Gln Asp Trp Leu Asn Gly Lys Glu Tyr Lys Cys Lys Val Ser Asn
                        340                 345                 350

Lys Ala Leu Pro Ala Pro Ile Glu Lys Thr Ile Ser Lys Ala Lys Gly
                    355                 360                 365

Gln Pro Arg Glu Pro Glu Val Ala Thr Phe Pro Pro Ser Arg Asp Glu
                370                 375                 380

Leu Thr Lys Asn Gln Val Thr Leu Val Cys Leu Val Thr Gly Phe Tyr
        385                 390                 395                 400

Pro Ser Asp Ile Ala Val Glu Trp Glu Ser Asn Gly Gln Pro Glu Asn
                        405                 410                 415

Asn Tyr Lys Thr Asp Pro Pro Leu Leu Glu Ser Asp Gly Ser Phe Ala
                        420                 425                 430

Leu Ser Arg Leu Arg Val Asp Lys Ser Arg Trp Gln Gln Gly Asn
                    435                 440                 445

Val Phe Ser Cys Ser Val Met His Glu Ala Leu His Asn His Tyr Thr
            450                 455                 460

Gln Lys Ser Leu Ser Leu Ser Pro Gly Lys
        465                 470

<210> SEQ ID NO 62
<211> LENGTH: 851
<212> TYPE: PRT
<213> ORGANISM: Artificial Sequence
<220> FEATURE:
<223> OTHER INFORMATION: Synthetic polypeptide

<400> SEQUENCE: 62

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
```

```
                35                  40                  45
Asn Tyr Asp Leu Ser Phe Leu Lys Thr Ile Gln Glu Val Ala Gly Tyr
 50                  55                  60
Val Leu Ile Ala Leu Asn Thr Val Glu Arg Ile Pro Leu Glu Asn Leu
 65                  70                  75                  80
Gln Ile Ile Arg Gly Asn Met Tyr Tyr Glu Asn Ser Tyr Ala Leu Ala
                 85                  90                  95
Val Leu Ser Asn Tyr Asp Ala Asn Lys Thr Gly Leu Lys Glu Leu Pro
                100                 105                 110
Met Arg Asn Leu Gln Glu Ile Leu His Gly Ala Val Arg Phe Ser Asn
                115                 120                 125
Asn Pro Ala Leu Cys Asn Val Glu Ser Ile Gln Trp Arg Asp Ile Val
                130                 135                 140
Ser Ser Asp Phe Leu Ser Asn Met Ser Met Asp Phe Gln Asn His Leu
145                 150                 155                 160
Gly Ser Cys Gln Lys Cys Asp Pro Ser Cys Pro Asn Gly Ser Cys Trp
                165                 170                 175
Gly Ala Gly Glu Glu Asn Cys Gln Lys Leu Thr Lys Ile Ile Cys Ala
                180                 185                 190
Gln Gln Cys Ser Gly Arg Cys Arg Gly Lys Ser Pro Ser Asp Cys Cys
                195                 200                 205
His Asn Gln Cys Ala Ala Gly Cys Thr Gly Pro Arg Glu Ser Asp Cys
                210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
                260                 265                 270
Arg Asn Tyr Val Val Thr Asp His Gly Ser Cys Val Arg Ala Cys Gly
                275                 280                 285
Ala Asp Ser Tyr Glu Met Glu Glu Asp Gly Val Arg Lys Cys Lys Lys
                290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
                340                 345                 350
Arg Gly Asp Ser Phe Thr His Thr Pro Pro Leu Asp Pro Gln Glu Leu
                355                 360                 365
Asp Ile Leu Lys Thr Val Lys Glu Ile Thr Gly Phe Leu Leu Ile Gln
                370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
                420                 425                 430
Ser Asp Gly Asp Val Ile Ile Ser Gly Asn Lys Asn Leu Cys Tyr Ala
                435                 440                 445
Asn Thr Ile Asn Trp Lys Lys Leu Phe Gly Thr Ser Gly Gln Lys Thr
450                 455                 460
```

```
Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser Gly Gly Gly
    610                 615                 620

Gly Gly Thr His Thr Cys Pro Pro Cys Pro Ala Pro Glu Leu Leu Gly
625                 630                 635                 640

Gly Pro Ser Val Phe Leu Phe Pro Pro Lys Pro Lys Asp Thr Leu Met
                645                 650                 655

Ile Ser Arg Thr Pro Glu Val Thr Cys Val Val Val Asp Val Ser His
            660                 665                 670

Glu Asp Pro Glu Val Lys Phe Asn Trp Tyr Val Asp Gly Val Glu Val
        675                 680                 685

His Asn Ala Lys Thr Lys Pro Arg Glu Glu Gln Tyr Asn Ser Thr Tyr
    690                 695                 700

Arg Val Val Ser Val Leu Thr Val Leu His Gln Asp Trp Leu Asn Gly
705                 710                 715                 720

Lys Glu Tyr Lys Cys Lys Val Ser Asn Lys Ala Leu Pro Ala Pro Ile
                725                 730                 735

Glu Lys Thr Ile Ser Lys Ala Lys Gly Gln Pro Arg Glu Pro Gln Val
            740                 745                 750

Tyr Thr Leu Pro Pro Ser Arg Glu Glu Met Thr Lys Asn Gln Val Ser
        755                 760                 765

Leu Thr Cys Leu Val Lys Gly Phe Tyr Pro Ser Asp Ile Ala Val Glu
    770                 775                 780

Trp Glu Ser Asn Gly Gln Pro Glu Asn Asn Tyr Lys Thr Thr Pro Pro
785                 790                 795                 800

Val Leu Asp Ser Asp Gly Ser Phe Phe Leu Tyr Ser Lys Leu Thr Val
                805                 810                 815

Asp Lys Ser Arg Trp Gln Gln Gly Asn Val Phe Ser Cys Ser Val Met
            820                 825                 830

His Glu Ala Leu His Asn His Tyr Thr Gln Lys Ser Leu Ser Leu Ser
        835                 840                 845

Pro Gly Lys
    850

<210> SEQ ID NO 63
<211> LENGTH: 862
```

```
<212> TYPE: PRT
<213> ORGANISM: Artificial Sequence
<220> FEATURE:
<223> OTHER INFORMATION: Synthetic polypeptide

<400> SEQUENCE: 63

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380
```

```
Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
            405                 410                 415

Gly Ala Tyr Ser Leu Thr Leu Gln Gly Leu Gly Ile Ser Trp Leu Gly
        420                 425                 430

Leu Arg Ser Leu Arg Glu Leu Gly Ser Gly Leu Ala Leu Ile His His
    435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
        500                 505                 510

Leu Arg Gly Gln Glu Cys Val Glu Glu Cys Arg Val Leu Gln Gly Leu
    515                 520                 525

Pro Arg Glu Tyr Val Asn Ala Arg His Cys Leu Pro Cys His Pro Glu
530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
        580                 585                 590

Lys Phe Pro Asp Glu Glu Gly Ala Cys Gln Pro Cys Pro Ile Asn Cys
    595                 600                 605

Thr His Ser Cys Val Asp Leu Asp Asp Lys Gly Cys Pro Ala Glu Gln
610                 615                 620

Arg Ala Ser Pro Leu Thr Glu Pro Lys Ser Cys Asp Lys Thr His Thr
625                 630                 635                 640

Cys Pro Pro Cys Pro Ala Pro Glu Leu Leu Gly Gly Pro Ser Val Phe
            645                 650                 655

Leu Phe Pro Pro Lys Pro Lys Asp Thr Leu Met Ile Ser Arg Thr Pro
        660                 665                 670

Glu Val Thr Cys Val Val Val Asp Val Ser His Glu Asp Pro Glu Val
    675                 680                 685

Lys Phe Asn Trp Tyr Val Asp Gly Val Glu Val His Asn Ala Lys Thr
690                 695                 700

Lys Pro Arg Glu Glu Gln Tyr Asn Ser Thr Tyr Arg Val Val Ser Val
705                 710                 715                 720

Leu Thr Val Leu His Gln Asp Trp Leu Asn Gly Lys Glu Tyr Lys Cys
            725                 730                 735

Lys Val Ser Asn Lys Ala Leu Pro Ala Pro Ile Glu Lys Thr Ile Ser
        740                 745                 750

Lys Ala Lys Gly Gln Pro Arg Glu Pro Gln Val Tyr Thr Leu Pro Pro
    755                 760                 765

Ser Arg Glu Glu Met Thr Lys Asn Gln Val Ser Leu Thr Cys Leu Val
770                 775                 780

Lys Gly Phe Tyr Pro Ser Asp Ile Ala Val Glu Trp Glu Ser Asn Gly
785                 790                 795                 800

Gln Pro Glu Asn Asn Tyr Lys Thr Thr Pro Pro Val Leu Asp Ser Asp
```

| | | | 805 | | | | | 810 | | | | | 815 | | |
|---|---|---|---|---|---|---|---|---|---|---|---|---|---|---|---|
Gly Ser Phe Phe Leu Tyr Ser Lys Leu Thr Val Asp Lys Ser Arg Trp
820 825 830

Gln Gln Gly Asn Val Phe Ser Cys Ser Val Met His Glu Ala Leu His
835 840 845

Asn His Tyr Thr Gln Lys Ser Leu Ser Leu Ser Pro Gly Lys
850 855 860

<210> SEQ ID NO 64
<211> LENGTH: 2577
<212> TYPE: DNA
<213> ORGANISM: Artificial Sequence
<220> FEATURE:
<223> OTHER INFORMATION: Synthetic polynucleotide

<400> SEQUENCE: 64

```
ctggaggaaa agaaagtttg ccaaggcacg agtaacaagc tcacgcagtt gggcactttt      60
gaagatcatt ttctcagcct ccagaggatg ttcaataact gtgaggtggt ccttgggaat     120
ttggaaatta cctatgtgca gaggaattat gatctttcct tcttaaagac catccaggag     180
gtggctggtt atgtcctcat tgccctcaac acagtggagc gaattccttt ggaaaacctg     240
cagatcatca gaggaaatat gtactacgaa aattcctatg ccttagcagt cttatctaac     300
tatgatgcaa ataaaaccgg actgaaggag ctgcccatga aatttacag gaaatcctg      360
catggcgccg tgcggttcag caacaaccct gccctgtgca acgtggagag catccagtgg     420
cgggacatag tcagcagtga ctttctcagc aacatgtcga tggacttcca gaaccacctg     480
ggcagctgcc aaaagtgtga tccaagctgt cccaatggga gctgctgggg tgcaggagag     540
gagaactgcc agaaactgac caaaatcatc tgtgcccagc agtgctccgg cgcgctgcgt     600
ggcaagtccc ccagtgactg ctgccacaac cagtgtgctg caggctgcac aggccccgg      660
gagagcgact gcctggtctg ccgcaaattc cgagacgaag ccacgtgcaa ggacacctgc     720
cccccactca tgctctacaa ccccaccacg taccagatgg atgtgaaccc cgagggcaaa     780
tacagctttg gtgccacctg cgtgaagaag tgtccccgta ttatgtggt gacagatcac     840
ggctcgtgcg tccgagcctg tggggccgac agctatgaga tggaggaaga cggcgtccgc     900
aagtgtaaga agtgcgaagg ccttgccgc aaagtgtgta cggaatagg tattggtgaa     960
tttaaagact cactctccat aaatgctacg aatattaaac acttcaaaaa ctgcacctcc    1020
atcagtggcg atctccacat cctgccggtg gcatttaggg gtgactcctt cacacatact    1080
cctcctctgg atccacagga actggatatt ctgaaaaccg taaaggaaat cacagggttt    1140
ttgctgattc aggcttggcc tgaaaacagg acggacctcc atgcctttga aacctagaa    1200
atcatacgcg gcaggaccaa gcaacatggt cagtttctc ttgcagtcgt cagcctgaac    1260
ataacatcct gggattacg ctccctcaag gagataagtg atggagatgt gataatttca    1320
ggaaacaaaa atttgtgcta tgcaaataca ataaactgga aaaaactgtt tgggacctcc    1380
ggtcagaaaa ccaaaattat aagcaacaga ggtgaaaaca gctgcaaggc cacaggccag    1440
gtctgccatg ccttgtgctc ccccgagggc tgctggggcc cggagcccag ggactgcgtc    1500
tcttgccgga atgtcagccg aggcagggaa tgcgtggaca gtgcaacct tctggagggt    1560
gagccaaggg agtttgtgga gaactctgag tgcatacagt gccacccaga gtgcctgcct    1620
caggccatga acatcacctg cacaggacgg ggaccagaca actgtatcca gtgtgcccac    1680
tacattgacg gcccccactg cgtcaagacc tgcccggcag gagtcatggg agaaaacaac    1740
```

| | |
|---|---:|
| accctggtct ggaagtacgc agacgccggc catgtgtgcc acctgtgcca tccaaactgc | 1800 |
| acctacggat gcactgggcc aggtcttgaa ggctgtccaa cgaatgggcc taagatcccg | 1860 |
| tccggtggtg gtggtggtac ccacacctgc cccccctgcc ctgcccctga gctgctgggc | 1920 |
| ggacccagcg tgttcctgtt cccccccaag cccaaggaca ccctgatgat cagccggacc | 1980 |
| cccgaggtga cctgcgtggt ggtggacgtg agccacgagg accctgaggt gaagttcaat | 2040 |
| tggtacgtgg acggcgtgga ggtgcacaac gccaagacca gccccgggga ggagcagtac | 2100 |
| aactccacct accgggtggt gtccgtgctg accgtgctgc accaggactg gctgaacggc | 2160 |
| aaggaataca gtgcaaggt gtccaacaag gccctgcctg cccccatcga aagaccatc | 2220 |
| agcaaggcca agggccagcc cagggagccc caggtgtaca ccctgccccc cagccgggag | 2280 |
| gagatgacca gaaccaggt gtccctgacc tgcctggtga agggcttcta ccccagcgac | 2340 |
| atcgccgtgg agtgggagag caacggccag cccgagaaca actacaagac cacccccct | 2400 |
| gtgctggaca cgacggcag cttcttcctg tacagcaagc tgaccgtgga caagagcagg | 2460 |
| tggcagcagg gcaacgtgtt cagctgcagc gtgatgcacg aggccctgca caaccactac | 2520 |
| acccagaaga gcctgagcct gtcccccggc aagagcgccc atcatcacca tcaccat | 2577 |

<210> SEQ ID NO 65
<211> LENGTH: 2586
<212> TYPE: DNA
<213> ORGANISM: Artificial Sequence
<220> FEATURE:
<223> OTHER INFORMATION: Synthetic polynucleotide

<400> SEQUENCE: 65

| | |
|---|---:|
| acccaagtgt gcaccggcac agacatgaag ctgcggctcc ctgccagtcc cgagacccac | 60 |
| ctggacatgc tccgccacct ctaccagggc tgccaggtgg tgcagggaaa cctggaactc | 120 |
| acctacctgc ccaccaatgc cagcctgtcc ttcctgcagg atatccagga ggtgcagggc | 180 |
| tacgtgctca tcgctcacaa ccaagtgagg caggtcccac tgcagaggct gcggattgtg | 240 |
| cgaggcaccc agctctttga ggacaactat gccctggccg tgctagacaa tggagacccg | 300 |
| ctgaacaata ccaccccctgt cacagggggcc tccccaggag gctgcgggga gctgcagctt | 360 |
| cgaagcctca cagagatctt gaaaggaggg gtcttgatcc agcggaaccc ccagctctgc | 420 |
| taccaggaca cgattttgtg gaaggacatc ttccacaaga caaccagct ggctctcaca | 480 |
| ctgatagaca ccaaccgctc tcgggcctgc cacccctgtt ctccgatgtg taagggctcc | 540 |
| cgctgctggg gagagagttc tgaggattgt cagagcctga cgcgcactgt ctgtgccggt | 600 |
| ggctgtgccc gctgcaaggg gccactgccc actgactgct gccatgagca gtgtgctgcc | 660 |
| ggctgcacgg gccccaagca ctctgactgc ctggcctgcc tccacttcaa ccacagtggc | 720 |
| atctgtgagc tgcactgccc agccctggtc acctacaaca gagacgtt tgagtccatg | 780 |
| cccaatcccg agggcggta acattcggc gccagctgtg tgactgcctg tccctacaac | 840 |
| tacctttcta cggacgtggg atcctgcacc ctcgtctgcc ccctgcacaa ccaagaggtg | 900 |
| acagcagagg atggaacaca gcggtgtgag aagtgcagca gccctgtgc ccgagtgtgc | 960 |
| tatggtctgg gcatggagca cttgcgagag gtgagggcag ttaccagtgc caatatccag | 1020 |
| gagtttgctg gctgcaagaa gatctttggg agcctggcat ttctgccgga gagctttgat | 1080 |
| ggggacccag cctccaacac tgccccgctc cagccagagc agctccaagt gtttgagact | 1140 |
| ctggaagaga tcagaggtta cctatacatc tcagcatggc cggacagcct gcctgacctc | 1200 |
| agcgtcttcc agaacctgca agtaatccgg ggacgaattc tgcacaatgg cgcctactcg | 1260 |

```
ctgaccctgc aagggctggg catcagctgg ctggggctgc gctcactgag ggaactgggc    1320
agtggactgg ccctcatcca ccataacacc cacctctgct tcgtgcacac ggtgccctgg    1380
gaccagctct ttcggaaccc gcaccaagct ctgctccaca ctgccaaccg gccagaggac    1440
gagtgtgtgg gcgagggcct ggcctgccac cagctgtgcg cccgagggca ctgctggggt    1500
ccagggccca cccagtgtgt caactgcagc cagttccttc ggggccagga gtgcgtggag    1560
gaatgccgag tactgcaggg gctccccagg gagtatgtga atgccaggca ctgtttgccg    1620
tgccaccctg agtgtcagcc ccagaatggc tcagtgacct gttttggacc ggaggctgac    1680
cagtgtgtgg cctgtgccca ctataaggac cctcccttct gcgtggcccg ctgccccagc    1740
ggtgtgaaac ctgacctctc ctacatgccc atctggaagt ttccagatga ggagggcgca    1800
tgccagcctt gccccatcaa ctgcacccac tcctgtgtgg acctggatga caagggctgc    1860
cccgccgagc agagagccag ccctctgacg gagcccaaga gctgcgacaa gacccacacc    1920
tgccccccct gccctgcccc tgagctgctg ggcggaccca gcgtgttcct gttccccccc    1980
aagcccaagg acaccctgat gatcagccgg accccgagg tgacctgcgt ggtggtggac    2040
gtgagccacg aggaccctga ggtgaagttc aattggtacg tggacggcgt ggaggtgcac    2100
aacgccaaga ccaagccccg ggaggagcag tacaactcca cctaccgggt ggtgtccgtg    2160
ctgaccgtgc tgcaccagga ctggctgaac ggcaaggaat acaagtgcaa ggtgtccaac    2220
aaggccctgc ctgcccccat cgaaaagacc atcagcaagg ccagggcca gcccagggag    2280 ccccaggtgt acaccctgcc ccccagccgg gaggagatga ccaagaacca ggtgtccctg    2340
acctgcctgg tgaagggctt ctaccccagc gacatcgccg tggagtggga gagcaacggc    2400
cagcccgaga caactacaa gaccacccc cctgtgctgg acagcgacgg cagcttcttc    2460
ctgtacagca agctgaccgt ggacaagagc aggtggcagc agggcaacgt gttcagctgc    2520
agcgtgatgc acgaggccct gcacaaccac tacacccaga gagcctgag cctgtccccc    2580 ggcaag                                                               2586
```

<210> SEQ ID NO 66
<211> LENGTH: 1365
<212> TYPE: DNA
<213> ORGANISM: Artificial Sequence
<220> FEATURE:
<223> OTHER INFORMATION: Synthetic polynucleotide

<400> SEQUENCE: 66

```
caggtgcagt tgcaggagag cggcccaggc ctggtgaagc ccagcgagac actgagcctg     60
acctgcaccg tgagcggctt cagcctgacc aactacggca tccactggat caggcagccc    120
ccaggcaagg gctggagtg gctgggcgtg atctgggcca ggggcttcac caactacaac    180
agcgccctga tgagcaggct gaccatcagc aaggacaaca gcaagaacca ggtgtccctg    240
aagctgtcca gcgtgacagc cgccgacacc gccgtgtact actgcgccag gccaacgac    300 ggcgtgtact acgccatgga ctactggggc cagggcaccc tggtcaccgt cagctcagcg    360
tcgaccaagg gccccagcgt gttcccgcta gcccccagca gcaagagcac cagcggcggc    420
acagccgccc tgggctgcct ggtgaaggac tacttccccg agcccgttac cgtgtcctgg    480
aactctggag ccctgacctc cggcgtgcac accttccccg ccgtgctcca gagcagcggc    540
ctgtacagcc tgagcagcgt ggtgacagtg cccagcagca gcctgggaac ccagacctac    600
atctgcaacg tgaaccacaa gcccagcaac accaaggtgg acaagaaggt ggagcccaag    660
```

```
agctgcgaca aaactcacac atgccccccc tgccctgccc ctgagctgct gggcggaccc    720
tccgtgttcc tgttccccca caagcccaag gacaccctga tgatcagccg acccccgag    780 gtgacctgcg tggtggtgga cgtgagccac gaggaccctg aggtgaagtt caattggtac    840
gtggacggcg tggaggtgca caacgccaag accaagcccc gggaggaaca gtacaacagc    900
acctaccggg tggtgtccgt gctgaccgtg ctgcaccagg actggctgaa cggcaaggaa    960
tacaagtgca aggtctccaa caaggccctg cctgccccca tcgagaaaac catctccaaa   1020
gccaaaggcc agcccagaga accccaggtg tacaccctgc cccccagcag agatgagctg   1080
accaagaacc aggtcaagct cgtgtgcctg gtcaccggct tctacccag cgatatcgcc    1140 gtggagtggg agagcaacgg ccagcctgaa aacaactact acaccacccc ccctgtgctg   1200
gacagcgacg gcagcttcag cctggtgtcc tggctgaacg tggacaagag ccggtggcag   1260
cagggcaacg tgttcagctg cagcgtgatg cacgaggccc tgcacaacca ctacacccag   1320
aagtccctga gcctgtctcc tggcaagcat caccatcacc atcac                   1365
```

<210> SEQ ID NO 67
<211> LENGTH: 639
<212> TYPE: DNA
<213> ORGANISM: Artificial Sequence
<220> FEATURE:
<223> OTHER INFORMATION: Synthetic polynucleotide

<400> SEQUENCE: 67

```
gacttcgtga tgacccagag ccccgccttc ctgagcgtga ccccaggcga aaggtgacc     60 atcacctgca gcgcccagag cagcgtgaac tacatccact ggtaccagca gaagcccgac   120
caggccccca gaagctgat ctacgacacc agcaagctgg ccagcggcgt gcccagcagg    180
ttcagcggca gcggctccgg caccgactac accttcacca tcagcagcct ggaggccgag   240
gacgccgcca cctactactg ccagcagtgg accaccaacc ccctgacctt cggccagggc   300
accaaggtgg agatcaagag gaccgtggcc gcccccagcg tgttcatctt ccccccagc    360 gacgagcagc tgaagagcgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgacccctg   540 agcaaggccg actacgagaa gcacaaggtg tacgcctgcg aggtgaccca ccagggcctg   600
tccagccccg tgaccaagag cttcaacagg ggcgagtgc                          639
```

<210> SEQ ID NO 68
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 68

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
```

```
                65                  70                  75                  80
Lys Leu Ser Ser Val Thr Ala Ala Asp Thr Ala Val Tyr Tyr Cys Ala
                    85                  90                  95

Arg Ala Asn Asp Gly Val Tyr Tyr Ala Met Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Lys Leu Val
            355                 360                 365

Cys Leu Val Thr Gly Phe Tyr Pro Ser Asp Ile Ala Val Glu Trp Glu
        370                 375                 380

Ser Asn Gly Gln Pro Glu Asn Asn Tyr Tyr Thr Thr Pro Pro Val Leu
385                 390                 395                 400

Asp Ser Asp Gly Ser Phe Ser Leu Val Ser Trp Leu Asn Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys His His His His His His
    450                 455

<210> SEQ ID NO 69
<211> LENGTH: 213
<212> TYPE: PRT
<213> ORGANISM: Artificial Sequence
```

<220> FEATURE:
<223> OTHER INFORMATION: Synthetic polypeptide

<400> SEQUENCE: 69

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 70
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 70

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val 115                 120                 125
Phe Pro Met Ala Pro Ser Ser Lys Ser Thr Ser Gly Gly Thr Ala Asn
            130                 135                 140

Leu Ala Cys Leu Val Lys Glu Tyr Phe Pro Glu Pro Val Thr Val Ser
145                 150                 155                 160

Trp Asn Ser Gly Ala Leu Thr Ser Gly Val Phe Thr Ala Pro Ala Val
                165                 170                 175

Leu Ser Ser Ser Gly Leu Tyr Asn Leu Val Ser Leu Val Lys Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Ala
            340                 345                 350

Thr Phe Pro Pro Ser Arg Asp Glu Leu Thr Lys Asn Gln Val Thr Leu
        355                 360                 365

Val Cys Leu Val Thr Gly Phe Tyr Pro Ser Asp Ile Ala Val Glu Trp
    370                 375                 380

Glu Ser Asn Gly Gln Pro Glu Asn Asn Tyr Lys Thr Asp Pro Pro Leu
385                 390                 395                 400

Leu Glu Ser Asp Gly Ser Phe Ala Leu Ser Ser Arg Leu Arg Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 71
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 71

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr

Gly Val Ser Trp Val Arg Gln Ala Pro Gly Lys Gly Leu Glu Trp Val
            20                  25                  30
Ala Val Ile Trp Gly Ser Glu Thr Thr Tyr Tyr Asn Ser Ala Leu Lys
        35                  40                  45
Ser Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys His Tyr Tyr Tyr Gly Gly Ser Tyr Ala Met Asp Tyr Trp Gly Gln
            100                 105                 110
Gly Thr Leu Val Thr Val Ser Ser Ala Ser Thr Lys Gly Pro Gln Val
        115                 120                 125
Tyr Pro Leu Ala Pro Ser Ser Asp Glu Thr Ser Gly Gly Gln Ala Ser
    130                 135                 140
Leu Thr Cys Leu Val Lys Asp Tyr Phe Pro Glu Pro Val Thr Val Ser
145                 150                 155                 160
Trp Asn Ser Gly Ala Leu Thr Ser Gly Val Lys Thr Thr Pro Ala Val
                165                 170                 175
Leu Asp Ser Ser Gly Leu Tyr Phe Leu Tyr Ser Lys Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Ala Thr Phe Pro Pro Ser
            340                 345                 350
Arg Asp Glu Leu Thr Lys Asn Gln Val Thr Leu Val Cys Leu Val Thr
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Asp Pro Pro Leu Leu Glu Ser Asp Gly
385                 390                 395                 400
Ser Phe Ala Leu Ser Ser Arg Leu Arg Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 72
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 72

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Lys Leu Val
        355                 360                 365
```

```
Cys Leu Val Thr Gly Phe Tyr Pro Ser Asp Ile Ala Val Glu Trp Glu
        370                 375                 380

Ser Asn Gly Gln Pro Glu Asn Asn Tyr Tyr Thr Thr Pro Pro Val Leu
385                 390                 395                 400

Asp Ser Asp Gly Ser Phe Ser Leu Val Ser Trp Leu Asn Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 73
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 73

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Lys
130                 135                 140

Leu Val Cys Leu Val Thr Gly Phe Tyr Pro Ser Asp Ile Ala Val Glu
145                 150                 155                 160

Trp Glu Ser Ser Gly Gln Pro Glu Asn Asn Tyr Tyr Thr Thr Pro Pro
                165                 170                 175

Met Leu Asp Ser Asp Gly Ser Phe Ser Leu Val Ser Trp Leu Asn Val
            180                 185                 190

Asp Lys Ser Arg Trp Gln Gln Gly Asn Ile Phe Ser Cys Ser Val Met
        195                 200                 205

His Glu Ala Leu His Asn Arg Phe Thr Gln Lys Ser Leu Ser Leu Ser
210                 215                 220

Pro Gly Lys
225
```

<210> SEQ ID NO 74
<211> LENGTH: 227
<212> TYPE: PRT
<213> ORGANISM: Artificial Sequence
<220> FEATURE:

<223> OTHER INFORMATION: Synthetic polypeptide

<400> SEQUENCE: 74

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Ala Thr Phe Pro Pro Ser Arg Asp Glu Leu Thr Lys Asn Gln Val Thr
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Asp Gly Ser Phe Ala Leu Ser Ser Arg Leu Arg Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 75
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Cys Pro Ala Pro Glu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Glu Val Ala Thr Phe Pro
225                 230                 235                 240

Pro Ser Arg Asp Glu Leu Thr Lys Asn Gln Val Thr Leu Val Cys Leu
                245                 250                 255

Val Thr Gly Phe Tyr Pro Ser Asp Ile Ala Val Glu Trp Glu Ser Asn
            260                 265                 270

Gly Gln Pro Glu Asn Asn Tyr Lys Thr Asp Pro Pro Leu Leu Glu Ser
        275                 280                 285

Asp Gly Ser Phe Ala Leu Ser Ser Arg Leu Arg Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 76
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 76

Gly Gln Pro Arg Glu Pro Gln Val Tyr Thr Leu Pro Pro Ser Arg Glu
1               5                   10                  15

Glu Met Thr Lys Asn Gln Val Lys Leu Val Cys Leu Val Thr Gly Phe
            20                  25                  30

Tyr Pro Ser Asp Ile Ala Val Glu Trp Glu Ser Ser Gly Gln Pro Glu
        35                  40                  45

Asn Asn Tyr Tyr Thr Thr Pro Pro Met Leu Asp Ser Asp Gly Ser Phe
    50                  55                  60

Ser Leu Val Ser Trp Leu Asn Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 77
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 77

```
ggccagccca gagaacccca ggtgtacacc ctgcccccca gccgggaaga gatgaccaag    60
aaccaggtga aactggtgtg cctggtgaca ggcttctacc ccagcgatat cgccgtggaa   120
tgggagagca gcggccagcc tgagaacaac tactacacca ccccccccat gctggacagc   180
gacggcagct tcagcctggt gtcctggctg aacgtggaca gagccggtg gcagcagggc    240
aacatcttca gctgcagcgt gatgcacgag gccctgcaca accggttcac ccagaagtcc   300
ctgagcctga gccccggcaa g                                             321
```

<210> SEQ ID NO 78
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 78

```
Gly Gln Pro Arg Glu Pro Glu Val His Thr Leu Pro Pro Ser Arg Asp
1               5                   10                  15
Glu Leu Thr Lys Asn Gln Val Ser Leu Thr Cys Leu Val Arg Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Arg Leu Glu Ser Asp Gly Ser Phe
    50                  55                  60
Ala Leu Thr Ser Lys Leu Thr Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105
```

<210> SEQ ID NO 79
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 79

```
Gly Gln Pro Arg Glu Pro Gln Val Tyr Thr Leu Pro Pro Ser Arg Asp
1               5                   10                  15
Glu Leu Thr Lys Asn Gln Val Thr Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Leu Thr Trp Pro Pro Val Leu Asp Ser Asp Gly Ser Phe
    50                  55                  60
Phe Leu Tyr Ser Ile Leu Arg Val Asp Lys Ser Arg Trp Gln Gln Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Pro Gly Lys
            100                 105
```

```
<210> SEQ ID NO 80
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 80

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

His Thr Leu Pro Pro Ser Arg Asp Glu Leu Thr Lys Asn Gln Val Ser
    130                 135                 140

Leu Thr Cys Leu Val Arg Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Arg Leu Glu Ser Asp Gly Ser Phe Ala Leu Thr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 81
<211> LENGTH: 335
<212> TYPE: PRT
<213> ORGANISM: Artificial Sequence
<220> FEATURE:
<223> OTHER INFORMATION: Synthetic polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Thr Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Leu Thr Trp Pro Pro Val Leu Asp Ser
        275                 280                 285

Asp Gly Ser Phe Phe Leu Tyr Ser Ile Leu Arg Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 82
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 82
ggccagccta gagaacctga ggtgcacacc ctgcccccca gcagagatga gctgaccaag      60
aaccaggtgt ccctgacctg tctcgtgcgg ggcttctacc cctccgatat cgccgtggaa     120
tgggagagca acggccagcc cgagaacaac tacaagacca ccccccccag actggaaagc     180
gacggcagct tgccctgac cagcaagctg accgtggaca agagcagatg gcagcagggc      240
aacgtgttca gctgcagcgt gatgcacgag gccctgcaca accactacac ccagaagtcc     300
ctgagcctga gccccggcaa g                                               321

<210> SEQ ID NO 83
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 83

```
ggccagccta gagaacccca ggtgtacaca ctgcccccca gcagagatga gctgaccaag      60
aaccaagtga ccctgacctg cctcgtgaag ggcttctacc cctccgatat cgccgtggaa     120
tgggagagca acggccagcc cgagaacaac tacctgacct ggcccccctgt gctggacagc    180
gacggctcat tcttcctgta cagcatcctg cgggtggaca agagcagatg gcagcagggc    240
aacgtgttca gctgcagcgt gatgcacgag gccctgcaca accactacac ccagaagtcc    300
ctgagcctga gccccggcaa g                                              321
```

<210> SEQ ID NO 84
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 84

```
Gly Val Ala Leu His Arg Pro Asp Val Tyr Leu Leu Pro Pro Ala Arg
  1               5                  10                  15
Glu Gln Leu Asn Leu Arg Glu Ser Ala Lys Ile Val Cys Leu Val Thr
             20                  25                  30
Gly Phe Ser Pro Ala Asp Val Phe Val Gln Trp Met Gln Arg Gly Gln
         35                  40                  45
Pro Leu Ser Pro Glu Lys Tyr Tyr Thr Ser Ala Pro Met Pro Glu Pro
     50                  55                  60
Gln Ala Pro Gly Arg Tyr Ser Ala Val Ser Trp Leu Asn Val Ser Glu
 65                  70                  75                  80
Glu Glu Trp Asn Thr Gly Glu Thr Tyr Thr Cys Val Val Ala His Glu
                 85                  90                  95
Ala Leu Pro Asn Arg Val Thr Glu Arg Thr Val Asp Lys Ser Thr Gly
            100                 105                 110
Lys
```

<210> SEQ ID NO 85
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 85

```
Gly Val Ala Leu His Arg Pro Glu Val Ala Leu Phe Pro Pro Ala Arg
  1               5                  10                  15
Glu Gln Leu Asn Leu Arg Glu Ser Ala Thr Ile Val Cys Leu Val Thr
             20                  25                  30
Gly Phe Ser Pro Ala Asp Val Phe Val Gln Trp Met Gln Arg Gly Gln
         35                  40                  45
Pro Leu Ser Pro Glu Lys Tyr Val Thr Asp Ala Pro Leu Pro Glu Pro
     50                  55                  60
Gln Ala Pro Gly Arg Tyr Ala Ala Ser Arg Leu Arg Val Ser Glu
 65                  70                  75                  80
Glu Glu Trp Asn Thr Gly Glu Thr Tyr Thr Cys Val Val Ala His Glu
                 85                  90                  95
Ala Leu Pro Asn Arg Val Thr Glu Arg Thr Val Asp Lys Ser Thr Gly
            100                 105                 110
Lys
```

<210> SEQ ID NO 86
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 86

```
ggcgtggccc tgcacagacc cgacgtgtac ctgctgcctc ctgccagaga gcagctgaac     60
ctgcgggaaa gcgccaagat cgtgtgtctc gtgaccggct tctcccctgc cgacgtgttc    120
gtgcagtgga tgcagagagg ccagcccctg agccccgaga agtactacac aagcgccccc    180
atgcctgagc cacaggcccc tggaagatac agcgccgtgt cttggctgaa cgtgtccgag    240
gaagagtgga acaccggcga gacatacacc tgtgtggtgg cccatgaggc cctgcccaat    300
agagtgaccg agcggaccgt ggacaagagc accggaaag                           339
```

<210> SEQ ID NO 87
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 87

```
ggcgtggccc tgcacagacc agaggtggcc ctgtttccac ccgccagaga gcagctgaac     60
ctgcgggaaa gcgccaccat cgtgtgtctc gtgaccggct tcagccctgc cgacgtgttc    120
gtgcagtgga tgcagagagg ccagcccctg tccccgaga aatacgtgac agacgccccc    180
ctgcctgagc cacaggcccc tggaagatat gccgccagca gcagactgcg ggtgtccgag    240
gaagagtgga acaccggcga gacatacacc tgtgtggtgg cccatgaggc cctgcccaat    300
agagtgaccg aacggaccgt ggacaagagc accggcaag                           339
```

<210> SEQ ID NO 88
<211> LENGTH: 239
<212> TYPE: PRT
<213> ORGANISM: Artificial Sequence
<220> FEATURE:
<223> OTHER INFORMATION: Synthetic polypeptide

<400> SEQUENCE: 88

```
Asp Lys Thr His Thr Cys Pro Pro Cys Pro Ala Pro Glu Leu Leu Gly
1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Val Ala Leu His Arg Pro Asp
        115                 120                 125
```

```
Val Tyr Leu Leu Pro Pro Ala Arg Glu Gln Leu Asn Leu Arg Glu Ser
    130                 135                 140

Ala Lys Ile Val Cys Leu Val Thr Gly Phe Ser Pro Ala Asp Val Phe
145                 150                 155                 160

Val Gln Trp Met Gln Arg Gly Gln Pro Leu Ser Pro Glu Lys Tyr Tyr
                165                 170                 175

Thr Ser Ala Pro Met Pro Glu Pro Gln Ala Pro Gly Arg Tyr Ser Ala
            180                 185                 190

Val Ser Trp Leu Asn Val Ser Glu Glu Trp Asn Thr Gly Glu Thr
                195                 200                 205

Tyr Thr Cys Val Val Ala His Glu Ala Leu Pro Asn Arg Val Thr Glu
    210                 215                 220

Arg Thr Val Asp Lys Ser Thr Gly Lys His His His His His His
225                 230                 235
```

<210> SEQ ID NO 89
<211> LENGTH: 341
<212> TYPE: PRT
<213> ORGANISM: Artificial Sequence
<220> FEATURE:
<223> OTHER INFORMATION: Synthetic polypeptide

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Val Ala Leu His Arg Pro Glu Val Ala Leu Phe
225                 230                 235                 240

Pro Pro Ala Arg Glu Gln Leu Asn Leu Arg Glu Ser Ala Thr Ile Val
                245                 250                 255
```

```
Cys Leu Val Thr Gly Phe Ser Pro Ala Asp Val Phe Val Gln Trp Met
            260                 265                 270

Gln Arg Gly Gln Pro Leu Ser Pro Glu Lys Tyr Val Thr Asp Ala Pro
        275                 280                 285

Leu Pro Glu Pro Gln Ala Pro Gly Arg Tyr Ala Ala Ser Ser Arg Leu
    290                 295                 300

Arg Val Ser Glu Glu Glu Trp Asn Thr Gly Glu Thr Tyr Thr Cys Val
305                 310                 315                 320

Val Ala His Glu Ala Leu Pro Asn Arg Val Thr Glu Arg Thr Val Asp
                325                 330                 335

Lys Ser Thr Gly Lys
            340

<210> SEQ ID NO 90
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 90

Gly Pro Arg Ala Ala Pro Glu Val Tyr Ala Phe Ala Thr Pro Glu Trp
1               5                   10                  15

Pro Gly Ser Arg Asp Lys Arg Lys Leu Val Cys Leu Ile Thr Asn Phe
            20                  25                  30

Met Pro Glu Asp Ile Ser Val Gln Trp Leu His Asn Glu Val Gln Leu
        35                  40                  45

Pro Asp Ala Arg His Tyr Thr Thr Gln Pro Arg Lys Thr Lys Gly Ser
    50                  55                  60

Gly Phe Ser Val Val Ser Trp Leu Asn Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110

<210> SEQ ID NO 91
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 91

Gly Pro Arg Ala Ala Pro Glu Val Ala Ala Phe Ala Thr Pro Glu Trp
1               5                   10                  15

Pro Gly Ser Arg Asp Lys Arg Thr Leu Val Cys Leu Ile Thr Asn Phe
            20                  25                  30

Met Pro Glu Asp Ile Ser Val Gln Trp Leu His Asn Glu Val Gln Leu
        35                  40                  45

Pro Asp Ala Arg His Ser Thr Asp Gln Pro Leu Lys Glu Lys Gly Ser
    50                  55                  60

Gly Phe Ala Val Ser Ser Leu Leu Arg Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110
```

<210> SEQ ID NO 92
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 92

```
ggacctagag ccgcccctga ggtgtacgcc tttgccacac ctgagtggcc cggcagccgg      60
gacaagagaa aactcgtgtg cctgatcacc aacttcatgc ccgaggacat cagcgtgcag     120
tggctgcaca acgaggtgca gctgcccgac gccagacact acaccaccca gcccagaaag     180
accaagggca gcggcttcag cgtggtgtcc tggctgaatg tgaccagagc cgagtgggag     240
cagaaggacg agttcatctg cagagccgtg cacgaggccg ccagcccttc tcagacagtg     300
cagagggccg tgtccgtgaa ccctggaaaa                                      330
```

<210> SEQ ID NO 93
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 93

```
ggacctagag ccgctcctga agtggccgcc tttgccacac ctgagtggcc cggcagcaga      60
gacaagagaa ccctcgtgtg cctgatcacc aacttcatgc ccgaggacat cagcgtgcag     120
tggctgcaca acgaggtgca gctgcccgat gccagacaca gcaccgacca gcccctgaaa     180
gagaagggca gcggctttgc cgtgtccagc ctgctgagag tgaccagagc cgagtgggag     240
cagaaggacg agttcatctg cagagccgtg cacgaggccg ccagcccttc tcagacagtg     300
cagagggccg tgtccgtgaa ccctggaaaa                                      330
```

<210> SEQ ID NO 94
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 94

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Pro Arg Ala Ala Pro Glu Val
        115                 120                 125
```

```
Tyr Ala Phe Ala Thr Pro Glu Trp Pro Gly Ser Arg Asp Lys Arg Lys
    130                 135                 140

Leu Val Cys Leu Ile Thr Asn Phe Met Pro Glu Asp Ile Ser Val Gln
145                 150                 155                 160

Trp Leu His Asn Glu Val Gln Leu Pro Asp Ala Arg His Tyr Thr Thr
                165                 170                 175

Gln Pro Arg Lys Thr Lys Gly Ser Gly Phe Ser Val Val Ser Trp Leu
            180                 185                 190

Asn Val Thr Arg Ala Glu Trp Glu Gln Lys Asp Glu Phe Ile Cys Arg
        195                 200                 205

Ala Val His Glu Ala Ala Ser Pro Ser Gln Thr Val Gln Arg Ala Val
    210                 215                 220

Ser Val Asn Pro Gly Lys His His His His His
225                 230                 235

<210> SEQ ID NO 95
<211> LENGTH: 338
<212> TYPE: PRT
<213> ORGANISM: Artificial Sequence
<220> FEATURE:
<223> OTHER INFORMATION: Synthetic polypeptide

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg Asp Lys Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Pro Arg Ala Ala Pro Glu Val Ala Ala Phe Ala
225                 230                 235                 240

Thr Pro Glu Trp Pro Gly Ser Arg Asp Lys Arg Thr Leu Val Cys Leu
                245                 250                 255
```

```
Ile Thr Asn Phe Met Pro Glu Asp Ile Ser Val Gln Trp Leu His Asn
                260                 265                 270

Glu Val Gln Leu Pro Asp Ala Arg His Ser Thr Asp Gln Pro Leu Lys
            275                 280                 285

Glu Lys Gly Ser Gly Phe Ala Val Ser Ser Leu Leu Arg Val Thr Arg
        290                 295                 300

Ala Glu Trp Glu Gln Lys Asp Glu Phe Ile Cys Arg Ala Val His Glu
305                 310                 315                 320

Ala Ala Ser Pro Ser Gln Thr Val Gln Arg Ala Val Ser Val Asn Pro
                325                 330                 335

Gly Lys

<210> SEQ ID NO 96
<211> LENGTH: 111
<212> TYPE: PRT
<213> ORGANISM: Homo sapiens
<220> FEATURE:
<221> NAME/KEY: MISC_FEATURE
<222> LOCATION: (1)..(111)
<223> OTHER INFORMATION: human CH3 (isotype alpha 1) constant domain

<400> SEQUENCE: 96

Gly Asn Thr Phe Arg Pro Glu Val His Leu Leu Pro Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala
            100                 105                 110

<210> SEQ ID NO 97
<211> LENGTH: 111
<212> TYPE: PRT
<213> ORGANISM: Homo sapiens
<220> FEATURE:
<221> NAME/KEY: MISC_FEATURE
<222> LOCATION: (1)..(111)
<223> OTHER INFORMATION: human CH3 (isotype alpha 2) constant domain

<400> SEQUENCE: 97

Gly Asn Thr Phe Arg Pro Glu Val His Leu Leu Pro Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95
```

Ala Leu Pro Leu Ala Phe Thr Gln Lys Thr Ile Asp Arg Leu Ala
            100                 105                 110

<210> SEQ ID NO 98
<211> LENGTH: 353
<212> TYPE: PRT
<213> ORGANISM: Artificial Sequence
<220> FEATURE:
<223> OTHER INFORMATION: IGHA1

<400> SEQUENCE: 98

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 99
<211> LENGTH: 340
<212> TYPE: PRT
<213> ORGANISM: Artificial Sequence
<220> FEATURE:
<223> OTHER INFORMATION: IGHA2

<400> SEQUENCE: 99

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335

Gly Thr Cys Tyr
            340
```

```
<210> SEQ ID NO 100
<211> LENGTH: 384
<212> TYPE: PRT
<213> ORGANISM: Artificial Sequence
<220> FEATURE:
<223> OTHER INFORMATION: IGHD

<400> SEQUENCE: 100
```

| | | | | | | | | | | | | | | | |
|---|---|---|---|---|---|---|---|---|---|---|---|---|---|---|---|
|Ala|Pro|Thr|Lys|Ala|Pro|Asp|Val|Phe|Pro|Ile|Ile|Ser|Gly|Cys|Arg|
|1| | | |5| | | | |10| | | | |15| |
|His|Pro|Lys|Asp|Asn|Ser|Pro|Val|Val|Leu|Ala|Cys|Leu|Ile|Thr|Gly|
| | | | |20| | | | |25| | | | |30| |
|Tyr|His|Pro|Thr|Ser|Val|Thr|Val|Thr|Trp|Tyr|Met|Gly|Thr|Gln|Ser|
| | | | |35| | | | |40| | | | |45| |
|Gln|Pro|Gln|Arg|Thr|Phe|Pro|Glu|Ile|Gln|Arg|Arg|Asp|Ser|Tyr|Tyr|
| |50| | | | |55| | | | |60| | | | |
|Met|Thr|Ser|Ser|Gln|Leu|Ser|Thr|Pro|Leu|Gln|Gln|Trp|Arg|Gln|Gly|
|65| | | | |70| | | | |75| | | | |80|
|Glu|Tyr|Lys|Cys|Val|Val|Gln|His|Thr|Ala|Ser|Lys|Ser|Lys|Lys|Glu|
| | | | |85| | | | |90| | | | |95| |
|Ile|Phe|Arg|Trp|Pro|Glu|Ser|Pro|Lys|Ala|Gln|Ala|Ser|Ser|Val|Pro|
| | | | |100| | | | |105| | | | |110| |
|Thr|Ala|Gln|Pro|Gln|Ala|Glu|Gly|Ser|Leu|Ala|Lys|Ala|Thr|Thr|Ala|
| | | | |115| | | | |120| | | | |125| |
|Pro|Ala|Thr|Thr|Arg|Asn|Thr|Gly|Arg|Gly|Gly|Glu|Glu|Lys|Lys|Lys|
| |130| | | | |135| | | | |140| | | | |
|Glu|Lys|Glu|Lys|Glu|Glu|Gln|Glu|Glu|Arg|Glu|Thr|Lys|Thr|Pro|Glu|
|145| | | | |150| | | | |155| | | | |160|
|Cys|Pro|Ser|His|Thr|Gln|Pro|Leu|Gly|Val|Tyr|Leu|Leu|Thr|Pro|Ala|
| | | | |165| | | | |170| | | | |175| |
|Val|Gln|Asp|Leu|Trp|Leu|Arg|Asp|Lys|Ala|Thr|Phe|Thr|Cys|Phe|Val|
| | | | |180| | | | |185| | | | |190| |
|Val|Gly|Ser|Asp|Leu|Lys|Asp|Ala|His|Leu|Thr|Trp|Glu|Val|Ala|Gly|
| | | | |195| | | | |200| | | | |205| |
|Lys|Val|Pro|Thr|Gly|Gly|Val|Glu|Glu|Gly|Leu|Leu|Glu|Arg|His|Ser|
| |210| | | | |215| | | | |220| | | | |
|Asn|Gly|Ser|Gln|Ser|Gln|His|Ser|Arg|Leu|Thr|Leu|Pro|Arg|Ser|Leu|
|225| | | | |230| | | | |235| | | | |240|
|Trp|Asn|Ala|Gly|Thr|Ser|Val|Thr|Cys|Thr|Leu|Asn|His|Pro|Ser|Leu|
| | | | |245| | | | |250| | | | |255| |
|Pro|Pro|Gln|Arg|Leu|Met|Ala|Leu|Arg|Glu|Pro|Ala|Ala|Gln|Ala|Pro|
| | | | |260| | | | |265| | | | |270| |
|Val|Lys|Leu|Ser|Leu|Asn|Leu|Leu|Ala|Ser|Ser|Asp|Pro|Pro|Glu|Ala|
| | | | |275| | | | |280| | | | |285| |
|Ala|Ser|Trp|Leu|Leu|Cys|Glu|Val|Ser|Gly|Phe|Ser|Pro|Pro|Asn|Ile|
| |290| | | | |295| | | | |300| | | | |
|Leu|Leu|Met|Trp|Leu|Glu|Asp|Gln|Arg|Glu|Val|Asn|Thr|Ser|Gly|Phe|
|305| | | | |310| | | | |315| | | | |320|
|Ala|Pro|Ala|Arg|Pro|Pro|Gln|Pro|Arg|Ser|Thr|Thr|Phe|Trp|Ala|
| | | | |325| | | | |330| | | | |335|
|Trp|Ser|Val|Leu|Arg|Val|Pro|Ala|Pro|Pro|Ser|Pro|Gln|Pro|Ala|Thr|
| | | | |340| | | | |345| | | | |350| |
|Tyr|Thr|Cys|Val|Val|Ser|His|Glu|Asp|Ser|Arg|Thr|Leu|Leu|Asn|Ala|
| | | | |355| | | | |360| | | | |365| |

Ser Arg Ser Leu Glu Val Ser Tyr Val Thr Asp His Gly Pro Met Lys
    370                 375                 380

<210> SEQ ID NO 101
<211> LENGTH: 428
<212> TYPE: PRT
<213> ORGANISM: Artificial Sequence
<220> FEATURE:
<223> OTHER INFORMATION: IGHE

<400> SEQUENCE: 101

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Cys Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
    130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
            340                 345                 350

```
Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
            420                 425

<210> SEQ ID NO 102
<211> LENGTH: 330
<212> TYPE: PRT
<213> ORGANISM: Artificial Sequence
<220> FEATURE:
<223> OTHER INFORMATION: IGHG1

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 103
<211> LENGTH: 326
<212> TYPE: PRT
<213> ORGANISM: Artificial Sequence
<220> FEATURE:
<223> OTHER INFORMATION: IGHG2

<400> SEQUENCE: 103

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
290                 295                 300
Ser Val Met His Glu Ala Leu His Asn His Tyr Thr Gln Lys Ser Leu
305                 310                 315                 320

```
Ser Leu Ser Pro Gly Lys
            325

<210> SEQ ID NO 104
<211> LENGTH: 377
<212> TYPE: PRT
<213> ORGANISM: Artificial Sequence
<220> FEATURE:
<223> OTHER INFORMATION: IGHG3

<400> SEQUENCE: 104

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

```
Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 105
<211> LENGTH: 327
<212> TYPE: PRT
<213> ORGANISM: Artificial Sequence
<220> FEATURE:
<223> OTHER INFORMATION: IGHG4

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 106
<211> LENGTH: 431
<212> TYPE: PRT
<213> ORGANISM: Artificial Sequence
<220> FEATURE:
<223> OTHER INFORMATION: IGHGP

<400> SEQUENCE: 106

```
Ala Ser Thr Lys Gly Pro Ser Val Phe Pro Leu Val Pro Ser Ser Arg
1               5                   10                  15

Ser Val Ser Glu Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Arg
        35                  40                  45

Ser Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Pro Lys Thr Pro Cys Cys Asp Thr Thr His Thr Cys Pro Pro
            100                 105                 110

Cys Ala Thr Glu Pro Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Trp Glu
                165                 170                 175

Glu Gln Tyr Asn Ser Thr Tyr His Val Val Ser Val Leu Thr Val Val
            180                 185                 190

His Gln Asn Trp Leu Asn Gly Arg Glu Tyr Lys Cys Lys Val Ser Asn
        195                 200                 205

Lys Gly Leu Pro Ala Pro Ile Glu Lys Thr Ile Ser Lys Thr Lys Gln
    210                 215                 220

Pro Arg Glu Pro Gln Val Tyr Thr Leu Pro Pro Ser Gln Lys Met Thr
225                 230                 235                 240

Lys Asn Gln Val Thr Leu Thr Cys Leu Val Lys Gly Phe Tyr Pro Ser
                245                 250                 255

Asp Ile Thr Val Glu Trp Glu Ser Asn Gly Gln Pro Glu Asn Asn Tyr
            260                 265                 270

Lys Thr Thr Pro Pro Met Leu Asp Ser Asn Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Gly Leu His Asn His Tyr Thr Gln Lys
305                 310                 315                 320

Ser Leu Ser Leu Ser Pro Gly Lys Gln Pro Arg Glu Pro Gln Val Tyr
                325                 330                 335

Thr Leu Pro Pro Ser Gln Lys Met Thr Lys Asn Gln Val Thr Leu Thr
            340                 345                 350

Cys Leu Val Lys Gly Phe Tyr Pro Ser Asp Ile Thr Val Glu Trp Glu
        355                 360                 365
```

```
Ser Asn Gly Gln Pro Glu Asn Asn Tyr Lys Thr Thr Pro Pro Met Leu
370                 375                 380

Asp Ser Asn Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
            405                 410                 415

Gly Leu His Asn His Tyr Thr Gln Lys Ser Leu Ser Leu Ser Pro
            420                 425                 430

<210> SEQ ID NO 107
<211> LENGTH: 452
<212> TYPE: PRT
<213> ORGANISM: Artificial Sequence
<220> FEATURE:
<223> OTHER INFORMATION: IGHM

<400> SEQUENCE: 107

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Ser Glu Glu Glu
290                 295                 300
```

```
Trp Asn Thr Gly Glu Thr Tyr Thr Cys Val Ala His Glu Ala Leu Pro
305                 310                 315                 320

Asn Arg Val Thr Glu Arg Thr Val Asp Lys Ser Thr Gly Lys Pro Thr
                325                 330                 335

Leu Tyr Asn Val Ser Leu Val Met Ser Asp Thr Ala Gly Thr Cys Tyr
            340                 345                 350

Phe Thr Cys Thr Val Thr His Thr Asp Leu Pro Ser Pro Leu Lys Gln
        355                 360                 365

Thr Ile Ser Arg Pro Lys Gly Val Ala Leu His Arg Pro Asp Val Tyr
    370                 375                 380

Leu Leu Pro Pro Ala Arg Glu Gln Leu Asn Leu Arg Glu Ser Ala Thr
385                 390                 395                 400

Ile Thr Cys Leu Val Thr Gly Phe Ser Pro Ala Asp Val Phe Val Gln
                405                 410                 415

Trp Met Gln Arg Gly Gln Pro Leu Ser Pro Glu Lys Tyr Val Thr Ser
                420                 425                 430

Ala Pro Met Pro Glu Pro Gln Ala Pro Gly Arg Tyr Phe Ala His Ser
            435                 440                 445

Ile Leu Thr Val
    450

<210> SEQ ID NO 108
<211> LENGTH: 107
<212> TYPE: PRT
<213> ORGANISM: Artificial Sequence
<220> FEATURE:
<223> OTHER INFORMATION: IGKC

<400> SEQUENCE: 108

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 109
<211> LENGTH: 104
<212> TYPE: PRT
<213> ORGANISM: Artificial Sequence
<220> FEATURE:
<223> OTHER INFORMATION: IGLC1

<400> SEQUENCE: 109

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45
```

```
Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 110
<211> LENGTH: 105
<212> TYPE: PRT
<213> ORGANISM: Artificial Sequence
<220> FEATURE:
<223> OTHER INFORMATION: IGLC2

<400> SEQUENCE: 110

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 111
<211> LENGTH: 104
<212> TYPE: PRT
<213> ORGANISM: Artificial Sequence
<220> FEATURE:
<223> OTHER INFORMATION: IGLC3

<400> SEQUENCE: 111

```
Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
                20                  25                  30

Pro Gly Ala Val Thr Val Ala Trp Lys Ala Asp Ser Ser Pro Val Lys
            35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 112
<211> LENGTH: 105
<212> TYPE: PRT

```
<213> ORGANISM: Artificial Sequence
<220> FEATURE:
<223> OTHER INFORMATION: IGLC6

<400> SEQUENCE: 112

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Ala Glu Cys Ser
            100                 105

<210> SEQ ID NO 113
<211> LENGTH: 106
<212> TYPE: PRT
<213> ORGANISM: Artificial Sequence
<220> FEATURE:
<223> OTHER INFORMATION: IGLC7

<400> SEQUENCE: 113

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Ala Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 114
<211> LENGTH: 141
<212> TYPE: PRT
<213> ORGANISM: Artificial Sequence
<220> FEATURE:
<223> OTHER INFORMATION: TRAC
<220> FEATURE:
<221> NAME/KEY: misc_feature
<222> LOCATION: (1)..(1)
<223> OTHER INFORMATION: Xaa can be any naturally occurring amino acid

<400> SEQUENCE: 114

Xaa Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
```

```
                 35                  40                  45
Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Pro Glu Ser Ser Cys Asp
                 85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
                115                 120                 125

Gly Phe Asn Leu Leu Met Thr Leu Arg Leu Trp Ser Ser
                130                 135                 140

<210> SEQ ID NO 115
<211> LENGTH: 177
<212> TYPE: PRT
<213> ORGANISM: Artificial Sequence
<220> FEATURE:
<223> OTHER INFORMATION: TRBC1

<400> SEQUENCE: 115

Glu Asp Leu Asn Lys Val Phe Pro Pro Glu Val Ala Val Phe Glu Pro
1               5                  10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
                35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Val Ser Tyr Gln Gln Gly Val Leu Ser
                130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 116
<211> LENGTH: 178
<212> TYPE: PRT
<213> ORGANISM: Artificial Sequence
<220> FEATURE:
<223> OTHER INFORMATION: TRBC2

<400> SEQUENCE: 116

Asp Leu Lys Asn Val Phe Pro Pro Glu Val Ala Val Phe Glu Pro Ser
1               5                  10                  15

Glu Ala Glu Ile Ser His Thr Gln Lys Ala Thr Leu Val Cys Leu Ala
```

```
                   20                  25                  30
Thr Gly Phe Tyr Pro Asp His Val Glu Leu Ser Trp Trp Val Asn Gly
                35                  40                  45
Lys Glu Val His Ser Gly Val Ser Thr Asp Pro Gln Pro Leu Lys Glu
         50                  55                  60
Gln Pro Ala Leu Asn Asp Ser Arg Tyr Cys Leu Ser Ser Arg Leu Arg
 65                  70                  75                  80
Val Ser Ala Thr Phe Trp Gln Asn Pro Arg Asn His Phe Arg Cys Gln
                85                  90                  95
Val Gln Phe Tyr Gly Leu Ser Glu Asn Asp Glu Trp Thr Gln Asp Arg
               100                 105                 110
Ala Lys Pro Val Thr Gln Ile Val Ser Ala Glu Ala Trp Gly Arg Ala
               115                 120                 125
Asp Cys Gly Phe Thr Ser Glu Ser Tyr Gln Gln Gly Val Leu Ser Ala
               130                 135                 140
Thr Ile Leu Tyr Glu Ile Leu Leu Gly Lys Ala Thr Leu Tyr Ala Val
145                 150                 155                 160
Leu Val Ser Ala Leu Val Leu Met Ala Met Val Lys Arg Lys Asp Ser
               165                 170                 175

Arg Gly

<210> SEQ ID NO 117
<211> LENGTH: 154
<212> TYPE: PRT
<213> ORGANISM: Artificial Sequence
<220> FEATURE:
<223> OTHER INFORMATION: TRDC
<220> FEATURE:
<221> NAME/KEY: misc_feature
<222> LOCATION: (1)..(1)
<223> OTHER INFORMATION: Xaa can be any naturally occurring amino acid

<400> SEQUENCE: 117

Xaa Ser Gln Pro His Thr Lys Pro Ser Val Phe Val Met Lys Asn Gly
 1               5                  10                  15
Thr Asn Val Ala Cys Leu Val Lys Glu Phe Tyr Pro Lys Asp Ile Arg
                20                  25                  30
Ile Asn Leu Val Ser Ser Lys Lys Ile Thr Glu Phe Asp Pro Ala Ile
                35                  40                  45
Val Ile Ser Pro Ser Gly Lys Tyr Asn Ala Val Lys Leu Gly Lys Tyr
         50                  55                  60
Glu Asp Ser Asn Ser Val Thr Cys Ser Val Gln His Asp Asn Lys Thr
 65                  70                  75                  80
Val His Ser Thr Asp Phe Glu Val Lys Thr Asp Ser Thr Asp His Val
                85                  90                  95
Lys Pro Lys Glu Thr Glu Asn Thr Lys Gln Pro Ser Lys Ser Cys His
               100                 105                 110
Lys Pro Lys Ala Ile Val His Thr Glu Lys Val Asn Met Met Ser Leu
               115                 120                 125
Thr Val Leu Gly Leu Arg Met Leu Phe Ala Lys Thr Val Ala Val Asn
               130                 135                 140
Phe Leu Leu Thr Ala Lys Leu Phe Phe Leu
145                 150

<210> SEQ ID NO 118
<211> LENGTH: 173
<212> TYPE: PRT
```

<213> ORGANISM: Artificial Sequence
<220> FEATURE:
<223> OTHER INFORMATION: TRGC1

<400> SEQUENCE: 118

```
Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170
```

<210> SEQ ID NO 119
<211> LENGTH: 109
<212> TYPE: PRT
<213> ORGANISM: Artificial Sequence
<220> FEATURE:
<223> OTHER INFORMATION: TRGC2 (2X)

<400> SEQUENCE: 119

```
Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
            20                  25                  30

Leu Glu Lys Phe Phe Pro Asp Ile Ile Lys Ile His Trp Gln Glu Lys
        35                  40                  45

Lys Ser Asn Thr Ile Leu Gly Ser Gln Glu Gly Asn Thr Met Lys Thr
    50                  55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr
            100                 105
```

<210> SEQ ID NO 120
<211> LENGTH: 204
<212> TYPE: PRT
<213> ORGANISM: Artificial Sequence
<220> FEATURE:
<223> OTHER INFORMATION: TRGC2 (3X)

<400> SEQUENCE: 120

-continued

Lys Gln Leu Asp Ala Asp Val Ser Pro Lys Pro Thr Ile Phe Leu Pro
1               5                   10                  15

Ser Ile Ala Glu Thr Lys Leu Gln Lys Ala Gly Thr Tyr Leu Cys Leu
            20                  25                  30

Leu Glu Lys Phe Phe Pro Asp Ile Ile Lys Ile His Trp Gln Glu Lys
            35                  40                  45

Lys Ser Asn Thr Ile Leu Gly Ser Gln Glu Gly Asn Thr Met Lys Thr
50                      55                  60

Asn Asp Thr Tyr Met Lys Phe Ser Trp Leu Thr Val Pro Glu Glu Ser
65                  70                  75                  80

Leu Asp Lys Glu His Arg Cys Ile Val Arg His Glu Asn Asn Lys Asn
                85                  90                  95

Gly Ile Asp Gln Glu Ile Ile Phe Pro Pro Ile Lys Thr Asp Val Thr
            100                 105                 110

Thr Val Asp Pro Lys Asp Ser Tyr Ser Lys Asp Ala Asn Asp Val Thr
        115                 120                 125

Thr Val Asp Pro Lys Tyr Asn Tyr Ser Lys Asp Ala Asn Asp Val Ile
        130                 135                 140

Thr Met Asp Pro Lys Asp Asn Trp Ser Lys Asp Ala Asn Asp Thr Leu
145                 150                 155                 160

Leu Leu Gln Leu Thr Asn Thr Ser Ala Tyr Tyr Met Tyr Leu Leu Leu
                165                 170                 175

Leu Leu Lys Ser Val Val Tyr Phe Ala Ile Ile Thr Cys Cys Leu Leu
            180                 185                 190

Gly Arg Thr Ala Phe Cys Cys Asn Gly Glu Lys Ser
            195                 200

<210> SEQ ID NO 121
<211> LENGTH: 214
<212> TYPE: PRT
<213> ORGANISM: Artificial Sequence
<220> FEATURE:
<223> OTHER INFORMATION: IGHEP1

<400> SEQUENCE: 121

Asn Pro Arg Gly Val Ser Ala Tyr Leu Ser Arg Pro Ser Pro Phe Asp
1               5                   10                  15

Leu Phe Ile Arg Lys Ser Pro Thr Ile Thr Cys Leu Val Val Asp Leu
            20                  25                  30

Ala Pro Ser Lys Trp Thr Val Asn Leu Thr Trp Ser Arg Ala Ser Gly
            35                  40                  45

Lys Pro Val Asn His Ser Thr Arg Lys Glu Glu Lys Gln Arg Asn Gly
50                  55                  60

Thr Leu Thr Val Thr Ser Thr Val Pro Val Gly Thr Arg Asp Trp Ile
65                  70                  75                  80

Glu Gly Glu Thr Tyr Gln Cys Arg Val Thr His Pro Gln Leu Pro Arg
                85                  90                  95

Ala Leu Val Arg Ser Thr Thr Lys Thr Ser Gly Pro Arg Ala Ala Pro
            100                 105                 110

Glu Val Tyr Ala Phe Ala Thr Pro Glu Trp Leu Gly Ser Arg Asp Lys
        115                 120                 125

Arg Thr Leu Thr Cys Leu Ile Gln Asn Phe Met Pro Glu Asp Ile Ser
        130                 135                 140

Val Gln Trp Leu His Asn Glu Val Gln Leu Pro Asp Ala Arg His Ser
145                 150                 155                 160

```
Thr Thr Gln Pro Arg Lys Thr Lys Gly Ser Gly Phe Phe Ile Phe Ser
                165                 170                 175

Arg Leu Glu Val Thr Arg Ala Glu Trp Glu Gln Lys Asp Glu Phe Ile
            180                 185                 190

Cys Arg Ala Val His Glu Ala Ala Ile Pro Ser Gln Thr Val Gln Arg
        195                 200                 205

Ala Val Ser Val Asn Pro
        210

<210> SEQ ID NO 122
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human IgG1 CH3 domain

<400> SEQUENCE: 122

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 123
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: CH3-BT alpha domain

<400> SEQUENCE: 123

Gly Gln Pro Arg Glu Pro Gln Val Tyr Thr Leu Pro Pro Ser Arg Asp
1               5                   10                  15

Glu Leu Thr Lys Asn Gln Val Lys Leu Val Cys Leu Val Thr Gly Phe
            20                  25                  30

Tyr Pro Ser Asp Ile Ala Val Glu Trp Glu Ser Asn Gly Gln Pro Glu
        35                  40                  45

Asn Asn Tyr Tyr Thr Thr Pro Pro Val Leu Asp Ser Asp Gly Ser Phe
    50                  55                  60

Ser Leu Val Ser Trp Leu Asn Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

```
<210> SEQ ID NO 124
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: CH3-BT beta domain

<400> SEQUENCE: 124

Gly Gln Pro Arg Glu Pro Glu Val Ala Thr Phe Pro Pro Ser Arg Asp
1               5                   10                  15

Glu Leu Thr Lys Asn Gln Val Thr Leu Val Cys Leu Val Thr Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Asp Pro Pro Leu Leu Glu Ser Asp Gly Ser Phe
    50                  55                  60

Cys Leu Ser Ser Arg Leu Arg Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```